US012698478B2

(12) United States Patent
Woods et al.

(10) Patent No.: US 12,698,478 B2
(45) Date of Patent: Aug. 4, 2026

(54) COMPOSITIONS AND METHODS FOR EXTRACTION OF MESENCHYMAL STEM CELLS

(71) Applicant: OSSIUM HEALTH, INC., San Francisco, CA (US)

(72) Inventors: Erik J. Woods, Carmel, IN (US); Brian H. Johnstone, Fishers, IN (US); Dongsheng Gu, Indianapolis, IN (US); Hannah Marie Miller, Speedway, IN (US)

(73) Assignee: OSSIUM HEALTH, INC., San Francisco, CA (US)

( * ) Notice: Subject to any disclaimer, the term of this patent is extended or adjusted under 35 U.S.C. 154(b) by 0 days.

(21) Appl. No.: 18/448,864

(22) Filed: Aug. 11, 2023

(65) Prior Publication Data

US 2024/0240151 A1     Jul. 18, 2024

Related U.S. Application Data

(63) Continuation of application No. 18/086,537, filed on Dec. 21, 2022, now abandoned, which is a continuation of application No. 17/684,277, filed on Mar. 1, 2022, now abandoned, which is a continuation of application No. PCT/US2021/055066, filed on Oct. 14, 2021.

(60) Provisional application No. 63/091,904, filed on Oct. 14, 2020.

(51) Int. Cl.
| | |
|---|---|
| *C12N 5/0775* | (2010.01) |
| *C12N 9/52* | (2006.01) |

(52) U.S. Cl.
CPC ............. *C12N 5/0663* (2013.01); *C12N 9/52* (2013.01); *C12N 2509/00* (2013.01)

(58) Field of Classification Search
CPC ..... C12N 5/0663; C12N 9/52; C12N 2509/00
See application file for complete search history.

(56) References Cited

U.S. PATENT DOCUMENTS

| | | | |
|---|---|---|---|
| 4,674,184 A | 6/1987 | Anderson | |
| 4,710,472 A | 12/1987 | Saur et al. | |
| 5,474,687 A | 12/1995 | Van Vlasselaer | |
| 5,672,346 A | 9/1997 | Srour et al. | |
| 5,766,944 A | 6/1998 | Ruiz | |
| 5,840,580 A | 11/1998 | Terstappen et al. | |
| 5,858,782 A | 1/1999 | Long et al. | |
| 6,739,112 B1 | 5/2004 | Marino | |
| 6,900,029 B1 | 5/2005 | Coulter et al. | |
| 7,470,538 B2 | 12/2008 | Laughlin et al. | |
| 7,547,210 B1 | 6/2009 | Valen | |
| 7,604,930 B1 | 10/2009 | Gao et al. | |
| 7,794,705 B2 | 9/2010 | Pecora et al. | |
| 7,883,698 B2 | 2/2011 | Michejda | |

| | | | |
|---|---|---|---|
| 7,915,043 B2 | 3/2011 | Caligiuri et al. | |
| 7,927,785 B2 | 4/2011 | Milhem et al. | |
| 8,048,618 B2 | 11/2011 | Luk et al. | |
| 8,088,370 B2 | 1/2012 | Pecora et al. | |
| 8,343,485 B2 | 1/2013 | Pecora et al. | |
| 8,425,899 B2 | 4/2013 | Pecora et al. | |
| 8,637,005 B2 | 1/2014 | Pecora et al. | |
| 8,709,403 B2 | 4/2014 | Pecora et al. | |
| 8,956,862 B2 | 2/2015 | Pal et al. | |
| 9,034,316 B2 | 5/2015 | Pecora et al. | |
| 9,078,429 B2 | 7/2015 | McGann et al. | |
| 9,192,695 B2 | 11/2015 | Shi | |
| 9,241,959 B2 | 1/2016 | Tang | |
| 9,402,377 B2 | 8/2016 | Flavell et al. | |
| 9,409,906 B2 | 8/2016 | Sauvageau et al. | |
| 9,499,792 B2 | 11/2016 | Chretien et al. | |
| 9,504,717 B2 | 11/2016 | Strober et al. | |
| 9,533,010 B2 | 1/2017 | Pecora et al. | |
| 9,534,202 B2 | 1/2017 | Pecora et al. | |
| 9,561,253 B2 | 2/2017 | Strober et al. | |
| 9,675,643 B2 | 6/2017 | Weston et al. | |
| 9,675,644 B2 | 6/2017 | Weston et al. | |
| 9,687,511 B2 | 6/2017 | Weston et al. | |
| 9,808,558 B2 | 11/2017 | Shi | |
| 9,814,803 B2 | 11/2017 | Shi | |
| 9,828,586 B2 | 11/2017 | Tom et al. | |
| 9,945,854 B2 | 4/2018 | Altman et al. | |
| 9,963,678 B2 | 5/2018 | Tom et al. | |
| 9,974,807 B2 | 5/2018 | Strober et al. | |

(Continued)

FOREIGN PATENT DOCUMENTS

| | | |
|---|---|---|
| CN | 1058991 C | 11/2000 |
| CN | 104357396 A | 2/2015 |

(Continued)

OTHER PUBLICATIONS

Gorantla VS et al. Development and validation of a procedure to isolate viable bone marrow cells from the vertebrae of cadveric organ donors for composite organ grafting. Cryotherapy. 2012. 14(1):104-113. (Year: 2012).*

AATB. Guidance Document, in Evaluation of Body Cooling at Standard D5.400. 2013. American Association of Tissue Banks: McLean, VA. p. 13.

Ahrens et al., Mesenchymal stem cell content of human vertebral bone marrow. Transplantation, 2004. 78(6): 925-929.

Aimulhem N., Cryopreservation and Hypothermal Storage of Hemotopoietic Stem Cells. Thesis; University of Cincinnati. May 30, 2013; (Year 2015) in 72 pages.

Banfi et al., Replicative Aging and Gene Expression in Long-term Cultures of Human Bone Marrow Stromal Cells. Tissue Eng, 2002. 8(6): p. 901-910.

(Continued)

*Primary Examiner* — Paul J Holland
(74) *Attorney, Agent, or Firm* — KNOBBE, MARTENS, OLSON & BEAR, LLP

(57) ABSTRACT

Compositions and methods for the extraction mesenchymal cells from deceased donor bone, and therapeutic applications thereof, along with combination therapeutic applications comprising mesenchymal cells from deceased donors and bone marrow derived from deceased donors are presented.

23 Claims, 15 Drawing Sheets

(56) References Cited

U.S. PATENT DOCUMENTS

| | | | |
|---|---|---|---|
| 10,047,344 B2 | 8/2018 | Poon et al. |
| 10,076,113 B2 | 9/2018 | Chretien et al. |
| 10,076,542 B2 | 9/2018 | Strober et al. |
| 10,080,769 B2 | 9/2018 | Strober et al. |
| 10,143,562 B2 | 12/2018 | Malinin |
| 10,159,694 B2 | 12/2018 | Strober et al. |
| 10,183,043 B2 | 1/2019 | Strober et al. |
| 10,258,648 B2 | 4/2019 | Strober et al. |
| 10,286,112 B2 | 5/2019 | Govil |
| 10,400,218 B2 | 9/2019 | Itescu et al. |
| 10,472,608 B2 | 11/2019 | Bader et al. |
| 10,513,690 B2 | 12/2019 | Ganey et al. |
| 10,550,369 B2 | 2/2020 | Tom et al. |
| 10,603,340 B2 | 3/2020 | Strober et al. |
| 10,645,921 B2 | 5/2020 | Temple et al. |
| 10,660,329 B2 | 5/2020 | Ivanovic et al. |
| 10,660,954 B2 | 5/2020 | Mitchell et al. |
| 10,669,528 B2 | 6/2020 | Rossi et al. |
| 10,995,318 B2 | 5/2021 | Woods et al. |
| 11,085,024 B2 | 8/2021 | Woods et al. |
| 11,104,882 B2 | 8/2021 | Woods et al. |
| 11,447,750 B2 | 9/2022 | Woods et al. |
| 11,697,799 B2 | 7/2023 | Woods et al. |
| 11,702,637 B2 | 7/2023 | Woods et al. |
| 11,744,243 B2 | 9/2023 | Woods et al. |
| 2002/0039786 A1 | 4/2002 | Reid et al. |
| 2002/0182186 A1 | 12/2002 | Loeb |
| 2003/0082158 A1 | 5/2003 | Symonds et al. |
| 2003/0161817 A1 | 8/2003 | Young et al. |
| 2004/0072347 A1 | 4/2004 | Schuler et al. |
| 2004/0107453 A1 | 6/2004 | Furcht et al. |
| 2004/0156834 A1 | 8/2004 | Slavin et al. |
| 2004/0258670 A1 | 12/2004 | Laughlin et al. |
| 2005/0233299 A1 | 10/2005 | Sawa et al. |
| 2007/0036734 A1 | 2/2007 | Tahara et al. |
| 2007/0190023 A1 | 8/2007 | Battista et al. |
| 2007/0224587 A1 | 9/2007 | Forsell et al. |
| 2010/0178279 A1 | 7/2010 | Cunningham-Rundles et al. |
| 2010/0260721 A1 | 10/2010 | McGonagie et al. |
| 2010/0310535 A1 | 12/2010 | Nakamura et al. |
| 2010/0310536 A1 | 12/2010 | Nakamura et al. |
| 2012/0020934 A1 | 1/2012 | Ma |
| 2012/0052049 A1* | 3/2012 | Woods .................... A61P 29/00 |
| | | 424/93.7 |
| 2012/0276581 A1 | 11/2012 | Arav et al. |
| 2012/0276628 A1 | 11/2012 | Khan et al. |
| 2013/0011376 A1 | 1/2013 | Peled et al. |
| 2013/0216495 A1 | 8/2013 | Motlagh et al. |
| 2013/0236433 A1 | 9/2013 | Webster |
| 2013/0302293 A1 | 11/2013 | Webster |
| 2014/0363437 A1 | 12/2014 | Reisner et al. |
| 2015/0203820 A1 | 7/2015 | Wang et al. |
| 2015/0216911 A1 | 8/2015 | Vines et al. |
| 2016/0000062 A1 | 1/2016 | Chen et al. |
| 2016/0089401 A1 | 3/2016 | Woods et al. |
| 2016/0101134 A1 | 4/2016 | Tang |
| 2016/0175198 A1 | 6/2016 | Warner et al. |
| 2017/0035935 A1 | 2/2017 | Uveges et al. |
| 2017/0151287 A1 | 6/2017 | Von Maltzahn et al. |
| 2017/0198257 A1 | 7/2017 | Bader et al. |
| 2017/0239390 A1 | 8/2017 | Ganey et al. |
| 2017/0240862 A1 | 8/2017 | Ganey et al. |
| 2017/0247659 A1 | 8/2017 | Ganey et al. |
| 2018/0169301 A1 | 6/2018 | Temple et al. |
| 2018/0214487 A1 | 8/2018 | Fiorina et al. |
| 2018/0221410 A1 | 8/2018 | Strober et al. |
| 2018/0243337 A1 | 8/2018 | Strober et al. |
| 2018/0282762 A1 | 10/2018 | Gori |
| 2018/0326122 A1 | 11/2018 | Ganey et al. |
| 2018/0334655 A1 | 11/2018 | Ganey et al. |
| 2018/0353541 A1 | 12/2018 | Delaney |
| 2019/0000877 A1 | 1/2019 | Strober et al. |
| 2019/0083530 A1 | 3/2019 | Strober et al. |
| 2019/0091262 A1 | 3/2019 | Strober et al. |
| 2019/0151506 A1 | 5/2019 | Ganey et al. |
| 2019/0191694 A1 | 6/2019 | Temple et al. |
| 2019/0192561 A1 | 6/2019 | Strober et al. |
| 2019/0192562 A1 | 6/2019 | Strober et al. |
| 2019/0298762 A1 | 10/2019 | Strober et al. |
| 2019/0336528 A1 | 11/2019 | Strober et al. |
| 2019/0343112 A1 | 11/2019 | Woods et al. |
| 2019/0345450 A1 | 11/2019 | Radtke et al. |
| 2019/0358257 A1 | 11/2019 | Strober et al. |
| 2020/0016198 A1 | 1/2020 | Jongen et al. |
| 2020/0054788 A1 | 2/2020 | Temple et al. |
| 2020/0054789 A1 | 2/2020 | Temple et al. |
| 2020/0088718 A1 | 3/2020 | Zdanowski et al. |
| 2020/0205399 A1 | 7/2020 | Shao et al. |
| 2020/0254015 A1 | 8/2020 | Strober et al. |
| 2020/0325451 A1 | 10/2020 | Woods et al. |
| 2020/0337648 A1 | 10/2020 | Saripalli et al. |
| 2020/0399604 A1 | 12/2020 | Woods et al. |
| 2020/0399605 A1 | 12/2020 | Woods et al. |
| 2020/0399606 A1 | 12/2020 | Woods et al. |
| 2020/0399607 A1 | 12/2020 | Woods et al. |
| 2021/0214688 A1 | 7/2021 | Woods et al. |
| 2021/0369782 A1 | 12/2021 | Agarwal et al. |
| 2022/0183275 A1 | 6/2022 | Woods et al. |
| 2022/0186187 A1 | 6/2022 | Woods et al. |
| 2022/0241342 A1 | 8/2022 | Woods et al. |
| 2024/0164371 A1 | 5/2024 | Woods et al. |
| 2024/0207322 A1 | 6/2024 | Woods et al. |
| 2024/0271097 A1 | 8/2024 | Woods et al. |

FOREIGN PATENT DOCUMENTS

| | | |
|---|---|---|
| CN | 107012119 A | 8/2017 |
| CN | 110777114 A | 2/2020 |
| EP | 3107995 B1 | 10/2019 |
| RU | 2012151191 A | 6/2014 |
| WO | WO 1993/007824 A1 | 4/1993 |
| WO | WO 1999/025367 A2 | 5/1999 |
| WO | WO 2000/036090 A2 | 6/2000 |
| WO | WO 2003/024215 A1 | 3/2003 |
| WO | WO 2005/001033 A2 | 1/2005 |
| WO | WO 2005/032251 A1 | 4/2005 |
| WO | WO 2008/121120 A1 | 10/2008 |
| WO | WO 2011069117 A1 | 6/2011 |
| WO | WO 2011/151452 A1 | 12/2011 |
| WO | WO 2016/210292 A1 | 12/2016 |
| WO | WO 2017/127755 A1 | 7/2017 |
| WO | WO 2017/216775 A3 | 2/2018 |
| WO | WO 2017/218948 A3 | 2/2018 |
| WO | WO 2018/022651 A1 | 2/2018 |
| WO | WO 2018/051340 A1 | 3/2018 |
| WO | WO 2019/006328 A1 | 1/2019 |
| WO | WO 2020/047236 A1 | 3/2020 |
| WO | WO 2020/058324 A1 | 3/2020 |
| WO | WO 2020/061180 A1 | 3/2020 |
| WO | WO 2019/026910 A1 | 7/2020 |
| WO | WO 2020/214400 A1 | 10/2020 |
| WO | WO 2020/247341 A1 | 12/2020 |
| WO | WO 2022/020210 A1 | 1/2022 |
| WO | WO 2022/081909 A1 | 4/2022 |
| WO | WO 2022/133282 A1 | 6/2022 |
| WO | WO 2022/140296 A1 | 6/2022 |
| WO | WO 2022/159824 A1 | 7/2022 |

OTHER PUBLICATIONS

Bara et al., Concise Review: Bone Marrow-Derived Mesenchymal Stem Cells Change Phenotype Following In Vitro Culture: Implications for Basic Research and the Clinic. Stem Cells, 2014. 32(7): p. 1713-1723.

Baumert et al., Bone Marrow of Multiorgan Donors Underutilized: Implications for Improvement ofAccessibility of Hematopoietic Cells for Transplantations. Transplantation Jan. 27, 2012;93(2): p. 165-171.

Baxter et al., Study of Telomere Length Reveals Rapid Aging of Human Marrow Stromal Cells Following In Vitro Expansion. Stem Cells, 2004. 22(5): p. 675-682.

Bender et al., Impact of Freeze-Thaw on Isolation of Viable CD34+ Cells from Human Cadaveric Bone Marrow. The FASEB J. Apr. 2020;34(S1): Abstract.

(56)         References Cited

OTHER PUBLICATIONS

Bensidhoum et al., Homing of In Vitro Expanded Stro-1- or Stro-1+ Human Mesenchymal Stem Cells into the NOD/SCIO Mouse and Their Role in Supporting Human CD34 Cell Engraftment. Blood, 2004. 103(9): p. 3313-3319.

Berz et al., Cryopreservation of Hematopoietic Stem Cells. Am J Hematol. Jun. 2007;82(6): p. 463-472.

Bieback et al., Human Alternatives to Fetal Bovine Serum for the Expansion of Mesenchymal Stromal Cells from Bone Marrow. Stem Cells. Sep. 1, 2009;27(9): p. 2331-2341.

Blashki et al., Mesenchymal Stem Cells from Cortical Bone Demonstrate Increased Clonal Incidence, Potency, and Developmental Capacity Compared to their Bone Marrow-Derived Counterparts. J Tissue Eng, Aug. 1, 2016;7: p. 2041731416661196 in 14 pages.

Blazar et al., Successful Donor Cell Engraftment in a Recipient of Bone Marrow from a Cadaveric Donor. Blood 1986;67(6): p. 1655-1660.

Bork et al., DNA Methylation Pattern Changes Upon Long-term Culture and Aging of Human Mesenchymal Stromal Cells. Aging Cell, Feb. 2010;9(1): p. 54-63.

Bruder et al., Growth Kinetics, Self-Renewal, and the Osteogenic Potential of Purified Human Mesenchymal Stem Cells During Extensive Subcultivation and Following Cryopreservation. J Cell Biochem, Feb. 1997;64(2): p. 278-294.

Busilacchi et al., A Novel Method to Evaluate Prethawing Viability of Cryopreserved CD34+ hematopoietic stem cells for autologous transplantation. J Aabb. Transf. Jul. 2020;60(7): 1529-1535.

Chilima et al., Designing the Optimal Manufacturing Strategy for an Adherent Allogeneic Cell Therapy. BioProcess International, 2016; 14(9): p. 24-32 https://bioprocessintl.com/manufacturing/cell-therapies/designing-optimal-manufacturing-strategy-adherent-allogeneic-cell-therapy/.

Chinnadurai et al., Immune dysfunctionality of replicative senescent mesenchymal stromal cells is corrected by IFNgamma priming. Blood Adv. Apr. 25, 2017;1(11): p. 628-643.

Choi et al., Dissecting Cellular Heterogeneity Using Single-Cell RNA Sequencing. Mol Cells. Mar. 3, 2019;42(3): p. 189-199.

ClinicalTrials.gov Identifier: NCT01459107 (2011).

Cox et al., High Abundance of CD271+ Multipotential Stromal Cells (MSCs) in Intramedullary Cavities of Long Bones. Bone. Feb. 1, 2012;50(2): p. 510-517.

CRYO2018: The 55th Annual Meeting of The Society for Cryobiology. CSIC (2018) p. 1-2 Abstract.

CRYO2019: The 56th Annual Meeting of The Society for Cryobiology. CSIC (2019) p. 1-6 Abstracts.

Delloyd's Lab Tech. Standard Sieves and Mesh Sizes. Online publication. http://delloyd.50megs.com/moreinfo/mesh.html. pp. 2-3 (2018).

Dennis et al., The STRO-1+ Marrow Cell Population is Multipotential. Cells Tissues Organs, Jul. 1, 2002;170(2-3): p. 73-82.

DiGirolamo et al., Propagation and Senescence of Human Marrow Stromal Cells in Culture: A Simple Colony Forming Assay Identifies Samples with the Greatest Potential to Propagate and Differentiate. Br J Haematol. Nov. 1999; 107(2): p. 275-281.

Dominici et al., Minimal Criteria for Defining Multipotent Mesenchymal Stromal Cells: The international society for cellular therapy position statement. Cytotherapy, 2006. 8(4): p. 315-317.

Donnenberg et al., Clinical Implementation of a Procedure to Prepare Bone Marrow Cells from Cadaveric Vertebral Bodies. Regen Med. Nov. 2011;6(6): 701-706.

Donnenberg, PhD., Working with Bone Marrow on a Grand Scale McGowan Retreat, University of Pittsburgh Publication; Mar. 2011, 34 pages.

Du et al., Rational Design of a Fluorescent Hydrogen Peroxide Probe Based on the Umbelliferone Fluorophore. Tetrahedron Lett. May 5, 2008;49(19): 3045-3048.

Dykstra et al., Concise Review: Fat and Furious: Harnessing the Full Potential of Adipose-Derived Stromal Vascular Fraction. Stem Cells Transl Med. Apr. 2017;6(4): p. 1096-1108.

Eagle et al., Assessment of an Improved Bone Washing Protocol for Deceased Donor Human Bone. Cell Tissue Bank. Mar. 2015;16: p. 83-90.

Eckardt et al., Comparison of Engraftment and Acute GVHD in Patients Undergoing Cryopreserved or Fresh Allogeneic BMT. Bone Marrow Transplant, Feb. 1, 1993;11(2): p. 125-131.

Ferrari et al., Beta Regression for Modeling Rates and Proportions. J Appl Stat. Aug. 1, 2004;31(7): p. 799-815.

Ferrebee et al., The Collection, Storage and Preparation of Viable Cadaver Marrow for Intravenous Use. Blood. Feb. 1, 1959;14(2): 140-147.

Flood et al., Does Practice Make Perfect? Part I: The Relations Between Hospital Volume and Outcomes for Selected Diagnostic Categories. Med Care. Feb. 1, 1984;22(2): p. 98-114.

Flood et al., Does Practice Make Perfect? Part II: The Relation Between Volumes and Other Hospital Characteristics. Med Care. Feb. 1, 1984;22(2): p. 115-125.

Fresenius Kabi AG. 510(k) Summary. Bone Marrow Collection Stand. (2017) https://www.fda.gov/media/106490/download in 6 pages.

Fu et al., "Lymphohematopoietic graft-versus-host responses promote mixed chimerism in patients receiving intestinal transplantation," J Clin Invest. Apr. 21, 2021; 131(8):e141698 inn 16 pages; doi: 10.1172/JCI141698.

Galipeau et al., International Society for Cellular Therapy Perspective on Immune Functional Assays for Mesenchymal Stromal Cells as Potency Release Criterion for Advanced Phase Clinical Trials. Cytotherapy, Feb. 1, 2016;18(2): p. 151-159.

Galipeau et al., Mesenchymal Stromal Cells: Clinical Challenges and Therapeutic Opportunities. Cell Stem Cell, Jun. 1, 2018;22(6): p. 824-833.

GE Healthcare Life Sciences. Cell Separation Media Reference. 2014; 80 pages.

Gorantla et al., Development and Validation of a Procedure to Isolate Viable Bone Marrow Cells from the Vertebrae of Cadaveric Organ Donors for Composite Organ Grafting. Cytotherapy. Jan. 1, 2012;14(1): 104-113.

Gronthos et al., Molecular and cellular characterisation of highly purified stromal stem cells derived from human bone marrow. J Cell Sci. May 1, 2003;116(Pt 9): p. 1827-1835.

Han et al., Optimization of Human Umbilical Cord Mesenchymal Stem Cell Isolation and Culture Methods. Cytotechnology. Oct. 2013;65: 819-827.

Harrel Jr., Regression Modeling Strategies with Applications to Linear Models, Logistic Regression, and Survival Analysis. 2nd ed. Springer Series in Statistics. 2001, New York: Springer. 582.

Harrison et al., Cell Therapy-Processing Economics: Small-Scale Microfactories as a Stepping Stone Toward Large-Scale Macrofactories. Regen Med, Mar. 2018;13(2): p. 159-173.

Heathman et al., Characterization of Human Mesenchymal Stem Cells from Multiple Donors and the Implications for Large Scale Bioprocess Development. Biochem Eng J. Apr. 15, 2016;108: p. 14-23.

HEMACARE Corporation. Isolation of Peripheral Blood Mononuclear Cells (PBMCs) Using a Density Gradient Reagent. Technical Protocol. PROT-IPBMC-V1 .1 1018 (2016).

Hibino et al., Comparison of Human Bone Marrow Mononuclear Cells Isolation Methods for Creating Tissue-Engineered Vascular Grafts: Novel Filter System Versus Traditional Density Centrifugation Method. Tissue Eng Part C: Methods. Oct. 1, 2011;17(10): 993-998.

Hotta et al., Long-term Nonhuman Primate Renal Allograft Survival Without Ongoing Immunosuppression in Recipients of Delayed Donor Bone Marrow Transplantation. Transplantation, Apr. 2018; 102(4): p. e128-e136.

Hunt C.J., Cryopreservation of Human Stem Cells for Clinical Application: A Review. Transfus Med Hemother. Mar. 16, 2011;38(2): 107-123.

Hwang et al., Single-cell RNA Sequencing Technologies and Bioinformatics Pipelines. Exp Mol Med. Aug. 2018; 50(8): p. 1-4.

(56)     References Cited

OTHER PUBLICATIONS

Johnstone, Edit Identification and Characterization of a Large Source of Primary Mesenchymal Stem Cells Tightly Adhered to Bone Surfaces of Human Vertebral Body Marrow Cavities. ISSCR Abstract (2020).

Johnstone et al., Identification and Characterization of a Large Source of Primary MesenchymalStem Cells Tightly Adhered to Bone Surfaces of Human Vertebral Body Marrow Cavities. Cytotherapy. Nov. 1, 2020;(22)11:617-628.

Jones et al., Large-scale Extraction and Characterization of CD271+ Multipotential Stromal Cells from Trabecular Bone in Health and Osteoarthritis: Implications for Bone Regeneration Strategies Based on Uncultured or Minimally Cultured Multipotential Stromal Cells. Arthritis Rheum. Jul. 2010;62(7): p. 1944-1954.

Jossen et al., Manufacturing Human Mesenchymal Stem Cells at Clinical Scale: Process and Regulatory Challenges. Appl Microbial Biotechnol. May 2018; 102(9): p. 3981-3994.

Kawai et al., Long-term Results in Recipients of Combined HLA-Mismatched Kidney and Bone Marrow Transplantation Without Maintenance Immunosuppression. Am J Transplant, Jul. 1, 2014;14(7): p. 1599-1611.

Kenyon et al., Effect of Depletion of Class II Bright Cells on the Immunogenicity and Stem Cell Content of Human Vertebral Body Bone Marrow. Transplant Proc. Dec. 1995; 27(6): 3419.

Knebel et al., Allocation of Scarce Resources after a Nuclear Detonation: Setting the Context. Disaster Med Public Health Prep, Mar. 2011;5(Suppl 1): p. S20-531.

Lechanteur et al., Large-scale Clinical Expansion of Mesenchymal Stem Cells in the GMP-Compliant, Closed Automated Quantum® Cell Expansion System: Comparison with Expansion in Traditional T-Flasks. Stem Cell Research & Therapy, 2014;4(8): p. 1-11.

Li et al., Therapeutic Delivery Specifications Identified Through Compartmental Analysis of a Mesenchymal Stromal Cell-Immune Reaction. Sci Rep, May 1, 2018;8(1): p. 6816 in 12 pages.

Linch et al., Bone Marrow Processing and Cryopreservation. J Clin Path. Feb. 1, 1982; 35(2): p. 186-190.

Lioznov et al., Transportation and Cryopreservation may Impair Haematopoietic Stem Cell Function and Engraftment of Allogeneic PBSCs, but not BM. Bone Marrow Transplant, Jul. 2008;42(2): p. 121-128.

Lipsitz et al., A Roadmap for Cost-of-Goods Planning to Guide Economic Production of Cell Therapy Products. Cytotherapy, Dec. 1, 2017;19(12): p. 1383-1391.

Lockhart et al., Use of Freshly Isolated Human Adipose Stromal Cells for Clinical Applications. Aesthet Surg J. Jul. 1, 2017; 37(suppl 3): p. S4-S8.

Long et al., Accumulation of CD11b+Gr-1+ Cells in the Lung, Blood and Bone Marrow of Mice Infected with Highly Pathogenic H5N1 and H1N1 Influenza Viruses. Arch Virol. Jun. 2013; 158: 1305-1322.

Mendicino et al., MSC-Based Product Characterization for Clinical Trials: an FDA Perspective. Cell Stem Cell, Feb. 6, 2014;14(2): p. 141-145.

Michalova et al., Hematopoietic Stem Cells Survive Circulation Arrest and Reconstitute Hematopoiesis in Myeloablated Mice. Biol Blood Marrow Transpl. Sep. 1, 2011;17(9): 1273-1281.

Miller et al., Phenotypic and Functional Equivalency of Digested Bone Marrow Mesenchymal Stem Cells to Aspirated Bone Marrow Mesenchymal Stem Cells. FASEB J. Apr. 2019;33(S1) (2019) Abstract.

MILTENYI Biotec. Isolation of Mononuclear Cells from Human Bone Marrow Aspirates by Density Gradient Centrifugation. 2008; 1 page.

Mizukami et al., Technologies for Large-Scale Umbilical Cord-Derived MSC Expansion: Experimental Performance and Cost of Goods Analysis. Biochem Eng J. Jul. 15, 2018;135: p. 36-48.

Moravcikova et al., Proteomic Profiling of Native Unpassaged and Culture-Expanded Mesenchymal Stromal Cells (MSC). Cytometry A, Sep. 2018;93(9): p. 894-904.

Morgenstern et al., Post-Thaw Viability of Cryopreserved Peripheral Blood Stem Cells (PBSC) does not Guarantee Functional Activity: Important Implications for Quality Assurance of Stem Cell Transplant Programmes. Br J Haematol. Sep. 2016; 174(6): p. 942-951.

Muraglia et al., Clonal Mesenchymal Progenitors from Human Bone Marrow Differentiate in vitro According to a Hierarchical Model. J Cell Sci. Apr. 1, 2000;113 ( Pt 7): p. 1161-1166.

Oetjen et al., Human Bone Marrow Assessment by Single-Cell RNA Sequencing, Mass Cytometry, and Flow Cytometry. JCI Insight. Dec. 12, 2018;3(23): e124928 in 9 pages.

Olsen et al., Peak MSC—Are We There Yet? Front Med (Lausanne), 2018. 5: p. 178.

Oseni et al., Optimization of Chondrocyte Isolation and Characterization for Large-Scale Cartilage Tissue Engineering. J Surg Res. May 1, 2013;181(1): 41-48.

Pennington et al., Evaluation of a Sterling Cycle Controlled Rate Freezing Device for Simultaneous Cryopreservation of Multiple Units. Cryobiology. 2019; 91:146-197—Abstract P36.

Pereira et al., Impact of Allogeneic Stem Cell Manufacturing Decisions on Cost of Goods, Process Robustness and Reimbursement. Biochem Engin J. Sep. 1, 20185;137: 132-151.

Picard et al., Cross-validation of regression models. J Am Stat Assoc. Sep. 1, 1984;79(428): p. 575-583.

Pittenger et al., Multilineage Potential of Adult Human Mesenchymal Stem Cells. Science. Apr. 2, 1999;284(5411): p. 143-147.

Quah et al., Monitoring Lymphocyte Proliferation In Vitro and In Vivo with the Intracellular Fluorescent Dye Carboxyfluorescein Diacetate Succinimidyl Ester. Nat Protoc. Sep. 2007;2(9): p. 2049-2056.

Redaelli et al., From Cytogenomic to Epigenomic Profiles: Monitoring the Biologic Behavior of In Vitro Cultured Human Bone Marrow Mesenchymal Stem Cells. Stem Cell Res Ther. Dec. 2012; 3(6): p. 1-7.

Rybka et al., Hematopoietic Progenitor Cell Content of Vertebral Body Marrow Used for Combined Solid Organ and Bone Marrow Transplantation. Transplantation. Mar. 3, 1995;59(6): 871-874.

Saegeman et al., Influence of Postmortem Time on the Outcome of Blood Cultures Among Cadaveric Tissue Donors. Eu J Clin Microbiol Infect Dis. Feb. 2009;28: 161-168.

Schneeberger et al., Upper-Extremity Transplantation Using a Cell-Based Protocol to Minimize Immunosuppression. Ann Surg. Feb. 2013;257(2): p. 345-351.

Schwartz et al., Explanatory and Pragmatic Attitudes in Therapeutical Trials. J Chronic Dis. Aug. 1, 1967; 20(8): p. 637-648.

Sherry et al., The Influence of Warm Ischemic Time on the Viability of Deceased Organ Donor Derived Bone Marrow. FASEB J. Apr. 2018;32(S1): in 5 pages.

Shu et al., Development of a Reliable Low-Cost Controlled Cooling Rate Instrument for the Cryopreservation of Hematopoietic Stem Cells. Cytotherapy Jan. 1, 2010;12(2): 161-169.

Siclari et al., Mesenchymal Progenitors Residing Close to the Bone Surface are Functionally Distinct from Those in the Central Bone Marrow. Bone. Apr. 1, 2013;53(2): p. 575-586.

Simaria et al., Allogeneic Cell Therapy Bioprocess Economics and Optimization: Single-Use Cell Expansion Technologies. Biotechnol Bioeng. Jan. 2014;111(1): p. 69-83.

Simmons et al., Identification of Stromal Cell Precursors in Human Bone Marrow by a Novel Monoclonal Antibody, STRO-1. Blood. 1991. 78(1): p. 55-62.

Soderdahl et al., Cadaveric Bone Marrow and Spleen Cells for Transplantation. Bone Marrow Transpl. Jan. 1998;21(1): 79-84.

Spitzer et al., Twenty Year Follow Up of Histocompatibility Leukocyte Antigen-Matched Kidney and Bone Marrow Co-Transplantation for Multiple Myeloma with End Stage Renal Disease: Lessons Learned. Transplantation. Nov. 2019;103(11): p. 2366-2372.

Squillaro et al., Clinical Trials With Mesenchymal Stem Cells: An Update. Cell Transplant. May 2016; 25(5): p. 829-848.

Stenn et al., Dispase, a Neutral Protease From Bacillus Polymyxa, Is a Powerful Fibronectinase and Type IV Collagenase. J Invest Dermatol. Aug. 1, 1989;93(2): p. 287-290.

(56) References Cited

OTHER PUBLICATIONS

Stockschläder et al., Use of Cryopreserved Bone Marrow in Allogeneic Bone Marrow Transplantation. Bone Marrow Transplant. 1995 15(4): p. 569-72.

Stockschläder et al., Use of Cryopreserved Bone Marrow in Unrelated Allogeneic Transplantation. Bone Marrow Transplant. Feb. 1, 1996; 17(2): p. 197-199 (Abstract).

Stockschläder et al., Long-term Follow-up of Leukemia Patients After Related Cryopreserved Allogeneic Bone Marrow Transplantation. Br J Haematol. Feb. 1997;96(2): p. 382-386.

Suire et al., Isolation of the Stromal-Vascular Fraction of Mouse Bone Marrow Markedly Enhances the Yield of Clonogenic Stromal Progenitors. Blood. Mar. 15, 2012;119(11): e86-95.

Sutherland et al., The ISHAGE Guidelines for CD34+ Cell Determination by Flow Cytometry. J Hematother, 1996;5(3): p. 213-226.

Thomas et al., Intravenous Infusion of Bone Marrow in Patients Receiving Radiation and Chemotherapy. N Engl J Med. Sep. 12, 1957;257(11): p. 491-496.

Thompson M.C., Preparing Skeletons for Research and Teaching from Preserved Human Specimens. Thesis California State University, Dec. 2015; 162 pages.

Thompson et al., Time and Temperature Dependent Ficoll Separation of Aged Whole Blood Neutrophils. FASEB J. 2019 33(S1) Abstract (2019).

Walter et al.: Molecular and Functional Phenotypes of Human Bone Marrow-Derived Mesenchymal Stromal Cells Depend on Harvesting Techniques. Int J Mol Sci. Jun. 19, 2020;21(12): 4382 in 12 pages.

Warwick et al., Collagenase Clostridium Histolyticum: Emerging Practice Patterns and Treatment Advances. J Plastic Surg Hand Surg.Sep. 2, 2016;50(5): p. 251-326.

Weinstock et al., Radiologic and Nuclear Events: Contingency Planning for Hematologists/Oncologists. Blood. Jun. 15, 2008;111(12): p. 5440-5445.

Woods et al., The Learning Curve and the Cost of Heart Transplantation. Health Sery Res. Jun. 1992;27(2): p. 219-238.

Woods et al., Packaging Considerations for Biopreservation. Transfus Med Hemother. Mar. 16, 2011;38(2): 149-156.

Woods et al., Off the Shelf Cellular Therapeutics: Factors to Consider During Cryopreservation and Storage of Human Cells for Clinical Use. Cytotherapy. Jun. 1, 2016;18(6): p. 697-711.

Woods et al., Ischemia Considerations for the Development of an Organ and Tissue Donor Derived Bone Marrow Bank. J Transl Med. Dec. 18, 2020(1): 300 in 11 pages.

Wuchter et al., Standardization of Good Manufacturing Practice—Compliant Production of Bone Marrow-Derived Human Mesenchymal Stromal Cells for Immunotherapeutic Applications. Cytotherapy. Feb. 1, 2015;17(2): p. 128-139.

Yamada et al., Overcoming Memory T-cell Responses for Induction of Delayed Tolerance in Nonhuman Primates. Am J Transplant. Feb. 1, 2012;12(2): p. 330-340.

Yusop et al., Isolation and Characterisation of Mesenchymal Stem Cells from Rat Bone Marrow and the Endosteal Niche: A Comparative Study. Stem Cells Int. Mar. 22, 2018; p. 6869128 in 14 pages.

Breite et al.: Characterization and functional assessment of class I (C1) collagenases and the synergistic degradation of native collagen in enzyme mixtures containing class II (C2) collagenase. In Transplantation Proceedings Nov. 1, 2011 (vol. 43, No. 9, pp. 3171-3175).

Brubaker et al., Tissue Recovery Practices and Bioburden: A Systemic Review. Cell Tissue Bank. Dec. 2016;17: 561-571.

Chiang et al., Allogeneic Mesenchymal Stem Cells in Combination with Hyaluronic Acid for the Treatment of Osteoarthritis in Rabbits. PLoS One. Feb. 25, 2016; 11(2): e149835 in 15 pages.

Chilima et al., Impact of Allogeneic Stem Cell Manufacturing Decisions on Cost of Goods, Process Robustness and Reimbursement. Biochem Engin J. Sep. 15, 2018;137: p. 132-151.

ClinicalTrials.gov Identifier: NCT00497757 https://clinicaltrials.gov/cl2/show/NCT004977571 Ildstad, S.T.: Induction of donor Specific Tolerance in Recipients of Cardiac Allografts by Donor Stem Cell Infusion; Aug. 31, 2020, in 12 pages.

Donnenberg A.D. PhD., Declaration Under 37 C.F.R. 1.132, dated Aug. 11, 2021 including Biography, submitted in U.S. Appl. No. 17/013,395, filed Sep. 4, 2020 in 78 pages.

Fragkakis et al.: Vertebral body versus iliac crest bone marrow as a source of multipotential stromal cells: Comparison of processing techniques, tri-lineage differentiation and application on a scaffold for spine fusion. PloS One. May 24, 2018;13(5): e0197969 in 20 pages.

Fuller et al., Applications and Optimization of Cryopreservation Technologies to Cellular Therapeutics, Cell Gene Thera Insights, Jun. 6, 2017; 3(5): 359-378.

Ghaneialvar et al.: Characterization and classification of mesenchymal stem cells in severeal species using markers for cell therapy purposes. Indian J Clin Biochem. Jan. 2018;33: 46-52.

Gorantla et al.: 2007-05-R11A Procedure for preparation of bone marrow cells from cadaveric vertebral bodies. University of Pittsburgh Medical Center. pp. 1-11 (2007).

Guan et al., Comparison of biological characteristics of mesenchymal stem cells derived from the human umbilical cord and decidua parietalis, Mol Med Rep. (2019); 20(1): 633-639.

Haitao et al., Progress in Bone Marrow Stem Cell Transplantation for the Treatment of Ischemic Cardiomyopathy. Tissue Engineering Research and Clinical Rehabilitation. Oct. 21, 2007; vol. 11, No. 42, 8565-8568.

Halfon et al.: Markers distinguishing mesenchymal stem cells from fibroblasts are downregulated with passaging. Stem Cells Devel. Jan. 1, 2011;20(1): 53-66.

Hefley, "Utilization of FPLC-Purified Bacterial Collagenase for the Isolation of Cells from Bone", Journal of Bone and Mineral Research (ASBMR 30th Annual Meeting), Blackweel Science, Inc., Jan. 1, 1987, vol. 2, No. 6, pp. 505-516.

Johnstone et al.: A large-scale bank of organ donor bone marrow and matched mesenchymal stem cells for promoting immunomodulation and transplant tolerance. Front Immunol. Feb. 26, 2021;12:622604 in 11 pages.

Kamble et al.: Orthotopic heart transplant facilitated autologous hematopoietic stem cell transplantation in light-chain amyloidosis. Blood Dec. 3, 2015; 126(23): 5364 Abstract in 2 pages.

McCarthy et al., Tissue dissociation enzymes for isolating human islets for transplantation: factors to consider in setting enzyme acceptance criteria, Transplantation. Jan. 27, 2011;91(2): 137-145.

Michalova et al., Cadaveric Bone Marrow as Potential Source of Hematopoietic Stem Cells for Transplantation. Chimerism Jul. 20, 2011;2(3): p. 86-87.

Nasca et al., "Use of Cryopreserved Bone in Spinal Surgery," Spine. Apr. 1, 1987;12(3): 222-227.

Schneeberger et al., 2007-05-R11A Procedure for preparation of bone marrow cells from cadaveric vertebral bodies, Regen Med. NIHMS339821—Supplement p. 1-11 (2014).

Urso et al., Short-Term Preservation of Mouse Bone Marrow at Refrigeration and Room Temperature for Irradiation Experiments. J Appl Physio. Mar. 1, 1957;10(2): 314-316.

Zhan et al.: A comparative study of biological characteristics and transcriptome profiles ofmesenchymal stem cells from different canine tissues. Int J Mol Scienc. Mar. 25, 2019;20(6): 1485 in 16 pages.

International Search Report and Written Opinion for International Application No. PCT/US2021/055066 dated Dec. 23, 2021.

European Extended Search Report for Application No. 21881119.8 dated Nov. 12, 2024.

* cited by examiner

FIG. 3

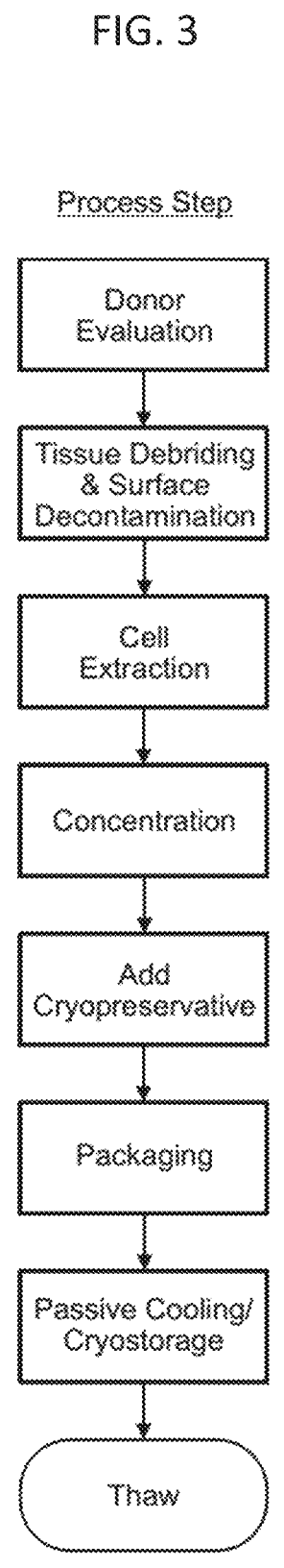

Process Step

```
┌─────────────────┐
│      Donor      │
│   Evaluation    │
└─────────────────┘
         │
         ▼
┌─────────────────┐
│ Tissue Debriding│
│    & Surface    │
│ Decontamination │
└─────────────────┘
         │
         ▼
┌─────────────────┐
│      Cell       │
│   Extraction    │
└─────────────────┘
         │
         ▼
┌─────────────────┐
│                 │
│  Concentration  │
│                 │
└─────────────────┘
         │
         ▼
┌─────────────────┐
│      Add        │
│ Cryopreservative│
└─────────────────┘
         │
         ▼
┌─────────────────┐
│                 │
│    Packaging    │
│                 │
└─────────────────┘
         │
         ▼
┌─────────────────┐
│ Passive Cooling/│
│   Cryostorage   │
└─────────────────┘
         │
         ▼
      (  Thaw  )
```

FIG. 11
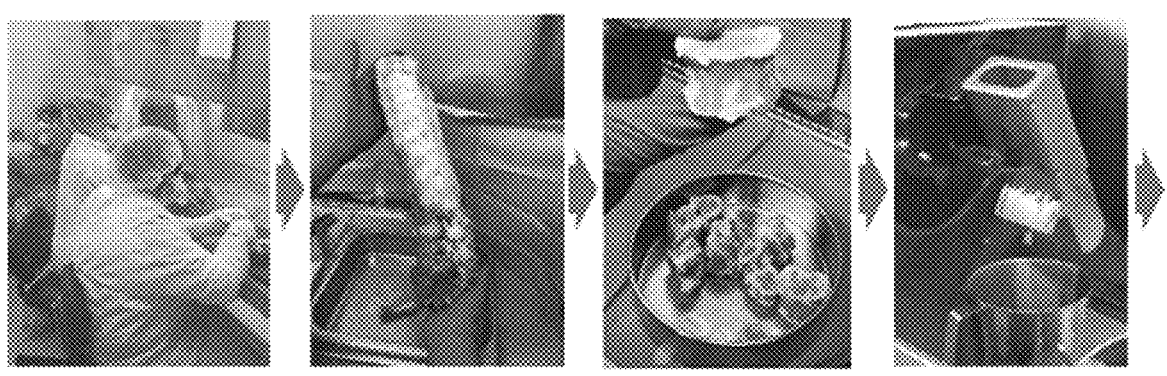
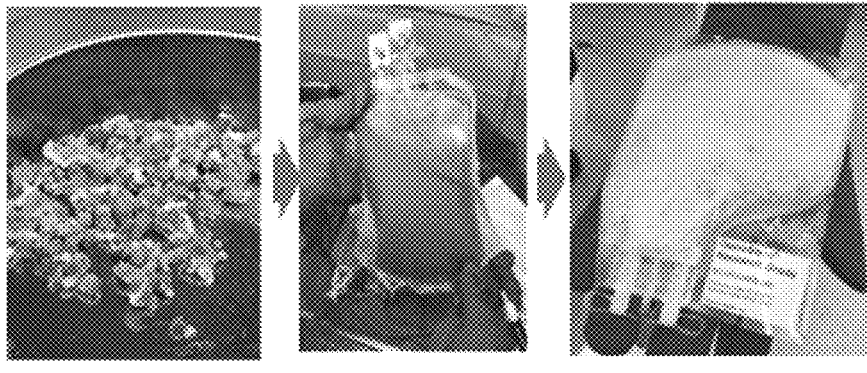

COMPOSITIONS AND METHODS FOR EXTRACTION OF MESENCHYMAL STEM CELLS

CROSS-REFERENCE

This application is a continuation application of U.S. patent application Ser. No. 18/086,537, filed Dec. 21, 2022, which is a continuation application of U.S. patent application Ser. No. 17/684,277, filed Mar. 1, 2022, now abandoned, which is a continuation application of PCT/US2021/055066, filed Oct. 14, 2021, which claims the benefit of U.S. Provisional Application No. 63/091,904, filed Oct. 14, 2020, which are incorporated herein by reference in their entirety.

BACKGROUND

Induction of immune tolerance with solid organ and vascular composite allografts is the gold standard for transplantation medicine, Induction of immune tolerance to mismatched grafts would obviate the need for life-long immunosuppression which is associated with serious adverse outcomes, such as renal failure, cancers, and infections. Currently the most promising means of tolerance induction is through establishing a mixed chimeric state by transplantation of donor hematopoietic stein cells; however, with the exception of tolerogenic organs such as kidneys. The mixed chimerism approach has not achieved durable immune tolerance in preclinical or clinical trials with most solid organs or vascular composite allotransplants (VCA).

Mesenchymal stem (stromal) cells (MSCs) have been identified as potentially useful adjuvant to stem cell transplants (SCT) for promoting mixed chimerism as well as promoting complementary peripheral immunomodulatory functions, along with solid organ transplants (SOT). However, there are many unresolved issues to address before clinical translation of these promising therapeutic cells. A primary, impediment is the source of MSCs, which are rare in all tissues and require invasive procedures for procurement. Low abundance mandates extensive expansion in culture to generate sufficient numbers for human dosing. It has been observed in the clinical setting that the degree of expansion is negatively correlated with outcomes, Therefore, there exists a need of a robust method of MSC extraction at high enough cellular density to improve clinical outcomes of SCT, SOT, and VCA.

SUMMARY

An aspect of the present disclosure comprises a composition, comprising about at least 10 million cadaveric human mesenchynmal stein cells (MSCs), wherein said composition is capable of inhibiting an immune response within a subject. In some embodiments, said composition comprises less than 5% CD45+ cells. In some embodiments, said composition comprises at least 90% CD105+ cells. In some embodiments, said composition comprises at least 90% CD166+ cells. In some embodiments, said cadaveric human MSCs comprise cadaveric human MSCs derived from bone marrow, adherent vertebral body MSCs (vBA-MSCs), or both. In some embodiments, said immune response is a rejection of a vascular composite allotransplant (VCAs) of art organ to said subject. In some embodiments-, said organ is limb. In some embodiments, said organ is a heart, kidney, liver, lung, pancreas, intestine, thymus, or uterus. In some embodiments, said organ is skin. In some embodiments, said composition comprises about at least 10 million, 100 million, 1 billion, or 10 billion cadaveric human MSCs.

Another aspect of the present disclosure is a composition comprising a population of human mesenchymal stem cells (MSCs) derived from a population of un-passaged or fresh MSCs, wherein the population of human MSCs is passaged at least 4 times and comprises a doubling rate of at least about 16 to 36 hours. In some embodiments, the population of human MSCs is derived from vertebral bodies. In some embodiments, the population of human MSCs is derived from a population of un-passaged/fresh vertebral bone adherent (vBA) MSCs. In some embodiments, the population of human MSCs is immune-suppressive. In some embodiments, the population of human MSCs suppresses CD4+ Immune cell expansion by at least 1 fold. In some embodiments, the population of human MSCs suppresses CD4-f immune cell expansion by at least 2 fold. In some embodiments, the population of human MSCs suppresses CD4+ immune cell expansion by at least 3 fold. In some embodiments, the population of human MSCs suppresses CD4+ immune cell expansion by at least 4 fold. In some embodiments, the population of human MSCs suppresses CD8+ immune cell expansion by at least 1 fold. In some embodiments, the population of human MSCs suppresses CD8+ immune cell expansion by at least 2 fold. In some embodiments, the population of human MSCs suppresses CD8+ immune cell expansion by at least 3 fold. In some embodiments, the vertebral bodies are derived from a cadaver. In some embodiments, the population of human MSCs comprises less than 5% CD45+ cells. In some embodiments, the population of human MSCs comprises more than 1.75% CD45+ cells. In some embodiments, the population of human MSCs comprises at least 90% CD105+ cells. In some embodiments, the population of human MSCs comprises at least 90% CD166+ cells. In some embodiments, the population of human MSCs is passaged at least 5 times. In some embodiments, the population of human MSCs is passaged at least 6 times. In some embodiments, the population of human MSCs is passaged at least 7 times. In some embodiments, the population of human MSCs is passaged at least 8 times. In some embodiments, the population of human MSCs is passaged at least 9 times. In some embodiments, the population of human MSCs is passaged at least 10 times. In some embodiments, the population of human MSCs comprises a doubling rate of at least about 16 to 36 hours over the at least 4 passages. In some embodiments, the population of human MSCs comprises a doubling rate of at least about 16 to 36 hours over each of the at least 4 passages. In some embodiments, the population of human MSCs comprises a doubling rate of at least about 16 to 36 hours over the at least 5 passages. In some embodiments, the population of human MSCs comprises a doubling rate of at least about 16 to 36 hours over each of the at least 5 passages. In some embodiments, the population of human MSCs comprises a doubling rate of at least about 16 to 36 hours over the at least 6 passages. In some embodiments, the population of human MSCs comprises a doubling rate of at least about 16 to 36 hours over each of the at least 6 passages. In some embodiments, the population of human MSCs comprises a doubling rate of at least about 16 to 36 hours over the at least 7 passages. In some embodiments, the population of human MSCs comprises a doubling rate of at least about 16 to 36 hours over each of the at least 7 passages. In some embodiments, the population of human MSCs comprises a doubling rate of at least about 16 to 36 hours over the at least 8 passages. In some embodiments, the population of human MSCs comprises a doubling rate of at least about 16 to 36 hours over each of the at least 8 passages. In some embodiments, the population of human MSCs comprises a doubling rate of at least about 16 to 36 hours over the at least 9 passages. In some embodiments, the population of human MSCs comprises a doubling rate of at least about 16 to 36 hours over each of the at least 9 passages. In some embodiments, the population of human MSCs comprises a doubling rate of at least about 16 to 36 hours over the at least 10 passages. In some embodiments, the population of human MSCs comprises a doubling rate of at least about 16 to 36 hours over each of the at least 10 passages. In some embodiments, the population of human MSCs comprises a doubling rate of less than about 29 hours. In some embodiments, the population of human MSCs comprises a doubling rate of less than about 29 hours. In some embodiments, the population of human MSCs comprises a doubling rate of less than about 29 hours. In some embodiments, the population of human MSCs comprises a doubling rate of less than about 29 hours. In some embodiments, the population of human MSCs comprises a doubling rate of less than about 29 hours. In some embodiments, the population of human MSCs comprises a doubling rate of less than about 29 hours. In some embodiments, the population of human MSCs comprises a doubling rate of less than about 29 hours. In some embodiments, the population of human MSCs comprises at least 40% cells in the S phase of the cell cycle. In some embodiments, the population of human MSCs comprises at least 45% cells in the S phase of the cell cycle. In some embodiments, the population of human MSCs comprises at least 50% cells in the S phase of the cell cycle. In some embodiments, the population of human MSCs comprises at least 55% cells in the S phase of the cell cycle.

Another aspect described herein is a method of generating a population of mesenchymal stem cells (MSCs), the method comprising: grinding a bone into one or more ground bone segments; contacting the one or more ground bone segments with a digestion solution; extracting a sample of fresh MSCs from the one or more ground bone segments; passaging the sample of fresh MSCs at least 4 times, wherein the sample of fresh MSCs comprise a doubling rate of at least about 16 to 36 hours over the at least 4 passages, thereby generating the population of MSCs, in some embodiments, the digestion solution comprises one or more distinct enzymes. In some embodiments, the one or more distinct enzymes comprise a collagenase. In some embodiments, the one or more distinct enzymes comprise a neutral protease. ID some embodiments, the collagenase comprises collagenase isoforms C1 and C2 at a ratio comprising more collagenase isoform C1 than collagenase isoform C2. In some embodiments, the ratio of collagenase isoform C1 to collagenase isoform C2 is about 30:10 to about 70:29. In some embodiments, the ratio of collagenase isoform C1 to collagenase C2 is 35:15. In some embodiments, the digestion solution comprises about 2 to about 20 U/ml of the neutral protease. In some embodiments, the digestion solution comprises the neutral protease at an activity of about 19.6 U/ml, in some embodiments, the digestion solution is present at a ratio of volume to weight of the bone of about 1:1 to about 15:1. In some embodiments, the digestion solution is contacted with the bone for up to about 3 hours. In some embodiments, the population of MSCs is passaged at least 5 times. In some embodiments, the population of MSCs is passaged at least 6 times. In some embodiments, the population of MSCs is passaged at least 7 times. In some embodiments, the population of MSCs is passaged at least 8 times. In some embodiments, the population of MSCs is passaged at least 9 times. In some embodiments, the population of MSCs is passaged at least 10 times. In some embodiments, the population of MSCs comprises a doubling rate of at least about 16 to 36 hours over each of the at least 4 passages. In some embodiments, the population of MSCs comprises a doubling rate of at least about 16 to 36 hours over the at least 5 passages. In some embodiments, the population of MSCs comprises a doubling rate of at least about 16 to 36 hours over each of the at least 5 passages. In some embodiments, the population of MSCs comprises a doubling rate of at least about 16 to 36 hours over the at least 6 passages. In some embodiments, the population of MSCs comprises a doubling rate of at least about 16 to 36 hours over each of the at least 6 passages. In some embodiments, the population of MSCs comprises a doubling rate of at least about 16 to 36 hours over the at least 7 passages. In some embodiments, the population of MSCs comprises a doubling rate of at least about 16 to 36 hours over each of the at least 7 passages. In some embodiments, the population of MSCs comprises a doubling rate of at least about 16 to 36 hours over the at least 8 passages. In some embodiments, the population of MSCs comprises a doubling rate of at least about 16 to 36 hours over each of the at least 8 passages. In some embodiments, the population of MSCs comprises a doubling rate of at least about 16 to 36 hours over the at least 9 passages. In some embodiments, the population of MSCs comprises a doubling rate of at least about 16 to 36 hours over each of the at least 9 passages. In some embodiments, the population of MSCs comprises a doubling rate of at least about 16 to 36 hours over the at least 10 passages in some embodiments, the population of MSCs comprises a doubling rate of at least about 16 to 36 hours over each of the at least 10 passages. In some embodiments, the population of MSCs comprises a doubling rate of less than about 29 hours. In some, embodiments, the population of MSCs comprises less than 5% CD45+ cells. In some embodiments, the population of MSCs comprises more than 1.75% CD45+ cells. In some embodiments, the population of MSCs comprises at least 90% CD105+ cells. In some embodiments, the population of MSCs comprises at least 90% CD166+ cells. In some embodiments, the bone is a vertebral body. In some embodiments, the sample of MSCs comprises vertebral bone adherent (vBA) MSCs. In some embodiments, the bone is derived from a cadaver.

Another aspect described herein is a method of treating a medical condition in a subject suffering therefrom, the method comprising administering a composition comprising a population of mesenchymal stem cells (MSCs), wherein the population of MSCs comprises more than 1.75% CD45+ cells. In some embodiments, the population of MSCs suppresses CD4+ immune cell expansion by at least 1 fold. In some embodiments, the population of MSCs suppresses CD4+ immune cell expansion by at least 2 fold. In some embodiments, the population of MSCs suppresses CD4+ immune cell expansion by at least 3 fold. In some embodiments, the population of MSCs suppresses CD4+ immune cell expansion by at least 4 fold. In some embodiments, the population of MSCs suppresses CD8+ immune cell expansion by at least 1 fold. In some embodiments, the population of MSCs suppresses CD8+ immune cell expansion by at least 2 fold. In some embodiments, the population of MSCs suppresses CD8+ immune cell expansion by at least 3 fold. In some embodiments, die population of MSCs are passaged at least 4 times. In some embodiments, the population of MSCs are passaged at least 5 times. In some embodiments, the population of MSCs are passaged at least 6 times. In some embodiments, the population of MSCs are passaged at least 7 times. In some embodiments, the population of MSCs are passaged at least 9 times. In some embodiments, the population of MSCs are passaged at least 9 times. In some embodiments, the population of MSCs are passaged at least 10 times. In some embodiments, the population of MSCs comprises a doubling rate of at least about 16 to 36 hours over the at least 4 passages. In some embodiments, the population of MSCs comprises a doubling rate of at least about 16 to 36 hours over each of the at least 4 passages. In some embodiments, the population of MSCs comprises a doubling rate of at least about 16 to 36 hours over the at least 5 passages. In some embodiments, the population of MSCs comprises a doubling rate of at least about 16 to 36 hours over each of the at least 5 passages. In some embodiments, the population of MSCs comprises a doubling rate of at least about 16 to 36 hours over the at least 6 passages. In some embodiments, the population of MSCs comprises a doubling rate of at least about 16 to 36 hours over each of the at least 6 passages. In some embodiments, the population of MSCs comprises a doubling rate of at least about 16 to 36 hours over the at least 7 passages. In some embodiments, the population of MSCs comprises a doubling rate of at least about 16 to 36 hours over each of the at least 7 passages. In some embodiments, the population of MSCs comprises a doubling rate of at least about 16 to 36 hours over the at least 8 passages. In some embodiments, the population of MSCs comprises a doubling rate of at least about 16 to 36 hours over each of the at least 8 passages. In some embodiments, the population of MSCs comprises a doubling rate of at least about 16 to 36 hours over the at least 9 passages. In some embodiments, the population of MSCs comprises a doubling rate of at least about 16 to 36 hours over each of the at least 9 passages. In some embodiments, the population of MSCs comprises a doubling rate of at least about 16 to 36 hours over the at least 10 passages. In some, embodiments, the population of MSCs comprises a doubling rate of at least about 16 to 36 hours over each of the at least 10 passages. In some embodiments, the population of MSCs comprises a doubling rate of less than about 29 hours. In some embodiments, the population of MSCs comprises less than 5% CD45+ cells. In some embodiments, the population of MSCs comprises at least 90% CD105+ cells. In some embodiments, the population of MSCs comprises at least 90% CD166+ cells. In some embodiments, the population of MSCs is derived from a bone. In some embodiments, the bone is a vertebral body. In some embodiments, the sample of MSCs comprises vertebral bone adherent (vBA) MSCs. In some embodiments, the bone is derived from a cadaver. In some embodiments, the medical condition is a rejection of a vascular composite allotransplant (VCAs) of an organ to the subject. In some embodiments, the organ is limb. In some embodiments, the organ is skin, heart, kidney, liver, lung, pancreas, intestine, thymus, or uterus. In some embodiments, the medical condition is myocardial infarction, chronic obstructive pulmonary disease (COPD), acute respiratory distress syndrome (ARDS), osteogenesis imperfection, cartilage defects, Crohn's disease, fistula, liver cirrhosis, osteo arthritis, asthma, or graft vs. host disease (GVHD). In some embodiments, the medical condition is an autoimmune disease. In some embodiments, the autoimmune disease is rheumatoid arthritis, lupus, celiac disease, multiple sclerosis, polymyalgia rheumatica, ankylosing spondylitis, type 1 diabetes, alopecia areata, vasculitis or temporal arteritis.

Another aspect of the present disclosure comprises a method of treating a medical condition in a subject suffering thereof, comprising administering to said subject a composition comprising at least 10 million cadaveric human MSCs. In some embodiments, said cell composition inhibits an immune response within said subject. In some embodiments, said medical condition is an autoimmune disease. In some embodiments, said medical condition is a myocardial infarction. In some embodiments, said medical condition is chronic obstructive pulmonary disease (COPD) or acute respiratory distress syndrome (ARDS). In some embodiments, said medical condition is arthritis. In some embodiments, said composition comprises at least 10 million, 100 million, 1 billion, or 10 billion cadaveric human MSCs. In some embodiments, the method further comprises generating CD45−huCD73+huCD90+ cells within said subject. In some embodiments, said cadaveric human MSCs comprise cadaveric human MSC's derived from bone marrow, adherent vertebral body MSCs (vBA-MSCs), or both.

Another aspect of the present disclosure comprises a method of preparing a composition comprising cadaveric human MSCs, comprising: providing a bone derived from a deceased donor; grinding said bone into one or more ground bone segments; filtering said one or more ground bone segments; and extracting said cadaveric human MSCs from said one or more ground bone segments. In some embodiments, said extracting of said cadaveric human MSCs comprises contacting said bone with a digestion solution. In some embodiments, said digestion solution comprises one or more distinct enzymes. In some embodiments, said one or more distinct enzymes comprise one or more collagenases and a neutral protease. In some embodiments, said one or more collagenases comprise collagenase isoforms C1 and C2 at a ratio comprising more collagenase isoform C1 than collagenase isoform C2. In some embodiments, said ratio of collagenase isoform C1 to collagenase isoform C2 is about 30 to about 70:about 10 to about 29. In some embodiments, said ratio of collagenase isoform C1 to collagenase C2 is 35:15. In some embodiments, said digestion solution is present at a ratio of volume to weight of said bone and said digestion solution of about 1:1 to about 15:1. In some embodiments, said digestion solution comprises about 2 to about 20 U/ml of said neutral protease. In some embodiments, said digestion solution comprises said neutral protease at an activity of about 19.6 U/ml. In some embodiments, said digestion solution is contacted with said bone for up to about 3 hours. In some embodiments, at least 10 million, 100 million, 1 billion, or 10 billion cadaveric human MSCs are extracted from said one or more ground bone segments.

Another aspect of the present disclosure comprises a composition, comprising: at least about 10 million cadaveric human mesenchymal stem cells MSCs; and at least about 500,000 nucleated bone marrow cells or derivatives thereof, wherein said composition is capable of inhibiting an immune response. In some embodiments, said composition further comprises a human organ. In some embodiments, said human organ is a heart, kidney, liver, lung, pancreas, intestine, thymus, or uterus. In some embodiments, said nucleated bone marrow cells or derivatives thereof comprise hematopoietic stem cells (HSCs). In some embodiments, said cadaveric human MSCs comprises a matched HLA haploid type as said nucleated bone marrow cells or derivatives thereof. In some embodiments, said cadaveric human MSCs comprises a matched HLA haploid type as said human organ. In some embodiments, said cadaveric human MSCs comprises a mis-matched HLA haploid type as said human organ. In some embodiments, said cadaveric human MSCs and said nucleated bone marrow cells or derivatives thereof comprise a mis-matched HLA haploid type as said human organ. In some embodiments, said composition comprises at least 100 million, 1 billion, or 10 billion cadaveric human MSCs. In some embodiments, said composition comprises at least 1 million, 1.5 million, or 2 million nucleated bone marrow cells or derivatives thereof. In some embodiments, said cadaveric human MSCs comprise cadaveric human MSCs derived from bone marrow, adherent vertebral body MSCs (vBA-MSC's), or both.

Another aspect of the present disclosure comprises a method of treating a medical condition in a subject suffering thereof, comprising: administering at least 500,000 nucleated bone marrow cells or derivatives thereof to said in need thereof, and administering at least 10 million cadaveric human mesenchymal stem cells (MSCs) to said subject suffering thereof. In some embodiments, said medical condition comprises an autoimmune disease. In some embodiments, said autoimmune disease comprises graft verses host disease (GVHD). In some embodiments, said nucleated bone marrow cells or derivatives thereof comprise hematopoietic stem cells (HSCs). In some embodiments, said cadaveric human MSCs comprises a matched HLA haploid type as said nucleated bone marrow cells or derivatives thereof. In some embodiments, said cadaveric human MSCs comprises a mis-matched HLA haploid type as said nucleated bone marrow cells or derivatives thereof. In some embodiments, the method further comprises, prior to (a), transplanting an organ into said subject suffering from said medical condition. In some embodiments, said cadaveric human MSCs and said nucleated bone marrow cells or derivatives thereof comprise a mis-matched HLA haploid type as said human organ. In some embodiments, the method further comprises administering rapamycin to said subject in need thereof for between about 0 days to about 21 days from said transplanting said organ. In some embodiments, the method further comprises administering about 0.1 mg/kg to about 1 mg/kg of rapamycin to said subject on one or more days. In some embodiments, the method further comprises administering CTLA4-Ig to said subject. In some embodiments, said CTLA4-Ig is administered on the same day as said transplanting of said human organ, 2 days after said transplanting of said human organ, 4 days after said transplanting of said human organ. 6 days after said transplanting of said human organ, or any combination thereof. In some embodiments, the method further comprises generating CD45+H2d+ cells in a background of CD45+H2b+ cells. In some embodiments, the method further comprises generating CD45−huCD73+huCD90+ cells. In some embodiments, the method further comprises generating a mixed chimerism within said subject. In some embodiments, said mixed chimerism is maintained for at least 120 days from administration of said nucleated bone marrow cells. In some embodiments, the method further comprises additionally administering at least 10 million cadaveric human mesenchymal stein cells (MSCs) to said subject in need thereof 1 day after (h), 2 days after (b), 3 days after (b), 4 days after (b), or any combination thereof.

In another aspect, a composition of donor-matched vBA-MSC is provided to augment mechanisms of mixed chimerism with BM transplant as well as provide peripheral immunomodulatory functions to achieve durable tolerance for major histocompatibility complex mismatched solid organ and vascular composite tissue transplants.

Additional aspects and advantages of the present disclosure will become readily apparent to those skilled in this art from the following detailed description, wherein only illustrative embodiments of the present disclosure are shown and described. As will be realized, the present disclosure is capable of other and different embodiments, and its several details are capable of modifications in various obvious respects, all without departing from the disclosure. Accordingly, the drawings and description are to be regarded as illustrative in nature, and not as restrictive.

INCORPORATION BY REFERENCE

All publications, patents, and patent applications mentioned in this specification are herein incorporated by reference to the same extent as if each individual publication, patent, or patent application was specifically and individually indicated to be incorporated by reference. To the extent publications and patents or patent applications incorporated by reference contradict the disclosure contained in the specification, the specification is intended to supersede and/or take precedence over any such contradictory material.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings (also "Figure" and "FIG." herein), of which:

FIG. 3 is a flowchart of one method according to the present disclosure.

FIG. 11 illustrates the current "industrialized" BM recovery and processing workflow.

FIG. 12 illustrates that at passages 2 and 4, the vBA-MSC population comprises a higher percentage of cells in the S phase of the cell cycle relative to the bone marrow derived MSCs (BM-MSCs).

FIG. 13 illustrates the difference in T cell expansion index (progeny/parent populations) without stimulation (i.e., basal) and IFNg stimulation (fully induced).

DETAILED DESCRIPTION

Figure 1:
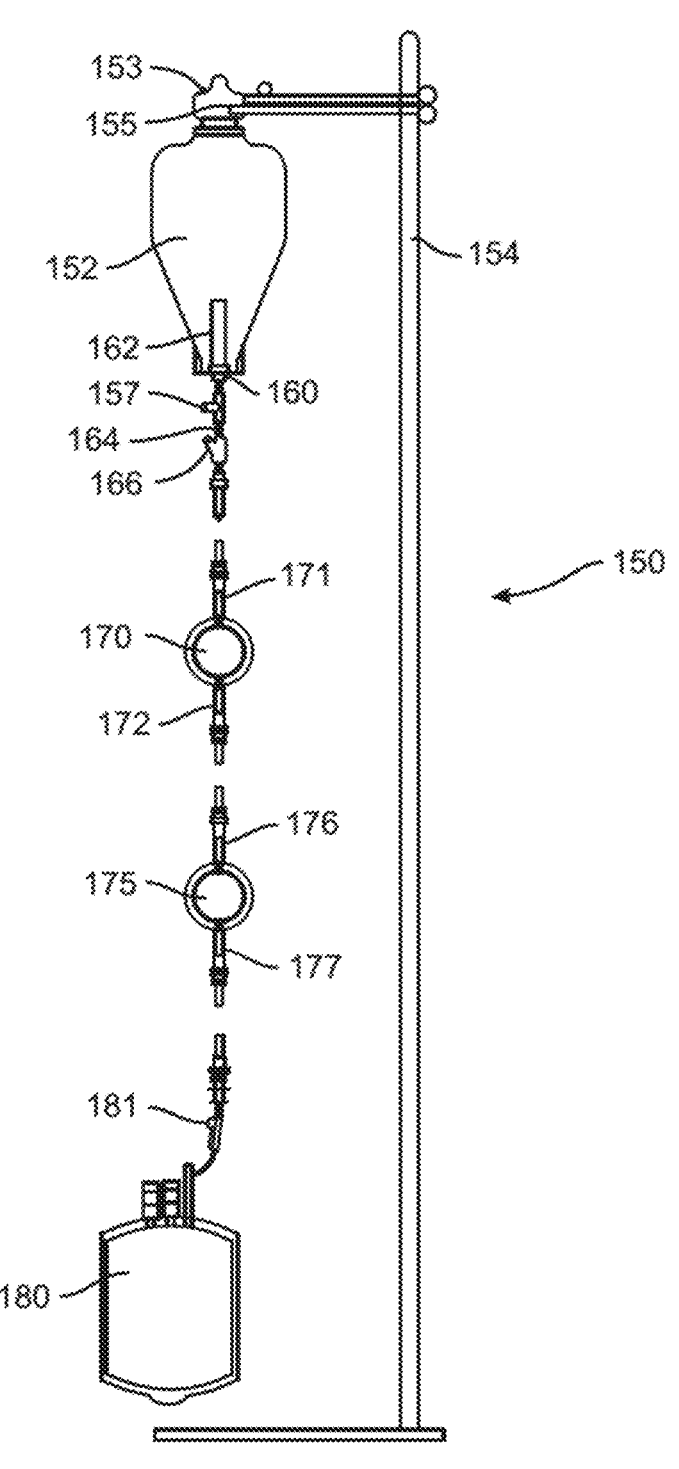
FIG. 1 is a view of a filtration system according to one feature of the present disclosure.
Figure 2:
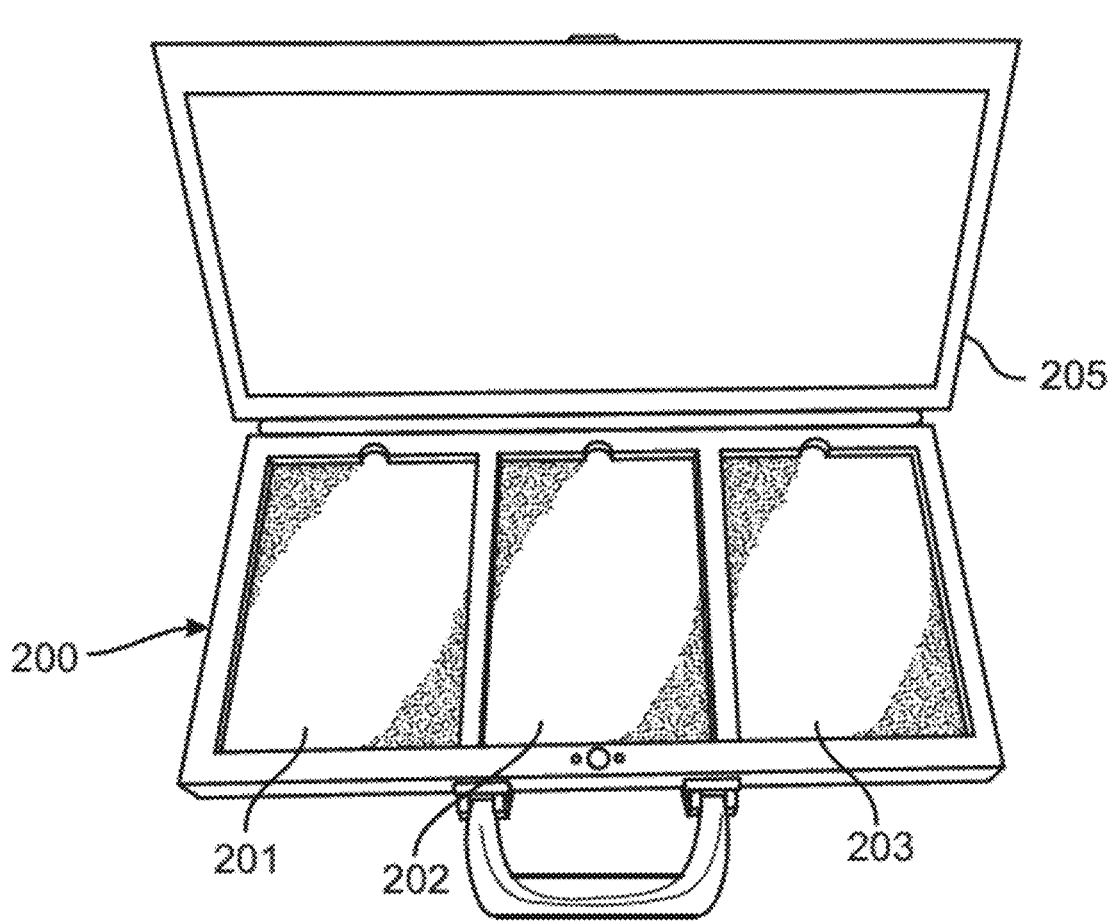
FIG. 2 is a perspective view of a cooling box according to one aspect of the present disclosure.

Typically, patients undergoing lifesaving procedures of SCT, SOT, and VCA are subjected to a life-long requirement of immune suppressing drugs that prevent their body from rejecting the organ or tissue graft. Unfortunately, immunosuppression drugs have been found to be associated with severe medical issues such as cancer, kidney failure and infections. Therefore, new medical procedures that reduce or overcome the need for immunosuppressive drugs are greatly needed. Previously deceased donor vertebral bodies (VB) BM SCT transplants from matched diseased organ donors have been found to induce immune tolerance following SOT and VCA. It is suggested that immunosuppression induction from transplanted VB BM STC rely on establishing mixed chimerism by SCT. It has also been suggested that MSCs promote stem cell engraftment in the BM and induce FoxP3+ TREG cell expansion as wells as possess additional synergistic immunomodulatory properties. Additionally, MSCs have been shown to possess potent immune system modulating activities which has contributed to widespread testing in clinical trials for various diseases associated with immune system dysfunction. Unfortunately, MSCs are extremely hard to obtain and subsequently grow in the laboratory to generate sufficient numbers required to treat typical adult patients. To address this shortcoming, the systems and methods disclosed herein provide a needed complement to existing MSC and BM sources and extraction methodologies capable of producing MSCs and BM in sufficient quantity for the aforementioned applications.

The methods and systems disclosed herein enable the extraction of large quantities of MSCs front human vertebral bone termed (vBA-MSCs) wherein MSCs have been found in >2×10⁷/donor of primary uncultured MSCs tightly adhered to the medullary cavity bone matrix.

Additionally, compositions of vBA-MSCs, HSC, donor bone marrow, and combinations thereof are disclosed herein for therapeutic immunomodulatory and adjunctive disease treatment.

Definitions

While preferred embodiments of the present disclosure have been shown and described herein, it will be obvious to those skilled in the art that such embodiments are provided by way of example only. Numerous variations, changes, and substitutions will now occur to those skilled in the art without departing from the disclosure. It should be understood that various alternatives to the embodiments of the disclosure described herein may be employed in practicing the disclosure. It is intended that the following claims define the scope of the disclosure and that methods and structures within the scope of these claims and their equivalents be covered thereby.

Use of absolute or sequential terms, for example, "will," "will not," "shall." "shall not," "must," "must not," "first," "initially," "next," "subsequently," "before," "after," "lastly," and "finally," are not meant to limit scope of the present embodiments disclosed herein but as exemplary.

As used herein, the singular forms "a", "an" and "the" are intended to include the plural forms as well, unless the context clearly indicates otherwise. Furthermore, to the extent that the terms "including", "includes", "having", "has", "with", or variants thereof are used in either the detailed description and/or the claims, such terms are intended to be inclusive in a manner similar to the term "comprising."

As used herein, the phrases "at least one", "one or more", and "and/or" are open-ended expressions that are both conjunctive and disjunctive in operation. For example, each of the expressions "at least one of A, B and C", "at least one of A, B, or C", "one or more of A, B, and C", "one or more of A, B, or C" and "A, B, and/or C" means A alone, B alone, C alone, A and B together, A and C together. B and C together, or A, B and C together.

As used herein, "or" may refer to "and", "or," or "and/or" and may be used both exclusively and inclusively. For example, the term "A or B" may refer to "A or B", "A but not B", "B but not A", and "A and B". In some cases, context may dictate a particular meaning.

Any systems, methods, software, and platforms described herein are modular. Accordingly, terms such as "first" and "second" do not necessarily imply priority, order of importance, or order of acts.

The term "about" when referring to a number or a numerical range means that the number or numerical range referred to is an approximation within experimental variability (or within statistical experimental error), and the number or numerical range may vary from, for example, front 1% to 15% of the stated number or numerical range. In examples, the term "about" refers to ±10% of a stated number or value.

The terms "increased", "increasing", or "increase" are used herein to generally mean an increase by a statically significant amount. In some aspects, the terms "increased," or "increase," mean an increase of at least 10% as compared to a reference level, for example an increase of at least about 10%, at least about 20%, or at least about 30%, or at least about 40%, or at least about 50%, or at least about 60%, or at least about 70%, or at least about 80%, or at least about 90% or up to and including a 100% increase or any increase between 10-100% as compared to a reference level, standard, or control, Other examples of "increase" include an increase of at least 2-fold, at least 5-fold, at least 10-fold, at least 20-fold, at least 50-fold, at least 100-fold, at least 1000-fold or more as compared to a reference level.

The terms, "decreased", "decreasing", or "decrease" are used herein generally to mean a decrease by a statistically significant amount. In some aspects, "decreased" or "decrease" means a reduction by at least 10% as compared to a reference level, for example a decrease by at least about 20%, or at least about 30%, or at least about 40%, or at least about 50%, or at least about 60%, or at least about 70%, or at least about 80%, or at least about 90% or up to and including a 100% decrease (e.g., absent level or non-detectable level as compared to a reference level), or any decrease between 10-100% as compared to a reference level. In the context of a marker or symptom, by these terms is meant a statistically significant decrease in such level. The decrease can be, for example, at least 10%, at least 20%, at least 30%, at least 40% or more, and is preferably down to a level accepted as within the range of normal for an individual without a given disease.

Preparing the Donor Bone

In some embodiments, the donor bone is vertebral bodies. However, it is understood that the methods described herein can be used on the ilium, a combination of the vertebral bodies and ilium, or other bones suitable for extraction of MSCs, even donor bones with lower expected yields.

It is understood that the donor bones can be procured according to fixed protocols for clinical recovery. Bones can be recovered by surgeons or by personnel at a trained OPO (organ procurement organization) using an osteotome and mallet from consented organ and tissue donors. Unprocessed bones are preferably wrapped in sponges and towels soaked in saline to ensure moisture retention during hypothermic shipment on wet ice at a temperature of 0 to 10° F. to a processing facility.

The process for preparing the donor bone can occur soon after the bone is obtained from the deceased donor or can occur after the donor bone has been shipped in a hypothermic environment to a processing facility. Since the donor bone can experience prolonged periods of ischemia during recovery and shipment to the processing facility, care must be taken to track the length and type of ischemia—i.e., warm ischemia and cold ischemia. As described in more detail herein, bone subject to predetermined periods of warm and/or cold ischemia are suitable for obtaining meaningful quantities of viable bone marrow cells.

During the processing of the donor bone, the bone is debrided in an ISO-5 (class 100) environment (biosafety cabinet) with an ISO-7, (class 10,000) background (clean room), with special care taken to sterilize the bag containing the donor bone, such as by spraying with 70% isopropanol. In one embodiment, the debridement is conducted manually using scalpels, osteotomes and gouges. In processing vertebrae, typically a spinal segment including multiple vertebral levels will be provided. In a typical case, the spine segment runs from T8 to L5, for ten vertebral bodies. During initial debridement of the spinal segment, when enough soft tissue has been removed to visualize the pedicels, the pedicles are removed using either a tissue processing band saw or a bone saw, such as the Stryker System 6 Saw (Stryker, Kalamazoo, MI). Special care is taken to avoid breaching the cortical bone which would expose the cancel bone, to ensure that the hypoxic cancellous bone marrow remains protected throughout the entire debriding process. The anterior element of the vertebral bodies remain, while the policies and posterior elements are discarded.

Using a boning knife or tissue processing band saw, the vertebral bodies are separated at the intervertebral discs. The intervertebral disc and soft tissue remaining on each vertebral body is removed with a scalpel, scissors and/or osteotomes, leaving clean, separated VBs. In the case of donor ilium, the soft tissue can be removed with gouges and a scalpel, with special care again taken to ensure that the cortical bone is not breached. Any anatomical pathologies or injuries of the bone are noted and recorded as part of the batch record for the marrow ultimately obtained from the bones. Bones damaged during the recovery process are discarded.

The VBs are placed into a sterile bag and submerged in a 10% bleach solution, yielding a concentration of 5,000 ppm free chlorine, for a predetermined period, typically 5 or more minutes. Bleach has a broad spectrum of anti-microbial activity, does not leave a Toxic residue, is unaffected by water hardness and is fast acting. At the end of the period, the bones are transferred to another sterile bag and submerged in a 3% hydrogen peroxide ($H_2O_2$) solution. The hag is closed and shaken briefly to ensure that the entire surface of the bone is in contact with the solution. Most living cells include catalase, which is an enzyme that catalyzes the breakdown of $H_2O_2$ into $H_2O$ and $O_2$. This breakdown manifests as foam or froth when the $H_2O_2$ solution contacts soft tissue but not bone. The foam level can be observed as an indication of the amount of soft tissue remaining on the bone. This observation can be performed manually by a human processor or, in another embodiment, by an automated processor. The automated processor incorporates a visualization device, such as a camera, and object recognition software that can determine foam levels within the bag. The addition of an inert contrast dye can help the human or automated processor detect the foam level. If any foam or froth is observed, the bone is returned for further processing to remove all of the remaining soft tissue from the bone. Once the VBs or ilium has been cleaned of all soft tissue, the bones are transferred to a new sterile bag. The bag is filled with IL of PLASMA-LYTE™ (multiple electrolytes injection obtained from Baxter Healthcare, Ltd.), or other suitable sterile, nonpyrogenic isotonic solution. The bag is closed and shaken briefly to ensure that the entire bone is contacted with the PLASMA-LYTE™.

Bone marrow from each group of VBs processed at different duration of bleach treatment can be tested by flow cytometry to assess the viability of the cells isolated front the bone marrow (Table 1). As seen from Table, soaking the VBs for more than 10 minutes yields no significant difference in cell viability compared to when the VBs are soaked for up to 25 minutes.

TABLE 1

| Bleach Soak of Vertebral Bodies | | | |
|---|---|---|---|
| Time Point (min) | CD45+ % Viability | CD34+ % Viability | CD3+ % Viability |
| 10 | 88.59 | 95.92 | 80.50 |
| 15 | 88.78 | 97.95 | 75.61 |
| 20 | 87.12 | 96.85 | 71.14 |
| 25 | 86.81 | 96.75 | 71.67 |
| Avg. | 87.825 | 96.8675 | 74.73 |
| SD | 0.869554 | 0.721747 | 3.752299 |

In some embodiments, the bleach treatment comprises using 1%. 2%, 3%, 4%, 5%, 6% 7%, 8%, 9%, 10%, 11%, 12%, 13%, 14%, 15%, 20%, 25%, 30%, 35%, 40%, 45%, 50%, or higher percentage of bleach. In some embodiments, the bleach treatment comprises contacting the VBs with bleach for at least 1 minute, 2 minutes, 3 minutes, 4 minutes, 5 minutes, 6 minutes, 7 minutes, minutes, 9 minutes, 10 minutes, 11, minutes, 12, minutes, 13 minutes, H minutes, 15 minutes. 20 minutes, 25 minutes, 30 minutes, 35 minutes, 40 minutes, 45 minutes, 50 minutes, or longer duration. In some embodiments, the viability of the bone marrow cells isolated from the VBs treated with the bleach treatment is not significantly decreased at any duration of bleach treatment described herein compared to bone marrow cells isolated from the VBs without the bleach treatment. In some embodiments, the viability of the bone marrow cells isolated from the VBs treated with 11 minutes, 12 minutes, 13 minutes, 14 minutes, 15 minutes, 20 minutes, 25 minutes, 30 minutes, 35 minutes, 40 minutes, 45 minutes, 50 minutes, or longer duration of the bleach treatment is not decreased or is decreased by less than 3% compared to the viability of the bone marrow cells isolated from the VBs treated with the 10 minutes bleach treatment. In some embodiments, the viability of the bone marrow cells isolated from the VBs treated with more than 10 minutes decreased by less than 2% compared to the viability of the bone marrow cells isolated from the VBs treated with the 10 minutes bleach treatment. In some embodiments, the viability of the bone marrow cells isolated from the VBs treated with more than 10 minutes decreased by less than 1% compared to the viability of the bone marrow cells isolated from the VBs treated with the 10 minutes bleach treatment.

The bone is removed from the bag and from the PLASM-LYTE™, and a sterile gauze or sponge is used to absorb any liquid remaining on the VBs. In one approach, a saw and/or anvil shears are used to cut the VBs are cut into smaller pieces, such as 1.5 cm² pieces, that are small enough for fragmenting with a bone grinder. In order to simplify, the process and for increased safety to the processing personnel, a custom bone cutting tool as described in PCT/US2020/025778, which is hereby incorporated by reference in its entirety, is provided is used to cut the VBs into the smaller pieces.

Recovery of MSCs from Processed Bone

In another feature of the systems and methods disclosed herein, a method is provided for preparing a composition of cadaveric human MSCs from bone. In some embodiments, the preparation may include providing a bone derived from a deceased donor, grinding the bone into one or more ground bone segments, filtering the one or more ground bone segments and extracting the cadaveric human MSCs from the one or more ground bone segments. In some embodiments, the MSCs may be recovered from thawed or cryopreserved VB bone fragments. In some embodiments, the extracted cadaveric human MSCs may be adherent, vertebral body mesenchymal stem cells (vBA-MSCs). In some embodiments, the extracted cadaveric human MSCs are derived from a bone or fragments thereof that has already been processed to remove bone marrow or derivates thereof associated with the bone or fragment thereof (e.g. bone marrow derived cells, hematopoietic stein cells). In some embodiments, the extracted cadaveric human MSCs are derived from a bone or fragments thereof that has been processed for bone marrow and/or bone marrow-derived cells (e.g. hematopoietic stem cells) as described herein. In some embodiments, the extracted cadaveric human MSCs are derived from the bone grindings and/or segments described herein following filtration and/or extraction and/or isolation of bone marrow and/or bone marrow-derived cells as described herein. The processing and extraction of viable vBA-MSCs from the bone and/or derivates thereof (e.g. bone grindings described herein, bone segments described herein) results in significant improvements in cell yield, especially with respect to total cell yield (vBA-MSCs and hematopoietic stem cells) per weight of bone derived from a donor, and viability of cells with respect to the state of the art. In some embodiments, the vBA-MSCs described herein can be combined with bone marrow-derived MSCs isolated from bone marrow isolated and processed as described herein.

In some, embodiments, the extraction of cadaveric human MSCs may include contacting the bone or derivatives thereof with a digestion solution. In some embodiments, the digestion solution may include one or more distinct enzymes. In some embodiments, the one or more distinct enzymes may include one or more collagenases and neutral proteases. In some embodiments, the digestion solution may be present at a ratio of volume to weight of the one or more ground bone segments and digestion solution of about 1:1 to about 15:1. In some embodiments, the ratio may be 1:1, 2.5:1, 5:1, 7.5:1, 10:1 and 15:1 (volume:weight). In some embodiments, the combination of one or more collagenases and neutral proteases is used to obtain the highest possible yields of vBA-MSC.

In some embodiments, a collagenase may include *Clostridium histolyticum* further comprising two active isoforms, C1 and C2. In some embodiments, one or more collagenases comprising isoforms C1 and C2 may be present in the digestion solution at a ratio comprising more collagenase isoform C1 than collagenase isoform C2. In some embodiments, the ratio of collagenase isoform C1 to collagenase isoform C2 may be about 30 to about 70:about 10 to about 29. In some embodiments, the ratio of collagenase isoform C1 to collagenase C2 may be 35:115. In some embodiments, the mass ratio of C1 and C2 for each concentration may be 70:30, 54:46, 37:63, 82:18, 54:46, and 90:10.

In some embodiments, the neutral protease may be *Paenibacillus polymyxa* neutral protease. In some embodiments, the neutral protease concentration may be about 2 U/ml to about 21 U/ml. In some embodiments, the neutral protease concentration may be about 2 U/ml to about 7 U/ml, about 2 U/ml to about 12 U/ml, about 2 U/ml to about 17 U/ml, about 2 U/ml to about 21 U/ml, about 7 U/ml to about 12 U/ml, about 7 U/ml to about 17 U/ml, about 7 U/ml to about 21 U/ml, about 12 U/ml to about 17 U/ml, about 12 U/ml to about 21 U/ml, or about 17 U/ml to about 21 U/ml. In some embodiments, the neutral protease concentration may be about 2 U/ml, about 7 U/ml, about 12 U/ml, about 117 U/ml, or about 21 U/ml. In some embodiments, the neutral protease concentration may be at least about 2 U/ml, about 7 U/ml, about 12 U/ml, or about 17 U/ml. In some embodiments, the neutral protease concentration may be at most about 7 U/ml about 12 U/ml, about 17 U/ml, or about 21 U/ml. In some embodiments, the digestion solution may comprise the neutral protease at an activity of about 19.6 U/ml.

Ili some embodiments, the collagenase concentration is about 005 U/ml to about 1.6 U/ml. In some embodiments, the collagenase concentration is about 005 U/ml to about 0.1 U/ml, about 0.05 U/ml to about 015 U/ml, about 0.05 U/ml to about 0.2 U/ml, about 005 U/ml to about 025 U/ml, about 0.05 U/ml to about 0.3 U/ml, about 0.05 U/ml to about 0.35 U/ml, about 0.05 U/ml to about 0.4 U/ml, about 0.05 U/ml to about 0.8 U/ml, about 0.05 U/ml to about 1.2 U/ml, about 0.05 U/ml to about 1.6 U/ml, about 0.1 U/ml to about 0.15 U/ml, about 0.1 U/ml to about 0.2 U/ml, about 0.1 U/ml to about 0.25 U/ml, about 0.1 U/ml to about 0.3 U/ml, about 0.1 U/ml to about 0.35 U/ml, about 0.1 U/ml to about 0.4 U/ml, about 0.1 U/ml to about 0.8 U/ml, about 0.1 U/ml to about 1.2 U/ml, about 0.1 U/ml to about 1.6 U/ml, about 0.15 U/ml to about 0.2 U/ml, about 0.15 U/ml to about 0.25 U/ml, about 0.15 U/ml to about 0.3 U/ml, about 0.15 U/ml to about 0.35 U/ml, about 0.15 U/ml to about 0.4 U/ml, about 0.15 U/ml to about 0.8 U/ml, about 0.15 U/ml to about 1.2 U/ml, about 0.15 U/ml to about 1.6 U/ml, about 0.2 U/ml to about 0.25 U/ml, about 0.2 U/ml to about 0.3 U/ml, about 0.2 U/ml to about 0.35 U/ml, about 0.2 U/ml to about 0.4 U/ml, about 0.2 U/ml to about 0.8 U/ml, about 0.2 U/ml to about 1.2 U/ml, about 0.2 U/ml to about 1.6 U/ml, about 0.25 U/ml to about 0.3 U/ml, about 0.25 U/ml to about 0.35 U/ml, about 0.25 U/ml to about 0.4 U/ml, about 0.25 U/ml to about 0.8 U/ml, about 0.25 U/ml to about 1.2 U/ml, about 0.25 Ural to about 1.6 U/ml, about 0.3 U/ml to about 0.35

U/ml, about 0.3 U/ml to about 0.4 U/ml, about 0.3 U/ml to about 0.8 U/ml, about 0.3 U/ml to about 1.2 U/ml, about 0.3 U/ml to about 1.6 U/ml, about 0.35 U/ml to about 0.4 U/ml, about 0.35 U/ml to about 0.8 U/ml, about 0.35 U/ml to about 1.2 U/ml, about 0.35 U/ml to about 1.6 U/ml, about, 0.4 U/ml to about 0.8 U/ml, about 0.4 U/ml to about 1.2 U/ml, about 0.4 U/ml to about 1.6 U/ml, about 0.8 U/ml to about 1.2 U/ml, about 0.8 U/ml to about 1.6 U/ml, or about 1.2 U/ml to about 1.6 U/ml. In some embodiments, the collagenase concentration is about 0.05 U/ml, about 0.1 U/ml, about 0.15 U/ml, about 0.2 U/ml, about 0.25 U/ml, about 0.3 U/ml, about 0.35 U/ml, about 0.4 U/ml, about 0.8 U/ml, about 1.2 U/ml, or about 16 U/ml. In some embodiments, the collagenase concentration is at least about 0.05 U/ml, about 0.1 U/ml, about 0.15 U/ml, about 0.2 U/ml, about 0.25 U/ml, about 0.3 U/ml, about 0.35 U/ml, about 0.4 U/ml, about 0.8 U/ml, or about 1.2 U/ml. In some embodiments, the collagenase concentration is at most about 0.1 U/ml, about 0.15 U/ml, about 0.2 U/ml, about 0.25 U/ml, about 0.3 U/ml, about 0.35 U/ml, about 0.4 U/ml, about 0.8 U/ml, about 1.2 U/ml, or about 1.6 U/ml.

In accordance with one aspect of the disclosure, neutral protease concentration and collagenase concentrations (C1 and C2 collagenase) and ratio of solution volume (mis) to bone fragment weight (MOs are determined.

In some embodiments, the total collagenase concentrations (C1 and C2 collagenase) are about 25 µg/ml to about 100 µg/ml. In some embodiments, the total collagenase concentrations are about 25 µg/ml to about 32.5 µg/ml, about 25 µg/ml to about 47.5 µg/ml, about 25 µg/ml to about 42.5 µg/ml, about 25 µg/ml to about 50 µg/ml, about 2.5 mg/mi to about 65 µg/ml, about 25 µg/ml to about 77.5 µg/ml, about 25 µg/ml to about 85 µg/ml, about 25 µg/ml to about 100 µg/ml, about 32.5 µg/ml to about 47.5 µg/ml, about. 32.5 µg/ml to about 42.5 µg/ml, about 32.5 µg/ml to about 50 µg/ml, about 32.5 µg/ml to about 65 µg/ml, about 32.5 µg/ml to about 77.5 g/mi, about 32.5 µg/ml to about 85 g/ml, about 32.5 µg/ml to about 100 µg/ml, about 47.5 µg/ml to about 42.5 µg/ml, about 47.5 µg/ml to about 50 µg/ml, about 47.5 µg/ml to about 65 µg/ml, about 47.5 µg/ml to about 77.5 µg/ml, about 47.5 µg/ml to about 85 µg/ml, about 47.5 g/ml to about 100 g/ml, about 42.5 µg/ml to about 50 µg/ml, about 42.5 µg/ml to about 65 µg/ml, about 42.5 µg/ml to about 77.5 µg/ml, about 42.5 µg/ml to about 85 µg/ml, about 42.5 µg/ml to about 100 µg/ml, about 50 µg/ml to about 65 g/ml, about 50 µg/ml to about 77.5 µg/ml, about 50 µg/ml to about 85 µg/ml, about 50 µg/ml to about 100 µg/ml, about 65 µg/ml to about 77.5 µg/ml, about 65 µg/ml to about 85 µg/ml, about 65 µg/ml to about 100 µg/ml, about 77.5 µg/ml to about 85 µg/ml, about 77.5 µg/ml to about 100 µg/ml, or about 85 µg/ml to about 100 µg/ml. In some embodiments, the total collagenase concentrations are about 25 µg/ml, about 32.5 µg/ml, about 47.5 µg/ml, about 42.5 µg/ml, about 50 µg/ml, about 65 µg/ml, about 77.5 µg/ml, about 85 µg/ml, or about 100 µg/ml. In Some embodiments, the total collagenase concentrations are at least about 25 µg/ml, about 32.5 µg/ml, about 47.5 µg/ml, about 42.5 µg/ml, about 50 µg/ml, about 65 µg/ml, about 77.5 µg/ml, or about 85 µg/ml. In some embodiments, the total collagenase concentrations are at most about 32.5 µg/ml, about 47.5 µg/ml, about 42.5 µg/ml, about 50 µg/ml, about 65 µg/ml, about 77.5 µg/ml, about 85 µg/ml, or about 100 µg/ml.

In some embodiments, the mass ratio of C1 and C2 for each concentration are 70:30, 54:46, 37:63, 82:18 and 90:10, respectively.

According to the process, fragments of VB bone are placed in cryoprotectant solution comprised of PLASMA- LYTE™, 2.5% human serum albumin and 10% dimethyl sulfoxide (DMSO) and incubated for 1 hour at 4° C. In some embodiments, the incubation period is about 1 hour to about 3 hours. In some embodiments, the incubation period is about 1 hour to about 1.5 hours, about 1 hour to about 2 hours, about 1 hour to about 2.5 hours, about 1 hour to about 3 hours, about 1.5 hours to about 2 hours, about 1.5 hours to about 2.5 hours, about 1.5 hours to about 3 hours, about 2 hours to about 2.5 hours, about 2 hours to about 3 hours, or about 2.5 hours to about 3 hours. In some embodiments, the incubation period is about 1 hour, about 1.5 hours, about 2 hours, about 2.5 hours, or about 3 hours. In some embodiments, the incubation period is at least about 1 hour, about 1.5 hours, about 2 hours, or about 2.5 hours. In some embodiments, the incubation period is at most about 1.5 hours, about 2 hours, about 2.5 hours, or about 3 hours. The solution is removed and the bone fragments cooled at a rate of ~1°/min to −86° C. and then plunged into liquid nitrogen. After 24-48 hours in liquid nitrogen, the bone fragments are thawed rapidly in a water bath set at 37° C. and then washed in saline and digested using the collagenase/protease solution described above.

In some embodiments, the volume-to-weight ratio was 5:1 at an incubation time of 2.5 hours. In some embodiments, the protease produced neutral protease activity of 19.6 U/ml.

The population of cells liberated by digesting VB bone fragment is cultured on tissue-coated plastic in the presence of Mesencult medium to select proliferative vBA-MSC. Freshly digested preparations as well as different passages of vBA-MSC can be characterized by flow cytometry, colony forming unit-fibroblast (CFU-F) potential, population doubling time (PDT) and trilineage (adipogenic, chondrogenic, and osteogenic) differentiation in vitro. In some embodiments, the population of human MSCs is passaged and comprises a doubling rate of at least about 16 to 36 hours. In some embodiments, the population of human MSCs is passaged at least about 1 time to about 12 times. In some embodiments, the population of human MSCs is passaged at least about 1 time to about 2 times, about 1 time to about 3 times, about 1 time to about 4 times, about 1 time to about 5 times, about 1 time to about 6 times, about 1 time to about 7 times, about 1 time to about 8 times, about 1 time to about 9 times, about 1 time to about 10 times, about 1 time to about 11 times, about 1 time to about 12 times, about 1 times to about 3 times, about 2 times to about 4 times, about 2 times to about 5 times, about 2 times to about 6 times, about 2 times to about 7 times, about 2 times to about 8 times, about 2 times to about 9 times, about 2 times to about 10 times, about 2 times to about 11 times, about 2 times to about 12 times, about 3 times to about 4 times, about 3 times to about 5 times, about 3 times to about 6 times, about 3 times to about 7 times, about 3 times to about 8 times, about 3 times to about 9 times, about 3 times to about 10 times, about 3 times to about 11 times, about 3 times to about 12 times, about 4 times to about 5 times, about 4 times to about 6 times, about 4 times to about 7 times, about 4 times to about 8 times, about 4 times to about 9 times, about 4 times to about 10 times, about 4 times to about 11 times, about 4 times to about 12 times, about 5 times to about 6 times, about 5 times to about 7 times, about 5 times to about 8 times, about 5 times to about 9 times, about 5 times to about 10 times, about 5 times to about 11 times, about 5 times to about 12 times, about 6 times to about 7 times, about 6 times to about 8 times, about 6 times to about 9 times, about 6 times to about 10 times, about 6 times to about 11 times, about 6 times to about 12 times, about 7 times to about 8 times, about 7 times to about 9 times, about 7 times to about 10 times, about 7 times to about 11 times, about 7 times to about 12 times, about 8 times to about 9 times, about 8 times to about 10 times, about 8 times to about 11 times, about 8 times to about 12 times, about 9 times to about 10 times, about 9 times to about 11 times, about 9 times to about 12 times, about 10 times to about 11 times, about 10 times to about 12 times, or about 11 times to about 12 times. In some embodiments, the population of human MSCs is passaged at least about 1 time, about 2 times, about 3 times, about 4 times, about 5 times, about 6 times, about 7 times, about 8 times, about 9 times, about 10 times, about 11 times, or about 12 times, in some embodiments, the population of human MSCs is passaged at least at least about 1 time, about 2 times, about 3 times, about 4 times, about 5 times, about 6 times, about 7 times, about 8 times, about 9 times, about 10 times, or about 11 times. In some embodiments, the population of human MSCs is passaged at least at most about 2 times, about 3 times, about 4 times, about 5 times, about 6 times, about 7 times, about 8 times, about 9 times, about 10 times, about 11 times, or about 12 times.

In some embodiments, the population of human MSCs comprises a doubling rate of at least about 16 to 36 hours over the passages. In some embodiments, the population of human MSCs comprises a doubling rate of about 14 hours to about 36 hours. In some embodiments, the population of human MSCs comprises a doubling rate of about 14 hours to about 16 hours, about 14 hours to about 18 hours, about 14 hours to about 20 hours, about 14 hours to about 22 hours, about 14 hours to about 24 hours, about 14 hours to about 26 hours, about 14 hours to about 28 hours, about 14 hours to about 30 hours, about 14 hours to about 32 hours, about 14 hours to about 34 hours, about 14 hours to about 36 hours, about 16 hours to about 18 hours, about 16 hours to about 20 hours, about 16 hours to about 22 hours, about 16 hours to about 24 hours, about 16 hours to about 26 hours, about 16 hours to about 28 hours, about 16 hours to about 30 hours, about 16 hours to about 32 hours, about 16 hours to about 34 hours, about 16 hours to about 36 hours, about 18 hours to about 20 hours, about 18 hours to about 22 hours, about 18 hours to about 24 hours, about 18 hours to about 26 hours, about 18 hours to about 28 hours, about 18 hours to about 30 hours, about 18 hours to about 32 hours, about 18 hours to about 34 hours, about 18 hours to about 36 hours, about 20 hours to about 22 hours, about 20 hours to about 24 hours, about 20 hours to about 26 hours, about 20 hours to about 28 hours, about 20 hours to about 30 hours, about 20 hours to about 32 hours, about 20 hours to about 34 hours, about 20 hours to about 36 hours, about 22 hours to about 24 hours, about 22 hours to about 26 hours, about 22 hours to about 28 hours, about 22 hours to about 30 hours, about 22 hours to about 32 hours, about 22 hours to about 34 hours, about 22 hours to about 36 hours, about 24 hours to about 26 hours, about 24 hours to about 28 hours, about 24 hours to about 30 hours, about 24 hours to about 32 hours, about 24 hours to about 34 hours, about 24 hours to about 36 hours, about 26 hours to about 28 hours, about 26 hours to about 30 hours, about 26 hours to about 32 hours, about 26 hours to about 34 hours, about 26 hours to about 36 hours, about 28 hours to about 30 hours, about 28 hours to about 32 hours, about 28 hours to about 34 hours, about 28 hours to about 36 hours, about 30 hours to about 32 hours, about 30 hours to about 34 hours, about 30 hours to about 34 hours, about 32 hours to about 34 hours, about 32 hours to about 36 hours, or about 34 hours to about 36 hours. In some embodiments, the population of human MSCs comprises a doubling rate of about 14 hours, about 16 hours, about 18 hours, about 20 hours, about 22 hours, about 24 hours, about 26 hours, about 28 hours, about 30 hours, about 32 hours, about 34 hours, or about 36 hours. In some embodiments, the population of human MSCs comprises a doubling rate of at least about 14 hours, about 16 hours, about 18 hours, about 20 hours, about 22 hours, about 24 hours, about 26 hours, about 28 hours, about 30 hours, about 32 hours, or about 34 hours. In some embodiments, the population of human MSCs comprises a doubling rate of at most about 16 hours, about 18 hours, about 20 hours, about 22 hours, about 24 hours, about 26 hours, about 28 hours, about 30 hours, about 32 hours, about 34 hours, or about 36 hours.

In some embodiments, the population of human MSCs comprises a doubling rate of at least about 16 to 36 hours over each of the at least 4 passages. In some embodiments, the population of human MSCs comprises a doubling rate of at least about 16 to 36 hours over the at least 5 passages. In some embodiments, the population of human MSCs comprises a doubling rate of at least about 16 to 36 hours over each of the at least 5 passages. In some embodiments, the population of human MSCs comprises a doubling rate of at least about 16 to 36 hours over the at least 6 passages. In some embodiments, the population of human MSCs comprises a doubling rate of at least about 16 to 36 hours over each of the at least 6 passages. In some embodiments, the population of human MSCs comprises a doubling rate of at least about 16 to 36 hours over the at least 7 passages. In some embodiments, the population of human MSCs comprises a doubling rate of at least about 16 to 36 hours over each of the at least 7 passages. In some embodiments, the population of human MSCs comprises a doubling rate of at least about 16 to 36 hours over the at least 8 passages. In some embodiments, the population of human MSCs comprises a doubling rate of at least about 16 to 36 hours over each of the at least 8 passages. In some embodiments, the population of human MSCs comprises a doubling rate of at least about 16 to 36 hours over the at least 9 passages. In some embodiments, the population of human MSCs comprises a doubling rate of at least about 16 to 36 hours over each of the at least 9 passages. In some embodiments, the population of human MSCs comprises a doubling rate of at least about 16 to 36 hours over the at least 10 passages. In some embodiments, the population of human MSCs comprises a doubling rate of at least about 16 to 36 hours over each of the at least 10 passages. In some embodiments, the population of human MSCs comprises a doubling rate of less than about 29 hours. In some embodiments, the population of human MSCs comprises a doubling rate of less than about 29 hours. In some embodiments, the population of human MSCs comprises a doubling rate of less than about 29 hours. In some embodiments, the population of human MSCs comprises a doubling rate of less than about 29 hours. In some embodiments, the population of human MSCs comprises a doubling rate of less than about 29 hours. In some embodiments, the population of human MSCs comprises a doubling rate of less than about 29 hours. In some embodiments, the population of human MSCs comprises a doubling rate of less than about 29 hours.

In some embodiments, the method of cadaveric human MSC extraction disclosed herein may be capable of extracting quantities of about 10 million to about 10 billion. In some embodiments, cadaveric human MSCs mar be administered in quantities of about 10 million to about 100 million, about 10 million to about 1 billion, about 10 million to about 10 billion, about 100 million to about 1 billion, about 100 million to about 10 billion, or about 1 billion to about 10 billion. In some embodiments, cadaveric human MSCs may be administered in quantities of about 10 million, about 100 million, about 1 billion, or about 10 billion. In some embodiments, cadaveric human MSCs may be administered in quantities of at least about 10 million, about 100 million, or about 1 billion. In some embodiments, cadaveric human MSCs may be administered in quantities of at most about 100 million, about 1 billion, or about 10 billion.

Extracting Bone Marrow and Bone Marrow-Derived Cells (e.g. Hematopoietic Stein Cells)

The pieces produced by the bone cutting tool are immediately placed into a sterile pitcher and submerged in 300-500 ml of a grind media. In one aspect of the present system and method, the grind media uses PLASMA-LYTE™-A as a base with 10 U/ml heparin, 2.5% human serum albumin (HSA), and 3 U/ml Benzonase® reagent (Merck KGAA Corporation). Heparin is used as an anticoagulant. Other anticoagulants at various quantities can also be used. HSA provides a protein source to prevent cell adherence and adsorption to surfaces, as well as reactive oxygen scavenging. It is noted that conventional grind media utilizes DNase, but for the present disclosure Benzonase® reagent is substituted for DNase™ reagent (Qiagen Sciences LLC), Whereas DNase works only on DNA, modern pharmaceutical biotechnology processing relies on enzymes that can cleave all forms of DNA and RNA, and can reduce the viscosity of the solution in which the cells are suspended. It is noted that IMDM (Iscove's Modified Dulbecco's Media) can substitute for the PLASMA-LYTE™-A, since IMDM is suitable for rapidly proliferating high-density cell cultures and ideal for supporting T- and B-lymphocytes. It is further noted that Denarase reagent (C-Lecta GmbH) is equivalent to Benzonase reagent in the same quantity in the present process.

In some embodiments, the amount of heparin in the grind media is about 5 U/ml to about 15 U/ml. In some embodiments, the amount of heparin in the grind media is about 5 U/ml to about 6 U/ml, about 5 U/ml to about 7 Ural, about 5 Ural to about 8 U/ml, about 5 U/ml to about 9 U/ml, about 5 U/ml to about 10 U/ml, about 5 U/ml to about 11 Unit about 5 U/ml to about 12 U/ml, about 5 U/ml to about 13 U/ml, about 5 U/ml to about 14 U/ml, about 5 U/ml to about 15 U/ml, about 6 U/ml to about 7 U/ml, about 6 U/ml to about 8 U/ml, about 6 U/ml to about 9 U/ml, about 6 U/ml to about 10 U/ml, about 6 U/ml to about 11 U/ml, about 6 U/ml to about 12 U/ml, about 6 U/ml to about 13 U/ml, about 6 U/ml to about 14 U/ml, about 6 U/ml to about 15 U/ml, about 7 U/ml to about 8 U/ml, about 7 U/ml to about 9 U/ml, about 7 U/ml to about 10 U/ml, about 7 U/ml to about 11 U/ml, about 7 U/ml to about 12 U/ml, about 7 U/ml to about 13 U/ml, about 7 U/ml to about 14 U/ml, about 7 U/ml to about 15 U/ml, about 8 U/ml to about 9 U/ml, about 8 U/ml to about 10 U/ml, about 8 U/ml to about 11 U/ml, about 8 U/ml to about 12 U/ml, about 8 U/ml to about 13 U/ml, about 8 U/ml to about 14 U/ml, about 8 U/ml to about 15 U/ml, about 9 U/ml to about 10 U/ml, about 9 U/ml to about 11 U/ml, about 9 U/ml to about 12 U/ml, about 9 U/ml to about 13 U/ml, about 9 U/ml to about 14 U/ml, about 9 U/ml to about 15 U/ml, about 10 U/ml to about 11 U/ml, about 10 U/ml to about 12 U/ml, about 10 U/ml to about 13 U/ml, about 10 U/ml to about 14 U/ml, about 10 U/ml to about 15 U/ml, about 11 U/ml to about 12 U/ml, about 11 U/ml to about 13 U/ml, about 11 U/ml to about 14 U/ml, about 11 U/ml to about 15 U/ml, about 12 U/ml to about 13 U/ml, about 12 U/ml to about 14 U/ml, about 12 U/ml to about 15 U/ml, about 13 U/ml to about 14 U/ml, about 13 U/ml to about 15 U/ml, or about 14 U/ml to about 15 U/ml.

In some embodiments, the amount of heparin in the grind media is about 5 U/ml, about 6 U/ml, about 7 U/ml, about 8 U/ml, about 9 U/ml, about 10 U/ml, about 11 U/ml, about 12 U/ml, about 13 U/ml, about 14 U/ml, or about 15 U/ml. In some embodiments, the amount of heparin in the grind media is at least about 5 U/ml, about 6 U/ml, about 7 U/ml, about 8 U/ml, about 9 U/ml, about 10 U/ml, about 11 U/ml, about 12 U/ml, about 13 U/ml, or about 14 U/ml. In some embodiments, the amount of heparin in the grind media is at most about 6 U/ml, about 7 U/ml, about 8 U/ml, about 9 U/ml, about 10 U/ml, about 11 U/ml, about 12 U/ml, about 13 U/ml, about 14 U/ml, or about 15 U/ml. In some embodiments, the amount of Benzonase in the grind media is about 11 U/ml to about 55 U/ml. In some embodiments, the amount of Benzonase in the grind media is about 11 U/ml to about 15 U/ml, about 11 U/ml to about 20 U/ml, about 11 U/ml to about 25 U/ml, about 11 U/ml to about 30 U/ml, about 11 U/ml to about 35 U/ml, about 11 U/ml to about 40 U/ml, about 11 U/ml to about 45 U/ml, about 11 U/ml to about 50 U/ml, about 11 U/ml to about 55 U/ml, about 15 U/ml to about 20 U/ml, about 15 U/ml to about 25 U/ml, about 15 U/ml to about 30 U/ml, about 15 U/ml to about 35 U/ml, about 15 U/ml to about 40 U/ml, about 15 U/ml to about 45 U/ml, about 15 U/ml to about 50 U/ml, about 15 U/ml to about 55 U/ml, about 20 U/ml to about 25 U/ml, about 20 U/ml to about 30 U/ml, about 20 U/ml to about 35 U/ml, about 20 U/ml to about 40 U/ml, about 20 U/ml to about 45 U/ml, about 20 U/ml to about 50 U/ml, about 20 U/ml to about 55 U/ml, about 25 U/ml to about 30 U/ml, about 25 U/ml to about 35 U/ml, about 25 U/ml to about 40 U/ml, about 25 U/ml to about 45 U/ml, about 25 U/ml to about 50 U/ml, about 25 U/ml to about 55 U/ml, about 30 U/ml to about 35 U/ml, about 30 U/ml to about 40 U/ml, about 30 U/ml to about 45 U/ml, about 30 U/ml to about 50 U/ml, about 30 U/ml to about 55 U/ml, about 35 U/ml to about 40 U/ml, about 35 U/ml to about 45 U/ml, about 35 U/ml to about 50 U/ml, about 35 U/ml to about 55 U/ml, about 40 U/ml to about 45 U/ml, about 40 U/ml to about 50 U/ml, about 40 U/ml to about 55 U/ml, about 45 U/ml to about 50 U/ml, about 45 U/ml to about 55 U/ml, or about 50 U/ml to about 55 U/ml. In some embodiments, the amount of Benzonase in the grind media is about 11 U/ml, about 15 U/ml, about 20 U/ml, about 25 U/ml, about 30 U/ml, about 35 U/ml, about 40 U/ml, about 45 U/ml, about 50 U/ml, or about 55 U/ml. In some embodiments, the amount of Benzonase in the grind media is at least about 11 U/ml, about 15 U/ml, about 20 U/ml, about 25 U/ml, about 30 U/ml, about 35 U/ml, about 40 U/ml, about 45 U/ml, or about 50 U/ml. In some embodiments, the amount of Benzonase in the grind media is at most about 15 U/ml, about 20 U/ml, about 25 U/ml, about 30 U/ml, about 35 U/ml, about 40 U/ml, about 45 U/ml, about 50 U/ml, or about 55 U/ml.

In some embodiments, the amount of Benzonase in the grind media is about 1 U/ml to about 10 U/ml. In some embodiments, the amount of Benzonase in the grind media is about 1 U/ml to about 2 U/ml, about 1 U/ml to about 3 U/ml, about 1 U/ml to about 4 U/ml, about 1 U/ml to about 5 U/ml, about. 1 U/ml to about 6 U/ml, about 1 U/ml to about 7 U/ml, about 1 U/ml to about 8 U/ml, about 1 U/ml to about 9 U/ml, about 1 U/ml to about 10 U/ml, about 2 U/ml to about 3 U/ml, about 2 U/ml to about 4 U/ml, about 2 U/ml to about 5 U/ml, about 2 U/ml to about 6 U/ml, about 2 U/ml to about 7 U/ml, about 2 U/ml to about 8 U/ml, about 2 U/ml to about 9 U/ml, about 2 U/ml to about 10 U/ml, about 3 U/ml to about 4 U/ml, about 3 U/mli to about 5 U/ml, about 3 U/ml to about 6 U/ml, about 3 U/ml to about 7 U/ml, about 3 U/ml to about 8 U/ml, about 3 U/ml to about 9 U/ml, about 3 U/ml to about 10 U/ml, about 4 U/ml to about 5 U/ml, about 4 U/ml to about 6 U/ml, about 4 U/ml to about 7 U/ml, about 4 U/ml to about 8 U/ml, about 4 U/ml to about 9 U/ml, about 4 U/ml to about 10 U/ml, about 5 U/ml to about 6 U/ml, about 5 U/ml to about 7 U/ml, about 5 U/ml to about 8 U/ml, about 5 U/ml to about 9 U/ml, about 5 U/ml to about 10 U/ml, about 6 U/ml to about 7 U/ml, about 6 U/ml to about 8 U/ml, about 6 U/ml to about 9 U/ml, about 6 U/ml to about 10 U/ml, about 7 U/ml to about 8 U/ml, about 7 U/ml to about 9 U/ml, about 7 U/ml to about 10 U/ml, about 8 U/ml to about 9 U/in, about 8 U/ml to about 10 U/ml, or about 9 U/ml to about 10 U/ml. In some embodiments, the amount of Benzonase in the grind media is about 1 U/ml, about 2 U/ml, about 3 U/ml, about 4 U/ml, about 5 U/ml, about 6 U/ml, about 7 U/ml, about 8 U/ml, about 9 U/ml, or about 10 U/ml in some embodiments, the amount of Benzonase in the grind media is at least about 1 U/ml, about 2 U/ml, about 3 U/ml, about 4 U/ml, about 5 U/ml, about 6 U/ml, about 7 U/ml, about 8 U/ml, or about 9 U/ml. In some embodiments, the amount of Benzonase in the grind media is at most about 2 U/ml, about 3 U/ml, about 4 U/ml, about 5 U/ml, about 6 U/ml, about 7 U/ml, about 8 U/ml, about 9 U/ml, or about 10 U/ml.

In some embodiments, HSA is present in the grind media at about 0.5% to about 5%. In some embodiments, i-ISA is present in the grind media at about 0.5% to about 1%, about 0.5% to about 1.5%, about 0.5% to about 2%, about 0.5% to about 2.5%, about 0.5% to about 3%, about 0.5% to about 3.5 about 0.5% to about 4%, about 0.5% to about 4.5%, about 0.5% to about 5%, about 1% to about 1.5%, about 1% to about 2%, about 1% to about 2.5%, about 1% to about 3%, about 1% to about 3.5%, about 1% to about 4%, about 1% to about 4.5%, about 1% to about 5%, about 1.5% to about 2%, about 1.5% to about 2.5%, about 1.5% to about 3%, about 1.5% to about 3.5%, about 1.5% to about 4%, about 1.5% to about 4.5%, about 1.5% to about 5%, about 2% to about 2.5%, about 2% to about 3 %, about 2% to about 3.5%, about 2% to about 4%, about 2% to about 4.5%, about 2% to about 5%, about 2.5% to about 3%, about 2.5% a to about 3.5%, about 2.5% a to about 4%, about 2.5% to about 4.5%, about 2.5% to about 5%, about 3% to about 3.5%, about 3% to about 4%, about 3% to about 4.5%, about 3% to about 5%, about 3.5% to about 4%, about 3. % to about 4.5%, about 3.5% to about %, about 4% to about 4.5%, about 4% to about 5%, or about 4.5% to about 5%. In some embodiments, HSA is present in the grind media at about 0.5%, about 1%, about 1.5%, about 2%, about 2.5%, about 3%, about 3.5%, about 4%, about 4.5%, or about 5%. In some embodiments, HSA is present in the grind media at least about 0.5%, about 1%, about 1.5%, about 2%, about 2.5%, about 3%, about 3.5%, about 4%, or about 4.5%. In some embodiments, HSA is present in the grind media at most about 1%, about 1.5%, about 2%, about 2.5%, about 3%, about 3.5%, about 4%, about 4.5%, or about 5%.

Another pitcher of about 300 to about 500 ml of grind media is retained for collecting the bone fragments after grinding, and another supply of about 100 ml or the grind media is retained for rinsing through the grinder during the grinding process to prevent bone fragments from sticking to the surface of the pitcher of the grinding components. In some embodiments, the additional grind media may have different quantities of heparin. HSA, and Beazonase as compared to the initial grind media.

An electric bone grinder or a purpose-built bone grinder, such as the grinder of Biorep Technologies Inc, (Miami, FL) can be used in an ISO-5 environment within an TSO-7 clean room. Bone types are kept separate if both VB and ilium from the same donor are being processed. The bone is kept submerged in grind media at all times during and after the grinding process. Once all of the donor bone pieces are ground, the chamber of the bone grinder is thoroughly rinsed with fresh processing media. The bone fragments are discharged from the grinder into the pitcher containing grind media.

The contents of the pitcher are, transferred to sterile bags. Next, the contents of the sterile bags are filtered to extract the solid components. In one embodiment, the contents of each bag are passed through a series of stainless steel sieves. In this embodiment, a No. 40 (42.5 μm) sieve is stacked on top of a No. 80 (177 μm) sieve, which is seated over a catch-pan to receive the liquid filter contents. The sterile bags containing the output from the grinder is swirled and then poured evenly over the sieve stack or filtration sets. The filtering process is observed to ensure that excessive clumping is not occurring, which can signal the presence of soft tissue or other contaminants. Bone fragments retained on the surface of the sieves are distributed evenly on the sieves and rinsed with 250 ml of fresh processing medium. In one embodiment, the processing medium used for rinsing is the grind media described above or PLASMA-LYTE™ with 2.5% HSA. The sieved bone marrow product, which can be approximately 1000 and in a well-performed process, is transferred to sterile packs for subsequent processing, and analysis. The contents of each bag are visually inspected to confirm that the contents do not include any visible bone fragments or soft tissue.

In some embodiments, the rinse media can contain the various amounts of HSA as described for the grind media. In some embodiments, the rinse media can contain, additionally, heparin and/or Benzonase.

In another embodiment, the contents of each bag are passed through bone marrow filtration units, as depicted in FIG. 1. In this embodiment, the system 150 includes a stand 154 configured to support a sterile collection bag 152 which contains the bone fragments and media from the grinding operation described above. The stand includes a container hanger 155 configured to engage the cap 153 of the sterile bag to suspend the container. The bottom of the bag includes a discharge assembly 160 that includes a pre-filter 162 projecting into the body of the collection bag. In one specific embodiment, the pre-filter 162 is an 850 μm filter. The filter 162 is connected to an output tube 164 that is connected by a container clamp 166 to the input line 171 of a first in-line filter 170. In the specific embodiment, the first in-line filter is a 200 μm or a 500 μm filter. The output line 172 of the first in-line filter is connected to the input line 176 of a second in-line filter 175. The second in-line filter is a 200 μm or a 500 μm filter. The two in-line filters are initially both 500 μm for a first pass through the filter system 150. A second rinse is then performed on the grindings with the two in-line filters being 200 μm. This double-pass filtration results in a cleaner suspension and enhances removal of fat from the suspension. The second in-line filter 175 has an output line 177 that can be engaged to a sterile bag, such as bag 152 for the second filtration pass. On the second pass through the system, the output line 177 of the second in-line filter 175 can be engaged to a container clamp 181 of a transfer pack container 180. The transfer pack container can be a 600-2000 ml bag to accommodate the filtered bone marrow product, which can be approximately 1000 ml in a well-performed process.

Fat Removal and Concentration

The bone marrow product collected from the filtering is essentially a fatty emulsion. The fat content of the suspension obtained from the sieve filtering approach disclosed above is greater than the fat content of the suspension obtained from the double-pass filtration system 150. However, in both cases, there is a need to remove the fat content from the suspension. The suspension obtained from the filtering is recovered into 250 ml bags which are hermetically sealed with tube welders. Pairs of sterile bags and taring sticks are mounted within a centrifuge with bag ports facing down, and balanced. Volume compensating plates are used to prevent creasing of the bags during centrifugation. In one embodiment, the bags are centrifuged at 500×g for 15 minutes at room temperature to concentrate the cells, preferably to 2-3×10⁸/mi, After centrifugation is complete, each bag is individually hung on a ring stand. The distinct layers within the bag are visible, with the fat layer clearly delineated on top of the supernatant with the bone marrow pellet at the bottom, as described in U.S. Ser. No. 16/734,713, which is hereby incorporated by reference in its entirety. A new sterile bag is welded to the bag removed from the centrifuge. A bag clamp or clip is placed on the bag just below the fat layer to clamp off or squeeze the bag closed beneath the fat layer, as described in U.S. Ser. No. 16/734, 713. The pellet is then drained from the centrifuge bag into the new sterile bag, with the hag clip preventing passage of the fat layer. The pellet is agitated as it is drained to resuspend all of the pellet. After about half of the pellet has drained into the new bag, the tubing is closed with a hemostat or tube scaler. The second centrifuge bag is then welded to the new bag containing the pellet, and the contents of this second centrifuge bag are drained into the new bag.

The result is new sterile bags containing the bone marrow centrifuged to remove the fat. These bags of dc-fatted bone marrow are then centrifuged at 500×g for 15 minutes at room temperature-, with volume compensating plates to prevent creasing of the bags. Each hag is removed and suspended on a ring stand and a waste bag is welded to the bag, and a plasma extractor is used to remove the supernatant into the waste bag, as described in U.S. Ser. No. 16/734,713. The tubing is clamped with a hemostat when the pellet rises or breaks. The tubing is then sealed and severed to remove the pellet . . . containing bag, from the waste bag, which is discarded. A Luer connection is welded to the pellet-containing bag. The pellets from each bag are combined into a bulk bag using a large syringe. The pellet-containing bags are rinsed into the bulk bag using a rinse media. The bulk hag is inverted several times to ensure that all of the pellet is resuspended. A small quantity of the processed BM, such as 0.5 mL, can be removed for quality control testing for density and cell count. The test sample can also be evaluated for human leukocyte antigens, CCR5delta 32 mutation and apolipoprotein (APOE), among other things.

In some embodiments, the centrifuge settings at one or more steps can be increased. In some embodiments, the centrifuge is spun at about 400 g to about 650 g. In some embodiments, the centrifuge is spun at about 400 g to about 450 g, about 400 g to about 500 g, about 400 g to about 550 g, about 400 g to about 600 g, about 400 g to about 650 g, about 450 g to about 500 g, about 450 g to about 550 g, about 450 g to about 600 g, about 450 g to about 650 g, about 500 g to about 550 g, about 500 g to about 600 g, about 500 g to about 650 g, about 550 g to about 600 g, about 550 g to about 650 g, or about 600 g to about 650 g. In some embodiments, the centrifuge is spun at about 400 g, about 450 g, about 500 g, about 550 g, about 600 g, or about 650 g. In some embodiments, the centrifuge is spun at least about 400 g, about 450 g, about 500 g, about 550 g, or about 600 g. In some embodiments, the centrifuge is spun at most about 450 g, about 500 g, about 550 g, about 600 g, or about 650 g. In some embodiments, the centrifuge is spun for about 10 minutes to about 40 minutes. In some embodiments, the centrifuge is spun for about 10 minutes to about 15 minutes, about 10 minutes to about 20 minutes, about 10 minutes to about 25 minutes, about 10 minutes to about 30 minutes, about 10 minutes to about 35 minutes, about 10 minutes to about 40 minutes, about 15 minutes to about 20 minutes, about 15 minutes to about 25 minutes, about 15 minutes to about 30 minutes, about 15 minutes to about 35 minutes, about 15 minutes to about 40 minutes, about 20 minutes to about 25 minutes, about 20 minutes to about 30 minutes, about 20 minutes to about 35 minutes, about 20 minutes to about 40 minutes, about 25 minutes to about 30 minutes, about 25 minutes to about 35 minutes, about 25 minutes to about 40 minutes, about 30 minutes to about 35 minutes, about 30 minutes to about 40 minutes, or about 35 minutes to about 40 minutes. In some embodiments, the centrifuge is spun for about 10 minutes, about 15 minutes, about 20 minutes, about 25 minutes, about 30 minutes, about 35 minutes, or about 40 minutes. In some embodiments, the centrifuge is spun for at least about 10 minutes, about 15 minutes, about 20 minutes, about 25 minutes, about 30 minutes, or about 35 minutes. In some embodiments, the centrifuge is spun for at most about 15 minutes, about 20 minutes, about 25 minutes, about 30 minutes, about 35 minutes, or about 40 minutes. In some embodiments, the centrifuge is stopped without the use of a brake. In some embodiments, the centrifuge is stopped with a brake. In some embodiments, the centrifuge brake is set at about 25% to about 100%. In some embodiments, the centrifuge brake is set at about 25% to about 50%, about 25% to about 75%, about 25% to about 100%, about 50% to about 75%, about 50% to about 100%, or about 75% to about 100%. In some embodiments, the centrifuge brake is set at about 25%, about 50%, about 75%, or about 100%. In some embodiments, the centrifuge brake is set at least about 25%, about 50%, or about 75%. In some embodiments, the centrifuge brake is set at most about 50%, about 75%, or about 100%.

Automated System for Recovery of Bone Marrow

Figure 4A:
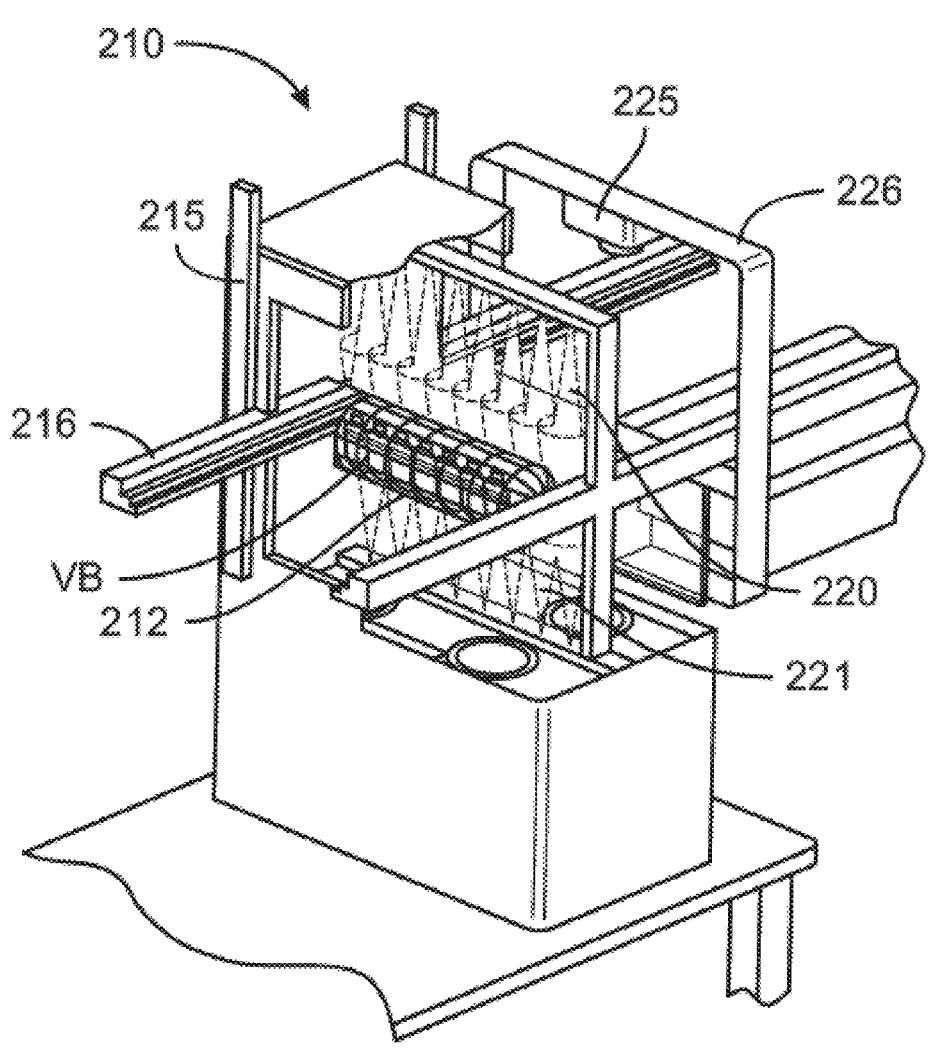
FIGS. 4A and 4B are perspective views of a bone debriding station.
Figure 4B:
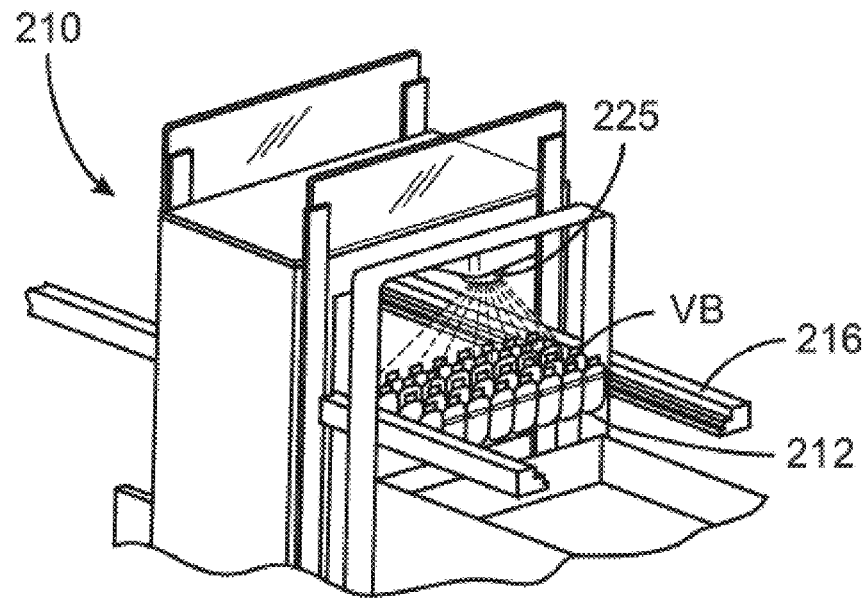

The present disclosure contemplates an automated process for recovery of the bone marrow, and even selection of cells front the bone marrow. In one aspect, an automated system includes sequential stations, described in U.S. Ser. No. 16/734,713. The first station of the automated process debrides the VBs to remove all soft tissue as shown in FIGS. 4A-4B. In contrast to the manual process that operates on one VB at a time, the automated process is configured to debride an entire donor VB set (which can be at least ten vertebral bodies). The VBs are mounted on a rack or tray 212 that is configured to support the vertebral body set from a given donor. The tray 212 is placed on transfer rails 216 of a housing 215, as shown in FIGS. 4A-4B, with the tray advanced automatically or manually into the interior of the housing. The housing 215 supports a plurality of hydrojets 220 that direct high pressure and high velocity jets of saline onto the VBs. In the known manual process, a manual hydrojet, operating at lower velocities and pressures, directs a stream of detergent onto the VB. In the manual process, the detergent is needed to clean the VBs of the soft tissue. In contrast, the automated cleaning station 210 of the present disclosure uses a saline medium, with the velocity and pressure of the water jets being sufficient to dislodge all soft tissue from the VBs. The automated cleaning station of the present disclosure includes jets configured to produce a direct stream or narrow "V" water/saline jet that generates a high concentrated impact force at varying distances. To achieve good coverage of the VBs, the device includes many direct jets at close spacing at different orientations relative to the VBs, which allows for uniform cleaning independent of position of the VB in the device. In the illustrated embodiment of FIG. 4A, the hydrojets are provided in an upper 220 and a lower row 221. The "V" jets are aligned at different angles to achieve full coverage of the surfaces of the VBs. In addition, or alternatively, the hydrojets 220, 221 can be configured to oscillate over the tray of VBs to ensure complete coverage.

A visualization device 225 is arranged at the outlet of the debridement station 210 that is operable to visualize and interpret the VBs exiting the station to determine if all of the soft tissue has been removed, as shown in FIG. 4B. If not, then the VBs are returned along the rails 216 back into the housing for further hydrojet processing. It is contemplated that a controller (not shown) can be provided to control the movement of the tray 212 along the rails 216 and to interpret the signals generated by the visualization device 225. The visualization device can include a camera that obtains an image of the VBs and the controller can include imaging software capable of recognizing the soft tissue in the acquired image. A dye can be applied to the cleaned VBs at the end of the hydro jet debridement process, in which the dye is absorbed by soft tissue but not bone. The dye can thus provide contrast to facilitate differentiation of any remaining soft tissue from the bone. The visualization device 225 can be configured to pan across the VBs, such as by translating along a frame 226 and by translating the frame in order to view the VBs at all angles.

Figure 5A:
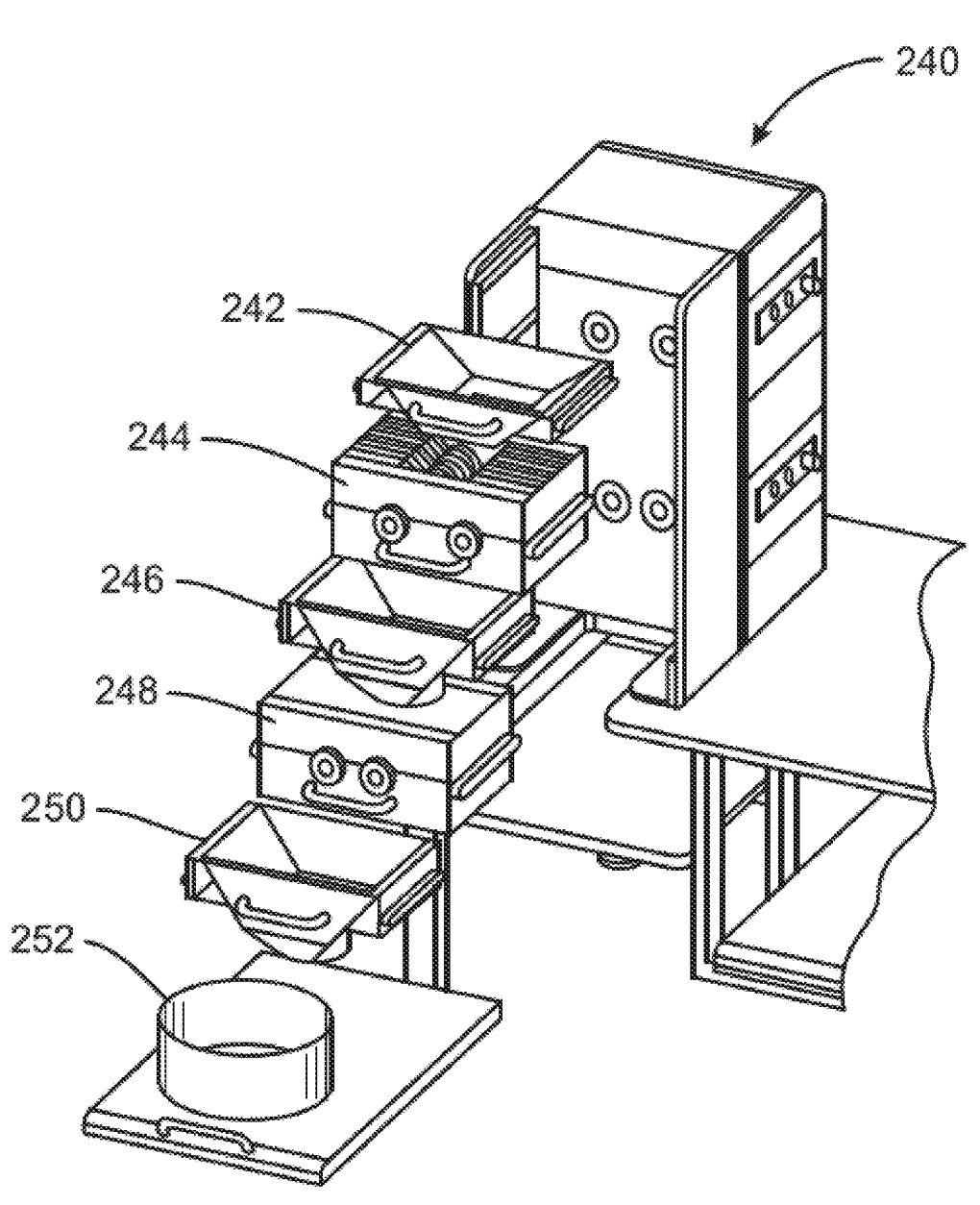
FIGS. 5A and 5B are perspective and front views of a bone grinding station.
Figure 5B:
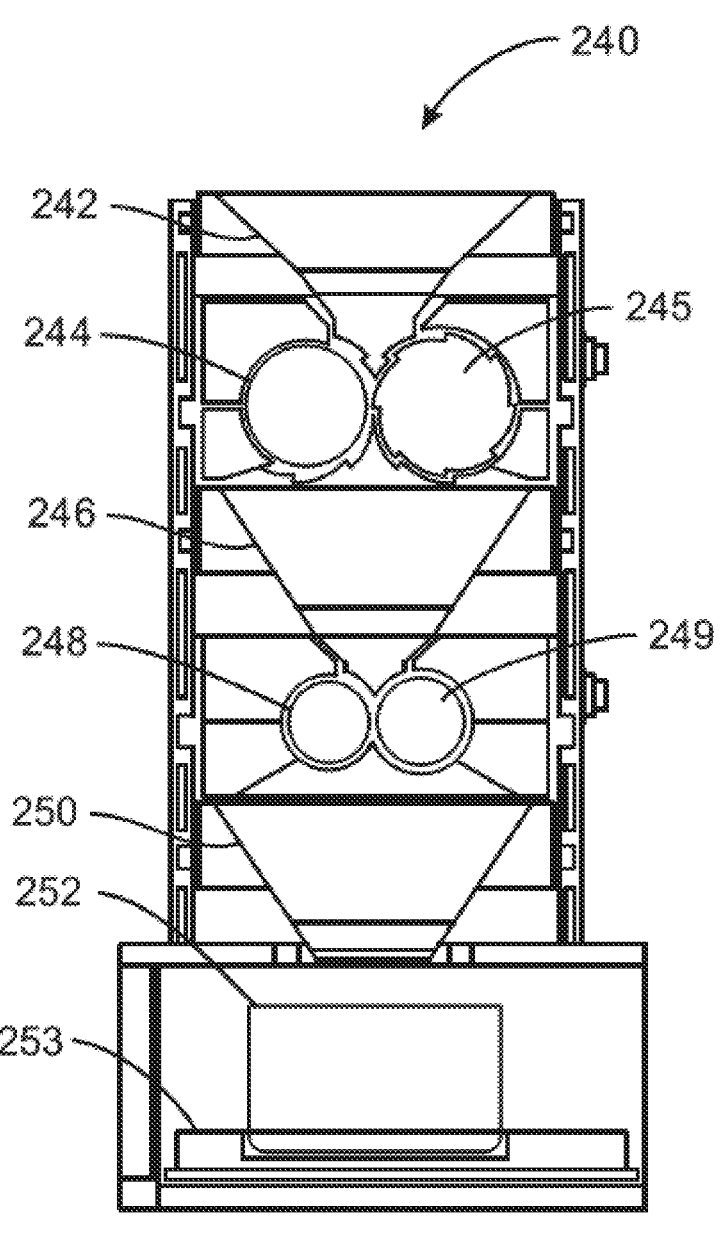

Once it is determined that the VBs are cleaned of all soft tissue, the debrided VBs are then fed by a conveyor to an automated grinding station 240, as shown in FIG. 5A, to produce appropriately sized pieces for tumbling and final cell extraction. The manual "cubing" process described above can be variable, time consuming, and potentially not safe for the operator. The automated system includes a grinding station that combines cubing the VBs (i.e., cutting the VBs into small pieces) and grinding the cubed VBs to reduce the VBs to 2-3 mm pieces. The rails 216 and tray 212, as shown in FIGS. 4A-4B can be configured to deposit the debrided VBs onto the conveyor which then automatically transfers the VBs to an input hopper 242 of the grinding station 240, shown in more detail in FIGS. 5A-5B. The VBs are directed through an initial mill cutter module 244, then through a funnel 246 to a fine mill cutter module 248, as shown in FIG. 5A. As shown in FIG. 5B the initial mill cutter module 242 includes opposed rotating grinding mills 245 that are separated by a predetermined cap, such as a 5-8 mm gap, so that the incoming VBs are ground into coarse-sized segments. The coarse ground segments are fed to the fine mill cutter module 248 in which smaller diameter grinding mills 249 are provided. The fine grind mills 249 are separated by a smaller gap, on the order of 2-3 mm, to produce finely ground VB segments. As shown in FIG. 5A, a funnel 246 conveys the coarse ground segments to the second grinding mill 248, and a funnel 250 directs the finely ground VB segments to a collection pan 252 supported on a plate 253. During the milling operation, a measured volume of processing/resuspension medium with DNAse can be directed through the upper hopper, onto grinding cutters. This medium can be manually introduced during the operation of the grinding station 240, or can be automatically implemented through nozzles incorporated into the hopper 242.

Figure 6:
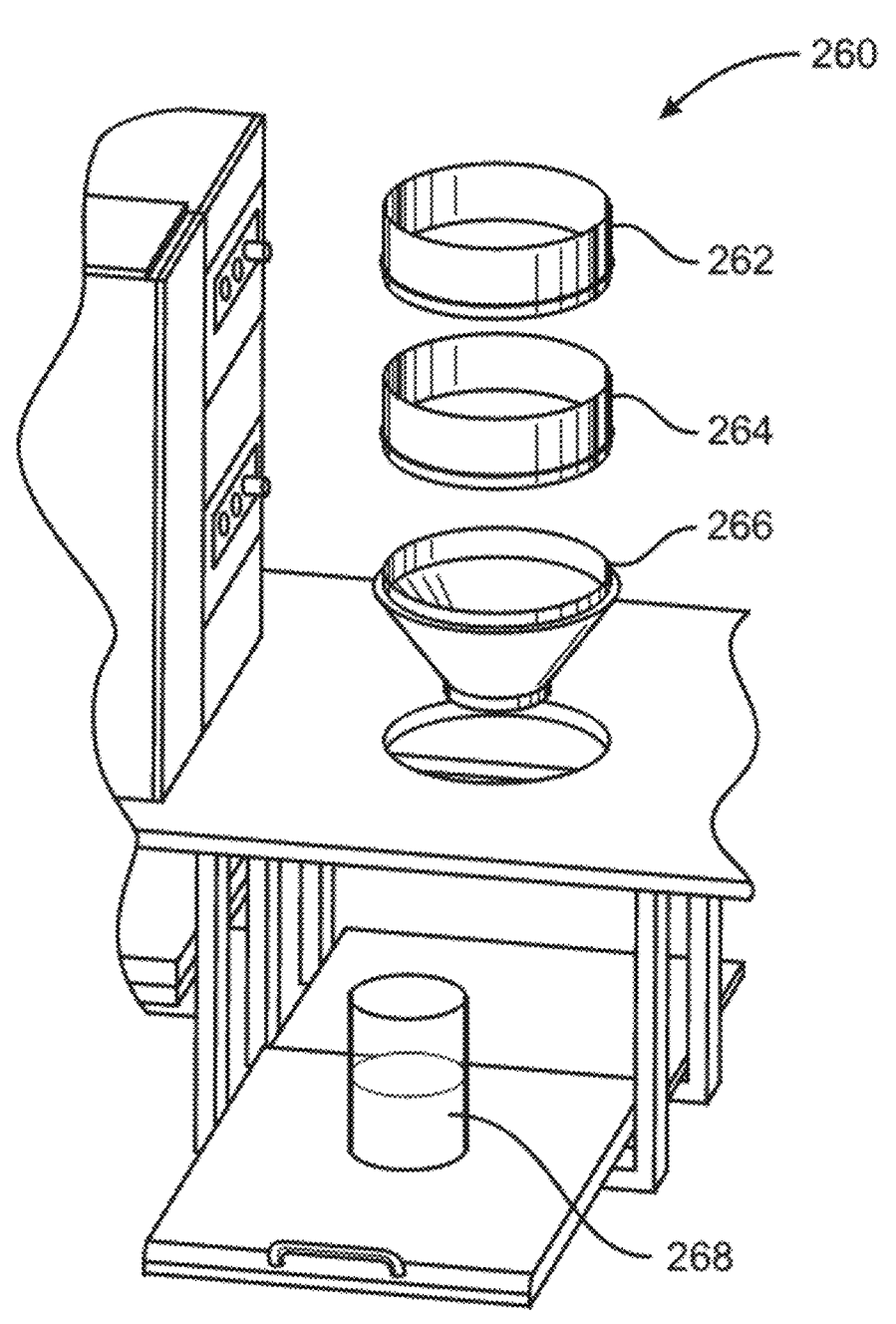
FIG. 6 is a perspective view of a sieve station.

The finely ground VB segments and processing medium are collected in the collection pan 252 and the plate 253 can be moved to a sieve station 260 (FIG. 6), whether manually or automatically. Once at the sieve station 260 the contents of the pan 252 are dropped into a sieve cartridge unit which includes two 12" diameter filter sieves—a #40 sieve 262 on top followed by a finer #80 sieve 264, as depicted in FIG. 6. A funnel 266 directs the filtered contents to a collection container 268. The grindings retained by the filters are rinsed within the sieve station 260 with processing/resuspension medium that does not include DNAse. The liquid bone marrow product in the collection container 268 can be analyzed to determine cell content and then concentrated and packaged in appropriate volumes for cryopreservation, as described below. Alternatively, some or all of the processed bone marrow can be further processed using automated cell selection approaches for specialized cell products such as CD34+ cells. Because large volumes of cells can be recovered from a single organ donor with this approach, one donor could yield multiple product types. Moreover, since the source is primary bone marrow (as opposed to G-CSF mobilized peripheral blood) the cell product will endure cryopreservation processing.

In one modification, the output from the grinding station 240 or the sieve station 260 can be automatically fed to a collection bag for cryogenic treatment. In this modification, the lower funnel 250 can be configured to direct the contents to a fluid line connected to a sterile bag. A peristaltic pump can engage the fluid line to pump the output from the grinding station to the sterile bag. A similar arrangement can be engaged to the funnel 266 of the sieve station.

The content of the collection container 268, which is essentially a bone marrow slurry, is conveyed, either manually or automatically, to an adjacent tumbler station 270 that includes a mechanical tumbler 272 and a large disposable vessel 274 that can contain the entire contents of ten processed VBs and associated processing/resuspension medium. The tumbler 272 has a paddle for agitation of the grinding shirr to mechanically liberate cells. When the tumbling cycle is complete, the contents of the tumbler are poured through a sieve magazine into the vessel 274. The contents of the vessel 274 can be processed further or prepared for cryogenic storage.

Cell Isolation from Bone Marrow

In one aspect of the present disclosure, a method is provided for selecting CD34-expressing (CD34+) cells from deceased donor bone marrow using density reduced Ficoll and an immunomagnetic CD34+ cell isolation kit. Surprisingly, it has been found that cell isolation using density reduced Ficoll prior to CD34 selection is beneficial to obtain high purity and viability CD45/CD34+ cells from freshly prepared deceased donor bone marrow. On the other hand, Ficoll at conventional density has been found to select for CD45/CD34+ cells from thawed cryopreserved deceased donor bone marrow.

Vertebral sections obtained from a recently deceased donor were processed as described above. Thus, in one embodiment, the bone is cleaned of all soft tissue and then cut into small pieces that were immediately submerged into 500 ml of grinding media. The grinding media can be PLASM A-LYTE™ A injection pH 7.4, multiple electrolytes, injection type 1 USP (PLASMA-LYTE™) containing 2.5% human serum albumin (HSA), 3 U/ml Denarase, and 10 U/ml heparin. The sectioned VB are ground using a bone grinder, filtered and rinsed with rinse media (such as PLASMA-LYTE™ with 2.5% HSA). The entire cell suspension is centrifuged to concentrate cells to $2-3 \times 10^8$/ml and the cell concentration is extracted. A portion or all of the resulting BM preparation call be used immediately for CD34 selection, while the remainder call be prepared for cryopreservation. The cryopreserved portion involves adding a final concentration of 10% DMSO and 5% HSA to the BM cells and bringing the preparation to −86° C. either by passive cooling or by controlled cooling at a rate of approximately −1° C./min, after which the cryopreserved portion is plunged into liquid nitrogen.

For selection of CD34+ cells, either the newly processed BM preparation is used or a previously cryopreserved portion is thawed for use. Ficoll-Paque PLUS is added to the BM preparation to separate the desired CD34+ cell component of the bone marrow. It has been found for cell selection from cryopreserved bone marrow that the conventional density for the Ficoll of 1.077 g/mi produces acceptable results. However, in one aspect or the present disclosure, for cell selection from freshly prepared deceased donor bone marrow the Ficoll density is reduced from the conventional density. In particular, the density is reduced by mixing Ficoll-Paque PLUS (density 1.077 g/mL, GE Company) with Plasma Lyte-A Injection pH 7.4 (Baxter Healthcare 2B2544X) in specific proportions to obtain an overall density of less than 1.077 g/ml, particularly, 1.063-1.052 g/ml. In one specific embodiment, the density of 1.063 g/ml was found for isolation of CD34+ cells, taking into account quantity, viability and purity of the CD34+ cells.

In one embodiment, 5 ml of the 1.063 g/ml density Ficoll solutions is pipetted into 15-mi centrifuge tubes, and the BM solution generated from VBs of deceased donors is carefully layered over the Ficoll gradient. The tubes are centrifuged for 30 ill in at 400 g without break at room temperature. After centrifugation, buffy coat cells are harvested carefully, and the cells are washed in phosphate-buffered saline (PBS) containing 0.5% HSA and 2 mM Ethylenediaminetetraacetic acid (EDTA) (MACS buffer, Miltenyi). In one specific embodiment, centrifugation is performed for 5 min at 400 g, and the resulting cell pellets are resuspended in 10 ml PBS, followed by a second centrifugation for 5 rain at 400 g.

Nucleated cells in the isolated huffy coat can be counted using a Sysmex XP-300. A Ceilometer Vision Nexcelom) or flow cytometer can be used to determine cell counts of purified CD34 cells. 20 microliters of AOPI can be added to 20 microliters of cells and after mixing total viable cells cart be determined. The CD34+ cells can be selected by a positive immune separation method using a CliniMAX system (Miltenyi, Bergisch Gladbach, Germany) or an Easy Sep CD34 kit (Stemcell Technologies, Vancouver, BC, Canada) in accordance with the protocol of the manufacturer. From testing at various Ficoll densities it has been surprisingly determined that the lower Ficoll density contemplated in the present disclosure (i.e., 1.063-1.052 μm/ml vs, the conventional 1.077 μm/ml density) leads to more optimum cell recovery. Optimization is based on purity, viability and yield of selected CD34 cells, A target of >90% purity and >90% viable CD34+ cells is preferred. While lower Ficoll densities resulted in greater purity and fewer dead cells, it was surprisingly found that a greater portion of the CD34+ cells present in the deceased donor whole bone marrow before selection are lost using the lower Ficoll densities to prepare buffy coat. Thus, the high viability and purity of CD45/CD34+ cells achieved at the conventional Ficoll density gradient also leads to a large loss in yield (approximately 60% loss of input CD34+ cells).

Thus, in accordance with one aspect of the present disclosure, for freshly prepared the density of Ficoll for selection of CD45/CD34+ cells at >90% purity and viability is less than 1,077 and particularly 1.063-1.052. This Ficoll density provides a higher yield of CD45/CD34+ cells with similar purity and cell viability to the conventional Ficoll density approach.

In another aspect of the present disclosure, the CD34+ cells can be initially acquired from a freshly prepared deceased donor bone marrow using the reduced density Ficoll-Paque described above. The BM can be cryogenically frozen and then the CD34+ cells can be acquired later using conventional density Ficoll-Paque. This approach essentially allows selective recovery, of cells from deceased donor bone marrow either before freezing, using the modified Ficoll density or after freezing and thawing using conventional Ficoll density.

Described herein, in some embodiments, is a method of processing bone marrow to obtain bone marrow cells. In some embodiments, the method comprises the contacting the bone marrow or the bone marrow cells with the stabilization buffer described herein. In some embodiments, the stabilization buffer comprises serum albumin. In some embodiments, the serum albumin can be human serum albumin. In some embodiments, the stabilization buffer comprises about 0.01% HSA, 0.05% HSA, 0.1% HSA, 0.2% HSA, 0.3% HSA, 0.4% HSA, 0.5% HSA, 0.6% HSA, 0.7% HSA, 0.8% HSA, 0.9% HSA, 1.0% HSA, 1.5% HSA, 2% HSA, 2.5% HSA, 5% HSA, 10% HSA, 20% HSA, or more HSA. In some embodiments, the stabilization buffer comprises nuclease. In some embodiments, the nuclease is Benzonase. In some embodiments, the stabilization buffer comprises nuclease at about 1 unit/ml (U/ml), 2 U/ml, 3 U/ml, 4 U/ml, 5 U/ml, 6 U/ml, 7 U/ml, 8 U/ml, 9 U/ml, 10 U/ml, 11 U/ml, 12 U/ml, 13 U/ml, 14 U/ml, 15 U/ml, 16 U/ml, 17 U/ml, 18 U/ml, 19 U/ml, 20 U/ml, 21 U/ml, 22 U/ml, 23 U/ml, 24 U/ml, 25 U/ml, 26 U/ml, 27 U/ml, 28 U/ml, 29 U/ml, 30 U/ml, 50 U/ml. 100 U/ml, 200 U/ml, or more U/ml. In some embodiments, the stabilization buffer comprises an anticoagulant. In some cases, the anticoagulant is Heparin. In some instances, the stabilization buffer comprises anticoagulant at about 1 U/ml, 2 U/ml, 3 U/ml, 4 U/ml, 5 U/ml, 6 U/ml, 7 U/ml, 8 U/ml, 9 U/ml, 10 U/ml, 11 U/ml, 12 U/ml, 13 U/ml, 14 U/ml, 15 U/ml, 16 U/ml, 17 U/ml, 18 U/ml, 19 U/ml, 20 U/ml, 21 U/ml. 22 U/ml, 23 U/ml, 24 U/ml. 25 U/ml, 26 U/ml, 27 U/ml, 28 U/ml, 29 U/ml, 30 U/ml, 50 U/ml, 100 U/ml, 200 U/ml, or more U/ml.

In some embodiments, processing or contacting the bone marrow or bone marrow cells described herein with the stabilization buffer increases the yield of the bone marrow cells obtained from the methods described herein compared to the yield of the bone marrow cells processed in the absence of the stabilization buffer. In some instances, processing or contacting the bone marrow or bone marrow cells described herein with the stabilization buffer increases the yield of the bone marrow cells by at least about 10%, 20%, 30%, 40%, 50%, 60%, 70%, 80%, 90%, 100%, 2 folds, 3 folds, 4 folds, 5 folds, 10 folds, 20 folds, 50 folds, or more compared to yield of bone marrow cells processed in the absence of the stabilization buffer. In some embodiments, processing or contacting the bone marrow or bone marrow cells described herein with the stabilization buffer increases the viability of the bone marrow cells obtained from the methods described herein compared to the viability of the bone marrow cells processed in the absence of the stabilization buffer. In some instances, processing or contacting the bone marrow or bone marrow cells described herein with the stabilization buffer increases the viability of the bone marrow cells by at least about 10%, 20%, 30%, 40%, 50%, 60%, 70%, 80%. 90%, 100%, 2 folds, 3 folds. 4 folds, 5 folds, 10 folds, 20 folds, 50 folds, or more compared to viability of bone marrow cells processed in the absence of the stabilization buffer.

In some embodiments, processing or contacting the bone marrow or bone marrow cells described herein with the stabilization buffer increases the number of CD34+ bone marrow cells compare to the number of CD34+ bone marrow cells processed in the absence of the stabilization buffer. In some cases, the number of CD34+ bone marrow obtained from processing with the stabilization buffer is increased by at least about 10%, 20%, 30%, 40%, 50%, 60%, 70%, 80%. 90%. 100%, 2 folds, 3 folds. 4 folds, 5 folds, 10 folds, 20 folds, 50 folds, or more compared to the number of CD34+ bone marrow obtained from processing in the absence of stabilization buffer. In some, embodiments, processing or contacting the bone marrow or bone marrow cells described herein with the stabilization buffer increases the number of CD45+ bone marrow cells compare to the number of CD45+ bone marrow cells processed in the absence of the stabilization buffer. In some cases, the number of CD45+ bone marrow obtained from processing with the stabilization buffer is increased by at least about 10%, 20%, 30%, 40%. 50%. 60%. 70%, 80%. 90%, 100%, 2 folds, 3 folds, 4 folds, 5 folds. 10 folds, 20 folds, 50 folds, or more compared to the number of CD45+ bone marrow obtained from processing in the absence of stabilization buffer.

MSCs Combination Treatments Promote Immune Tolerance of Vascular Composite Allotransplants and Solid Organ Transplantation In one aspect of the present disclosure, a method and composition are provided for inhibiting an immune response within a subject following vascularized composite allotransplantation (VCA). In some embodiments, the vascularized composite may include transplantation of an organ to a subject referred to as a solid organ transplant (SOT). In some embodiments, the SOT may be a limb, heart, kidney liver, lung, pancreas, intestine, thymus, or uterus, skin or combination thereof.

It has been shown that MSC are a potentially useful adjuvant to stem cell transplants (SCT) for promoting mixed chimerisms as well as promoting complementary peripheral immunomodulatory functions, li has been demonstrated therapeutic potential of MSC for inducing operational tolerance of SOT and VCA, providing proof-of-principle for clinical testing in the transplant setting. The effect of MSC infusion, including in humans and nonhuman primates, is to skew the T cell population in favor of $T_{REG}$ over $T_{EM}$ cells. It is evident that mixed chimerism is essential for central tolerance of SOT and VCA, which is complemented by expansion of peripheral alloantigen-specific regulatory T cells ($T_{REGS}$) and donor-derived tolerogenic dendritic cells (TolDC).

In some embodiments, cadaveric MSCs may administered prophylactically, perioperatively or postoperatively with SOT or other VCA procedures. In some embodiments, cadaveric MSCs administered may comprise cadaveric human MSCs derived from bone marrow, adherent vertebral body MSCs (vBA-MSCs), or both.

In some embodiments, the composition of cadaveric human MSCs provided for inhibiting an immune response may be administered in quantities of about 10 million to about 10 billion. In some embodiments, cadaveric human MSCs may be administered in quantities of about 10 million to about 100 million, about 10 million to about 1 billion, about 10 million to about 10 billion, about 100 million to about 1 billion, about 100 million to about 10 billion, or about 1 billion to about 10 billion. In some embodiments, cadaveric human MSCs may be administered in quantities of about 10 million, about 100 million, about 1 billion, or about 10 billion. In some embodiments, cadaveric human MSCs may be administered in quantities of at least about 10 million, about 100 million, or about 1 billion. In some embodiments, cadaveric human MSC's may be administered in quantities of at most about 100 million, about 1 billion, or about 10 billion.

In some embodiments, the composition of cadaveric MSCs (e.g. vBA-MSCs) may be comprised of less than 5% CD45+. In some embodiments, the composition of cadaveric MSCs may be comprised of less than about 0.5% CD45+ to about 10% CD45+. In some embodiments, the composition of cadaveric MSCs may be comprised of less than about 10% CD45+ to about 9% CD45+, about 10% CD45+ to about 8% CD45+, about 10% CD45+ to about 7% CD45+, about 10% CD45+ to about 6% CD45+, about 10% CD45+ to about 5% CD45+, about 10% CD45+ to about. 4% CD45+, about 10% CD45+ to about 3% CD45+, about 10% CD45+ to about 2% CD45+, about 10% CD45+ to about 1% CD45+, about 10% CD45+ to about 0.5% CD45+, about 9% CD45+ to about 8% CD45+, about 9% CD45+ to about 7% CD45+, about 9% CD45+ to about 6% CD45+, about 9% CD45+ to about 5% CD45+, about 9% CD45+ to about 4% CD45+, about 9% CD45+ to about 3% CD45+, about 9% CD45+ to about 2% CD45=, about 9% CD45+ to about 1% CD45+, about 9% CD45+ to about 0.5% CD45+, about 8% CD45+ to about 7% CD45+, about 8% CD45+ to about 6% CD45+, about 8% CD45+ to about 5% CD45+, about 8% CD45+ to about 4% CD45+, about 8% CD45+ to about 3% CD45+, about 8% CD45+ to about 2% CD45+, about 8% CD45+ to about 1% CD45+, about 8% CD45+ to about 0.5% CD45+, about 7% CD45+ to about 6% CD45+, about 7% CD45+ to about 5% CD45+, about 7% CD45+ to about 4% CD45+, about 7% CD45+ to about 3% CD45+, about 7% CD45+ to about 2% CD45+, about 7% CD45+ to about 1% CD45+, about 7% CD45+ to about 0.5% CD45+, about 6% CD45+ to about 5% CD45+, about 6% CD45+ to about 4% CD45+, about 6% CD45+ to about 3% CD45+, about 6% CD45+ to about 2% CD45+, about 6% CD45+ to about 1%, CD45+, about 6% CD45+ to about 0.5% CD45+, about 5% CD45+ to about 4% CD45+, about 6% CD45+ to about 3% CD45+, about 5% CD45+ to about 2% CD45+ about 5% CD45+ to about 1% CD45+, about 5% CD45+ to about 0.5% CD45+, about 4% CD45+ to about 3% CD45+, about 4% CD45+ to about 2% CD45+, about 4% CD45+ to about 1% CD45+, about 4% CD45+ to about 0.5% CD45+, about 3% CD45+ to about 2% CD45+, about 3% CD45+ to about 1% CD45+, about 3% CD45+ to about 0.5% CD45+, about 2% CD45+ to about 1% CD45+, about 2% CD45+ to about 0.5% CD45+, or about 1% CD45+, to about 0.5% CD45+.

In some embodiments, the composition of cadaveric MSCs may be comprised of less than about 10% CD45+, about 9% CD45+, about 8% CD45+, about 7% CD45+, about 6% CD45+, about 5% CD45+, about 4% CD45+, about 3% CD45+, about 2% CD45+, about 1% CD45+, or about 0.5% CD45+. In some embodiments, the composition of cadaveric MSCs may be comprised of less than at least about 10% CD45+, about 9% CD45+, about 8% CD45+, about 7% CD45+, about 6% CD45+, about 5% CD45+, about 4% CD45+, about 3% CD45+, about 2% CD45+, or about 1% CD45+. In some embodiments, the composition of cadaveric MSCs may be comprised of less than at most about 9% CD45+, about 8% CD45+, about 7% CD45+, about 6%

CD45+, about 5% CD45+, about 4% CD45+, about 3% CD45+, about 2% CD45+, about 1% CD45+, or about 0.5% CD45+.

In some embodiments, the composition of cadaveric MSCs (e.g. vBA-MSCs) may comprise more than 1% CD45+ cells. In some embodiments, the composition of cadaveric MSCs may comprise more than 1.1% CD45+ cells. In some embodiments, the composition of cadaveric MSCs may comprise more than 1.2% CD45+ cells. In some embodiments, the composition of cadaveric MSCs may comprise more than 1.3% CD45+ cells. In some embodiments, the composition of cadaveric MSCs may comprise more than 1.4% CD45+ cells. In some embodiments, the composition of cadaveric MSCs may comprise more than 1.5% CD45+ cells. In some embodiments, the composition of cadaveric MSCs may comprise more than 1.6% CD45+ cells. In some embodiments, the composition of cadaveric MSCs may comprise more than 1.7% CD45+ cells. In some embodiments, the composition of cadaveric MSCs may comprise more than 1.8% CD45+ cells. In some embodiments, the composition of cadaveric MSCs may comprise more than 1.9% CD45+ cells. In some embodiments, the composition of cadaveric MSCs may comprise more than 2% CD45+ cells.

In some embodiments, the composition of cadaveric. MSCs may be comprised of at least 90% CD105+ cells. In some embodiments, the composition of cadaveric MSCs may be comprised of at least about 70% CD105+ cells to about 100% CD105+ cells. In some embodiments, the composition of cadaveric MSCs may be comprised of at least about 100% CD105+ cells to about 95% CD105+ cells, about 100% CD105+ cells to about 94% CD105+ cells, about 100% CD105+ cells to about 93% CD105+ cells, about 100% CD105+ cells to about 92% CD105+ cells, about 100% CD105+ cells to about 91% CD105+ cells, about 100% CD105+ cells to about 90% CD105+ cells, about 100% CD105+ cells to about 85% CD105+ cells, about 100% CD105+ cells to about 80% CD105+ cells, about 100% CD105+ cells to about 75% CD105+ cells, about 100% CD105+ cells to about 70% CD105+ cells, about 95% CD105+ cells to about 94% CD105+ cells, about 95% CD105+ cells to about 93% CD105+ cells, about 95% CD105+ cells to about 92% CD105+ cells, about 95% CD105+ cells to about 91% CD105+ cells, about 95% CD105+ cells to about 90% CD105+ cells, about 95% CD105+ cells to about 85% CD105+ cells, about 95% CD105+ cells to about 80% CD105+ cells, about 95% CD105+ cells to about 75% CD105+ cells, about 95% CD105+ cells to about 70% CD105+ cells, about 94% CD105+ cells to about 93% CD105+ cells, about 94% CD105+ cells to about 92% CD105+ cells, about 94% CD105+ cells to about 91% CD105+ cells, about 94% CD105+ cells to about 90% CD105+ cells, about 94% CD105+ cells to about 85% CD105+ cells, about 94% CD105+ cells to about 80% CD105+ cells, about 94% CD105+ cells to about 75% CD105+ cells, about 94% CD105+ cells to about 70% CD105+ cells, about 93% CD105+ cells to about 92% CD105+ cells, about 93% CD105+ cells to about 91% CD105+ cells, about 93% CD105+ cells to about 90% CD105+ cells, about 93% CD105+ cells to about 85% CD105+ cells, about 93% CD105+ cells to about 80% CD105+ cells, about 93% CD105+ cells to about 75% CD105+ cells, about 92. % CD105+ cells to about 70% CD105+ cells, about 92% CD105+ cells to about 91% CD105+ cells, about 92% CD105+ cells to about 90% CD105+ cells, about 92% CD105+ cells to about 85% CD105+ cells, about 92%

CD105+ cells to about 80% CD105+ cells, about 92% CD105+ cells to about 75% CD105+ cells, about 92% CD105+ cells to about 70% CD105+ cells, about 91% CD105+ cells to about 90% CD105+ cells, about 91% CD105+ cells to about 85% CD105+ cells, about 91% CD105+ cells to about 80% CD105+ cells, about 91% CD105+ cells to about 75% CD105+ cells, about 91% CD105+ cells to about 70% CD105+ cells, about 90% CD105+ cells to about 85% CD105+ cells, about 90% CD105+ cells to about 80% CD105+ cells, about 90% CD105+ cells to about 75% CD105+ cells, about 90% CD105+ cells to about 70% CD105+ cells, about 85% CD105+ cells to about 80% CD105+ cells, about 85% CD105+ cells to about 15% CD105+ cells, about 85% CD105+ cells to about 70% CD105+ cells, about 80% CD105+ cells to about 75% CD105+ cells, about 80% CD105+ cells to about 70% CD105+ cells, or about 75% CD105+ cells to about 70% CD105+ cells. In some embodiments, the composition of cadaveric MSCs may be comprised of at least about 100% CD105+ cells, about 95% CD105+ cells, about 94% CD105+ cells, about 93% CD105+ cells, about 92% CD105+ cells, about 91% CD105+ cells, about 90% CD105+ cells, about 85% CD105+ cells, about 80% CD105+ cells, about 75% CD105+ cells, or about 70% CD105+ cells. In some embodiments, the composition of cadaveric MSCs may be comprised of at least at least about 100% CD105+ cells, about 95% CD105+ cells, about 94% CD105+ cells, about 93% CD105+ cells, about 92% CD105+ cells, about 91% CD105+ cells, about 90% CD105+ cells, about 85% CD105+ cells, about 80% CD105+ cells, or about 75% CD105+ cells. In some embodiments, the composition of cadaveric MSCs may be comprised of at least at most about 95% CD105+ cells, about 94% CD105+ cells, about 93% CD105+ cells, about 92% CD105+ cells, about 91% CD105+ cells, about 90% CD105+ cells, about 85% CD105+ cells, about 80% CD105+ cells, about 75% CD105+ cells, or about 70% CD105+ cells.

In some embodiments, the composition of cadaveric MSCs may be comprised of at least 90% CD166+ cells. In some embodiments, the composition of cadaveric MSCs may be comprised of at least about 70% CD166+ cells to about 100% CD166+ cells. In some embodiments, the composition of cadaveric MSCs may be comprised of at least about 100% CD166+ cells to about 95% CD166+ cells, about 100% CD166+ cells to about 94% CD166+ cells, about 100% CD166+ cells to about 93% CD166+ cells, about 100% CD166+ cells to about 92% CD166+ cells, about 100% CD166+ cells to about 91% CD166+ cells, about 100% CD166+ cells to about 90% CD166+ cells, about 100% CD166+ cells to about 85% CD166+ cells, about 100% CD166+ cells to about 80% CD166+ cells, about 100% CD166+ cells to about 75% CD166+ cells, about 100% CD166+ cells to about 70% CD166+ cells, about 95% CD166+ cells to about 94% CD166+ cells, about 95% CD166+ cells to about 93% CD166+ cells, about 95% CD166+ cells to about 92% CD166+ cells, about 95% CD166+ cells to about 91% CD166+ cells, about 95% CD166+ cells to about 90% CD166+ cells, about 95% CD166+ cells to about 85% CD166+ cells, about 95% CD166+ cells to about 80% CD166+ cells, about 95% CD166+ cells to about 75% CD166+ cells, about 95% CD166+ cells to about 70% CD166+ cells, about 94% CD166+ cells to about 93% CD166+ cells, about 94% CD166+ cells to about 92% CD166+ cells, about 94% CD166+ cells to about 91% CD166+ cells, about 94% CD166+ cells to about 90% CD166+ cells, about 94%

CD166+ cells to about 85% CD166+ cells, about 94%
CD166+ cells to about 80% CD166+ cells, about 94%
CD166+ cells to about 75% CD166+ cells, about 94%
CD166+ cells to about 70% CD166+ cells, about 93%
CD166+ cells to about 92% CD166+ cells, about 93%
CD166+ cells to about 91% CD166+ cells, about 93%
CD166+ cells to about 90% CD166+ cells, about 93%
CD166+ cells to about 85% CD166+ cells, about 93%
CD166+ cells to about 80% CD166+ cells, about 93%
CD166+ cells to about 75% CD166+ cells, about 93%
CD166+ cells to about 70% CD166+ cells, about 92%
CD166+ cells to about 91% CD166+ cells, about 92%
CD166+ cells to about 90% CD166+ cells, about 92%
CD166+ cells to about 85% CD166+ cells, about 92%
CD166+ cells to about 80% CD166+ cells, about 92%
CD166+ cells to about 75% CD166+ cells, about 92%
CD166+ cells to about 70% CD166+ cells, about 91%
CD166+ cells to about 90% CD166+ cells, about 91%
CD166+ cells to about 85% CD166+ cells, about 91%
CD166+ cells to about 80% CD166+ cells, about 91%
CD166+ cells to about 75% CD166+ cells, about 91%
CD166+ cells to about 70% CD166+ cells, about 90%
CD166+ cells to about 85% CD166+ cells, about 90%
CD166+ cells to about 80% CD166+ cells, about 90%
CD166+ cells to about 75% CD166+ cells, about 90%
CD166+ cells to about 70% CD166+ cells, about 85%
CD166+ cells to about 80% CD166+ cells, about 85%
CD166+ cells to about 75% CD166+ cells, about 85%
CD166+ cells to about 70% CD166+ cells, about 80%
CD166+ cells to about 75% CD166+ cells, about 80%
CD166+ cells to about 70% CD166+ cells, or about 75%
CAD 166+ cells to about 0% CD166+ cells. In some
embodiments, the composition of cadaveric MSCs may be
comprised of at least about 100% CD166+ cells, about 95%
CD166+ cells, about 94% CD166+ cells, about 93%
CD166+ cells, about 92% CD166+ cells, about 91%
CD166+ cells, about 90% CD166+ cells, about 85%
CD166+ cells, about 80% CD166+ cells, about 75%
CD166+ cells, or about 70% CD166+ cells. In some embodi-
ments, the composition of cadaveric MSCs may be com-
prised of at least at least about 100% CD166+ cells, about
95% CD166+ cells, about 94% CD166+ cells, about 93%
CD166+ cells, about 92% CD166+ cells, about 91%
CD166+ cells, about 90% CD166+ cells, about 85%
CD166+ cells, about 80% CD166+ cells, or about 75%
CD166+ cells. In some embodiments, the composition of
cadaveric MSCs may be comprised to at least at most about
95% CD166+ cells, about 94% CD166+ cells, about 93%
CD166+ cells, about 92% CD166+ cells, about 91%
CD166+ cells, about 90% CD166+ cells, about 85%
CD166+ cells, about 80% CD166+ cells, about 75%
CD166+ cells, or about 70% CD166+ cells.

In some embodiments, MSCs may be administered for
both tolerogenic and pro-tolerogenic SOT or VCA including
heart, limbs, kidney, skin and lung tissues, in some embodi-
ments, MSCs may be administered with hematopoietic stem
cells (HSC) to enhance mixed chimerism and to minimize
the number of HSC required for transplantation. It has been
shown that MSCs have been reported to facilitate and
enhance engraftment of allogeneic HSC clinically, even
after initial graft failure and rejection of conventional stem-
cell grafts.

The combination of promoting bone marrow (BM) chi-
merism and the immunomodulatory and HSC stabilizing
effects of MSC suggest that combining these cells with BM
transplants will be a potent combination for inducing
immune tolerance for SOT and VCA as well as facilitating function of the inherent BM component of VCA. Thus, in
some embodiments, MSCs may be administered in combi-
nation with bone marrow and HSCs to promote a state of
mixed chimerism.

MSCs for Treating Medical Conditions

Another aspect described herein is a method of treating a
medical condition in a subject suffering therefrom, the
method comprising administering a composition comprising
a population of mesenchymal stem cells (MSCs), wherein
the population of MSCs comprises more than 1.75% CD45+
cells. In some embodiments, the composition of MSCs (e.g.
vBA-MSCs) may comprise more than 1% CD45+ cells. In
some embodiments, the composition of MSCs may com-
prise more than 1.1% CD45+ cells. In some embodiments,
the composition of MSCs may comprise more than 1.2%
CD45+ cells. In some embodiments, the composition of
MSCs may comprise more than 1.3% CD45+ cells. In some
embodiments, the composition of MSCs may comprise more
than 1.4% CD45+ cells. In some embodiments, the compo-
sition of MSCs may comprise more than 1.5% CD45+ cells.
In some embodiments, the composition of MSCs may com-
prise more than 11.6% CD45+ cells. In some embodiments,
the composition of MSCs may comprise more than 1.7%
CD45+ cells. In some embodiments, the composition of
MSCs may, comprise more than 1.8% CD45+ cells. In some
embodiments, the composition of MSCs may comprise more
than 1.9% CD45+ cells. In some embodiments, the compo-
sition of MSCs may comprise more than 2% CD45+ cells.
In some embodiments, the composition of MSCs (e.g.
vBA-MSCs) may be comprised of less than 5% CD45+. In
some embodiments, the composition of MSCs may be
comprised of less than about 0.5% CD45+ to about 10%
CD45+. In some embodiments, the composition of MSCs
may be comprised of less than about 10% CD45+ to about
9% CD45+, about 10% CD45+ to about 8% CD45+, about
10% CD45+ to about 7% CD45+, about 10% CD45+ to
about 6% CD45+, about 10% CD45+ to about 5% CD45+,
about 10% CD45+ to about 4% CD45+, about 10% CD45+
to about 3% CD45+, about 10% CD45+ to about 2%
CD45+, about 10% CD45+ to about 1% CD45+, about 10%
CD45+ to about 0.5% CD45+, about 9% CD45+ to about
8% CD45+, about 9% CD45+ to about 7% CD45+, about
9% CD45+ to about 6% CD45+, about 9% CD45+ to about
5% CD45+, about 9 CD45+ to about 4% CD45+, about 9%
CD45+ to about 3% CD45+, about 9% CD45+ to about 2%
CD45+, about 9% CD45+ to about 1% CD45+, about 9%
CD45+ to about 0.5% CD45+, about 8% CD45+ to about
7% CD45+, about 8% CD45+ to about 6% CD45+, about
8% CD45+ to about 5% CD45+, about 8% CD45+ to about
4% CD45+, about 8% CD45+ to about 3% CD45+, about
8% CD45+ to about 2% CD45+, about 8% CD45+ to about
1% CD45+, about 8% CD45+ to about 0.5% CD45+, about
7% CD45+ to about 6% CD45+, about 7% CD45+ to about
5% CD45+, about 7% CD45+ to about 4% CD45+, about
7% CD45+ to about 3% CD45+, about 7% CD45+ to about
2% CD45+, about 7% CD45+ to about 1% CD45+, about
7% CD45+ to about 0.5% CD45+, about 6'% CD45+ to
about 5% CD45+, about 6% CD45+ to about 4% CD45+,
about 6% CD45+ to about 3% CD45+, about 6% CD45+ to
about 2% CD45+, about 6% CD45+ to about 1% CD45+,
about 6% CD45+ to about 0.5% CD45+, about 5% CD45+
to about 4% CD45+, about 5% CD45+ to about 3% CD45+,
about 5% CD45+ to about 2% CD45+, about 5% CD45+ to
about 1% CD45+, about 5% CD45+ to about 0.5% CD45+,
about 4% CD45+ to about 3% CD45+, about 4% CD45+ to
about 2% CD45+, about 4% CD45+ to about 1% CD45+,
about 4% CD45+ to about 0.5% CD45+, about 3% CD45+ to about 2% CD45+, about 3% CD45+ to about 1% CD45+, about 3% CD45+ to about 0.5% CD45+, about 2 CD45+ to about 1% CD45+, about 2% CD45+ to about 0.5% CD45+, or about 1% CD45+ to about 0.5% CD45+. In some embodiments, the composition of MSCs may be comprised of less than about 10% CD45+, about 9% CD45+, about 8% CD45+, about 7% CD45+, about 6% CD45+, about 5% CD45+, about 4% CD45+, about 3% CD45+, about 2% CD45+, about 1% CD45+, or about 0.5% CD45+. In some embodiments, the composition of MSCs may be comprised of less than at least about 10% CD45+, about 9% CD45+, about 8% CD45+, about 7% CD45+, about 6% CD45+, about 5% CD45+, about 4% CD45+, about 3% CD45+, about 2% CD45+, or about 1% CD45+. In some embodiments, the composition of MSCs may be comprised of less than at most about 9% CD45+, about 8% CD45+, about 7% CD45+, about 6% CD45+, about 5% CD45+, about 4% CD45+, about 3% CD45+, about 2% CD45+, about 1% CD45+, or about 0.5% CD45+.

In some embodiments, the population of human MSCs is immune-suppressive. In some embodiments, the population of human MSCs suppresses CD4+ immune cell expansion by at least about 1 fold to about 4 fold. In some embodiments, the population of human MSCs suppresses CD4+ immune cell expansion by at least about 1 fold to about 2 fold, about 1 fold to about 3 fold, about 1 fold to about 4 fold, about 2 fold to about 3 fold, about 2 fold to about 4 fold, or about 3 fold to about 4 fold. In some embodiments, the population of human MSCs suppresses CD4+ immune cell expansion by at least about 1 fold, about 2 fold, about 3 fold, or about 4 fold. In some embodiments, the population of human MSCs suppresses CD4+ immune cell expansion by at least at least about 1 fold, about 2 fold, or about 3 fold. In some embodiments, the population of human MSCs suppresses CD4+ immune cell expansion by at least at most about 2 fold, about 3 fold, or about 4 fold. In some embodiments, the population of human MSCs suppresses CD4+ immune cell expansion by at least 1 fold. In some embodiments, the population of human MSCs suppresses CD4+ immune cell expansion by at least 2 fold. In some embodiments, the population of human MSCs suppresses CD4+ immune cell expansion by at least 3 fold. In some embodiments, the population of human MSCs suppresses CD4+ immune cell expansion by at least 4 fold. In some embodiments, the population of human MSCs suppresses CD4+ immune cell expansion by at least about 10% to about 95%. In some embodiments, the population of human MSCs suppresses CD4+ immune cell expansion by at least about 10% to about 20%, about 10% to about 30%, about 10% to about 40%, about 10% to about 50%, about 10% to about 60%, about 10% to about 70%, about 10% to about 80%, about 10% to about 90%, about 10% to about 95%, about 20% to about 30%, about 20% to about 40%, about 20% to about 50%, about 20% to about 60%, about 20% to about 70%, about 20% to about 80%, about 20% to about 90%, about 20% to about 95%, about 30% to about 40%, about 30% to about 50%, about 30% to about 60%, about 30% to about 70%, about 30% to about 80%, about 30% to about 90%, about 30% to about 95%, about 40% to about 50%, about 40% to about 60%, about 40% to about 70%, about 40% to about 80%, about 40% to about 90%, about 40% to about 95%, about 50% to about 60%, about 50% to about 70%, about 50% to about 80%, about 50% to about 90%, about 50% to about 95%, about 60% to about 70%, about 60% to about 80%, about 60% to about 90%, about 60% to about 95%, about 70% to about 80%, about 70% to about 90%, about 70% to about 95%, about 80% to about 90%, about 80% to about 95%, or about 90% to about 95%. In some embodiments, the population of human MSCs suppresses CD4+ immune cell expansion by at least about 10%, about 20%, about 30%, about 40%, about 50%, about 60%, about 70%, about 80%, about 90%, or about 95%. In some embodiments, the population of human MSCs suppresses CD4+ immune cell expansion by at least at least about 10%, about 20%, about 30%, about 40%, about 50%, about 60%, about 70%, about 80%, about 90%. In some embodiments, the population of human MSCs suppresses CD4+ immune cell expansion by at least at most about 20%, about 30%, about 40%, about 50%, about 60%, about 70%, about 80%, about 90%, or about 95%. In some embodiments, the population of human MSCs suppresses CD8+ immune cell expansion by at least about 1 fold to about 4 told. In some embodiments, the population of human MSCs suppresses CD8+ immune cell expansion by at least about 1 fold to about 2 fold, about 1 fold to about 3 fold, about 1 fold to about 4 fold, about 2 fold to about 3 fold, about 2 fold to about 4 fold, or about 3 fold to about 4 fold. In some embodiments, the population of human MSCs suppresses CD8+ immune cell expansion b at least about 1 fold, about 2 fold, about 3 fold, or about 4 fold. In some embodiments, the population of human MSCs suppresses CD8+ immune cell expansion by at least at least about 1 fold, about 2 fold, or about 3 fold. In some embodiments, the population of human MSCs suppresses CD8+ immune cell expansion by at least at most about 2 fold, about 3 fold, or about 4 fold. In some embodiments, the population of human MSCs suppresses CD8+ immune cell expansion by at least 1 fold. In some embodiments, the population of human MSC, suppresses CD8+ immune cell expansion by at least 2 fold. In some embodiments, the population of human MSCs suppresses CD8+ immune cell expansion by at least 3 fold. In some embodiments, the population of human MSCs suppresses CD8+ immune cell expansion by at least about 10% to about 95%. In some, embodiments, the population of human MSCs suppresses CD8+ immune cell expansion by at least about 10% to about 20%, about 10% to about 30%, about 10% to about 40%, about 10% to about 50%, about 10% to about 60%, about 10% to about 70%, about 10% to about 80%, about 10% to about 90%, about 10% to about 95%, about 20% to about 30%, about 20% to about 40%, about 20% to about 50%, about 20% to about 60%, about 20% to about 70%, about 20% to about 80%, about 20% to about 90%, about 20% to about 95%, about 30% to about 40%, about 30% to about 50%, about 30% to about 60%, about 30% to about 70%, about 30% to about 80%, about 30% to about 90%, about 30% to about 95%, about 40% to about 50%, about 40% to about 60%, about 40% to about 70%, about 40% to about 80%, about 40% to about 90%, about 40% to about 95%, about 50% to about 60%, about 50% to about 70%, about 50% to about 80%, about 50% to about 90%, about 50% to about 95%, about 60% to about 70%, about 60% to about 80%, about 60% to about 90%, about 60% to about 95%, about 70% to about 80%, about 70% to about 90%, about 70% to about 95%, about 80% to about 90%, about 80% to about 95%, or about 90% to about 95%. In some embodiments, the population of human MSCs suppresses CD8+ immune cell expansion by at least about 10%, about 20%, about 30%, about 40%, about 50%, about 60%, about 70%, about 80%, about 90%, or about 95%. In some embodiments, the population of human MSCs suppresses CD8+ immune cell expansion by at least at least about 10%, about 20%, about 30%, about 40%, about 50%, about 60%, about 70%, about 80%, or about 90%. In some embodiments, the population of human MSCs suppresses CD8+ immune cell expansion by at least at most about 20%, about 3%, about 40%, about 50%, about 60%, about 70%, about 80%, about 90%, or about 95%.

In some embodiments, the population of human MSCs is passaged at least about 1 time to about 12 times. In some embodiments, the population of human MSCs is passaged at least about 1 time to about 2 times, about 1 time to about 3 times, about 1 time to about 4 times, about 1 time to about 5 times, about 1 time to about 6 times, about 1 time to about 7 times, about 1 time to about 8 times, about 1 time to about 9 times, about 1 time to about 10 times, about 1 time to about 11 times, about 1 time to about 12 times, about 2 times to about 3 times, about 2 times to about 4 times, about 2 times to about 5 tines, about 2 times to about 6 times, about 2 times to about 7 times, about 2 times to about 8 tildes, about 2 times to about 9 times, about 2 times to about 10 times, about 1 times to about 11 times, about 2 time, to about 12 times, about 3 times to about 4 times, about 3 times to about 5 times, about 3 times to about 6 times, about 3 times to about 7 times, about 3 times to about 8 times, about 3 times to about 9 times, about 3 times to about 10 times, about 3 times to about 11 times, about 3 times to about 12 times, about 4 times to about 5 tines, about 4 times to about 6 times, about 4 times to about 7 times, about 4 times to about 8 times, about 4 times to about 9 times, about 4 elides to about 10 times, about 4 times to about 11 times, about 4 times to about 12 times, about 5 times to about 6 times, about 5 elides to about 7 times, about 5 times to about 8 times, about 5 times to about 9 times, about 5 times to about 10 times, about 5 times to about 11 times, about 5 tuxes to about 12 times, about 6 times to about 7 times, about 6 times to about 8 times, about 6 times to about 1 times, about 6 times to about 10 times, about 6 times to about 11 times, about 6 times to about 12 times, about 7 times to about 8 times, about 7 times to about 9 times, about 7 times to about 10 times, about 7 times to about 11 times, about 7 titles to about 12 times, about 8 times to about 9 times, about 8 times to about 10 times, about 8 times to about 11 times, about 8 times to about 12 tines, about 9 times to about 10 times, about 9 times to about 11 times, about 9 times to about 12 times, about 10 times to about 11 times, about 10 times to about 12 times, or about 11 times to about 12 times, in some embodiments, the population of human MSCs is passaged at least about 1 time, about 2 times, about 3 times, about 4 times, about 5 times, about 6 times, about 7 times, about 8 times, about 9 times, about 10 times, about 11 times, or about 12 times. In some embodiments, the population of human MSCs is passaged at least at least about 1 time, about 2 elides, about 3 times, about 4 times, about 5 times, about 6 times, about 7 times, about 8 times, about 9 times, about 10 tears, or about 11 times. In some embodiments, the population of human MSCs is passaged at least at most about 2 times, about 3 times, about 4 times, about 5 times, about 6 times, about 7 times, about 8 times, about 9 times, about 10 times, about 11 times, or about 12 times.

In some embodiments, the population of MSCs comprises a doubling rate of at least about 16 to 36 hours over the passages. In some embodiments, the population of MSCs comprises a doubling rate of at least about 16 to 36 hours over each of the at least 4 passages. In some embodiments, the population of MSCs comprises a doubling rate of at least about 16 to 36 hours over the at least 5 passages. In some embodiments, the population of MSCs comprises a doubling rate of at least about 16 to 36 hours over each of the at least 5 passages. In some embodiments, the population of MSCs comprises a doubling rate of at least about 16 to 36 hours over the at least 6 passages. In some embodiments, the population of MSCs comprises a doubling rate of at least about 16 to 36 hours over each of the at least 6 passages. In some embodiments, the population of MSCs comprises a doubling rate of at least about 16 to 36 hours over the at least 7 passages. In some embodiments, the population of MSCs comprises a doubling rate of at least about 16 to 36 hours over each of the at least 7 passages. In some embodiments, the population of MSCs comprises a doubling rate of at least about 16 to 36 hours over the at least 8 passages. In some embodiments, the population of MSCs comprises a doubling rate of at least about 16 to 36 hours over each of the at least 8 passages. In some embodiments, the population of MSCs comprises a doubling rate of at least about 16 to 36 hours over the at least 9 passages. In some embodiments, the population of MSCs comprises a doubling rate of at least about 16 to 36 hours over each of the at least 9 passages. In some embodiments, the population of MSCs comprises a doubling rate of at least about 16 to 36 hours over the at least 10 passages. In some embodiments, the population of MSCs comprises a doubling rate of at least about 16 to 36 hours over each of the at least 10 passages. In some embodiments, the population of MSCs comprises a doubling rate of less than about 29 hours.

In some embodiments, the population of MSCs comprises at least 90% CD105+ cells. In some embodiments, the population of human MSCs comprises at least 90% CD105+ cells. In some embodiments, the composition of MSCs may be comprised of at least 90% CD105+ cells. In some embodiments, the composition of MSCs may be comprised of at least about 70% CD105+ cells to about 100% CD105+ cells. In some embodiments, the composition of MSCs may be comprised of at least about 100% CD105+ cells to about 95% CD105+ cells, about 100% CD105+ cells to about 94% CD105+ cells, about 100% CD105+ cells to about 93% CD105+ cells, about 100% CD105+ cells to about 92% CD105+ cells, about 100% CD105+ cells to about 91% CD105+ cells, about 100% CD105+ cells to about 90% CD105+ cells, about 100% CD105+ cells to about 85% CD105+ cells, about 100% CD105+ cells to about 80% CD105+ cells, about 100% CD105+ cells to about 75% CD105+ cells, about 100% CD105+ cells to about 70% CD105+ cells, about 95% CD105+ cells to about 94% CD105+ cells, about 95% CD105+ cells to about 93% CD105+ cells, about 95% CD105+ cells to about 92% CD105+ cells, about 95% CD105+ cells to about 91% CD105+ cells, about 95% CD105+ cells to about 90% CD105+ cells, about 95% CD105+ cells to about 85% CD105+ cells, about 95% CD105+ cells to about 80% CD105+ cells, about 95% CD105+ cells to about 75% CD105+ cells, about 95% CD105+ cells to about 70% CD105+ cells, about 94% CD105+ cells to about 93% CD105+ cells, about 94% CD105+ cells to about 92% CD105+ cells, about 94% CD105+ cells to about 91% CD105+ cells, about 94% CD105+ cells to about 90% CD105+ cells, about 94% CD105+ cells to about 85% CD105+ cells, about 94% CD105+ cells to about 80% CD105+ cells, about 94% CD105+ cells to about 75% CD105+ cells, about 94% CD105+ cells to about 70% CD105+ cells, about 93% CD105+ cells to about 92% CD105+ cells, about 93% CD105+ cells to about 91% CD105+ cells, about 93% CD105+ cells to about 90% CD105+ cells, about 93% CD105+ cells to about 85% CD105+ cells, about 93% CD105+ cells to about 80% CD105+ cells, about 93% CD105+ cells to about 75% CD105+ cells, about 93% CD105+ cells to about 70% CD105+ cells, about 92% CD105+ cells to about 91% CD105+ cells, about 92% CD105+ cells to about 90%

CD105+ cells, about 92% CD105+ cells to about 85% CD105+ cells, about 92% CD105+ cells to about 80% CD105+ cells, about 92% CD105+ cells to about 75% CD105+ cells, about 92% CD105+ cells to about 70% CD105+ cells, about 91% CD105+ cells to about 90% CD105+ cells, about 91% CD105+ cells to about 85% CD105+ cells, about 91% CD105+ cells to about 80% CD105+ cells, about 91% CD105+ cells to about 75% CD105+ cells, about 91% CD105+ cells to about 70% CD105+ cells, about 90% CD105+ cells to about 85% CD105+ cells, about 90% CD105+ cells to about 80% CD105+ cells, about 90°%, CD105+ cells to about 75% CD105+ cells, about 90% CD105+ cells to about 70% CD105+ cells, about 85% CD105+ cells to about 80% CD105+ cells, about 85% CD105+ cells to about 75% CD105+ cells, about 85% CD105+ cells to about 70% CD105+ cells, about 80% CD105+ cells to about 75% CD105+ cells, about 80% CD105+ cells to about 70% CD105+ cells, or about 75% CD105+ cells to about 70% CD105+ cells. In some embodiments, the composition of MSCs may be comprised of at least about 100% CD105+ cells, about 95% CD105+ cells, about 94% CD105+ cells, about CD105+ cells, about 92% CD105+ cells, about 91% CD105+ cells, about 90% CD105+ cells, about 85% CD105+ cells, about 80% CD105+ cells, about 75% CD105+ cells, or about 70% CD105+ cells. In some embodiments, the composition of MSCs may be comprised of at least at least about 100% CD105+ cells, about 95% CD105+ cells, about 94% CD105+ cells, about 93% CD105+ cells, about 92% CD105+ cells, about 91% CD105+ cells, about 90% CD105+ cells, about 85% CD105+ cells, about 80% CD105+ cells, or about 75% CD105+ cells. In some embodiments, the composition of MSCs may be comprised of at least at moist about 95% CD105+ cells, about 94% CD105+ cells, about 93% CD105+ cells, about 92% CD105+ cells, about 91% CD105+ cells, about 90% CD105+ cells, about 85% CD105+ cells, about 80% CD105+ cells, about 75% CD105+ cells, or about 70% CD105+ cells.

In some embodiments, the population of MSCs comprises at least 90% CD166+ cells. In some embodiments, the population of MSCs comprises at least 90% CD166+ cells. In some embodiments, the composition of MSCs may be comprised of at least 90% CD166+ cells. In some embodiments, the composition of MSCs may be comprised of at least about 70% CD166+ cells to about 100% CD166+ cells. In some embodiments, the composition of MSCs may be comprised of at least about 100% CD166+ cells to about 95% CD166+ cells, about 100% CD166+ cells to about 94% CD166+ cells, about 100% CD166+ cells to about 93% CD166+ cells, about 100% CD166 f cells to about 92% CD166+ cells, about 100% CD166+ cells to about 91% CD166+ cells, about 100% CD166+ cells to about 90% CD166+ cells, about 100% CD166+ cells to about 85% CD166+ cells, about 100% CD166+ cells to about 80% CD166+ cells, about 100% CD166+ cells to about 75% CD166+ cells, about 100% CD166+ cells to about 70% CD166+ cells, about 95% CD166+ cells to about 94% CD166+ cells, about 95% CD166+ cells to about 93% CD166+ cells, about 95% CD166+ cells to about 92% CD166+ cells, about 95% CD166+ cells to about 91% CD166+ cells, about 95% CD166+ cells to about 90% CD166+ cells, about 95% CD166-f cells to about 85% CD166+ cells, about 95% CD166+ cells to about 80% CD166+ cells, about 95% CD166+ cells to about 75% CD166+ cells, about 95% CD166+ cells to about 70% CD166+ cells, about 94% CD166+ cells to about 93% CD166-f cells, about 94% CD166+ cells to about 92%

CD166+ cells, about 94% CD166+ cells to about 91% CD166+ cells, about 94% CD166+ cells to about 90% CD166+ cells, about 94% CD166+ cells to about 85% CD166+ cells, about 94% CD166+ cells to about 80% CD166+ cells, about 94% CD166+ cells to about 75% CD166+ cells, about 94% CD166+ cells to about 70% CD166+ cells, about 93%, CD166+ cells to about 92% CD166+ cells, about 93% CD166+ cells to about 91% CD166+ cells, about 93% CD166+ cells to about 90% CD166+ cells, about 93% CD166+ cells to about 85% CD166+ cells, about 93% CD166+ cells to about 80% CD166+ cells, about 93% CD166+ cells to about 75% CD166+ cells, about 93% CD166+ cells to about 70% CD166+ cells, about 92% CD166+ cells to about 91% CD166+ cells, about 92% CD166+ cells to about 90% CD166+ cells, about 92. % CD166+ cells to about 85% CD166+ cells, about 92% CD166+ cells to about 80% CD166+ cells, about 92% CD166+ cells to about 75% CD166+ cells, about 92% CD166+ cells to about 70% CD166+ cells, about 91% CD166+ cells to about 90% CD166+ cells, about 91% CD166+ cells to about 85% CD166+ cells, about 91% CD166+ cells to about 80% CD166+ cells, about 91% CD166+ cells to about 75% CD166+ cells, about 91% CD166+ cells to about 70% CD166+ cells, about 90% CD166+ cells to about 85% CD166+ cells, about 90% CD166+ cells to about 80% CD166+ cells, about 90% CD166+ cells to about 75% CD166+ cells, about 90% CD166+ cells to about 70% CD166+ cells, about 85% CD166+ cells to about 80% CD166+ cells, about 85% CD166+ cells to about 75% CD166+ cells, about 85% CD166+ cells to about 70% CD166+ cells, about 80% CD166+ cells to about 75% CD166+ cells, about 80% CD166+ cells to about 70% CD166+ cells, or about 75% CD166+ cells to about 70% CD166+ cells. In some embodiments, the composition of MSCs may be comprised of at least about 100% CD166+ cells, about 95% CD166+ cells, about 94% CD166+ cells, about 93% CD166+ cells, about 92. % CD166+ cells, about 91% CD166+ cells, about 90% CD166+ cells, about 85% CD166+ cells, about 80% CD166+ cells, about 75% CD166+ cells, or about 70% CD166+ cells. In some embodiments, the composition of MSCs may be comprised of at least at least about 100% CD166+ cells, about 95% CT 166+ cells, about 94% CD166+ cells, about 93% CD166+ cells, about 92% CD166+ cells, about 91% CD166+ cells, about 90% CD166+ cells, about 85% CD166+ cells, about 80% CD166+ cells, or about 75% CD166+ cells. In some embodiments, the composition of MSCs may be comprised of at least at most about 95% CD166+ cells, about 94% CD166+ cells, about 93% CD166+ cells, about 92% CD166+ cells, about 91% CD166+ cells, about 90% CD166 cells, about 85% CD166+ cells, about 80% CD166+ cells, about 75% CD166+ cells, or about 70% CD166+ cells.

In some embodiments, the population of human MSCs comprises at least about 20% cells in the S phase of the cell cycle to about 60% cells in the S phase of the cell cycle. In some embodiments, the population of human MSCs comprises at least about 20% cells in the S phase of the cell cycle to about 30% cells in the S phase of the cell cycle, about 20% a cells in the S phase of the cell cycle to about 35% cells in the S phase of the cell cycle, about 20% cells in the S phase of the cell cycle to about 40% cells in the S phase of the cell cycle, about 20% cells in the S phase of the cell cycle to about 45% cells in the S phase of the cell cycle, about 20% cells in the S phase, of the cell cycle, to about 50% cells in the S phase of the cell cycle, about 20% cells in the S phase of the cell cycle to about 55% cells in the S phase of the cell cycle, about 20% cells in the S phase of the cell cycle to about 60% cells in the S phase of the cell cycle, about 30% cells in the S phase of the cell cycle to about 35% cells in the S phase of the cell cycle, about 30% cells in the S phase of the cell cycle to about 40% cells in the S phase of the cell cycle, about 30% cells in the S phase of the cell cycle to about 45% cells in the S phase of the cell cycle, about 30% cells in the S phase of the cell cycle to about 50% cells in the S phase of the cell cycle, about 30% cells in the S phase of the cell cycle, to about 55% cells in the S phase of the cell cycle, about 30% cells in the S phase of the cull cycle to about 60% cells in the S phase of the cell cycle, about 35% cells in the S phase of the cell cycle to about 40% cells in the S phase of the cell cycle, about 35% cells in the S phase of the cell cycle to about 45% cells in the S phase of the cell cycle, about 35% cells in the S phase of the cell cycle to about 50% cells in the S phase of the cell cycle, about 35% cells in the S phase of the cell cycle to about 55% cells in the S phase of the cell cycle, about 35% cells in the S phase of the cell cycle to about 60% cells in the S phase of the cell cycle, about 40% cells in the S phase of the cell cycle to about 45% cells in the S phase of the cell cycle, about 40% cells in the S phase of the cell cycle to about 50% cells in the S phase of the cell cycle, about 40% cells in the S phase of the cell cycle to about 55% cells in the S phase of the cell cycle, about 40% cells in the S phase of the cell cycle, to about 60% cells in the S phase of the cell cycle, about 45% cells in the S phase of the cell cycle, to about 50% cells in the S phase of the cell cycle, about 45% cells in the S phase of the cell cycle to about 55% cells in the S phase of the cell cycle, about 45% cells in the S phase of the cell cycle to about 60% cells in the S phase of die cell cycle, about 50% cells in the S phase of the cell cycle to about 55% cells in the S phase of the cell cycle, about 50% cells in the S phase of the cell cycle to about 60% cells in the S phase of the cell cycle, or about 55% cells in the S phase of the cull cycle to about 60% cells in the S phase of the cell cycle. In some embodiments, the population of human MSCs comprises at least about 20% cells in the S phase of the cell cycle, about 30% cells in the S phase of the cell cycle, about 35% cells in the S phase of the cell cycle, about 40% cells in the S phase of the cell cycle, about 45% cells in the S phase of the cell cycle, about 50% cells in the S phase of the cell cycle, about 55% cells in the S phase of the cell cycle, or about 60% cells in the S phase of the cell cycle. In some embodiments, the population of human MSCs comprises at least at least about 20% cells in the S phase of the cell cycle, about 30% cells in the S phase of the cell cycle, about 35% cells in the S phase of the cell cycle, about 40% cells in the S phase of the cell cycle, about 45% cells in the S phase of the cell cycle, about 50% cells in the S phase of the cell cycle, or about 55% cells in the S phase of the cell cycle. In some embodiments, the population of human MSCs comprises at least at most about 30% cells in the S phase of the cell cycle, about 35% cells in the S phase of the cell cycle, about 40% cells in the S phase of the cell cycle, about 45% cells in the S phase of the cell cycle, about 50% cells in the S phase of the cell cycle, about 55% cells in the S phase of the cell cycle, or about 60% cells in the S phase of the cell cycle. In some embodiments, the population of human MSCs comprises at least 40% cells in the S phase of the cell cycle. In some embodiments, the population of human MSCs comprises at least 45% cells in the S phase of the cell cycle. In some embodiments, the population of human MSCs comprises at least 50% cells in the S phase of the cell cycle. In some embodiments, the population of human MSCs comprises at least 55% cells in the S phase of the cell cycle.

In some embodiments, the population of MSCs is derived from a bone. In some embodiments, the bone is a vertebral body. In some embodiments, the sample of MSCs comprises vertebral bone adherent (vBA) MSCs. In some embodiments, the bone is derived from a cadaver.

In some embodiments, the medical condition is a rejection of a vascular composite allotransplant (VCAs) of an organ to the subject. In some embodiments, the organ is limb. In some embodiments, the organ is skin, heart, kidney, Liver, lung, pancreas, intestine, thymus, or uterus. In some embodiments, the medical condition is myocardial infarction, chronic obstructive pulmonary disease (COPD), acute respiratory distress syndrome (ARDS) osteogenesis imperfection, cartilage defects, Crap n s disease, fistula, liver cirrhosis, osteo arthritis, asthma, or graft vs. host disease (GVHD). In some embodiments, the medical condition is art autoimmune disease. In some embodiments, the autoimmune disease is rheumatoid arthritis, lupus, celiac disease, multiple sclerosis, polymyalgia rheumatica, ankylosing spondylitis, type 1 diabetes, alopecia areata, vasculitis or temporal arteritis.

In one aspect of the present disclosure, a method and composition are provided for treating a medical condition of a subject by administering a cell composition comprising cadaveric human MSCs. In some embodiments, the composition of cadaveric human MSCs provided for treating a medical condition may be administered in quantities of about 10 million to about 10 billion. In some embodiments, cadaveric human MSCs may be administered in quantities of about 10 million to about 100 million, about 10 million to about 1 billion, about 10 million to about 10 billion, about 100 million to about 1 billion, about 100 million to about 10 billion, or about 1 billion to about 10 billion. In some embodiments, the cadaveric human MSCs may be administered in quantities of about 10 million, about 100 million, about 1 billion, or about 10 billion. In some embodiments, cadaveric human MSCs may be administered in quantities of at least about 10 million, about 100 million, or about 1 billion. In some embodiments, cadaveric human MSCs may be administered in quantities of at most about 100 million, about 1 billion, or about 10 billion. In some embodiments, the cadaveric human MSCs are isolated and processed as described herein.

In some embodiments the cell composition may aid in producing a state of mixed chimerism. In some embodiments, the administered cell composition within a subject of cadaveric human MSCs may generate CD45–huCD73+ huCD90+ cells within said subject. In some embodiments, the administered human MSCs may be derived from bone marrow, adherent vertebral body MSCs (vBA-MSCs), or both.

In some embodiments, the treated medical condition may be an autoimmune disease such as rheumatoid arthritis, lupus, celiac disease, multiple sclerosis, polymyalgia rheumatica, ankylosing spondylitis, type 1 diabetes, alopecia areata, vasculitis or temporal arteritis. In some embodiments, the treated medical condition may be a myocardial infarction. In some embodiments, the treated medical condition may be chronic obstructive pulmonary disease (COPD). In some embodiments, the treated medical condition may be acute respiratory distress syndrome (ARDS). In some embodiments, the treated medical condition may be arthritis. In some embodiments, the treated medical condition is osteogenesis imperfection, cartilage defects, Crohns disease, fistula, liver cirrhosis, osteo arthritis, asthma, or graft vs. host disease (GVHD).

In another aspect of the present disclosure, a method and composition are provided for treating a medical condition by administering a composition of at least 10 million cadaveric human MSCs and at least 500,000 nucleated BM cells or derivatives thereof. In some embodiments, prior to administering a composition of cadaveric human MSCs and nucleated BM cells or derivates thereof, an organ may be transplanted into a subject suffering from a medical condition. In some embodiments, the cadaveric human MSCs and nucleated BM cells or derivatives thereof administered prior to transplanting the organ into a subject may comprise a mis-matched HLA haploid type as the transplanted human organ. In some embodiments, rapamycin may be administered prior to transplanting the human organ into the subject for between about 0 days to about 21 days from the day of human organ transplantation. In some embodiments, 0.1 mg/kg to about 1 mg/kg of rapamycin may be administered to a subject prior to transplanting the human organ into the subject. In some embodiments, CTLA4-Ig, may be administered prior to transplanting the organ into the subject. In some embodiments, CTLA4-Ig may be administered about 2 days to about 6 days after transplanting the human organ. In some embodiments, CTLA4-Ig may be administered about 2 days to about 3 days, about 2 days to about 4 days, about 2 days to about 5 days, about 2 days to about 6 days, about 3 days to about 4 days, about 3 days to about 5 days, about 3 days to about 6 days, about 4 days to about 5 days, about 4 days to about 6 days, or about 5 days to about 6 days after transplanting the human organ. In some embodiments, CTLA4-Ig may be administered about 2 days, about 3 days, about 4 days, about 5 days, about 6 days or any combination thereof after transplanting the human organ. In some embodiments, CTLA4-Ig may be administered at least about 2 days, about 3 days, about 4 days, or about 5 days after transplanting the human organ. In some embodiments, CTLA4-Ig may be administered at most about 3 days, about 4 days, about 5 days, or about 6 days after transplanting the human organ.

In some embodiments, the method of administrating a composition of cadaveric human MSCs and nucleated BM cells or derivatives thereof into a subject may result in successful engraftment of at least a subset of the nucleated BM cells within the subject in some embodiments, the method of administrating a composition of cadaveric human MSCs and nucleated BM cells or derivatives thereof into a subject may result in successful engraftment of an organ transplant within the subject. In some embodiments, the method of administrating a composition of cadaveric human MSCs and nucleated BM cells or derivatives thereof into a subject may generate hematopoietic cells of a particular HLA haploid in a background of hematopoietic cells of another particular HLA haploid wherein the another particular HLA haploid is mis-matched with the former HLA haploid. In some embodiments, the method of administrating a composition of cadaveric human MSCs and nucleated BM cells or derivatives thereof into a subject may generate hematopoietic cells of a particular HLA haploid specific to the donor of the cadaveric human MSCs and nucleated BM cells or derivatives thereof in a background of hem antipoetic cells of a particular HLA haploid specific to the subject. In some embodiments, the hematopoietic cells generated in the subject following administration of cadaveric human MSCs and nucleated BM cells or derivatives thereof are CD45+ cells. In some embodiments, the method of administrating a composition of cadaveric human MSCs and nucleated BM cells or derivatives thereof may generate CD45+H2d+ cells in a background of CD45H2b+ cells. In some embodiments, the method of administrating a composition of cadaveric human MSCs and nucleated BM cells or derivatives thereof may generate CD45−huCD73+huCD90+ cells. In some embodiments, the method of administrating a composition of cadaveric human MSCs and nucleated BM cells or derivatives thereof may generate a mixed chimerism within the subject. In some embodiments, the generated mixed chimerism within the subject may be maintained for at least 120 days from administration of the nucleated BM cells. In some embodiments, the generated mixed chimerism within the subject may be maintained for about 1 month to about 12 months. In some embodiments, the generated mixed chimerism within the subject may be maintained for about 1 month to about 2 months, about 1 month to about 3 months, about 1 month to about 4 months, about 1 month to about 5 months, about 1 month to about 6 months, about 1 month to about 7 months, about 1 month to about 8 months, about 1 month to about 9 months, about 1 month to about 10 months, about 1 month to about 11 months, about 1 month to about 12 months, about 2 months to about 3 months, about 2 months to about 4 months, about 2 months to about 5 months, about 2 months to about 6 months, about 2 months to about 7 months, about 2 months to about 8 months, about 2 months to about 9 months, about 2 months to about 10 months, about 2 months to about 11 months, about 2 months to about 12 months, about 3 months to about 4 months, about 3 months to about 5 months, about 3 months to about 6 months, about 3 months to about 7 months, about 3 months to about 8 months, about 3 months to about 9 months, about 3 months to about 10 months, about 3 months to about 11 months, about 3 months to about 12 months, about 4 months to about 5 months, about 4 months to about 6 months, about 4 months to about 7 months, about 4 months to about 8 months, about 4 months to about 9 months, about 4 months to about 10 months, about 4 months to about 11 months, about 4 months to about 12 months, about 5 months to about 6 months, about 5 months to about 7 months, about 5 months to about 8 months, about 5 months to about 9 months, about 5 months to about 10 months, about 5 months to about 11 months, about 5 months to about 12 months, about 6 months to about 7 months, about 6 months to about 8 months, about 6 months to about 9 months, about 6 months to about 10 months, about 6 months to about 11 months, about 6 months to about 12 months, about 7 months to about 8 months, about 7 months to about 9 months, about 7 months to about 10 months, about 7 months to about 11 months, about 7 months to about 12 months, about 8 months to about 9 months, about 8 months to about 10 months, about 8 months to about 11 months, about 8 months to about 12 months, about 9 months to about 10 months, about 9 months to about 11 months, about 9 months to about 12 months, about 10 months to about 11 months, about 10 months to about 12 months, or about 11 months to about 12 months. In some embodiments, the generated mixed chimerism within the subject may be maintained for about 1 month, about 2 months, about 3 months, about 4 months, about 5 months, about 6 months, about 7 months, about 8 months, about 9 months, about 10 months, about 11 months, or about 12 months. In some embodiments, the generated mixed chimerism within the subject may be maintained for at least about 1 month, about 2 months, about 3 months, about 4 months, about 5 months, about 6 months, about 7 months, about 8 months, about 9 months, about 10 months, or about 11 months. In some embodiments, the generated mixed chimerism within the subject may be maintained for at most about 2 months, about 3 months, about 4 months, about 5 months, about 6 months, about 7 months, about 8 months, about 9 months, about 10 months, about 11 months, or about 12 months.

In some embodiments, the generated mixed chimerism within the subject may be maintained for about 1 year to about 10 years. In some embodiments, the generated mixed chimerism within the subject may be maintained for about 1 year to about 2 years, about 1 year to about 3 years, about 1 year to about 4 years, about 1 year to about 5 years, about 1 year to about 6 years, about 1 year to about 7 years, about 1 year to about 8 years, about 1 year to about 9 years, about 1 year to about 10 years, about 2 years to about 3 years, about 2 years to about 4 years, about 2 years to about 5 years, about 2 years to about 6 years, about 2 years to about 7 years, about 2 years to about 8 years, about 2 years to about 9 years, about 2 years to about 10 years, about 3 years to about 4 years, about 3 years to about 5 years, about 3 years to about 6 years, about 3 years to about 7 years, about 3 years to about 8 years, about 3 years to about 9 years, about 3 years to about 10 years, about 4 years to about 5 years, about 4 years to about 6 years, about 4 years to about 7 years, about 4 years to about 8 years, about 4 years to about 9 years, about 4 years to about 10 years, about 5 years to about 6 years, about 5 years to about 7 years, about 5 years to about 8 years, about 5 years to about 9 years, about 5 years to about 10 years, about 6 years to about 7 years-, about 6 years to about 8 years, about 6 years to about 9 years, about 6 years to about 10 years, about 7 years to about 8 years, about 7 years to about 9 years, about 7 years to about 10 years, about 8 years to about 9 years, about 8 years to about 10 years, or about 9 years to about 10 years. M some embodiments, the generated mixed chimerism within the subject may be maintained for about 1 year, about 2 years, about 3 years, about 4 years, about 5 years, about 6 years, about 7 years, about 8 years, about 9 years, or about 10 years. In some embodiments, the generated mixed chimerism within the subject may be maintained for at least about 1 year, about 2 years, about 3 years, about 4 years, about 5 years, about 6 years, about 7 years, about 8 rears, or about 9 years. In some embodiments, the generated mixed chimerism within the subject may be maintained for at most about 2 years, about 3 years, about 4 years, about 5 years, about 6 years, about 7 years, about 8 years, about 9 years, or about 10 years.

In some embodiments, the method of first administrating a composition of cadaveric human MSCs and nucleated BM cells or derivatives thereof may further comprise a second administration of at least 10 million human MSCs to the subject in need thereof 1 day, 2 days, 3 days, 4 days, or any combination thereof after the first administration.

In some embodiments, the treated medical condition may be an immune response. In some embodiments, the treated medical condition may be an autoimmune disease. In some embodiments, the autoimmune disease may be graft verses host disease (GVHD).

In some embodiments, the composition of cadaveric human MSCs and nucleated BM cells or derivatives thereof may include cadaveric human MSCs derived from BM, adherent vertebral body MSCs (vBA-MSCs), or both. In some embodiments, the composition of cadaveric human MSCs and nucleated BM cells or derivatives thereof may include MSCs in quantities of about 10 million to about 10 billion. In some embodiments, the composition of cadaveric human MSCs and nucleated BM cells or derivatives thereof may include MSCs in quantities of about 10 million to about 100 million, about 10 million to about 1 billion, about 10 million to about 10 billion, about 100 million to about 1 billion, about 100 million to about 10 billion, or about 11 billion to about 10 billion. In some embodiments, the composition of cadaveric human MSCs and nucleated BM cells or derivatives thereof may include MSCs in quantities of about 10 million, about 100 million, about 1 billion, or about 10 billion. In some embodiments, the composition of cadaveric human MSCs and nucleated BM cells or derivatives thereof may include MSCs in quantities of at least about 10 million, about 100 million, or about 1 billion.

In some embodiments, the composition of cadaveric human MSCs and nucleated BM cells or derivatives thereof may include nucleated. BM in quantities about 1 million to about 2 million. In some embodiments, the composition of cadaveric human MSCs and nucleated BM cells or derivatives thereof may include nucleated BM in quantities about 1 million to about 1.5 million, about 1 million to about 2 million, or about 1.5 million to about 2 million. In some embodiments, the composition of cadaveric human MSCs and nucleated BM cells or derivatives thereof may include nucleated BM in quantities about 1 million, about 1.5 million, or about 2 million. In some embodiments, the composition of cadaveric human MSCs and nucleated BM cells or derivatives thereof may include nucleated BM in quantities at least about 1 million, or about 1.5 million. In some embodiments, the composition of cadaveric human MSCs and nucleated BM cells or derivatives thereof may include nucleated BM in quantities at most about 1.5 million, or about 2 million.

In some embodiments, the human cadaveric MSCs (e.g. vBA-MSCs) may be derived from the same origin as the nucleated BM cells. In some embodiments, the human cadaveric MSCs may be derived from a different origin as the nucleated BM cells. In some embodiments, the composition may further comprise a human organ. In some embodiments, the human organ may be a heart, kidney, liver, lung, pancreases, intestine, thymus, or uterus. In some embodiments, the composition comprised of cadaveric human MSCs and nucleated BM cells or derivative thereof may include MSCs with a matched human leukocyte antigen (HLA) haploid type as the human organ. In some embodiments, the composition, comprised of cadaveric human MSCs and nucleated BM cells or derivative thereof may include MSCs with mis-matched HLA haploid type as the human organ. In some embodiments, the composition comprised of cadaveric human MSCs and nucleated BM cells or derivative thereof may include MSCs and nucleated BM cells or derivatives thereof with a mis-matched HLA haploid type as the human organ. In some, embodiments, the composition comprised of cadaveric human MSCs and nucleated BM cells or derivative thereof may include MSCs and nucleated BM cells or derivatives thereof with a matched HLA haploid type as the human organ.

In some embodiments, the nucleated BM cells or derivatives thereof may comprise hematopoietic stem cells (HSC). In some embodiments, the cadaveric human MSCs may comprise a mis-matched HLA haploid type as the nucleated BM cells or derivatives thereof.

Compositions of MSCs and BM for Treating Medical Conditions

Another aspect of the present disclosure comprises compositions comprising one or more of the cell types described herein.

In some embodiments, described herein is a composition comprising vBA-MSCs. In some embodiments, the vBA-MSCs are cadaveric. In some embodiments, the vBA-MSCs are isolated and processed as described herein. In some embodiments, the compositions described herein comprise at least about 500,000 vBA-MSCs to about 1,000,000,000 vBA-MSCs. In some embodiments, the compositions described herein comprise at least about 500,000 vBA-MSCs to about 1,000,000 vBA-MSCs, about 500,000 vBA-MSCs to about 10,000,000 vBA-MSCs, about 500,000 vBA-MSCs to about 100,000,000 vBA-MSCs, about 500,000 vBA-MSCs to about 1,000,000,000 vBA-MSCs, about 1,000,000 vBA-MSCs to about 10,000,000 vBA-MSCs, about 1,000,000 vBA-MSCs to about 100,000,000 vBA-MSCs, about 1,000,000 vBA-MSCs to about 1,000,000,000 vBA-MSCs, about 10,000,000 vBA-MSCs to about 100,000,000 vBA-MSCs, about 10,000,000 vBA-MSCs to about 1,000,000,000 vBA-MSCs, or about 100,000,000 vBA-MSCs to about 1,000,000,000 vBA-MSCs. In some embodiments, the compositions described herein comprise at least about 500,000 vBA-MSCs, about 1,000,000 vBA-MSCs, about 10,000,000 vBA-MSCs, about 100,000,000 vBA-MSCs, or about 1,000,000,000 vBA-MSCs. In some embodiments, the compositions described herein comprise at least at least about 500,000 vBA-MSCs, about 1,000,000 vBA-MSCs, about 10,000,000 vBA-MSCs, or about 100,000,000 vBA-MSCs. In some embodiments, the compositions described herein comprise at least at most about 1,000,000 vBA-MSCs, about 10,000,000 vBA-MSCs, about 100,000,000 vBA-MSCs, or about 1,000,000,000 vBA-MSCs. In some embodiments, the compositions described herein comprise vBA-MSCs and bone marrow-derived MSCs.

In some embodiments, described herein is a composition comprising Nucleated BM cells. In some embodiments, the nucleated BM cells are cadaveric. In some embodiments, the nucleated BM cells are isolated and processed as described herein. In some embodiments, the compositions described herein comprise at least about 500,000 nucleated BM cells to about 2,000,000 nucleated BM cells. In some embodiments, the compositions described herein comprise at least about 500,000 nucleated BM cells to about 1,000,000 nucleated BM cells, about 500,000 nucleated. BM cells to about 1,500,000 nucleated BM cells, about 500,000 nucleated BM cells to about 2,000,000 nucleated BM cells, about 1,000,000 nucleated BM cells to about 1,500,000 nucleated BM cells, about 1,000,000 nucleated BM cells to about 2,000,000 nucleated BM cells, or about 1,500,000 nucleated BM cells to about 2,000,000 nucleated BM cells. In some embodiments, the compositions described herein comprise at least about 500,000 nucleated BM cells, about 1,000,000 nucleated BM cells, about 1,500,000 nucleated BM cells, or about 2,000,000 nucleated BM cells. In some embodiments, the compositions described herein comprise at least at least about 500,000 nucleated BM cells, about 1,000,000 nucleated BM cells, or about 1,500,000 nucleated BM cells. In some embodiments, the compositions described herein comprise at least at most about 1,000,000 nucleated BM cells, about 1,500,000 nucleated BM cells, or about 2,000,000 nucleated BM cells.

In some embodiments, the compositions described herein comprise both vBA-MSCs and nucleated BM cells. In some embodiments, the vBA-MSG's and nucleated BM cells of a single composition are derived from a single donor. In some embodiments, the compositions described herein are administered to a subject who is preparing to undergo, is undergoing, or has undergone, an organ transplant in some embodiments, the vBA-MSCs and nucleated. BM cells of a single composition comprise human leukocyte antigen (HLA) haploid matched to the organ transplanted into the subject. In some embodiments, the vBA-MSCs and nucleated BM cells of a single composition comprise human leukocyte antigen (HLA) haploid miss-matched to the organ transplanted into the subject.

In some embodiments, the nucleated bone marrow cells or derivatives thereof comprise hematopoietic stem cells (HSCs). In some embodiments, the HSCs comprise CD34+ cells.

Culturing of MSCs in one aspect of the present disclosure, extracted MSCs may be (e.g. vBA-MSCs) cultured and passaged to realize clinical scale MSC preparation having a desired number of MSCs with the antigen profiles taught herein. In some embodiments, a clinical scale preparation may be obtained by serial passage expansion where each passage includes a step of splitting the previous culture into a plurality of cultures at a given ratio. Each passaging step increases the number of concurrent cultures in the preparation. In some embodiments, clinical scale preparations having the instant preparation profiles, e.g. antigen profile, TNFRI profile, cryopreservation profile, differentiation profile, and/or sterility (with respect to pathogens) are successfully produced.

In some embodiments, extracted MSC, are cultured in a medium wherein the medium is configured to generate MSCs having the instant preparation profiles, e.g. antigen profile, TNFRI profile, cryopreservation profile, differentiation profile, and/or sterility (with respect to pathogens). In some embodiments, the medium comprises minimal essential medium (MEM). In some embodiments, the medium comprises alpha MEM. In some embodiments, the medium comprises human platelet lysate (hPL). In some embodiments, the medium comprises carrier free Fibroblast growth factor (FGF). In some embodiments, the medium comprises carrier free epidermal growth factor (EGF). In some embodiments, the medium comprises alpha MEM, hPL, FGF, EGF, or any combination thereof. In some embodiments, the medium comprises alpha MEM, hPL, FGF, and EGF. In some embodiments, the medium does not further require heparin.

In some embodiments, hPL, is present in the medium at about 1% to about 21%. In some embodiments, hPL is present in the medium at about 1% to about 3%, about 1% to about 5%, about 1% to about 7%, about 1% to about 9%, about 1% to about 10%, about 1% to about 11%, about 1% to about 13%, about 1% to about 1%, about 1% to about 17%, about 1% to about 19%, about 1% to about 2.1%, about 3% to about 5%, about 3% to about 7%, about 3% to about 9%, about 3% to about 10%, about 3% to about 11%, about 3% to about 13%, about 3% to about 15%, about 3% to about 17%, about 18% to about 19%, about 3% to about 21%, about 5% to about 7%, about 5% to about 9%, about 5% to about 10%, about 5% to about 11%, about 5% to about 13%, about 5% to about 15%, about 5% to about 17%, about 5% to about 19%, about 5% to about 21%, about 7% to about 9%, about 7% to about 10%, about 7% to about 11%, about 7% to about 13%, about 7% to about 15%, about 7% to about 17%, about 7% to about 19%, about 7% to about 21%, about 9% to about 10%, about 9% to about 11%, about 9% to about 13%, about 9% to about 15%, about 9% to about 17%, about 9% a to about 19%, about 9% to about 21%, about 10% to about 11%, about 10% to about 13%, about 10% to about 15%, about 10% to about 17%, about 10% to about 19%, about 10% to about 21%, about 11%, to about 13%, about 11% to about 15%, about 11% to about 17%, about 11% to about 19%, about 11% to about 21%, about 13% to about 15%, about 13% to about 17%, about 13% to about 19%, about 13% to about 21%, about 15% to about 17%, about 15% to about 19%, about 15% to about 21%, about 17% to about 19%, about 17% to about 21%, or about 19% to about 21%. In some embodiments, hPL is present in the medium at about 1%, about 3%, about 5%, about 7%, about 9%, about 10%, about 11%, about 13%, about 15%, about 17%, about 19%, or about 2.1%. In some embodiments, hPL is present. In the medium at least about 1%, about 3%, about 5%, about 7%, about 9%, about 10%, about 11%, about 13%, about 15%, about 17%, or about 19%. In some embodiments, hPL is present in the medium at most about 3%, about 5%, about 7%, about 9%, about 10%, about 11%, about 13%, about 15%, about 17%, about 19%, or about 21%. In some embodiments, FGF is present in the medium at about 0.5 ng/mL to about 5 ng/mL. In some embodiments, FGF is present in the medium at about 0.5 ng/ml, to about 1 ng/mL, about 0.5 ng/mL to about 1.5 ng/mL, about 0.5 ng/mL to about 2 ng/mL, about 0.5 ng/mL to about 2.5 ng/mL, about 0.5 ng/mL to about 3 ng/mL, about 0.5 ng/mL to about 3.5 ng/mL, about 0.5 ng/mL to about 4 ng/mL, about 0.5 ng/mL to about 4.5 ng/mL, about 0.5 ng/mL to about 5 ng/mL, about 1 ng/mL to about 1.5 ng/mL, about 1 ng/mL to about 2 ng/mL, about 1 ng/mL to about 2.5 ng/mL, about 1 ng/mL to about 3 ng/mL, about 1 ng/mL to about 3.5 ng/mL, about 1 ng/mL to about 4 ng/mL, about 1 ng/mL to about 4.5 ng/mL, about 1 ng/mL to about 5 ng/mL, about 1.5 ng/mL to about 2 ng/mL, about 1.5 ng/mL to about 2.5 ng/mL, about 1.5 ng/mL to about 3 ng/mL, about 1.5 ng/mL, to about 3.5 ng/mL, about 1.5 ng/mL, to about 4 ng/mL, about 1.5 ng/mL to about 4.5 ng/mL, about 1.5 ng/mL to about 5 ng/mL, about 2 ng/mL to about 2.5 ng/mL, about 2 ng/mL to about 3 ng/mL, about 2 ng/nib: to about 3.5 ng/mL, about 2 ng/mL, to about 4 ng/mL, about 2 ng/ml, to about 4.5 ng/mL, about 2 ng/mL to about 5 ng/mL, about 2.5 ng/mL to about 3 ng/mL, about 2.5 ng/mL to about 3.5 ng/ml, about 2.5 ng/mL to about 4 ng/mL, about 2.5 ng/mL to about 4.5 ng/mL, about 2.5 ng/mL to about 5 ng/mL, about 3 ng/mL to about 3.5 ng/mL, about 3 ng/mL to about 4 ng/ml, about 3 ng/mL to about 4.5 ng/mL, about 3 ng/mL to about 5 ng/ml, about 3.5 ng/mL to about 4 ng/mL, about 3.5 ng/mL to about 4.5 ng/mL, about 3.5 ng/mL to about 5 ng/mL, about 4 ng/mL to about 4.5 ng/mL, about 4 ng/mL, to about 5 ng/ml, or about 4.5 ng/mL to about 5 ng/mL. In some embodiments, FGF is present in the medium at about 0.5 ng/mL, about 1 ng/mL, about 1.5 ng/mL, about 2 ng/mL, about 2.5 ng/mL, about 3 ng/mL, about 3.5 ng/mL, about 4 ng/mL, about 4.5 ng/mL, or about 5 ng/ml. In some embodiments. FGF is present in the medium at least about 0.5 ng/ml, about 1 ng/mL, about 1.5 ng/mL, about 2 ng/mL, about 2.5 ng/mL, about 3 ng/mL, about 3.5 ng/mL, about 4 ng/mL, or about 4.5 ng/ml. In some embodiments, FGF is present in the medium at most about 1 ng/mL, about 1.5 ng/mL, about 2 ng/mL, about 2.5 ng/mL, about 3 ng/mL, about 3.5 ng/mL, about 4 ng/mL, about 4.5 ng/mL, or about 5 ng/mL.

In some embodiments, EGF is present in the medium at about 0.5 ng/ml, to about 5 ng/ml. In some embodiments. EGF is present in the medium at about 0.5 ng/mL to about 1 ng/mL, about 0.5 ng/mL to about 1.5 ng/mL, about 0.5 ng/mL to about 2 ng/mL, about 0.5 ng/mL to about 2.5 ng/mL, about 0.5 ng/mL to about 3 ng/mL, about 0.5 ng/mL to about 3.5 ng/mL, about 0.5 ng/ml, to about 4 ng/mL, about 0.5 ng/mL to about 4.5 ng/mL, about 0.5 ng/mL to about 5 ng/mL, about 1 ng/ml to about 1.5 ng/mL, about 1 ng/mL to about 2 ng/mL, about 1 ng/mL to about 2.5 ng/mL, about 1 ng/ml to about 3 ng/mL, about 1 ng/mL to about 3.5 ng/mL, about 1 ng/mL to about 4 ng/mL, about 1 ng/ml to about 4.5 ng/mL, about 1 ng/mL to about 5 ng/ml, about 1.5 ng/mL to about 2 ng/mL, about 1.5 ng/mL to about 2.5 ng/mL, about 1.5 ng/mL to about 3 ng/mL, about 1.5 ng/mL to about 3.5 ng/ml, about 1.5 ng/mL to about 4 ng/mL, about 1.5 ng/mL to about 4.5 ng/mL, about 1.5 ng/mL to about 5 ng/mL, about 2 ng/ml, to about 2.5 ng/mL, about 2 ng/mL to about 3 ng/mL, about 2 ng/mL to about 3.5 ng/mL, about 2 ng/mL to about 4 ng/mL, about 2 ng/mL to about 4.5 ng/ml, about 2 ng/mL to about 5 ng/ml, about 2.5 ng/mL to about 3 ng/mL, about 2.5 ng/mL to about 3.5 ng/mL, about 2.5 ng/mL to about 4 ng/ml, about 2.5 ng/mL to about 4.5 ng/mL, about 2.5 ng/mL to about 5 ng/mL, about 3 ng/mL to about 3.5 ng/mL, about 3 ng/mL to about 4 ng/mL, about 3 ng/mL to about 4.5 ng/mL, about 3 ng/mL to about 5 ng/ml, about 3.5 ng/mL to about 4 ng/mL, about 3.5 ng/mL to about 4.5 ng/mL, about 3.5 ng/mL to about 5 ng/ml, about 4 ng/mL to about 4.5 ng/mL, about 4 ng/ml to about 5 ng/ml, or about 4.5 ng/mL to about 5 ng/mL. In some embodiments, EGF is present in the medium at about 0.5 ng/mL, about 1 ng/mL, about 1.5 ng/ml, about 2 ng/mL, about 2.5 ng/ml, about 3 ng/mL, about 3.5 ng/mL, about 4 ng/mL, about 4.5 ng/mL, or about 5 ng/mL. In some embodiments. EGF is present in the medium at least about 0.5 ng/mL, about 1 ng/mL, about 1.5 ng/mL, about 2 ng/mL, about 2.5 ng/mL, about 3 ng/mL, about 3.5 ng/mL, about 4 ng/mL, or about 4.5 ng/mL. In some embodiments. EGF is present in the medium at most about 1 ng/mL, about 1.5 ng/mL, about 2 ng/mL, about 2.5 ng/mL, about 3 ng/mL, about 3.5 ng/mL, about 4 ng/ml, about 4.5 ng/mL, or about ng/mL.

In some embodiments, the medium comprises a modified alpha MEM. In some embodiments, the modified alpha MEM comprises one or more inorganic salts, one or more amino acids, one or more vitamins, glucose, lipoic acid, sodium bicarbonate, sodium pyruvate, or any combination thereof.

In some embodiments, the one or more inorganic salts comprise calcium chloride (dihydrate), magnesium sulfate (heptahydrate), potassium chloride, sodium chloride, sodium phosphate monobasic (dehydrate), or any combination thereof. In some embodiments, each inorganic salt present in the medium is present at about 100 mg/Liter to about 800 mg/Liter. In some embodiments, each inorganic salt present in the medium is present at about 100 mg/Liter to about 200 mg/Liter, about 100 mg/Liter about 300 mg/Liter, about 100 mg/Liter to about 400 mg/Liter, about 100 mg/Liter to about 500 mg/Liter, about 100 mg/Liter to about 600 mg/Liter, about 100 mg/Liter to about 700 mg/Liter, about 100 mg/Liter to about 800 mg/Liter, about 200 mg/Liter to about 300 mg/Liter, about 200 mg/Liter to about 400 mg/Liter, about 200 rag/Liter to about 500 mg/Liter, about 200 mg/Liter to about 600 mg/Liter, about 200 mg/Liter to about 700 mg/Liter, about 200 mg/Liter to about 800 mg/Liter, about 300 mg/Liter to about 400 mg/Liter, about 300 mg/Liter to about 500 mg/Liter, about 300 mg/Liter to about 600 mg/Liter, about 300 mg/Liter to about 700 mg/Liter, about 300 mg/Liter to about 800 mg/Liter, about 400 mg/Liter to about 500 mg/Liter, about 400 mg/Liter to about 600 mg/Liter, about 400 mg/Liter to about 700 mg/Liter, about 400 mg/Liter to about 800 mg/Liter, about 500 mg/Liter to about 600 mg/Liter, about 500 mg/Liter to about 700 mg/Liter, about 500 mg/Liter to about 800 mg/Liter, about 600 mg/Liter to about 700 mg/Liter, about 600 mg/Liter to about 800 mg/Liter, or about 700 mg/Liter to about 800 mg/Liter. In some embodiments, each inorganic salt present in the medium is present at about 100 mg/Liter, about 200 mg/Liter, about 300 mg/Liter, about 400 mg/Liter, about 500 mg/Liter, about 600 rag/Liter, about 700 mg/Liter. or about 800 mg/Liter. In some embodiments, each inorganic salt present in the medium is present at least about 100 mg/Liter, about 200 mg/Liter, about 300 mg/Liter, about 400 mg/Liter, about 500 mg/Liter, about 600 mg/Liter, or about 700 mg/Liter. In some embodiments, each inorganic salt present in the medium is present at most about 200 mg/Liter, about 300 mg/Liter, about 400 mg/Liter, about 500 mg/Liter, about 600 mg/Liter, about 700 mg/Liter, or about 800 mg/Liter.

In some embodiments, the one or more amino acids comprise glycine, alanine, alanyl-glutamine, arginine (HCl), asparagine (monohydrate), aspartic acid, cysteine (HCl) (monohydrate), cystine, glutamic acid, histidine, isoleucine, leucine, lysine, methionine, phenylalanine, proline, serine, threonine, tryptophan, tyrosine, valine, or any combination thereof. In some embodiments, the one or more amino acids are present in the L isoform. In some embodiments, the one or more amino acids are present in the D isoform. In some embodiments, the one or more amino acids are present in both isoforms. In some embodiments, each amino acid present in the medium is present at about 10 mg/Liter to about 100 mg/Liter. In some embodiments, each amino acid present in the medium is present at about 10 mg/Liter to about 20 mg/Liter, about 10 mg/Liter to about 30 mg/Liter, about 10 mg/Liter to about 40 mg/Liter, about 10 mg/Liter to about 50 mg/Liter, about 10 mg/Liter to about 60 mg/Liter, about 10 mg/Liter to about 70 mg/Liter, about 10 mg/Liter to about 80 mg/Liter, about 10 mg/Liter to about 90 mg/Liter, about 10 mg/Liter to about 100 mg/Liter, about 20 mg/Liter to about 30 mg/Liter, about 20 mg/Liter to about 40 mg/Liter, about 20 mg/Liter to about 50 mg/Liter, about 20 mg/Liter to about 60 mg/Liter, about 20 mg/Liter to about 70 mg/Liter, about 20 mg/Liter to about 80 mg/Liter, about 20 mg/Liter to about 90 mg/Liter, about 20 mg/Liter to about 100 mg/Liter, about 30 mg/Liter to about 40 mg/Liter, about 30 mg/Liter to about 50 mg/Liter, about 30 mg/Liter to about 60 mg/Liter, about 30 mg/Liter to about 70 mg/Liter, about 30 mg/Liter to about 80 mg/Liter, about 30 mg/Liter to about 90 mg/Liter, about 30 mg/Liter to about 100 mg/Liter, about 40 mg/Liter to about 50 mg/Liter, about 40 mg/Liter to about 60 mg/Liter, about 40 mg/Liter to about 70 mg/Liter, about 40 mg/Liter to about 80 mg/Liter, about 40 mg/Liter to about 90 mg/Liter, about 40 mg/Liter to about 100 mg/Liter, about 50 mg/Liter to about 60 mg/Liter, about 50 mg/Liter to about 70 mg/Liter, about 50 mg/Liter to about 80 mg/Liter, about 50 mg/Liter to about 90 mg/Liter, about 50 mg/Liter to about 100 mg/Liter, about 60 mg/Liter to about 70 mg/Liter, about 60 mg/Liter to about 80 mg/Liter, about 60 mg/Liter to about 90 mg/Liter, about 60 mg/Liter to about 100 mg/Liter, about 70 mg/Liter to about 80 mg/Liter, about 70 mg/Liter to about 90 mg/Liter, about 70 mg/Liter to about 100 mg/Liter, about 80 mg/Liter to about 90 mg/Liter, about 80 mg/Liter to about 100 mg/Liter, or about 90 mg/Liter to about 100 mg/Liter. In some embodiments, each amino acid present in the medium is present at about 10 mg/Liter, about 20 mg/Liter, about 30 mg/Liter, about 40 mg/Liter, about 50 mg/Liter, about 60 mg/Liter, about 70 mg/Liter, about 80 mg/Liter, about 90 mg/Liter, or about 100 mg/Liter. In some embodiments, each amino acid present in the medium is present at least about 10 mg/Liter, about 20 mg/Liter, about 30 mg/Liter, about 40 mg/Liter, about 50 mg/Titer, about 60 mg/Liter, about 70 mg/Liter, about 80 mg/Liter, or about 90 mg/Liter. In some embodiments, each amino acid present in the medium is present at most about 20 mg/Liter, about 30 mg/Liter, about 40 mg/Liter, about 50 mg/Liter, about 60 mg/Liter, about 70 mg/Liter, about 80 mg/Liter, about 90 mg/Liter, or about 100 mg/Liter. In some embodiments, each amino acid present in the medium is present at about 100 mg/Liter to about 500 mg/Liter. In some embodiments, each amino acid present in the medium is present at about 100 mg/Liter to about 200 mg/Liter, about 100 mg/Liter to about 300 mg/Liter, about 100 mg/Liter to about 400 mg/Liter, about 100 mg/Liter to about 500 mg/Liter, about 200 mg/Liter to about 300 mg/Liter, about 200 mg/Liter to about 400 mg/Liter, about 200 mg/Liter to about 500 mg/Liter, about 300 mg/Liter to about 400 mg/Liter, about 300 mg/Liter to about 500 mg/Liter. or about 400 mg/Liter to about 500 mg/Liter. In some embodiments, each amino acid present in the medium is present at about 100 mg/Liter, about 200 mg/Liter, about 300 mg/Liter, about 400 mg/Liter. or about 500 mg/Liter. In some embodiments, each amino acid present in the medium is present at least about 100 mg/Liter, about 200 mg/Liter, about 300 mg/Liter, or about 400 mg/Liter. In some embodiments, each amino acid present in the medium is present at most about 200 mg/Liter, about 300 mg/Liter, about 400 mg/Liter, or about 500 mg/Liter.

In some embodiments, the one or more vitamins comprise ascorbic acid, biotin, choline chloride, calcium pantothenate, folic acid, myo-inositol, niacinamide, pyridoxal (HCl), pyruvic acid (sodium salt), riboflavin, thiamine (HCl), vitamin B12, or any combination thereof, hi some embodiments, the one or more vitamins are present in the L isoform. In some embodiments, the one of more vitamins are present in the D isoform. In some embodiments, the one or more vitamins are present in both isoforms. In some embodiments, each vitamin present in the medium is present at about 0.1 mg/Liter to about 2 mg/Liter. In some embodiments, each vitamin present in the medium is present at about 0.1 mg/Liter to about 0.3 mg/Liter, about 0.1 mg/Liter to about 0.5 mg/Liter, about 0.1 mu/Liter to about 0.7 mg/Liter, about 0.1 mg/Liter to about 0.9 mg/Liter, about 0.1 mg/Liter to about 1.1 mg/Liter, about 0.1 mg/Liter to about 1.3 mg/Liter, about 0.1 mg/Liter to about 1.5 mg/Liter, about 0.1 mg/Liter to about 1.7 mg/Liter, about 0.1 mg/Liter to about 1.9 mg/Liter, about 0.1 mg/Liter to about 2 mg/Liter, about 0.3 mg/Liter to about 0.5 mg/Liter, about 0.3 mg/Liter to about 0.7 mg/Liter, about 0.3 mg/Liter to about 0.9 mg/Liter, about 0.3 mg/Liter to about 1.1 mg/Liter, about 0.3 mg/Liter to about 1.3 mu/Liter, about 0.3 rag/Liter to about 1.5 mg/Liter, about 0.3 mg/Liter to about 1.7 mg/Liter, about 0.3 mg/Liter to about 1.9 mg/Liter, about 0.3 mg/Liter to about 2 mg/Liter, about 0.5 mu/Liter to about 0.7 mg/Liter, about 0.5 mg/Liter to about 0.9 mg/Liter, about 0.5 mg/Liter to about 1.1 mg/Liter, about 0.5 mg/Liter to about 1.3 mg/Liter, about 0.5 mg/Liter to about 1.5 mg/Liter, about 0.5 mg/Liter to about 1.7 mg/Liter, about 0.5 mg/Liter to about 1.9 mg/Liter, about 0.5 mg/Liter to about 2 mg/Liter, about 0.7 mg/Liter to about 0.9 mg/Liter, about 0.7 mg/Liter to about 1.1 mg/Liter, about 0.7 mg/Liter to about 1.3 mg/Liter, about 0.7 mg/Liter to about 1.5 mg/Liter, about 0.7 mg/Liter to about 1.7 mu/Liter, about 0.7 rag/Liter to about 1.9 mg/Liter, about 0.7 mg/Liter to about 2 mg/Liter, about 0.9 mg/Liter to about 1.1 mg/Liter, about 0.9 mg/Liter to about 1.3 mg/Liter, about 0.9 mg/Liter to about 1.5 mg/Liter, about 0.9 mg/Liter to about 1.7 mg/Liter, about 0.9 mg/Liter to about 1.9 mg/Liter, about 0.9 mg/Liter to about 2 mg/Liter, about 1.1 mg/Liter to about 1.3 mg/Liter, about 1.1 mg/Liter to about 1.5 mg/Liter, about 1.1 mg/Liter to about 1.7 mg/Liter, about 1.1 mg/Liter to about 1.9 mg/Liter, about 1.1 mg/Liter to about 2 mg/Liter, about 1.3 mg/Liter to about 1.5 mg/Liter, about 1.3 mg/Liter to about 1.7 mg/Liter, about 1.3 mg/Liter to about 1.9 mg/Liter, about 1.3 mg/Liter to about 2 mg/Liter, about 1.5 mg/Liter to about 1.7 mg/Liter, about 1.5 mg/Liter to about 1.9 mg/Liter, about 1.5 mg/Liter to about 2 mg/Liter, about 1.7 mg/Liter to about 1.9 mg/Liter, about 1.7 mg/Liter to about 2 mg/Liter, or about 1.9 mg/Liter to about 2 mg/Liter. In some embodiments, each vitamin present in the medium is present at about 0.1 mg/Liter, about 0.3 mg/Liter, about 0.5 mg/Liter, about 0.7 mg/Liter, about 0.9 mg/Liter, about 1.1 mg/Liter, about 1.3 mg/Liter, or about 1.5 mg/Liter, about 1.7 mg/Liter, about 1.9 mg/Liter, or about 2 mg/Liter. In some embodiments, each vitamin present in the medium is present at least about 0.1 mg/Liter, about 0.3 mg/Liter, about 0.5 mg/Liter, about 0.7 mg/Liter, about 0.9 mg/Liter, about 1.1 mg/Liter, about 1.3 mg/Liter, about 1.5 mg/Liter, about 1.7 mg/Liter, or about 1.9 mg/Liter. In some embodiments, each vitamin present in the medium is present at most about 0.3 mg/Liter, about 0.5 mg/Liter, about 0.7 mg/Liter, about 0.9 mg/Liter, about 1.1 mg/Liter, about 1.3 mg/Liter, about 1.5 mg/Liter, about 1.7 mg/Liter, about 1.9 rag/Liter, or about 2 mg/Liter. In some embodiments, each vitamin present in the medium is present at about 10 mg/Liter to about 120 mg/Liter. In some embodiments, each vitamin present in the medium is present at about 10 mg/Liter to about 20 mg/Liter, about 10 mg/Liter to about 30 mg/Liter, about 10 mg/Liter to about 40 mg/Liter, about 10 mg/Liter to about 50 mg/Liter, about 10 mg/Liter to about 60 mg/Liter, about 10 mg/Liter to about 70 mg/Liter, about 10 mg/Liter to about 80 mg/Liter, about 10 mg/Liter to about 90 mg/Liter, about 10 mg/Liter to about 100 mg/Liter, about 10 mg/Liter to about 110 mg/Liter, about 10 mg/Liter to about 120 mg/Liter, about 20 mg/Liter to about 30 mg/Liter, about 20 mg/Liter to about 40 mg/Liter, about 20 mg/Liter to about 50 mg/Liter, about 20 mg/Liter to about 60 mg/Liter, about 20 mg/Liter to about 70 mg/Liter, about 20 mg/Liter to about 80 mg/Liter, about 20 mg/Liter to about 90 mg/Liter, about 20 mg/Liter to about 100 mg/Liter, about 20 mg/Liter to about 110 mg/Liter, about 20 mg/Liter to about 120 mg/Liter, about 30 mg/Liter to about 40 mg/Liter, about 30 mg/Liter to about 50 mg/Liter, about 30 mg/Liter to about 60 mg/Liter, about 30 mg/Liter to about 70 mg/Liter, about 30 mg/Liter to about 80 mg/Liter, about 30 mg/Liter to about 90 mg/Liter, about 30 mg/Liter to about 100 mg/Liter, about 30 mg/Liter to about 110 mg/Liter, about 30 mg/Liter to about 120 mg/Liter, about 40 mg/Liter to about 50 mg/Liter, about 40 mg/Liter to about 60 mg/Liter, about 40 mg/Liter to about 70 mg/Liter, about 40 mg/Liter to about 80 mg/Liter, about 40 mg/Liter to about 90 mg/Liter, about 40 mg/Liter to about 100 mg/Liter, about 40 mg/Liter to about 110 mg/Liter, about 40 mg/Liter to about 120 mg/Liter, about 50 mg/Liter to about 60 mg/Liter, about 50 mg/Liter to about 70 mg/Liter, about 50 mg/Liter to about 80 mg/Liter, about 50 mg/Liter to about 90 mg/Liter, about 50 mg/Liter to about 100 mg/Liter, about 50 mg/Liter to about 110 mg/Liter, about 50 mg/Liter to about 120 mg/Liter, about 60 mg/Liter to about 70 mg/Liter, about 60 mg/Liter to about 80 mg/Liter, about 60 mg/Liter to about 90 mg/Liter, about 60 mg/Liter to about 100 mg/Liter, about 60 mg/Liter to about 110 mg/Liter, about 60 mg/Liter to about 120 mg/Liter, about 70 mg/Liter to about 80 mg/Liter, about 70 mg/Liter to about 90 mg/Liter, about 70 mg/Liter to about 100 mg/Liter, about 70 mg/Liter to about 110 mg/Liter, about 70 mg/Liter to about 120 mg/Liter, about 80 mg/Liter to about 90 mg/Liter, about 80 mg/Liter to about 100 mg/Liter, about 80 mg/Liter to about 110 mg/Liter, about 80 mg/Liter to about 120 mg/Liter, about 90 mg/Liter to about 100 mg/Liter, about 90 mg/Liter to about 110 mg/Liter, about 90 mg/Liter to about 120 mg/Liter, about 100 mg/Liter to about 110 mg/Liter, about 100 mg/Liter to about 120 mg/Liter, or about 110 mg/Liter to about 120 mg/Liter. In some embodiments, each vitamin present in the medium is present at about 10 mg/Liter, about 20 mg/Liter, about 30 mg/Liter, about 40 mg/Liter, about 50 mg/Liter, about 60 mg/Liter, about 70 mg/Liter, about 80 mg/Liter, about 90 mg/Liter, about 100 mg/Liter, about 110 mg/Liter, or about 1120 mg/Liter. In some embodiments, each vitamin present in the medium is present at least about 10 mg/Liter, about 20 mg/Liter, about 30 mg/Liter, about 40 mg/Liter, about 50 mg/Liter, about 60 En/Liter, about 70 mg/Liter, about 80 mg/Liter, about 90 mg/Liter, about 100 mg/Liter, or about 1110 mg/Liter. In some embodiments, each vitamin present in the medium is present at most about 20 mg/Liter, about 30 mg/Liter, about 40 mg/Liter, about 50 mg/Liter, about 60 mg/Liter, about 70 mg/Liter, about 80 mg/Liter, about 90 mg/Liter, about 100 mg/Liter, about 110 mg/Liter, or about 120 mg/Liter.

In some embodiments, the glucose comprised in the medium is anhydrous. In some embodiments, the glucose is present in the L isoform. In some embodiments, the glucose is present in the D isoform. In some embodiments, the glucose is present in both isoforms. In some embodiments, glucose present in the medium is present at about 500 mg/Liter to about 1,600 mg/Liter. In some embodiments, glucose present in the medium is present at about 500 mg/Liter to about 600 mg/Liter, about 500 mg/Liter to about 700 mg/Liter, about 500 mg/Liter to about 800 mg/Liter, about 500 mg/Liter to about 900 mg/Liter, about 500 mg/Liter to about 1,000 mg/Liter, about 500 mg/Liter to about 1,100 mg/Liter, about 500 mg/Liter to about 1,200 mg/Liter, about 500 mg/Liter to about 1,300 mg/Liter, about 500 mg/Liter to about 1,400 mg/Liter, about 500 mg/Liter to about 1,500 mg/Liter, about 500 mg/Liter to about 1,600 mg/Liter, about 600 mg/Liter to about 700 mg/Liter, about 600 mg/Liter to about 800 mg/Liter, about 600 mg/Liter to about 900 mg/Liter, about 600 mg/Liter to about 1,000 mg/Liter, about 600 mg/Liter to about 1,100 mg/Liter, about 600 mg/Liter to about 1,200 mg/Liter, about 600 mg/Liter to about 1,300 mg/Liter, about 600 mg/Liter to about 1,400 mg/Liter, about 600 mg/Liter to about 1,500 mg/Liter, about 600 mg/Liter to about 1,600 mg/Liter, about 700 mg/Liter to about 800 mg/Liter, about 700 mg/Liter to about 900 mg/Liter, about 700 mg/Liter to about 1,000 mg/Liter, about 700 mg/Liter to about 1,100 mg/Liter, about 700 mg/Liter to about 1,200 mg/Liter, about 700 mg/Liter to about 11,300 mg/Liter, about 700 mg/Liter to about 11,400 mg/Liter, about 700 mg/Liter to about 1,500 mg/Liter, about 700 mg/Liter to about 1,600 mg/Liter, about 800 mg/Liter to about 900 mg/Liter, about 800 mg/Liter to about 1,000 mg/Liter, about 800 mg/Liter to about 1,100 mg/Liter, about 800 mg/Liter to about 1,200 mg/Liter, about 800 mg/Liter to about 1,300 mg/Liter, about 800 mg/Liter to about 1,400 mg/Liter, about 800 mg/Liter to about 1,500 mg/Liter, about 800 mg/Liter to about 1,600 mg/Liter, about 900 mg/Liter to about 1,000 mg/Liter, about 900 mg/Liter to about 1,100 mg/Liter, about 900 mg/Liter to about 1,200 mg/Liter, about 900 mg/Liter to about 1,300 mg/Liter, about 900 mg/Liter to about 1,400 mg/Liter, about 900 mg/Liter to about 1,500 mg/Liter, about 900 mg/Liter to about 1,600 mg/Liter, about 1,000 mg/Liter to about 1,100 mg/Liter, about 1,000 mg/Liter to about 1,200 mg/Liter, about 1,000 mg/Liter to about 1,300 mg/Liter, about 1,000 mg/Liter to about 1,400 mg/Liter, about 1,000 mg/Liter to about 1,500 mg/Liter, about 1,000 mg/Liter to about 1,600 mg/Liter, about 1,100 mg/Liter to about 1,200 mg/Liter, about 1,100 mg/Liter to about 1,300 mg/Liter, about 1,1100 mg/Liter to about 1,400 mg/Liter, about 11.100 mg/Liter to about 1,500 mg/Liter, about 1,100 mg/Liter to about 1,600 mg/Liter, about 1,200 mg/Liter to about 1,300 mg/Liter, about 1,200 mg/Liter to about 1,400 mg/Liter, about 1.200 mg/Liter to about 1,500 mg/Liter, about 1,200 mg/Liter to about 1,600 mg/Liter, about 1,300 mg/Liter to about 1,400 mg/Liter, about 1,300 mg/Liter to about 1,500 mg/Liter, about 1,300 mg/Liter to about 1,600 mg/Liter, about 1,400 mg/Liter to about 1,500 mg/Liter, about 1,400 mg/Liter to about 1,600 mg/Liter, or about 1,500 mg/Liter to about 1,600 mg/Liter. In some embodiments, glucose present in the medium is present at about 500 mg/Liter, about 600 mg/Liter, about 700 mg/Liter, about 800 mg/Liter, about 900 mg/Liter, about 1,000 mg/Liter, about 1,100 mg/Liter, about 1.200 mg/Liter, about 1,300 mg/Liter, about 1,400 mg/Liter, about 1,500 mg/Liter, or about 1,600 mg/Liter. In some embodiments, glucose present in the medium is present at least about 500 mg/Liter, about 600 mg/Liter, about 700 mg/Liter, about 800 mg/Liter, about 900 mg/Liter, about 1,000 mg/Liter, about 1,100 mg/Liter, about 1,200 mg/Liter, about 1,300 mg/Liter, about 1,400 mg/Liter, or about 1,500 mg/Liter. In some embodiments, glucose, present in the medium is present at most about 600 mg/Liter, about 700 mg/Liter, about 800 mg/Liter, about 900 mg/Liter, about 1,000 mg/Liter, about 1,100 mg/Liter, about 1,200 mg/Liter, about 1,300 mg/Liter, about 1,400 mg/Liter, about 1,500 mg/Liter, or about 1,600 mg/Liter.

In some embodiments, lipoic acid present in the medium is present at about 0.05 mg/Liter to about 0.5 mg/Liter. In some embodiments, the lipoic acid is present in the medium in the form of DL-thioctic acid. In some embodiments, lipoic acid present in the medium is present at about 0.05 mg/Liter to about 0.1 mg/Liter, about 0.05 mg/Liter to about 0.15 mg/Liter, about 0.05 mg/Titer to about 0.2 mg/Liter, about 0.05 mg/Liter to about 0.25 mg/Liter, about 0.05 mg/Liter to about 0.3 mg/Liter, about 0.05 mg/Liter to about 0.35 mg/Liter, about 0.05 mg/Liter to about 0.4 mg/Liter, about 0.05 mg/Liter to about 0.45 mg/Liter, about 0.05 mg/Liter to about 0.5 mg/Liter, about 0.1 mg/Liter to about 0.15 mg/Liter, about 0.1 mg/Liter to about 0.2 mg/Liter, about 0.1 mg/Liter to about 0.25 mg/Liter, about 0.1 mg/Liter to about 0.3 mg/Liter, about 0.1 mg/Liter to about 0.35 mg/Liter, about 0.1 mg/Liter to about 0.4 mg/Liter, about 0.1 mg/Liter to about 0.45 mg/Liter, about 0.1 mg/Liter to about 0.5 mg/Liter, about 0.15 mg/Liter to about 0.2 mg/Liter, about 0.15 mg/Liter to about 0.25 mg/Liter, about 0.15 mg/Liter to about 0.3 mg/Liter, about 0.15 mg/Liter to about 0.35 mg/Liter, about 0.15 mg/Liter to about 0.4 mg/Liter, about 0.15 mg/Liter to about 0.45 mg/Liter, about 0.15 mg/Liter to about 0.5 mg/Liter, about 0.2 mg/Liter to about 0.25 mg/Liter, about 0.2 mg/Liter to about 0.3 mg/Liter, about 0.2 mg/Liter to about 0.35 mg/Liter, about 0.2 mg/Liter to about 0.4 mg/Liter, about 0.2 mg/Liter to about 0.45 mg/liter, about 0.2 mg/Liter to about 0.5 mg/Liter, about 0.25 mg/Liter to about 0.3 mg/Liter, about 0.25 mg/Liter to about 0.35 mg/Liter, about 0.25 mg/Liter to about 0.4 mg/Liter, about 0.25 mg/Liter to about 0.45 mg/Liter, about 0.25 mg/Liter to about 0.5 mg/Liter, about 0.3 mg/Liter to about 0.35 mg/Liter, about 0.3 mg/Liter to about 0.4 mg/Liter, about 0.3 mg/Liter to about 0.45 mg/Liter, about 0.3 mg/Liter to about 0.5 mg/Liter, about 0.35 mg/Liter to about 0.4 mg/Liter, about 0.35 mg/Liter to about 0.45 mg/Liter, about 0.35 mg/Liter to about 0.5 mg/Liter, about 0.4 mg/Liter to about 0.45 mg/Liter, about 0.4 mg/Liter to about 0.5 mg/Liter, or about 0.45 mg/Liter to about 0.5 mg/Liter. In some embodiments, lipoic acid present in the medium is present at about 0.05 mg/Liter, about 0.1 mg/Liter, about 0.15 mg/Liter, about 0.2 mg/Liter, about 025 mg/Liter, about 0.3 mg/Liter, about 0.35 mg/Liter, about 0.4 mg/Liter, about 0.45 mg/Liter, of about 0.5 mg/Liter. In some embodiments, lipoic acid present in the medium is present at least about 0.05 mg/Liter, about 0.1 mg/Liter, about 0.15 mg/Liter, about 0.2 mg/Liter, about 0.25 mg/Liter, about 0.3 mg/Liter, about 0.35 mg/Liter, about 0.4 mg/Liter, or about 0.45 mg/Liter. In some embodiments, lipoic acid present in the medium is present at most about 0.1 mg/Liter, about 0.15 mg/Liter, about 0.2 mg/Liter, about 0.25 mg/Liter, about 0.3 mg/Liter, about 0.35 mg/Liter, about 0.4 mg/Liter, about 0.45 mg/Liter, or about 0.5 mg/Liter.

In some embodiments, sodium bicarbonate present in the medium is present at about 250 mg/Liter to about 2,000 mg/Liter. In some embodiments, sodium bicarbonate present in the medium is present at about 250 mg/Liter to about 500 mg/Liter, about 250 mg/Liter to about 750 mg/Liter, about 250 mg/Liter to about 1,000 mg/Liter, about 250 mg/Liter to about 1,250 mg/Liter, about 250 mg/Liter to about 1,500 mg/Later, about 250 mg/Liter to about 1,750 mg/Liter, about 250 mg/Liter to about 2,000 mg/Liter, about 500 mg/Liter to about 750 mg/Liter, about 500 mg/Liter to about 1,000 mg/Liter, about 500 mg/Liter to about 1,250 mg/Liter, about 500 mg/Liter to about 1,500 mg/Liter, about 500 mg/Liter to about 1,750 mg/Liter, about 500 mg/Liter to about 2,000 mg/Liter, about 750 mg/Liter to about 1,000 Ent/Liter, about 750 mg/Liter to about 1,250 g/Liter, about 750 mg/Liter to about 1,500 mg/Liter, about 750 mg/Liter to about 1,750 mg/Liter, about 750 mg/Liter to about 2,000 mg/Liter, about 1,000 mg/Liter to about 1,250 mg/Liter, about 1,000 mg/Liter to about 1,500 mg/Liter, about 1,000 mg/Liter to about 1,750 mg/Liter, about 1,000 mg/Liter to about 2,000 mg/Liter, about 1,250 tit/Liter to about 1,500 mg/Liter, about 1,250 mg/Liter to about 1,750 mg/Liter, about 1,250 mg/Liter to about 2,000 mg/Liter, about 1,500 mg/Liter to about 1,750 mg/Liter, about 1,500 mg/Liter to about 2,000 mg/Liter, or about 1,750 mg/Liter to about 2,000 mg/Liter. In some embodiments, sodium bicarbonate present in the medium is present at about 250 mg/Liter, about 500 mg/Liter, about 750 mg/Liter, about 1,000 mg/Liter, about 1,250 mg/Liter, about 1,500 mg/Liter, about 1,750 mg/Liter, or about 2,000 mg/Liter. In some embodiments, sodium bicarbonate present in the medium is present at least about 250 mg/Liter, about 500 mg/Liter, about 750 mg/Liter, about 1,000 mg/Liter, about 1,250 mg/Liter, about 1,500 mg/Liter, or about 1,750 mg/Liter. In some embodiments, sodium bicarbonate present in the medium is present at most about 500 mg/Liter, about 750 mg/Liter, about 1,000 mg/Liter, about 1,250 mg/Liter, about 1,500 mg/Liter, about 1,750 mg/Liter, or about 2,000 mg/Liter.

In some embodiments, sodium pyruvate present in the medium is present at about 50 mg/Liter to about 160 mg/Liter. In some embodiments, sodium pyruvate present in the medium is present at about 50 mg/Liter to about 60 mg/Liter, about 50 mg/Liter to about 70 mg/Liter, about 50 mg/Liter to about 80 mg/Liter, about 50 mg/Liter to about 90 mg/Liter, about 50 mg/Liter to about 100 mg/Liter, about 50 mg/Liter to about 110 mg/Liter, about 50 mg/Liter to about 120 mg/Liter, about 50 mg/Liter to about 130 mg/Liter, about 50 mg/Liter to about 140 mg/Liter, about 50 mg/Liter to about 150 mg/Liter, about 50 mg/Liter to about 160 mg/Liter, about 60 mg/Liter to about 70 mg/Liter, about 60 mg/Liter to about 80 mu/Liter, about 60 mu/Liter to about 90 mg/Liter, about 60 mg/Liter to about 100 mg/Liter, about 60 mg/Liter to about 110 mg/Liter, about 60 mg/Liter to about 120 mg/Liter, about 60 mg/Liter to about 130 mg/Liter, about 60 mg/Liter to about 140 mg/Liter, about 60 mg/Liter to about 150 mg/Liter, about 60 mg/Liter to about 160 mg/Liter, about 70 mg/Liter to about 80 mg/Liter, about 70 mg/Liter to about 90 mg/Liter, about 70 mg/Liter to about 100 mg/Liter, about 70 mg/Liter to about 110 mg/Liter, about 70 mg/Liter to about 120 mg/Liter, about 70 mg/Liter to about 130 mg/Liter, about 70 mg/Liter to about 140 mg/Liter, about 70 mg/Liter to about 150 mg/Liter, about 70 mg/Liter to about 160 mg/Liter, about 80 mg/Liter to about 90 mg/Liter, about 80 mg/Liter to about 100 mg/Liter, about 80 mg/Liter to about 110 mg/Liter, about 80 mg/Liter to about 120 mg/Liter, about 80 mg/Liter to about 130 mg/Liter, about 80 mg/Liter to about 140 mg/Liter, about 80 mg/Liter to about 150 mg/Liter, about 80 mg/Liter to about 160 mg/Liter, about 90 mg/Liter to about 100 mg/Liter, about 90 mg/Liter to about 110 mg/Liter, about 90 mg/Liter to about 120 mg/Liter, about 90 mg/Liter to about 130 mg/Liter, about 90 mg/Liter to about 140 mg/Liter, about 90 mg/Liter to about 150 mg/Liter, about 90 mg/Liter to about 160 mg/Liter, about 100 mg/Liter to about 110 mg/Liter, about 100 mg/Liter to about 120 rug/Liter, about 100 mg/Liter to about 130 mg/Liter, about 100 mg/Liter to about 140 mg/Liter, about 100 mg/Liter to about 150 mg/Liter, about 100 mg/Liter to about 160 mg/Liter, about 110 mg/Liter to about 120 mg/Liter, about 110 mg/Liter to about 130 mg/Liter, about 110 mg/Liter to about 140 mg/Liter, about 110 mg/Liter to about 150 mg/Liter, about 110 mg/Liter to about 160 mg/Liter, about 120 mg/Liter to about 130 mg/Liter, about 120 mg/Liter to about 140 mg/Liter, about 120 mg/Liter to about 150 mg/Liter, about 120 mg/Liter to about 160 mg/Liter, about 130 mg/Liter to about 140 mg/Liter, about 130 mg/Liter to about 150 mg/Liter, about 130 mg/Liter to about 160 mg/Liter, about 140 mg/Liter to about 150 mg/Liter, about 140 mg/Liter to about 160 mg/Liter, or about 150 mg/Liter to about 160 mg/Liter. In some embodiments, sodium pyruvate present in the medium is present at about 50 mg/Liter, about 60 mg/Liter, about 70 mg/Liter, about 80 mg/Liter, about 90 mg/Liter, about 100 mg/Liter, about 110 mg/Liter, about 120 mg/Liter, about 130 mg/Liter, about 140 mg/Liter, about 150 mg/Liter, or about 160 mg/Liter. In some embodiments, sodium pyruvate present in the medium is present at least about 50 mg/Liter, about 60 mg/Liter, about 70 mg/Liter, about 80 mg/Liter, about 90 mg/Liter, about 100 mg/Liter, about 110 mg/Liter, about 120 mg/Liter, about 130 mg/Liter, about 140 mg/Liter, or about 150 mg/Liter. In some embodiments, sodium pyruvate present in the medium is present at most about 60 mg/Liter, about 70 mg/Liter, about 80 mg/Liter, about 90 mg/Liter, about 100 mg/Liter, about 110 mg/Liter, about 120 mg/Liter, about 130 mg/Liter, about 140 mg/Liter, about 150 mg/Liter, or about 160 mg/Liter.

In some embodiments, the pH of the alpha MEM is between 7.0 and 7.4.

In some embodiments, the alpha MEM comprises the ingredients are presented in Table 1.

TABLE 1

| Components | mg/Liter |
| --- | --- |
| INORGANIC SALTS | |
| Calcium Chloride, dihydrate (CaCl$_2$•2H$_2$0) | 264.00 |
| Magnesium Sulfate, heptahydrate | 200.00 |
| Potassium Chloride (KCI) | 400.00 |
| Sodium Chloride (NaCI) | 6800.0 |
| Sodium Phosphate Monobasic, dihydrate (NaF$_2$1,0$_4$•2H$_2$0) | 158.00 |
| OTHER COMPONENTS | |
| D-Glucose, Anhydrous (C$_6$11$_{12}$0$_6$) | 1000.00 |
| Lipoic Acid (DL-Thiotic Acid) (C81$^-$ | 0.20000 |
| Sodium Bicarbonate (NaHCO$_3$) | 2200.00 |
| Sodium Pyruvate (C$_3$H$_3$Na0$_3$) | 110.000 |

TABLE 1-continued

| Components | mg/Liter |
| --- | --- |
| AMINO ACIDS | |
| Glycine (C2H5NO2) | 50.0000 |
| L-Alanine (C3H7NO2) | 25.0000 |
| L-Alanyl-Glutamine (C$_8$H$_{15}$N$_3$0$_4$) | 406.000 |
| L-Arginine HCI (C$_6$H$_{15}$CIN$_4$0$_2$) | 105.000 |
| L-Asparagine, monohydrate (C$_4$H$_8$N$_2$0$_3$•1-1$_2$0) | 50.0000 |
| L-Aspartic Acid (C4H7N04) | 30.0000 |
| L-Cysteine HCI, monohydrate | 100.000 |
| L-Cystine (C6Hi2N20452) | 24.0000 |
| L-Glutamic Acid (C$_5$H$_9$N0$_4$) | 75.0000 |
| L-Histidine (C6H9N302) | 31.0000 |
| L-Isoleucine (C$_6$F1$_{13}$NO$_2$) | 52.4000 |
| L-Leucine (C$_6$F1$_{13}$NO$_2$) | 52.4000 |
| L-Lysine (C$_6$H$_{14}$N$_2$0$_2$) | 58.0000 |
| L-Methionine (C$_5$H$_{11}$NO$_2$S) | 15.0000 |
| L-Phenylalanine (C$_9$H$_{11}$NO$_2$) | 32.0000 |
| L-Proline (C5H9NO2) | 40.0000 |
| L-Serine (C$_3$H$_7$NO$_3$) | 25.0000 |
| L-Threonine (C$_4$H$_9$NO$_3$) | 48.0000 |
| L-Tryptophan (C11H12N2$^0$2) | 10.0000 |
| L-Tyrosine (C$_9$H$_9$NO$_3$) | 36.0000 |
| L-Valine (C$_5$H$_{11}$NO$_2$) | 46.0000 |
| VITAMINS | |
| L-Ascorbic Acid (C6H806) | 50.0000 |
| D-Biotin (C$_{10}$H$_{16}$N$_2$0$_3$S) | 0.1000 |
| Choline Chloride (C$_5$H$_{14}$CIN0) | 1.0000 |
| D-Calcium Pantothenate | 1.0000 |
| Folic Acid (C191$^-$119N706) | 1.0000 |
| Myo-Inositol (C$_6$11$_{12}$0$_6$) | 2.0000 |
| Niacinamide (C$_6$H$_6$N$_2$0) | 1.0000 |
| Pyridoxal HCI (C$_8$H$_9$NO$_3$•FICI) | 1.0000 |
| Pyruvic Acid, Sodium Salt (C$_3$H$_3$Na0$_3$) | 110.00 |
| Riboflavin (C$_{17}$H$_2$$_O$N$_4$0$_6$) | 0.1000 |
| Thimaine HCI (C$_{12}$H$_{17}$CIN$_4$0S•HCI) | 1.0000 |
| Vitamin B12 (C63H88CON14$^{\circ}$14P) | 1.3600 |

In some embodiments, the vBA-MSCs are cultured in a medium comprising alpha MEM as described in Table 1, 10% Stemulate hPL (no heparin required), 2 ng/mL recombinant, carrier free FGF, and 2 ng/mL recombinant, carrier free EGF.

In some embodiments, the primary MSCs may be further passaged to non-primary, cells (e.g. removed from the culture surface and expanded into additional area) by seeding at a density of about 1,000 to about one million nucleated cells/cm$^2$ of culture dish (e.g. about 5,900 cells/cm$^2$ plus and minus about 1,200), and then culturing for additional days, e.g. about 14±about 2 days. In suitable embodiments, the primary cells may be grown to confluence, and in some instances may be passaged to a second culture of non-primary cells by seeding the primary cells from a confluent primary cell culture in the second culture surface in an amount below confluence and growing the non-primary culture to confluence. This method can be repeated for additional passages.

In some embodiments, the MSCs in the treatment composition may originate from sequential generation number (i.e., they are within about 1 or about 2 or about 3 or about 4 cell doublings of each other). Optionally, the average number of cell doublings in the present composition treatment composition may be about 20 to about 25 doublings. Optionally, the average number of cell doublings in the present treatment composition may be about 9 to about 13 (e.g., about 11 or about 11.2) doublings arising from the primary culture, plus about 1, about 2, about 3, or about 4 doublings per passage (for example, about 2.5 doublings per passage). Exemplary average cell doublings in present preparations may be of about 13.5, about 16, about 18.5, about 21, about 23.5, about 26, about 28.5, about 31, about 33.5, or about 36 when produced by about 1, about 2, about 3, about 4, about 5, about 6, about 7, about 8, about 9, or about 10 passages, respectively.

In some embodiments, notwithstanding one or more population doublings, the MSCs in the treatment composition (e.g. vBA-MSCs) may originate from MSCs that were cultured through about 1, about 2, about 3, about 4, about 5, about 6, about 7, about 8, about 9, or about 10 passages.

In some embodiments, the preparations and compositions of the present disclosure may comprise at least 100 million vBA-MSCs having an antigen profile of more than about 1.75% CD45+ cells, at least about 95% CD105+ cells, and at least about 95% CD166+ cells and the cells may be expanded ex vivo from passage 2, until passage 4 while maintaining population uniformly based upon the antigen profile (i.e. more than about 1.75% CD45+ cells, at least about 95% CD105+ cells, and at least about 95% CD166+ cells).

In some embodiments, the preparations and compositions of the present disclosure may comprise vBA-MSCs having an antigen profile of reduced expression of one or more senescent cell markers, as compared to bone marrow-derived MSCs prepared according to known MSC culturing techniques. In some embodiments, the one or more senescent cell markers comprise MIC-A, MIC-B, ULBP2, or any combination thereof. NK cell-mediated immune responses are stimulated by MIC-A, MIC-B, and/or ULBP2.

In some embodiments, the vBA-MSC preparations and compositions described herein comprise an amount of cells that express one or more senescent cell markers of about 1% less than bone marrow-derived MSCs to about 100% less than bone marrow-derived MSCs. In some embodiments, the vBA-MSC preparations and compositions described herein comprise an amount of cells that express one or more senescent cell markers of about 100% less than bone marrow-derived MSCs to about 90% less than bone marrow-derived MSCs, about 100% less than bone marrow-derived MSCs to about 80% less than bone marrow-derived MSCs, about 100% less than bone marrow-derived MSCs to about 70% less than bone marrow-derived MSCs, about 100% less than bone marrow-derived MSCs to about 60% less than bone marrow-derived MSCs, about 100% less than bone marrow-derived. MSCs to about 50% less than bone marrow-derived MSCs, about 1100% less than bone marrow-derived MSCs to about 40% less than bone marrow-derived MSCs, about 100% less than bone marrow-derived MSCs to about 30% less than bone marrow-derived MSCs, about 100% less than bone marrow-derived MSCs to about 20% less than bone marrow-derived MSCs, about 100% less than bone marrow-derived MSCs to about 10% less than bone marrow-derived MSCs, about 100% less than bone marrow-derived. MSCs to about 5% less than bone marrow-thrived MSCs, about 100% less than bane marrow-derived MSCs to about 1% less than bone marrow-derived MSCs, about 90% less than bone marrow-derived MSCs to about 80% less than bone marrow-derived MSCs, about 90% less than bane marrow-derived MSCs to about 70% less than bone marrow-derived MSCs, about 90% less than bone marrow-derived MSCs to about 60% less than bone marrow-derived. MSCs, about 90% less than bone marrow-derived MSCs to about 50% less than bone marrow-derived MSCs, about 90% less than bone marrow-derived MSCs to about 40% less than bone marrow-derived MSCs, about 90% less than bone marrow-derived MSCs to about 30% less than bone marrow-thrived MSCs, about 90% less than bone marrow-derived MSCs to about 20% less than bone marrow-derived MSCs, about 90% less than bone marrow-derived MSCs to about 10% less than bone marrow-derived MSCs, about 90% less than bone marrow-derived MSCs to about 5% less than bone marrow-derived MSCs, about 90% less than bone marrow-derived MSCs to about 1% less than bone marrow-derived. MSCs, about 80% less than bone marrow-derived MSCs to about 70% less than bone marrow-derived MSCs, about 80% less than bone marrow-derived MSCs to about 60% less than bone marrow-derived MSCs, about 80% less than bone marrow-derived MSCs to about 50% less than bone marrow-thrived MSCs, about 80% less than bone marrow-derived MSCs to about 40% less than bone marrow-derived MSCs, about 80% less than bone marrow-derived MSCs to about 30% less than bone marrow-derived MSCs, about 80% less than bane marrow-derived MSCs to about 20% less than bone marrow-derived MSCs, about 80% less than bone marrow-derived MSCs to about 10% less than bone marrow-derived. MSCs, about 80% less than bone farrow-derived MSCs to about 5% less than bone marrow-derived MSCs, about 80% less than bane marrow-derived MSCs to about. 1% less than bone marrow-derived MSCs, about 80% less than bone marrow-derived MSCs to about 60% less than bone marrow-thrived MSCs, about 70% less than bone marrow-derived MSCs to about 50% less than bone marrow-derived MSCs, about 70% less than bone marrow-derived MSCs to about 40% less than bone marrow-derived MSCs, about 70% less than bone marrow-derived MSCs to about 30% less than bone marrow-derived MSCs, about 70% less than bone marrow-derived MSCs to about 20% less than bone marrow-derived. MSCs, about 70% less than bone farrow-derived MSCs to about 10% less than bone marrow-derived MSCs, about 70% less than bane marrow-derived MSCs to about 5% less than bone marrow-derived MSCs, about 70% less than bone marrow-derived MSCs to about 1% less than bone marrow-derived. MSCs, about 60% less than bone narrow-derived MSCs to about 50% less than bone marrow-derived MSCs, about 60% less than bone marrow-derived MSCs to about 40% less than bone marrow-derived MSCs, about 60% less than bone marrow-derived MSCs to about 30% less than bone marrow-derived MSCs, about 60% less than bone marrow-derived MSCs to about 20% less than bone marrow-derived MSCs, about 60% less than bone marrow-derived MSCs to about 10% less than bone marrow-derived MSCs, about 60% less than bone marrow-derived MSCs to about 5% less than bone marrow-derived MSCs, about 60% less than bone marrow-derived MSCs to about 1% less than bone marrow-derived MSCs, about 50% less than bone marrow-derived MSCs to about 40% less than bone marrow-derived MSCs, about 50% less than bone marrow-derived MSCs to about 30% less than bone marrow-derived MSCs, about 50% less than bone marrow-derived MSCs to about 20% less than bone marrow-derived MSCs, about 50% less than bone marrow-derived MSCs to about 10% less than bone marrow-derived MSCs, about 50% less than bone marrow-derived MSCs to about 5% less than bone marrow-derived MSCs, about 50% less than bone marrow-derived MSCs to about 1% less than bone marrow-derived MSCs, about 40% less than bone marrow-derived MSCs to about 30% less than bone marrow-derived MSCs, about 40% less than bone marrow-derived MSCs to about 20% less than bone marrow-derived MSCs, about 40% less than bone marrow-derived MSCs to about 10% less than bone marrow-derived MSCs, about 40% less than bone marrow-derived MSCs to about 5% less than bone marrow-derived MSCs, about 40% less than bone marrow-derived MSCs to about 1% less than bone marrow-derived MSCs, about 30% less than bone marrow-derived MSCs to about 20% less than bone marrow-derived MSCs, about 30% less than bone marrow-derived MSCs to about 10% less than bone marrow-derived MSCs, about 30% less than bone marrow-derived MSCs to about 5% less than bone marrow-derived MSCs, about 30% less than bone marrow-derived MSCs to about 1% less than bone marrow-derived MSCs, about 20% less than bone marrow-derived MSCs to about 10% less than bone marrow-derived MSCs, about 20% less than bone marrow-derived MSCs to about 5% less than bone marrow-derived MSCs, about 20% less than bone marrow-derived MSCs to about 1% less than bone marrow-derived MSCs, about 10% less than bone marrow-derived MSCs to about 5% less than bone marrow-derived MSCs, about 10% less than bone marrow-derived MSCs to about 1% less than bone marrow-derived MSCs, or about 5% less than bone marrow-derived MSCs to about 1% less than bone marrow-derived MSCs. In some embodiments, the vBA-MSC preparations and compositions described herein comprise an amount of cells that express one or more senescent cell markers of about 100% less than bone marrow-derived MSCs, about 90% less than bone marrow-derived MSCs, about 80% less than bone marrow-derived MSCs, about 70% less than bone marrow-derived MSCs, about 60% less than bone marrow-derived MSCs, about 50% less than bone marrow-derived MSCs, about 40% less than bone marrow-derived MSCs, about 30% less than bone marrow-derived MSCs, about 20% less than bone marrow-derived MSCs, about. 10% less than bone marrow-derived MSCs, about 5% less than bone marrow-derived MSCs, or about 1% less than bone marrow-derived MSCs. In some embodiments, the vBA-MSC preparations and compositions described herein comprise an amount of cells that express one or more senescent cell markers of at least about 100% less than bone marrow-derived MSCs, about 90% less than bone marrow-derived MSCs, about 80% less than bone marrow-derived MSCs, about 70% less than bone marrow-derived MSCs, about 60% less than bone marrow-derived MSCs, about 50% less than bone marrow-derived MSCs, about 40% less than bone marrow-derived MSCs, about 30% less than bone marrow-derived MSCs, about 20% less than bone marrow-derived MSCs, about 10% less than bone marrow-derived MSCs. or about 5% less than bone marrow-derived MSCs. In some embodiments, the vBA-MSC preparations and compositions described herein comprise an amount of cells that express one or more senescent cell markers of at most about 90% less than bone marrow-derived MSCs, about 80% less than bone marrow-derived MSCs, about 70% less than bone marrow-derived MSC's, about 60% less than bone marrow-derived MSCs, about 50% less than bone marrow-derived MSCs, about 40% less than bone marrow-derived MSCs, about 30% less than bone marrow-derived MSCs, about 20% less than bone marrow-derived. MSCs, about 10% less than bone marrow-derived MSCs, about 5% less than bone marrow-derived MSCs, or about 1% less than bone marrow-derived MSCs.

In some embodiments, the preparations and compositions of the present disclosure generate a lessened NK cell-mediated immune response upon administration to a subject comprising mis-matched MI-IC molecules (e.g. mis-matched human leukocyte antigens when the subject is a human), as compared to administration of a composition comprising bone marrow-derived MSCs. In some embodiments, the preparations and compositions of the present disclosure do not generate a NK cell-mediated immune response upon administration to a subject comprising mis-matched MHC molecules (e.g. mis-matched human leukocyte antigens when the subject is a human).

vBA-MSC Compositions

One aspect of the present disclosure is a composition comprising a population of human mesenchymal stem cells (MSCs) derived from a population of un-passaged or fresh MSCs, wherein the population of human MSCs is passaged and comprises a doubling rate of at least about 16 to 36 hours. In some embodiments, the population of human MSC's is passaged at least about 1 time to about 12 times. In some embodiments, the population of human MSCs is passaged at least about 1 time to about 2 times, about 1 time to about 3 times, about 1 time to about 4 times, about 1 time to about 5 times, about 1 time to about 6 times, about 1 time to about 1 times, about 1 time to about 8 times, about 1 time to about 9 times, about 1 time to about 10 times, about 1 time to about 11 times, about 1 time to about 12 times, about 2 times to about 3 times, about 2 times to about 4 times, about 2 times to about 5 times, about 2 times to about 6 times, about 2 times to about 7 times, about 2 times to about 8 times, about 2 times to about 9 times, about 2 times to about 10 times, about 2 times to about 11 times, about 2 times to about 12 times, about 3 times to about 4 times, about 3 times to about 5 times, about 3 times to about 6 times, about 3 times to about 7 times, about 3 times to about 8 times, about 3 times to about 9 times, about 3 times to about 10 times, about 3 times to about 11 times, about 3 times to about 12 times, about 4 times to about 5 times, about 4 times to about 6 times, about 4 times to about 7 times, about 4 times to about 8 times, about 4 times to about 9 times, about 4 times to about 10 times, about 4 times to about 11 times, about 4 times to about 12 times, about 5 times to about 6 times, about 5 times to about 7 times, about 5 times to about 8 times, about 5 times to about 9 times, about 5 times to about 10 times, about 5 times to about 11 times, about 5 times to about 12 times, about 6 times to about 7 times, about 6 times to about 8 times, about 6 times to about 9 times, about 6 times to about 10 times, about 6 times to about 11 times, about 6 times to about 12 times, about 7 times to about 8 times, about 7 times to about 9 times, about 7 times to about 10 times, about 7 times to about 11 times, about 7 times to about 12 times, about 8 times to about 9 times, about 8 times to about 10 times, about 8 times to about 11 times, about 8 times to about 12 times, about 9 times to about 10 times, about 9 times to about 11 times, about 9 times to about 12 times, about 10 times to about 11 times, about 10 times to about 12 times, or about 11 times to about 12 times. In some embodiments, the population of human MSCs is passaged at least about 1 time, about 2 times, about 3 times, about 4 times, about 5 times, about 6 times, about 7 times, about 8 times, about 9 times, about 10 times, about 11 times, or about 12 times. In some embodiments, the population of human MSCs is passaged at least at least about 1 time, about 2 times, about 3 times, about 4 times, about 5 times, about 6 times, about 7 times, about 8 times, about 9 times, about 10 times, or about 11 times. In some embodiments, the population of human MSCs is passaged at least at most about 2 times, about 3 times, about 4 times, about 5 times, about 6 times, about 7 times, about 8 times, about 9 times, about 10 times, about 11 times, or about 12 times.

In some embodiments, the population of human MSCs comprises a doubling rate of at least about 16 to 36 hours over the at least 4 passages. In some embodiments, the population of human MSCs comprises a doubling rate of about 14 hours to about 36 hours. In some embodiments, the population of human MSCs comprises a doubling rate of about 14 hours to about 16 hours, about 14 hours to about 18 hours, about 14 hours to about 20 hours, about 14 hours to about 22 hours, about 14 hours to about 24 hours, about 14 hours to about 26 hours, about 14 hours to about 28 hours, about 14 hours to about 30 hours, about 14 hours to about 32 hours, about 14 hours to about 34 hours, about 14 hours to about 36 hours, about 16 hours to about 18 hours, about 16 hours to about 20 hours, about 16 hours to about 22 hours, about 16 hours to about 24 hours, about 16 hours to about 26 hours, about 16 hours to about 28 hours, about 16 hours to about 30 hours, about 16 hours to about 32 hours, about 16 hours to about 34 hours, about 16 hours to about 36 hours, about 18 hours to about 20 hours, about 18 hours to about 22 hours, about 18 hours to about 24 hours, about 18 hours to about 26 hours, about 18 hours to about 28 hours, about 18 hours to about 30 hours, about 18 hours to about 32 hours, about 18 hours to about 34 hours, about 18 hours to about 36 hours, about 20 hours to about 22 hours, about 20 hours to about 24 hours, about 20 hours to about 26 hours, about 20 hours to about 28 hours, about 20 hours to about 30 hours, about 20 hours to about 32 hours, about 20 hours to about 34 hours, about 20 hours to about 36 hours, about 22 hours to about 24 hours, about 22 hours to about 26 hours, about 22 hours to about 28 hours, about 22 hours to about 30 hours, about 22 hours to about 32 hours, about 22 hours to about 34 hours, about 22 hours to about 36 hours, about 24 hours to about 26 hours, about 24 hours to about 28 hours, about 24 hours to about 30 hours, about 24 hours to about 32 hours, about 24 hours to about 34 hours, about 24 hours to about 36 hours, about 26 hours to about 28 hours, about 26 hours to about 30 hours, about 26 hours to about 32 hours, about 26 hours to about 34 hours, about 26 hours to about 36 hours, about 28 hours to about 30 hours, about 28 hours to about 32 hours, about 28 hours to about 34 hours, about 28 hours to about 36 hours, about 30 hours to about 32 hours, about 30 hours to about 34 hours, about 30 hours to about 36 hours, about 32 hours to about 34 hours, about 32 hours to about 36 hours, or about 34 hours to about 36 hours. In some embodiments, the population of human MSCs comprises a doubling rate of about 14 hours, about 16 hours, about 18 hours, about 20 hours, about 22 hours, about 24 hours, about 26 hours, about 28 hours, about 30 hours, about 32 hours, about 34 hours, or about 36 hours. In some embodiments, the population or human MSCs comprises a doubling rate of at least about 14 hours, about 16 hours, about 18 hours, about 2(1) hours, about 22 hours, about 24 hours, about 26 hours, about 28 hours, about 30 hours, about 32 hours, or about 34 hours. In some embodiments, the population of human MSCs comprises a doubling rate of at most about 16 hours, about 18 hours, about 20 hours, about 22 hours, about 24 hours, about 26 hours, about 28 hours, about 30 hours, about 32 hours, about 34 hours, or about 36 hours.

In some embodiments, the population of human MSCs comprises a doubling rate of at least about 16 to 36 hours over each of the at least 4 passages. In some embodiments, the population of human MSCs comprises a doubling rate of at least about 16 to 36 hours over the at least 5 passages. In some embodiments, the population of human MSCs comprises a doubling rate of at least about 16 to 36 hours over each of the at least 5 passages. In some embodiments, the population of human MSCs comprises a doubling rate of at least about 16 to 36 hours over the at least 6 passages. In some embodiments, the population of human MSCs comprises a doubling rate of at least about 16 to 36 hours over each of the at least 6 passages. In some embodiments, the population of human MSCs comprises a doubling rate of at least about 16 to 36 hours over the at least 7 passages. In some embodiments, the population of human MSCs comprises a doubling rate of at least about 16 to 36 hours over each of the at least 7 passages. In some embodiments, the population of human MSCs comprises a doubling rate of at least about 16 to 36 hours over the at least 8 passages. In some embodiments, the population of human MSCs comprises a doubling rate of at least about 16 to 36 hours over each of the at least IS passages. In some embodiments, the population of human MSCs comprises a doubling rate of at least about 16 to 36 hours over the at least 9 passages. In some embodiments, the population of human MSCs comprises a doubling rate of at least about 16 to 36 hours over each of the at least 9 passages. In some embodiments, the population of human MSCs comprises a doubling rate of at least about 16 to 36 hours over the at least 10 passages. In some embodiments, the population of human MSCs comprises a doubling rate of at least about 16 to 36 hours over each of the at least 10 passages. In some embodiments, the population of human MSCs comprises a doubling rate of less than about 29 hours. In some embodiments, the population of human MSCs comprises a doubling rate of less than about 29 hours. In some embodiments, the population of human MSCs comprises a doubling rate of less than about 29 hours. In some embodiments, the population of human MSCs comprises a doubling rate of less than about 29 hours. In some embodiments, the population of human MSCs comprises a doubling rate of less than about 29 hours. In some embodiments, the population of human MSCs comprises a doubling rate of less than about 29 hours. In some embodiments, the population of human MSCs comprises a doubling rate of less than about 29 hours.

In some embodiments, the population of human MSCs is derived from a bone. In some embodiments, the bone is a vertebral body. In some embodiments, the vertebral body is derived from a cadaver. In some embodiments, the population of human MSCs is derived from a population of un-passaged/fresh vertebral bone adherent (vBA) MSCs.

In some embodiments, the population of human MSCs is immune-suppressive. In some embodiments, the population of human MSCs suppresses CD4+ immune cell expansion by at least about 1 fold to about 4 fold. In some embodiments, the population of human MSCs suppresses CD4+ immune cell expansion by at least about 1 fold to about 2 fold, about 1 fold to about 3 fold, about 1 fold to about 4 fold, about 2 fold to about 3 fold, about 2 fold to about 4 fold, or about 3 fold to about 4 fold. In some embodiments, the population of human MSCs suppresses CD4+ immune cell expansion by at least about 1 fold, about 2 fold, about 3 fold, or about 4 fold. In some embodiments, the population of human MSCs suppresses CD4+ immune cell expansion by at least at least about 1 fold, about 2 fold, or about 3 fold. In some embodiments, the population of human MSCs suppresses CD4+ immune cell expansion by at least at most about 2 fold, about 3 fold, or about 4 fold. In some embodiments, the population of human MSCs suppresses CD4+ immune cell expansion by at least 1 fold. In some embodiments, the population of human MSCs suppresses CD4+ immune cell expansion by at least 2 fold. In some embodiments, the population of human MSCs suppresses CD4+ immune cell expansion by at least 3 fold. In some embodiments, the population of human MSCs suppresses CD4+ immune cell expansion by at least 4 fold. In some embodiments, the population of human MSCs suppresses CD4+ immune cell expansion by at least about 10% to about 95%. In some embodiments, the population of human MSCs suppresses CD4+ immune cell expansion by at least about 10% to about 20%, about 10% to about 30%, about 10% to about 40%, about 10% to about 50%, about 10% to about 60%, about 10% to about 70%, about 10% to about 80%, about 10% to about 90%, about 10% to about 95%, about 20% to about 30%, about 20% to about 40%, about 20% to about 50%, about 20% to about 60%, about 20% to about 70%, about 20% to about 80%, about 20% to about 90%, about 20% to about 95%, about 30% to about 40%, about 30% to about 50%, about 30% to about 60%, about 30% to about 70%, about 30% to about 80%, about 30% to about 90%, about 30% to about 95%, about 40% to about 50%, about 40% to about 60%, about 40% to about 70%, about 40% to about 80%, about 40% to about 90%, about 40% to about 95%, about 50% to about 60%, about 50% to about 70%, about 50% to about 80%, about 50% to about 90%, about 50% to about 95%, about 60% to about 70%, about 60% to about 80%, about 60% to about 90%, about 60% to about 95%, about 70% to about 80%, about 70% to about 90%, about 70% to about 95%, about 80% to about 90%, about 80% to about 95%, or about 90% to about 95%. In some embodiments, the population of human MSCs suppresses CD4+ immune cell expansion by at least about 10%, about 20%, about 30%, about 40%, about 50%, about 60%, about 70%, about 80%, about 90%, or about 95%. In some embodiments, the population of human MSCs suppresses CD4+ immune cell expansion by at least at least about 10%, about 20%, about 30%, about 40%, about 50%, about 60%, about 70%, about 80%, or about 90%. In some embodiments, the population of human MSCs suppresses CD4 immune cell expansion by at least at most about 2.0%, about 30%, about 40%, about 50%, about 60%, about 70%, about 80%, about 90%, or about 95%. In some embodiments, the population of human MSCs suppresses CD8+ immune cell expansion by at least about 1 fold to about 4 fold. In some embodiments, the population of human MSCs suppresses CD8+ immune cell expansion b at least about 1 fold to about 2 fold, about 1 fold to about 3 fold, about 1 fold to about 4 fold, about 2 fold to about 3 fold, about 2 fold to about 4 fold, or about 3 fold to about 4 fold. In some embodiments, the population of human MSCs suppresses CB8+ immune cell expansion by at least about 1 fold, about 2 fold, about 3 fold, or about 4 fold. In some embodiments, the population of human MSCs suppresses CD8+ immune cell expansion by at least at least about 1 fold, about 2 fold, or about 3 fold. In some embodiments, the population of human MSCs suppresses CD8+ immune cell expansion by at least at most about 2 fold, about 3 fold, or about 4 fold. In some embodiments, the population of human MSCs suppresses CD8+ immune cell expansion by at least 1 fold. In some embodiments, the population of human MSCs suppresses CD8+ immune cell expansion b at least 2 fold. In some embodiments, the population of human MSCs suppresses CD8+ immune cell expansion by at least 3 fold. In some embodiments, the population of human MSCs suppresses CD8+ immune cell expansion by at least about 10% to about 95%. In some embodiments, the population of human MSCs suppresses CD8+ immune cell expansion by at least about 10% to about 20%, about 10% to about 10%, about 10% to about 40%, about 10% to about 50%, about 10% to about 60%, about 10% to about 70%, about 10% to about 80%, about 10% to about 90%, about 10% to about 95%, about 20% to about 30%, about 20% to about 40%, about 20% to about 50% about 20% to about 60%, about 20% to about 70%, about 20% to about 80%, about 20% to about 90%, about 20% to about 95%, about 30% to about 40%, about 30% to about 50%, about 30% to about 60%, about 30% to about 70%, about 30% to about 80%, about 30% to about 90%, about 30% to about 95%, about 40% to about 50%, about 40% to about 60%, about 40% to about 70%, about 40% to about 80%, about 40% to about 90%, about 40% to about 95%, about 50% to about 60%, about 50% to about 70%, about 50% to about 80%, about 50% to about 90%, about 50% to about 95%, about 60% to about 70%, about 60% to about 80%, about 60% to about 90%, about 60% to about 95%, about 70% to about 80%, about 70% to about 90%, about 70% to about 95%, about 80% to about 90%, about 80% to about 95%, or about 90% to about 95%. In some embodiments, the population of human MSCs suppresses CD8+ immune cell expansion by at least about 10%, about 20%, about 30%, about 40%, about 50%, about 60%, about 70%, about 80%, about 90%, or about 95%. In some embodiments, the population of human MSCs suppresses CD8+ immune cell expansion by at least at least about 10%, about 20%, about 30%, about 40%, about 50%, about 60%, about 70%, about 80%, or about 90%. In some embodiments, the population of human MSCs suppresses CD8+ immune cell expansion by at least at most about 20%, about 30%, about 40%, about 50%, about 60%, about 70%, about 80%, about 90%, or about 95%.

In some embodiments, the population of human MSCs comprises less than 5% CD45+ cells. In some embodiments, the population of human MSCs comprises more than 1.75% CD45+ cells. In some embodiments, the composition of MSCs (e.g. vBA-MSCs) may be comprised of less than 5% CD45+. In some embodiments, the composition of MSCs may be comprised of less than about 0.5% CD45+ to about 10% CD45+. In some embodiments, the composition of MSCs may be comprised of less than about 10% CD45+ to about 9% CD45+, about 10% CD45+ to about 8% CD45+, about 10% CD45+ to about 7% CD45+, about 10% CD45+ to about 6% CD45+, about 10% CD45+ to about 5% CD45+, about 10% CD45+ to about 4% CD45+, about 10% CD45+ to about 3% CD45+, about 10% CD45+ to about 2% CD45+, about 10% CD45+ to about 1% CD45+, about 10% CD45+ to about 0.5% CD45+, about 9% CD45+ to about 8% CD45+, about 9% CD45+ to about 7% CD45+, about 9% CD45+ to about 6% CD45+, about 9% CD45+ to about 5% CD45+, about 9% CD45+ to about 4% CD45+, about 9% CD45+ to about 3% CD45+, about 9% CD45+ to about 2% CD45+, about 9% CD45+ to about 1% CD45+, about 9% CD45+ to about 0.5% CD45+, about 8% CD45+ to about 7% CD45+, about 8% CD45+ to about 6% CD45+, about 8% CD45+ to about 5% CD45+, about 8% CD45+ to about 4% CD45+, about 8% CD45+ to about 3% CD45+, about 8% CD45+ to about 2% CD45+, about 8% CD45+ to about 1% CD45+, about 8% CD45+ to about 0.5% CD45+, about 7% CD45+ to about 6% CD45+, about 7% CD45+ to about 5% CD45+, about 7% CD45+ to about 4% CD45+, about 7% CD45+ to about 3% CD45+, about 7% CD45+ to about 2% CD45+, about 7% CD45+ to about 1% CD45+, about 7% CD45+ to about 0.5% CD45+, about 6% CD45+ to about 5% CD45+, about 6% CD45+ to about 4% CD45+, about 6% CD45+ to about 3% CD45+, about 6% CD45+ about 2% CD45+, about 6% CD45+ to about 1% CD45+, about 6% CD45+ to about 0.5% CD45+, about 5% CD45+ to about 4% CD45+, about 5% CD45+ to about 3% CD45+, about 5% CD45+ to about 2% CD45+, about 5% CD45+ to about 1% CD45+, about 5% CD45+ to about 0.5% CD45+, about 4% CD45+ to about 3% CD45+, about 4% CD45+ to about 2% CD45+, about 4% CD45+ to about 1% CD45+, about 4% CD45+ to about 0.5% CD45+, about 3% CD45+ to about 2% CD45+, about 3% CD45+ to about 1% CD45+, about 3% CD45+ to about 0.5% CD45+, about 2% CD45+ to about 1% CD45+, about 2% CD45+ to about 0.5% CD45+, or about 1% CD45+ to about 0.5% CD45+. In some embodiments, the composition of MSCs may be comprised of less than about 10% CD45+, about 9% CD45+, about 8%

CD45+, about 7% CD45+, about 6% CD45+ about 5% CD45+ about 4% CD45+ about 3% CD45+, about 2% CD45+, about 1% CD45+, or about 0.5% CD45+. In some embodiments, the composition of MSCs may be comprised of less than at least about 10% CD45 about 9% CD45+, about 8% CD45+, about 7% CD45+, about 6% CD45+, about 5% CD45+, about 4% CD45+, about 3% CD45+, about 2% CD45+, or about 1 CD45+. In some embodiments, the composition of MSCs may be comprised of less than at most about 9% CD45+, about 8% CD45+, about 7% CD45+, about 6% CD45+, about 5% CD45+, about 4% CD4+, about 3% CD45+, about 2% CD45+, about 1% CD45+, or about 0.5% CD45+.

In some embodiments, the composition of MSCs (e.g. vBA-MSCs) may comprise, more than 1% CD45+ cells. In some embodiments, the composition of MSCs may comprise more than 1.1% CD45+ cells. In some embodiments, the composition of MSCs may comprise more than 12% CD45+ cells. In some embodiments, the composition of MSCs may comprise more than 1.3% CD45+ cells. In some embodiments, the composition of MSCs may comprise more than 1.4% CD45+ cells. In some embodiments, the composition of MSCs may comprise more than 1.5% CD45+ cells. In some embodiments, the composition of MSCs may comprise more than 1.6% CD45+ cells. In some embodiments, the composition of MSCs may comprise more than 1.7% CD45+ cells. In some embodiments, the composition of MSCs may comprise more than 1.8% CD45+ cells. In some embodiments, the composition of MSCs may comprise more than 19% CD45+ cells. In some embodiments, the composition of MSCs may comprise more than 1% CD45+ cells.

In some embodiments, the population of human MSCs comprises at least 90% CD105+ cells. In some embodiments, the composition of MSCs may be comprised of at least 90% CD105+ cells. In some embodiments, the composition of MSCs may be comprised of at least about 70% CD105+ cells to about 100% CD105+ cells. In some embodiments, the composition of MSCs may be comprised of at least about 100% CD105+ cells to about 95% CD105+ cells, about 100% CD105+ cells to about 94% CD105+ cells, about 100% CD105+ cells to about 93% CD105+ cells, about 100% CD105+ cells to about 92% CD105+ cells, about 100% CD105+ cells to about 91% CD105+ cells, about 100% CD105+ cells to about 90% CD105+ cells, about 100% CD105+ cells to about 85% CD105+ cells, about 100% CD105+ cells to about 80% CD105+ cells, about 100% CD105+ cells to about 75% CD105+ cells, about 100% CD105+ cells to about 70% CD105+ cells, about 95% CD105+ cells to about 94% CD105+ cells, about 95% CD105+ cells to about 93% CD105+ cells, about 95% CD105+ cells to about 92% CD105+ cells, about 95% CD105+ cells to about 91% CD105+ cells, about 95% CD105+ cells to about 90% CD105+ cells, about 95% CD105+ cells to about 85% CD105+ cells, about 95% CD105+ cells to about 80% CD105+ cells, about 95% CD105+ cells to about 75% CD105+ cells, about 95% CD105+ cells to about 70% CD105+ cells, about 94% CD105+ cells to about 93% CD105+ cells, about 94% CD105+ cells to about 92% CD105+ cells, about 94% CD105+ cells to about 91% CD105+ cells, about 94% CD105+ cells to about 90% CD105+ cells, about 94% CD105+ cells to about 85% CD105+ cells, about 94% CD105+ cells to about 80% CD105+ cells, about 94% CD105+ cells to about 75% CD105+ cells, about 93% CD105+ cells to about 92% CD105+ cells, about 93% CD105+ cells to about 91% CD105+ cells, about 93%

CD105+ cells to about 90% CD105+ cells, about 93% CD105+ cells to about 85% CD105+ cells, about 93% CD105+ cells to about 80% CD105+ cells, about 93% CD105+ cells to about 75% CD105+ cells, about 93% CD105+ cells to about 70% CD105+ cells, about 92% CD105+ cells to about 91% CD105+ cells, about 92% CD105+ cells to about 90% CD105+ cells, about 92% CD105+ cells to about 85% CD105+ cells, about 92% CD105+ cells to about 80% CD105+ cells, about 92% CD105+ cells to about 75% CD105+ cells, about 92% CD105+ cells to about 70% CD105+ cells, about 91% CD105+ cells to about 90% CD105+ cells, about 91% CD105+ cells to about 85% CD105+ cells, about 91% CD105+ cells to about 80% CD105+ cells, about 91% CD105+ cells to about 75% CD105+ cells, about 91% CD105+ cells to about 70% CD105+ cells, about 90% CD105+ cells to about 85% CD105+ cells, about 90% CD105+ cells to about 80% CD105+ cells, about 90% CD105+ cells to about 75% CD105+ cells, about 90% CD105+ cells to about 70% CD105+ cells, about 85% CD105+ cells to about 80% CD105+ cells, about 85% CD105+ cells to about 75% CD105+ cells, about 85% CD105+ cells to about 70% CD105+ cells, about 80% CD105+ cells to about 75% CD105+ cells, about 80% CD105+ cells to about 70% CD105+ cells, about 75% CD105+ cells to about 70% CD105+ cells, or about 75% CD105+ cells to about 70% CD105+ cells. In some embodiments, the composition of MSCs may be comprised of at least about 100% CD105+ cells, about 95% CD105+ cells, about 94% CD105+ cells, about 93% CD105+ cells, about 92% CD105+ cells, about 91% CD105+ cells, about 90% CD105+ cells, about 85% CD105+ cells, about 80% CD105+ cells, about 75% CD105+ cells, or about 70% CD105+ cells. In some embodiments, the composition of MSCs may be comprised of at least at least about 100% CD105+ cells, about 95% CD105+ cells, about 94% CD105+ cells, about 93% CD105+ cells, about 92% CD105+ cells, about 91% CD105+ cells, about 90% CD105+ cells, about 85% CD105+ cells, about 80% CD105+ cells, or about 75% CD105+ cells. In some embodiments, the composition of MSCs may be comprised of at least at most about 95% CD105+ cells, about 94% CD105+ cells, about 93% CD105+ cells, about 92% CD105+ cells, about 91% CD105+ cells, about 90% CD105+ cells, about 85% CD105+ cells, about 80% CD105+ cells, about 75% CD105+ cells, or about 70% CD105+ cells.

In some embodiments, the population of human MSCs comprises at least 90% CD166+ cells. In some embodiments, the composition of MSCs may be comprised of at least 90% CD166+ cells. In some embodiments, the composition of MSCs may be comprised of at least about 70% CD166+ cells to about 100% CD166+ cells. In some embodiments, the composition of MSCs may be comprised of at least about 100% CD166+ cells to about 95% CD166+ cells, about 100% CD166+ cells to about 94% CD166+ cells, about 100% CD166+ cells to about 93% CD166+ cells, about 100% CD166+ cells to about 92% CD166+ cells, about 100% CD166+ cells to about 91% CD166+ cells, about 100% CD166+ cells to about 90% CD166+ cells, about 100% CD166+ cells to about 85% CD166+ cells, about 100% CD166+ cells to about 80% CD166+ cells, about 100% CD166+ cells to about 75% CD166+ cells, about 100% CD166+ cells to about 70% CD166+ cells, about 95% CD166+ cells to about 94% CD166+ cells, about 95% CD166+ cells to about 93% CD166+ cells, about 95% CD166+ cells to about 92% CD166+ cells, about 95% CD166+ cells to about 91% CD166+ cells, about 95% CD166+ cells to about 90% CD166+ cells, about 95% CD166+ cells to about 85% CD166+ cells, about 95%
CD166+ cells to about 80% CD166+ cells, about 95%
CD166+ cells to about 75% CD166+ cells, about 95%
CD166+ cells to about 70% CD166+ cells, about 94%
CD166+ cells to about 93% CD166+ cells, about 94%
CD166+ cells to about 92% CD166+ cells, about 94%
CD166+ cells to about 91% CD166+ cells, about 94%
CD166+ cells to about 90% CD166+ cells, about 94%
CD166+ cells to about 85% CD166+ cells, about 94%
CD166+ cells to about 80% CD166+ cells, about 94%
CD166+ cells to about 75% CD166+ cells, about 94%
CD166+ cells to about 70% CD166+ cells, about 93%
CD166+ cells to about 92% CD166+ cells, about 93%
CD166+ cells to about 91% CD166+ cells, about 93%
CD166+ cells to about 90% CD166+ cells, about 93%
CD166+ cells to about 85% CD166+ cells, about 93%
CD166+ cells to about 80% CD166+ cells, about 93%
CD166+ cells to about 75% CD166+ cells, about 93%
CD166+ cells to about 70% CD166+ cells, about 92%
CD166+ cells to about 91% CD166+ cells, about 92%
CD166+ cells to about 90% CD166+ cells, about 92%
CD166+ cells to about 85% CD166+ cells, about 92%
CD166+ cells to about 80% CD166+ cells, about 92%
CD166+ cells to about 75% CD166+ cells, about 92%
CD166+ cells to about 70% CD166+ cells, about 91%
CD166+ cells to about 90% CD166+ cells, about 91%
CD166+ cells to about 85% CD166+ cells, about 91%
CD166+ cells to about 80% CD166+ cells, about 91%
CD166+ cells to about 75% CD166+ cells, about 91%
CD166+ cells to about 70% CD166+ cells, about 90%
CD166+ cells to about 85% CD166+ cells, about 90%
CD166+ cells to about 80% CD166+ cells, about 90%
CD166+ cells to about 75% CD166+ cells, about 90%
CD166+ cells to about 70% CD166+ cells, about 85%
CD166+ cells to about 80% CD166+ cells, about 85%
CD166+ cells to about 75% CD166+ cells, about 85%
CD166+ cells to about 70% CD166+ cells, about 80%
CD166+ cells to about 75% CD166+ cells, about 80%
CD166+ cells to about 70% CD166+ cells, or about 75%
CD166+ cells to about 70% CD166+ cells. In some embodiments, the composition of MSCs may be comprised of at least about 100% CD166+ cells, about 95% CD166+ cells, about 94% CD166+ cells, about 93% CD166+ cells, about 92% CD166+ cells, about 91% CD166+ cells, about 90% CD166+ cells, about 85% CD166+ cells, about 80% CD166+ cells, about 75% CD166+ cells, or about 70% CD166+ cells. In some embodiments, the composition of MSCs may be comprised of at least at least about 100% CD166+ cells, about 95% CD166+ cells, about 94% CD166+ cells, about 93% CD166+ cells, about 92% CD166+ cells, about 91% CD166+ cells, about 90% CD166+ cells, about 85% CD166+ cells, about 80% CD166+ cells, or about 75% CD166+ cells. In some embodiments, the composition of MSCs may be comprised of at least at most about 95% CD166+ cells, about 94% CD166+ cells, about 93% CD166+ cells, about 92% CD166+ cells, about 91% CD166+ cells, about 90% CD166+ cells, about 85% CD166+ cells, about 80% CD166+ cells, about 75% CD166+ cells, or about 70% CD166+ cells.

In some embodiments, the population of human MSCs comprises at least about 20% cells in the S phase of the cell cycle to about 60% cells in the S phase of the cell cycle. In some embodiments, the population of human MSCs comprises at least about 20% cells in the S phase of the cell cycle to about 30% cells in the S phase of the cell cycle, about 20% cells in the S phase of the cell cycle to about 35% cells in the S phase of the cell cycle, about 20% cells in the S phase of the cell cycle to about 40% cells in the S phase of the cell cycle, about 20% cells in the S phase, of the cell cycle, to about 45% cells in the S phase of the cell cycle, about 20% cells in the S phase of the cell cycle to about 50% cells in the S phase of the cell cycle, about 20% cells in the S phase of the cell cycle to about 55% cells in the S phase of the cell cycle, about 20% cells in the S phase of the cell cycle, to about 60% cells in the S phase of the cell cycle, about 30% cells in the S phase of the cell cycle to about 35% cells in the S phase of the cell cycle, about 30% cells in the S phase of the cell cycle to about 40% cells in the S phase of the cell cycle, about 30% cells in the S phase of the cell cycle to about 45% cells in the S phase of the cell cycle, about 30% cells in the S phase of the cell cycle, to about 50% cells in the S phase of the cell cycle, about 30% cells in the S phase of the cell cycle to about 55% cells in the S phase of the cell cycle, about 30% cells in the S phase of the cell cycle to about 60% cells in the S phase of the cell cycle, about 35% cells in the S phase of the cell cycle to about 40% cells in the S phase of the cell cycle, about 35% cells in the S phase of the cell cycle to about 45% cells in the S phase of the cell cycle, about 35% cells in the S phase of the cell cycle to about 50% cells in the S phase of the cell cycle, about 35% cells in the S phase of the cell cycle to about 55% cells in the S phase of the cell cycle, about 35% cells in the S phase of the cell cycle to about 60% cells in the S phase of the cell cycle, about 40% cells in the S phase of the cell cycle to about 45% cells in the S phase of the cell cycle, about 40% cells in the S phase of the cell cycle to about 50% cells in the S phase of the cell cycle, about 40% cells in the S phase of the cell cycle to about 55% cells in the S phase of the cell cycle, about 40% cells in the S phase of the cell cycle to about 60% cells in the S phase of the cell cycle, about 45% cells in the S phase of the cell cycle to about 50% cells in the S phase of the cell cycle, about 45% cells in the S phase of the cell cycle to about 55% cells in the S phase of the cell cycle, about 45% cells in the S phase of the cell cycle to about 60% cells in the S phase of the cell cycle, about 50% cells in the S phase of the cell cycle to about 55% cells in the S phase of the cell cycle, about 50% cells in the S phase of the cell cycle to about 60% cells in the S phase of the cell cycle, or about 55% cells in the S phase of the cell cycle, to about 60% cells in the S phase of the cell cycle. In some embodiments, the population of human MSCs comprises at least about 20% cells in the S phase of the cell cycle, about 30% cells in the S phase of the cell cycle, about 35% cells in the S phase of the cell cycle, about 40% cells in the S phase of the cell cycle, about 45% cells in the S phase of the cell cycle, about 50% cells in the S phase of the cell cycle, about 55% cells in the S phase of the cell cycle, or about 60% cells in the S phase of the cell cycle. In some embodiments, the population of human MSCs comprises at least at least about 20% cells in the S phase of the cell cycle, about 30% cells in the S phase of the cell cycle, about 35% cells in the S phase of the cell cycle, about 40% cells in the S phase of the cell cycle, about 45% cells in the S phase of the cell cycle, about 50% cells in the S phase of the cell cycle, or about 55% cells in the S phase of the cell cycle. In some embodiments, the population of human MSCs comprises at least at most about 30% cells in the S phase of the cell cycle, about 35% cells in the S phase of the cell cycle, about 40% cells in the S phase of the cell cycle, about 45% cells in the S phase of the cell cycle, about 50% cells in the S phase of the cell cycle, about 55% cells in the S phase of the cell cycle, or about 60% cells in the S phase of the cell cycle. In some embodiments, the population of human MSCs comprises at least 40% cells in the S phase of the cell cycle. In some embodiments, the population of human MSCs comprises at least 45% cells in the S phase of the cell cycle. In some embodiments, the population of human MSCs comprises at least 50% cells in the S phase of the cell cycle. In some embodiments, the population of human MSCs comprises at least 55% cells in the S phase of the cell cycle.

The present disclosure should be considered as illustrative and not restrictive in character. It is understood that only certain embodiments have been presented and that all changes, modifications and further applications that come within the spirit of the disclosure are desired to be protected.

While preferred embodiments of the present invention have been shown and described herein, it will be obvious to those skilled in the art that such embodiments are provided by way of example only. It is not intended that the invention be limited by the specific examples provided within the specification. While the invention has been described with reference to the aforementioned specification, the descriptions and illustrations of the embodiments herein are not meant to be construed in a limiting sense, Numerous variations, changes, and substitutions will now occur to those skilled in the ail without departing from the invention. Furthermore, it shall be understood that all aspects of the invention are not limited to the specific depictions, configurations or relative proportions set forth herein which depend upon a variety of conditions and variables. It should be understood that various alternatives to the embodiments of the invention described herein may be employed in practicing the invention. It is therefore contemplated that the invention shall also cover any such alternatives, modifications, variations or equivalents, it is intended that the following claims define the scope of the invention and that methods and structures within the scope of these claims and their equivalents be covered thereby.

EMBODIMENTS

1. A composition, comprising about at least 10 million cadaveric human mesenchymal stem cells (MSCs), wherein said composition is capable of inhibiting an immune response within a subject.

2. The composition of embodiment 1, wherein said composition comprises less than 5% CD45+ cells.

33. The composition of embodiment 1, wherein said composition comprises at least 90% CD105+ cells.

4. The composition of embodiment 1, wherein said composition comprises at least 90% CD166+ cells.

5. The composition of embodiment 1, wherein said cadaveric human MSCs comprise cadaveric human MSCs derived from bone marrow, adherent vertebral body MSCs (vBA-MSCs) or both.

6. The composition of embodiment 1, wherein said immune response is a rejection of a vascular composite allotransplant (VCAs) of an organ to said subject.

7. The composition of embodiment 6, wherein said organ is limb.

8. The composition of embodiment 6, wherein said organ is a heart, kidney, liver, lung, pancreas, intestine, thymus, or uterus.

9. The composition of embodiment 6, wherein said organ is skin.

10. The composition of embodiment 1, wherein said composition comprises about at least 10 million, 100 million, 1 billion, or 10 billion cadaveric human MSCs, 11. A method of treating a medical condition in a subject suffering thereof, comprising administering to said subject a composition comprising at least 10 million cadaveric human MSCs.

12. The method of embodiment 11, wherein said cell composition inhibits an immune response within said subject.

13. The method of embodiment 11, wherein said medical condition is an autoimmune disease.

14. The method of embodiment 11, wherein said medical condition is a myocardial infarction.

15. The method of embodiment 11, wherein said medical condition is chronic obstructive pulmonary disease (COPD) or acute respiratory distress syndrome 16. The method of embodiment 11, wherein said medical condition is arthritis.

17. The method of embodiment 11, wherein said composition comprises at least 10 million, 100 million, 1 billion, or 10 billion cadaveric human MSCs.

18. The method of embodiment 11, further comprising generating CD45−huCD73+huCD90+ cells within said subject.

19. The method of embodiment 11, wherein said cadaveric human MSCs comprise cadaveric human MSCs derived from bone marrow, adherent vertebral body MSCs (vBA-MSCs), or both.

20. A method of preparing a composition comprising cadaveric human MSCs, comprising:
   A. providing a bone derived from a deceased donor;
   B. grinding said bone into one or more ground bone segments.
   C. filtering said one or more ground bone segments; and
   D. extracting said cadaveric human MSCs from said one or more ground bone segments.

21. The method of embodiment 20, wherein said extracting of said cadaveric human MSCs comprises contacting said bone with a digestion solution.

22. The method of embodiment 21, wherein said digestion solution comprises one or more distinct enzymes.

23. The method of embodiment 22, wherein said one or more distinct enzymes comprise one or more collagenases and a neutral protease.

24. The method of embodiment 23, wherein said one or more collagenases comprise collagenase isoforms C1 and C2 at a ratio comprising more collagenase isoform C1 than collagenase isoform C2.

25. The method of embodiment 24, wherein said ratio of collagenase isoform C1 to collagenase isoform C2 is about 30 to about 70:about 10 to about 29.

26. The method of embodiment 25, wherein said ratio of collagenase isoform C1 to collagenase C2 is 35:15.

27. The method of embodiment 21, wherein said digestion solution is present at a ratio of volume to weight of said bane and said digestion solution of about 1:1 to about 15:1.

28. The method of embodiment 23, wherein said digestion solution comprises about 2 to about 20 U/ml of said neutral protease.

29. The method of embodiment 28, wherein said digestion solution comprises said neutral protease at an activity of about 19.6 U/ml.

30. The method of embodiment 21, wherein said digestion solution is contacted with said bone for tap to about 3 hours.

31. The method of embodiment 20, wherein at least 10 million, 100 million, 1 billion, or 10 billion cadaveric human MSCs are extracted from said one or more ground bone segments.

32. A composition, comprising:
at least about 10 million cadaveric human mesenchymal stem cells (MSCs) and at least about 500,000 nucleated bane marrow cells or derivatives thereof,
wherein said composition is capable of inhibiting an immune response.

33. The composition of embodiment 32, wherein said composition further comprises a human organ.

34. The composition of embodiment 33, wherein said human organ is a heart, kidney, liver, lung, pancreas, intestine, thymus, or uterus.

35. The composition of embodiment 32, wherein said nucleated bone marrow cells or derivatives thereof comprise hematopoietic stem cells (HSCs).

36. The composition of embodiment 32, wherein said cadaveric human MSCs comprises a matched HLA haploid type as said nucleated bone marrow cells or derivatives thereof.

37. The composition of embodiment 33, wherein said cadaveric human MSCs comprises a matched HLA haploid type as said human organ.

38. The composition of embodiment 33, wherein said cadaveric human MSCs comprises a mis matched HLA haploid type as said human organ.

39, The composition of embodiment 33, wherein said cadaveric human MSCs and said nucleated bone marrow cells or derivatives thereof comprise a mis-matched HLA haploid type as said human organ.

40. The composition of embodiment 32, wherein said composition comprises at least 100 million, 1 billion, or 10 billion cadaveric human MSCs.

41. The composition of embodiment 32, wherein said composition comprises at least 1 million, 1.5 million, or 2 million nucleated bone marrow cells or derivatives thereof.

42. The composition of embodiment 32, wherein said cadaveric human MSCs comprise cadaveric human MSCs derived from bone marrow, adherent vertebral body MSCs (vBA-MSCs), or both.

43. A method of treating a medical condition in a subject suffering thereof, comprising:
   a. administering at least 500,000 nucleated bone marrow cells or derivatives thereof to said in need thereof; and
   b. administering at least 10 million cadaveric human mesenchymal stem cells (MSCs) to said subject suffering thereof.

44. The method of embodiment 43, wherein said medical condition comprises an autoimmune disease.

45. The method of embodiment 44, wherein said autoimmune disease comprises graft verses host disease (GVHD).

46. The method of embodiment 43, wherein said nucleated bone marrow cells or derivatives thereof comprise hematopoietic stem cells (HSCs).

47. The method of embodiment 43, wherein said cadaveric human MSCs comprises a matched HLA haploid type as said nucleated bone marrow cells or derivatives thereof.

48. The method of embodiment 43, wherein said cadaveric human MSCs comprises a mis matched HLA haploid type as said nucleated bone marrow cells or derivatives thereof.

49, The method of embodiment 43, further comprising, prior to (a), transplanting an organ into said subject suffering from said medical condition.

50. The method of embodiment 49, wherein said cadaveric human MSCs and said nucleated bone marrow cells or derivatives thereof comprise a mis-matched HLA haploid type as said human organ.

51. The method of embodiment 49, further comprising administering rapamycin to said subject in need thereof.

52. The method of embodiment 49, further comprising administering CTLA4-Ig to said subject.

53. The method of embodiment 43, further comprising generating CD45+H2d+ cells in a background of CD45+H2b+ cells.

54. The method of embodiment 43, further comprising generating CD45−huCD73+huCD90+ cells.

55. The method of embodiment 43, further comprising generating a mixed chimerism within said subject.

56. The method of embodiment 55, wherein said mixed chimerism is maintained for at least 120 days from administration of said nucleated bone marrow cells.

57. The method of embodiment 43, further comprising additionally administering at least 10 million cadaveric human mesenchymal stein cells (MSCs) to said subject in need thereof 1 day after (b), 2 days after (b), 3 days after (b). 4 days after (b), or any combination thereof.

58. The composition of embodiment 1, wherein said at least 10 million cadaveric human MSCs comprise more than 1.75% CD45+ cells.

59. The composition of embodiment 1, wherein said at least 10 million cadaveric human comprise less MIC-A+ cells, MIC-B+ cells, ULBP2+ cells, or any combination thereof, relative to bone marrow-derived MSCs.

EXAMPLES

The following illustrative examples are representative of embodiments of the systems and methods described herein and are not meant to be limiting in any way.

Example 1. Tissue Processing

Described herein is an exemplary tissue processing protocol. In some cases, the tissue being processed can be vertebral bodies. In some cases, the tissue processing protocol can yield the bone marrow cells described herein.
A. Tissue Debriding
   1. Spray down the surface of the exterior bag of fresh VBs with 70% isopropanol. In hood, remove outer nonsterile bag and dispose. Open inner bag and dispose of bag.
   2. Unwrap specimen from blue towel and lap sponges. Record presence of packing materials and condition of the spine for: minimum 2 layers of sterile bags; blue towel; lap sponges; tissue moisture maintenance; and presence of pedicles.
   3. Record the start time for tissue debriding.
   4. Remove soft tissue surrounding pedicles to reveal correct sawing location. Scrape off exterior tissue with osteotomes.
   5. If present, saw through pedicles. Retain anterior VBs and discard pedicles and posterior elements. Avoid exposing cancellous tissue.
   6. Separate VBs by slicing through discs using the boning knife.
   7. Remove remaining soft tissue front each individual VB surface, using a combination of scissors, knives, and osteotomes, Make note of any anatomical pathologies or injury during recovery (e.g. bone spurs, herniated discs, and degenerative discs, cuts into VBs from recovery, of others such as brittle bones).

8. Count the number of intact VBs and determine the levels recovered (e.g. T8-L5) Discard any VBs that were damaged during recovery and have cancellous tissue exposed.

9. Spray balance (CS-5000 model) with 70% IPA and place in a clean area inside the Biosafety cabinet (BSC). Tare balance with the sterile bag. Place VBs that will be processed further into the sterile bag, and record mass. Record the # of VBs used for BM extraction.

B. Surface Decontamination

1. Record the temperature of the VBs.

2. Place VBs into a sterile bag, then add 1 L of 10% bleach solution to the bag and ensure all VBs are submerged. Once bleach is added to the VB bag, immediately start, a timer for 10 minutes. Allow 10 minutes of contact time before proceeding to BA.

3. Remove all used processing equipment and drapes from the hood and remove soiled gloves. Clean BSC with 70% IPA and allow to city before proceeding.

4. After 10 minutes of bleach solution contact time, immediately begin transfer of the VBs into a new sterile bag using a pair of sterile, long handled forceps.

5. Add 1 L of 3% hydrogen peroxide solution to the bag. Ensure TBs are completely submerged. Close the bag and shake briefly.

6. Transfer the VBs into a new sterile bag using new, sterile, long handled forceps.

7. Fill the bag with 1 L of Plasma-Lyte. Close the bag and shake briefly.

8. Transfer the VBs into a new sterile bag using new, sterile long handled forceps.

9. Fill the bag with 1 L of Plasma-Lyte. Close the bag and shake briefly.

10. Transfer the VBs to a sterile pan using long handled forceps. Use sterile gauze or lap sponges to absorb excessive liquid if needed.

11. Record the end time for surface decontamination.

C. Bone Grinding

1. Document the device used for grinding VBs and set tip per EO-4 Bone Grinder Operation and Maintenance or EO-39 CCF Bone Grinder.

2. Record the grinding start time.

3. Obtain 1 L Grind media prepared at the beginning of the process.

4. Pour—300 mL of Grind Media into one sterile, stainless-steel pitcher. This pitcher will be called "Pitcher 1" and will contain cut VB pieces. Pour—300 mL of Grind Media into another pitcher or catch pan named. "Pitcher 2", to catch grindings. An additional—300 mL will be used for rinsing, through grinder while grinding. The remaining—100 mL of Grind Media will be set aside for final rinsing of grinder and Pitcher 2 after all pieces are ground.

5. Place Pitcher 2 underneath the grinder head.

6. Using a clean drape and gloves donned, cut VBs into pieces of adequate size for the grinder using hand eating tool. Cut pieces should immediately be submerged in Pitcher 1 with Grind Media.

7. Verify that IL of grind media was used and is in Pitcher 2. Turn off grinder and record the grinding end time.

D. Filtration

1. Open a Bone Marrow Collection Kit and record the mass of one empty, 600 mL TRANSFER-PACK using the VWR-3000P balance. Empty Mass of 600 mL TRANSFER-PACK.

2. Assemble the bone marrow filtration kit and perform the bone marrow extraction following Bone Marrow Collection and Filtration of Example 1 using a total of 1000 mL of Rinse Media (2×500 mL). Note: Total media volume after is 2 L (1 L Grind media and 1 L Rinse Media.

3. Document the mass (g) of each filled 600 mL TRANSFER-PACK and calculate the total mass of all 6 TRANSFER-PACKs, 4. Calculate the total mass of bone marrow (BM) extract: Total Mass (g) (D.3 [B]), Empty Mass (g) (D.1 [A]), Empty Mass of all TRANSFER-PACKS (g) (A×6), and Total Mass of BM Extract (g) (B-C).

5. Intermediate Accountability: Total Mass of BM Extract>1800 g (if yes, proceed; if no alert supervisor).

6. Close the clamp on the extra 2000 mL, TRANSFER-PACK and save for later use.

7. Visually inspect the bone marrow (EM) in each TRANSFER-PACK to confirm there are no visible grindings or soft tissue. If excessive clumping is observed during filtration, notify area management.

8. Identify the first TRANSFER-PACK filtered. Mix TRANSFER-PACK by inversion and then remove 0.3 ml, of BM using a lii syringe inside BSC. Place sample in a pre-labeled tube with the ISBT # and "QC 1" along with the date and time. Submit sample to QC for testing on the Sysmex Hematology Analyzer. Record results below and calculate the TNC (use same number of significant figures from QC1 Sysmex WBC concentration). Processing may proceed prior to obtaining this result. Note: Assume density of 1 g/ml.

9. Seal the tubing near the connector on the end of each of the six TRANSFER-PACKs collected and label with the ISBT #.

10. Record the filtration end time.

E. Removal of Fat

1. Pair up TRANSFER-PACKs and use taring sticks so that the centrifuge is balanced prior to operation. Use volume compensating plates to prevent creasing of bags during centrifugation.

2. Set the centrifuge to 500× g for 15 minutes at room temperature, with a brake setting of 4 Centrifuge TRANSFER-PACKs with tubing down, 3. While TRANSFER-PACKS are in the centrifuge, remove all drapes and supplies from the BSC and clean all surfaces with 70% isopropyl alcohol (IPA).

4. Carefully remove TRANSFER-PACK, one at a time, from the centrifuge and hang on a ring stand.

5. Weld on an empty, new 600 mL Fenwal bag post-fat intermediate hag) to the centrifuged TRANSFER-PACK. Label the new post-fat intermediate bag with the ISBT #. Inspect the weld prior to proceeding.

6. With the centrifuged TRANSFER-PACK hanging on one ring stand, place a bag clamp just below the fat, and open the weld on the tubing and drain pellet into new post-fat intermediate bag Agitate the pellet and spike ports gently to resuspend all pellet. Allow at least half of the volume from the centrifuged bag to drain into the post-fat intermediate bag before proceeding. Note: It is best practice to not allow all the liquid to drain out from above the clamp. If liquid seems to be draining quickly, use one hand to press the clamp closed to slow the draining of liquid.

7, Close the tubing with a hemostat or tube sealer.

8. Weld the next centrifuged TRANSFER-PACK onto the same post-fat intermediate bag used to collect the pellet in E.6. Leave enough tubing on this bag for future welds.

9. Repeat E.6.-E.7.

10. For the next two centrifuged TRANSFER-PACKs, repeat E.4.-E.9, creating the second post-fat intermediate bag.

11. Repeat E.4.-E.9, for the final two centrifuged bags creating a third post-fat intermediate bag.

F. Concentrate

1. Set the centrifuge to 500× g for 15 minutes at room temperature, with a brake setting of 4 Centrifuge post-fat intermediate bags with tubing up. Use volume compensating plates to prevent creasing of bags during centrifugation.

2. Carefully remove a post-fat intermediate bag from the centrifuge and hang on the plasma press. Only remove one bag at a time from the centrifuge.

3. For each bag centrifuged, weld on a 1000 mL waste bag (label as "Waste") and use the plasma extractor to remove the supernatant into the waste bag, Use a hemostat to clamp tubing as soon as the pellet breaks or when the pellet rises close to the top.

4. Seal the tubing and cut through to remove the post-fat intermediate bag from the waste bag, leaving enough tubing attached for welding. Weld on a female lure extension.

5. Repeat F.2.-F.4. for each post-fat intermediate bag.

6. Discard waste bags in biohazard trash bag.

7. Label a new, empty 2 L bulk bag from the BM filtration kit with the ISBT #, then measure and record the mass. If the bag is removed from the BSC for weighting, clean the luer connection with sterile alcohol after returning to the BSC. Wait until dry before proceeding.

8. For the following materials, spray with 70% IPA, place inside the BSC and wait until thy before proceeding: 50 mL syringes (3), 30 mL syringe, 50 mL conical tube and rack, Rinse Media.

9. Combine pellets from each of the three small bags into the pre-weighed bulk bag using a new 50 mL syringe for each small bag. Note: Press down on the plunger of the syringe slowly and avoid creating bubbles.

10. Aseptically transfer 25 mL of rinse media into a 50 mL conical tube. Use a new 30 mL syringe to rinse each bag serially with –20 mL of Rinse Media and add to the bulk bag. Note: A 50 mL syringe may be used to carry volume between bags if 30 mL syringe is too small.

G. Sampling and Accountability

1. On the bulk bag, open the clamp and drain BM extract in the tubing back into the bag. Invert bag three times minimum to mix, ensuring all pellet is resuspended. Remove about 0.5 mL of BM extract using a 1 mL syringe inside BSC. Place sample volume in a pre-labeled sterile sample tube with the ISBT # and "QC2" along with the date and time of sample collection. Submit sample to QC for testing, along with at least 50 mL of Rinse Media. Record the time samples were submitted for testing.

2. Measure and record the mass of the bulk bag of bone marrow extract. Subtract the empty mass from the filled mass to get the mass of BM extract (one decimal place), including empty mass [G] (g), filled mass [H] (g), and mass of BM extract [H-G] (g).

3. Record results from QC2 printout below and calculate QC2 concentration and the QC2 TNC Count (use the same number of significant figures from QC2 Sysmex WBC concentration for QC2 TNC Count). Note: Assume density of 1 g/mL, including QC2 Sysmex WBC Concentration (cells/μL); QC2 Dilution Factor, QC2 Concentration (cells/mL) (K×L×1000); and QC2 TNC Count [M×G.2 (J)].

4. Calculate the TNC % Yield to one decimal place for QC2 TNC Count (G.3 [N]); QC1 (D.8 [F]); and % Yield=(N÷F)×100.

H. Determining the Number of Bags

1. Record the QC2 TNC count from [G.3 (N)]. Calculate the total volume needed (one decimal place), Total Volume Needed (mL) [N÷(140×106)] NOTE: if the volume is less that) 228.9 mL, alert production supervisor.

2. Determine the number of bags and vials to prepare using the total volume needed previously.

3. Calculate the volume of freeze media needed, volume of Rinse Media, and volume of DMSO to add. Round calculated numbers to one decimal place (Total Volume Needed (H.1 [P]; Mass of BM Extract [G.2.J] (g is approximately ml); Total Vol. Freeze Media (Q-R); Vol. of DMSO (Q×0.1); and Vol. of Rinse Media (S-T). Note: Assume density of BM extract is 1 g/ml.

I. Cryoprotectant Addition

1. Prepare the freeze media using rinse media prepared per B-6 of and 100% DMSO. Add the volume of rinse media calculated in H.3 [U] to a sterile bottle labeled "Freeze Media" with the date prepared.

2. Add the volume of DMSO calculated in H.3 [T] to the freeze media bottle. Gently invert the bottle once to mix.

3. Record the temperature of the Freeze Media.

4. If temperature of the Freeze Media is >25.0° C., wait until the temperature of the Freeze media decreases to <25.0° C. Record the new temperature of the Freeze Media prior to use if applicable.

5. inside BSC place the BM bulk bag on a rocker for mixing. Remove the plunger of a large syringe and connect to the lure port on the bulk bag. Keep the syringe upright during the entire addition.

6. Calculate the volume of Freeze media to add per minute to the bulk bag as determined by volume of Freeze Media (H.3. [S]) and volume to Add per Minute (S×0.1).

7. Set a tinier for 10 Minutes and begin adding freeze media through the syringe at a rate of 10% of the freeze media volume per minute, calculated in 1.6, 8. Record the start and end time of the DMSO addition. Aim for elapsed time between 9-11 minutes.

J. Cryopreservation

1. Determine the number of cryopreservation bags and surrogate vials needed. Close clamps and label cryo-preservation bags with the prepared product labels, containing the ISBT number, product name, and date processed. Note: Label is placed inside the pocket on the top right of each bag. Use the tube sealer to tack the pocket so that the label will not fall out.

2. Use a 10 ml syringe to pull the entire volume for surrogate vials needed and fill with bone marrow (1 ml per vial).

3. For each cryopreservation bag, inside the BSC, use a new 100 ml syringe to fill the bag with 65 ml of bone marrow.

4. Unscrew the syringe to allow the tubing to drain back into the bag, then re-attach the syringe and draw air out of the bag while holding system upright.

5. Clamp tubing when bone marrow fills tubing, just before passing the Y connector. Discard syringe and replace cap.

6. Mix the bulk bag by inversion before removing more volume. Repeat J.3-J.5 for each cryopreservation bag of product to prepare.

7. Record the actual number of bags prepared.

8. If there is bone marrow left in the bulk bag, vials for research use may be prepared. Label the required number of 5 ail, cryovials and fill each one with 5 mL of BM by syringe or pipette.

9. Use the tube scaler to seal the tubing to create four segments oil each product bag for cryopreservation.

10. Record the end time for bagging. Note: Product and samples must be frozen as quickly as possible after addition of DMSO.

11. Notify QC that bags are ready for cryopreservation. Note: QC will perform a packaging inspection prior to freezing product bags.

12. For each cryopreservation bag, cut through the seal lira the tubing to remove 4 segments.

13. Document SmartCool boxes and Green CoolCells used.

14. Record the date and time the cassettes and samples were placed in the freezer.

15. Document Purple CoolCells used and freeze vials prepared for research use according to Cryopreservation (J) of Example 1 Record the date and time vials were placed in the freezer.

Example 2, Optimizing Digestion and MSC Recovery from Vertebral Bone Fragments Using a Combination of Purified Collagenase and Neutral Protease The scope of this experiment encompassed the investigation of a ratio and concentrations of collagenase and neutral protease for vertebral bone digestion and MSC recovery. The ratio and concentrations of collagenase and neutral protease was determined using DE collagenase (Vitacyte), wherein DE collagenase was comprised of purified *Clostridium histolyticum* collagenase and *Paenibacillus polymyxa* neutral protease. To determine the neutral protease activity (NPA), collagenase concentration was held constant at 0.4 U/ml while varying the neutral protease concentration between 2.4 and 19.6 U/ml. The specific neutral protease concentrations used were 2.4, 3.3, 4.9, 9.8 and 19.6 U/ml.

To determine the collagenase concentration for maximizing liberation of MSC from bone fragments, a series of tubes with a set neutral protease concentration and increasing collagenase concentrations was prepared. The collagenase concentrations used were 0.05, 0.1, 0.15, 0.2, 0.25, 0.3, 0.35, 0.4, 0.8, 1.2 and 1.6 U/ml.

Different concentrations and ratios of recombinant collagenase isoforms C1 and C2 were also purchased from Vitacyte. Total collagenase (C1 and C2) concentrations tested were 25, 32.5, 47.5, 42.5, 50, 65, 77.5, 85 and 100 micrograms/mi. The mass ratios of C1 and C2 for each concentration were 70:30, 54:46, 37:63, 82:18, 70:30, 54:46, 90:10, 82:18 and 70:30, respectively. For each concentration, neutral protease activity (NPA) was held constant at 4.9

U/ml. To evaluate the dependence of cell recovery on collagenase, the recombinant form (devoid of arty potential protease contamination) was used. Vertebral bone fragments bone grindings were digested with either 0 or 50 microgram/ml of the C1:C2 combination at the ratio of 35:15 in combination with 4.9 U/ml neutral protease. To evaluate the requirement for neutral protease. 50 micrograms/ml of C1:C2 at the ratio of 35:15 was used in the absence of 4.9 U/ml neutral protease.

Additionally. The volume of enzyme solution to bone fragment weight was assessed using ratios of 1:1, 2.5:1, 5:1, 7.5:1, 10:1, and 15:1 (volume:weight). Digestion time was evaluated by incubating bone fragments with protease solution for 1, 1.5, 2, 2.5, and 3 hours. The digestion protocol used is described below.

All experimental digestion was accomplished by incubating tubes for 10 minutes in a water bath set at 37° C. and then transferred to a shaking incubator and incubated for an additional 120 minutes at 37° C. while shaking at 100 rpm. Protease activity was then neutralized by adding 2 ml of Stemulate (Cook Regentec) and suspensions were filtered through a 70-micron tube top filter into 50 ml conical screw cap tubes. The filter-retained bone fragments were washed with 25 ml DPBS which was combined with the original filtrate. Tubes were centrifuged at 350 rpm for five mutes, supernatant aspirated, and the pellets are resuspended in 10 ml DPBS. The suspension was centrifuged again at 350 rpm for five inmates, supernatant aspirated, and the pellet resuspended in DPBS for cell count analysis.

Cell count analysis was performed by a Cellometer Vision (Nexcelom) to determine total viable cell counts. 20 microliters of HOPI were added to an Eppendorf tube containing 20 microliters of cells. Once mixed, 20 microliters of the solution were added to a Cellometer slide and total cells, live cells, and viability were calculated.

Figure 7:
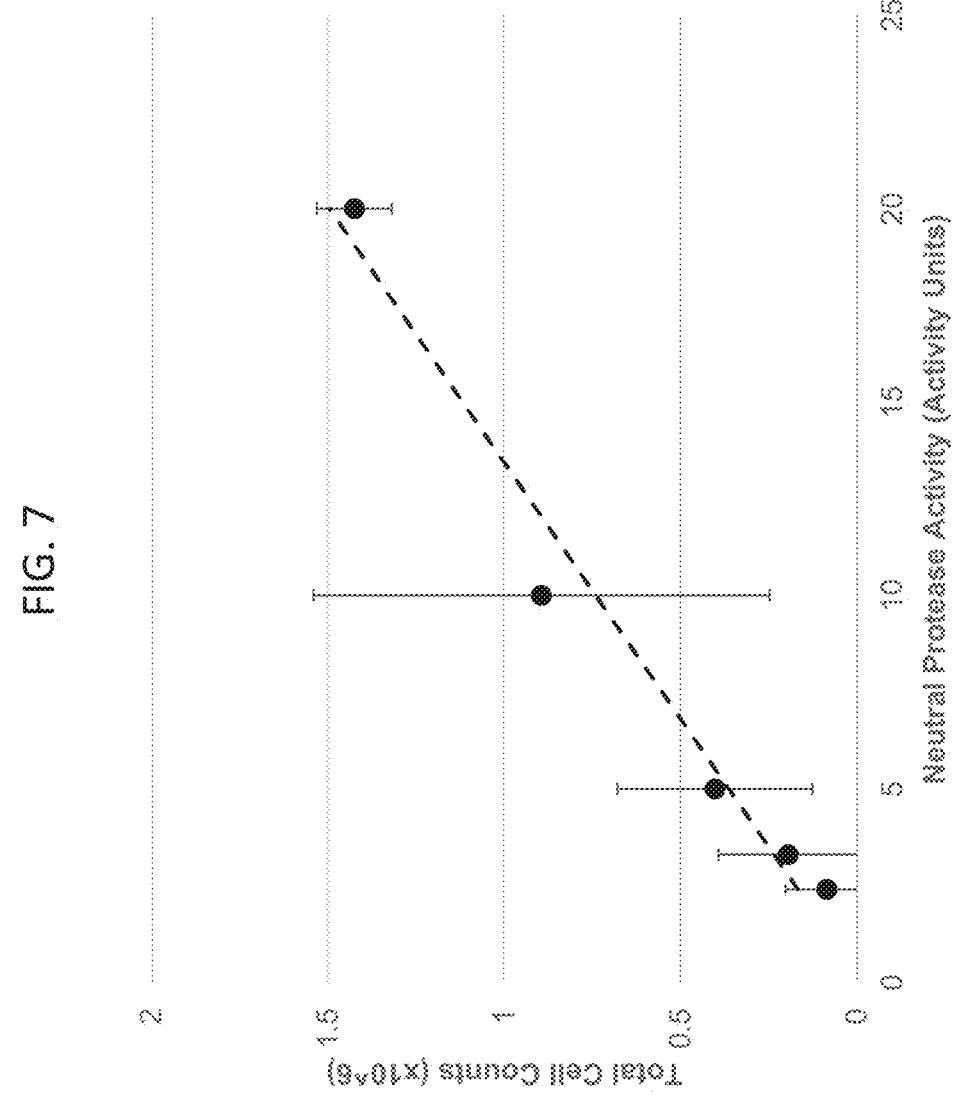
FIG. 7 is a chart showing the neutral protease activity at a fixed concentration of collagenase enzyme. Collagenase concentration was held constant at 0.4 U/ml and the activity of added neutral protease were 2.4, 3.3, 4.9, 9.8 and 19.6 U/ml. Recovered cells were plated at $2 \times 10^5$ cells/cm$^2$ and allowed to reach confluence and then counted. Values are means+standard deviations of triplicate experiments.

With respect to NPA for digestion and MSC recovery, it was determined that the maximum neutral protease activity (NPA) tested (1961 U/ml) was the best under these conditions based total viable vBA-MSC counts recovered per gram of bone digested represented in FIG. 7, Cell counts in freshly digested bane are enumerated and cells were plated at 100,000/cm$^2$ in a T-22.5 flask. Cells were trypsinized at ~90% confluency and counted.

Figure 8:
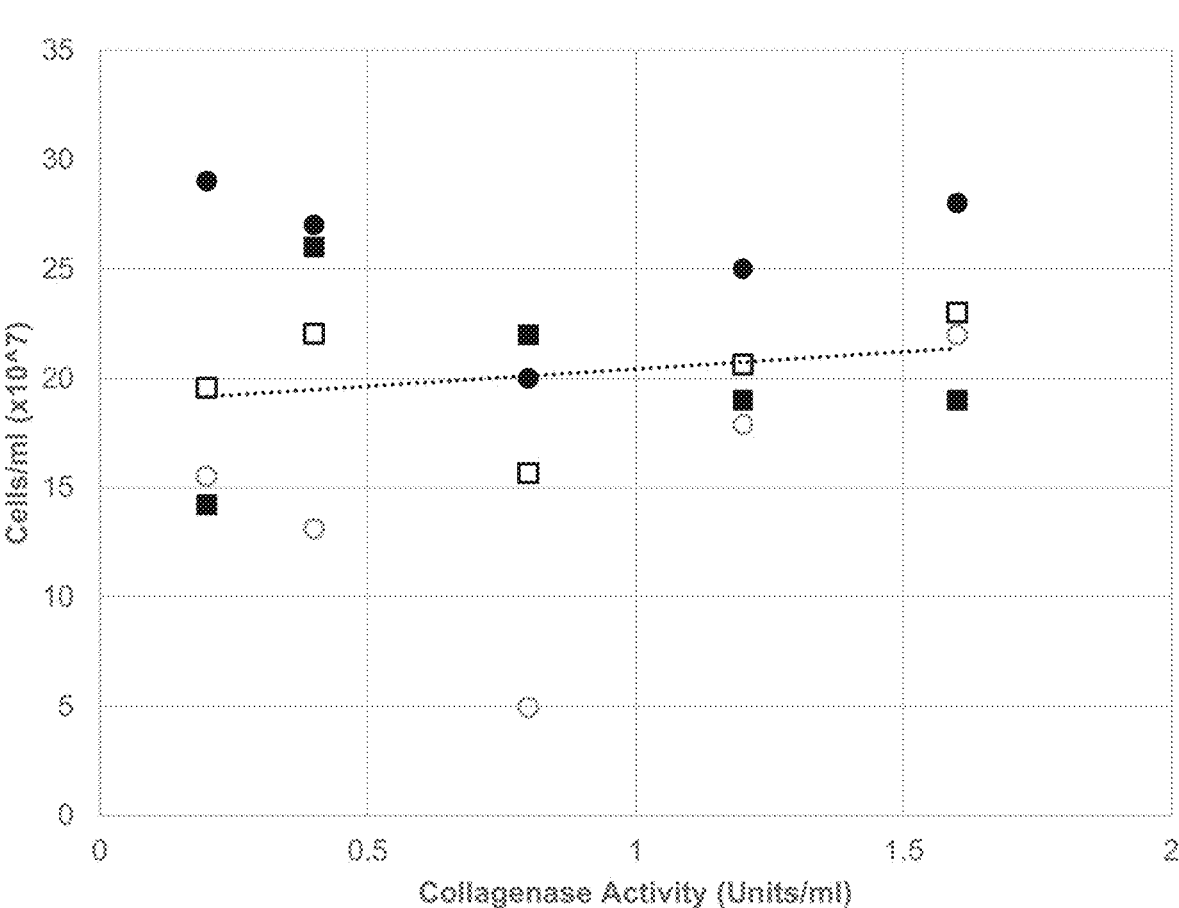
FIG. 8 is a chart showing the collagenase activity at a fixed concentration of neutral protease. Neutral protease concentration was held constant at 19.4 U/ml and a series of collagenase activities, ranging between 0.2 and 1.8 U/ml, was tested for release of cells from 1 g of VB bone fragments. The was no difference in total viable cell yield between any of the levels of collagenase. Values are means 4-standard deviations of triplicate experiments.

With respect to collagenase activity on MSC cell yield, it was found that the total viable MSC cell count was insensitive to collagenase concentration in the range used (FIG. 8).

Based on total viable cell counts recovered from digested bane it can be concluded that a ratio of 5:1 (volume/weight) yielded the highest number of viable cells (Table 2). Incubation times of 2.5 hours

TABLE 2

| Varying the ratio of protease solution volume to bone weight. | |
| --- | --- |
| Ratio | vTNC/g bone |
| 1:1 | $5.99 \times 10^7$ |
| 2.5:1 | $3.63 \times 10^7$ |
| 5:1 | $5.75 \times 10^7$ |
| 7.5:1 | $5.43 \times 10^7$ |
| 10:1 | $4.75 \times 10^7$ |
| 15:1 | $5.49 \times 10^7$ |

TABLE 3

| Optimizing digestion time | |
| --- | --- |
| Time (hr) | vTNC/g bone |
| 1 | $6.27 \times 10^7$ |
| 1.5 | $6.97 \times 10^7$ |
| 2 | $7.73 \times 10^7$ |
| 2.5 | $8.34 \times 10^7$ |
| 3 | $7.90 \times 10^7$ |

Example 3. In Vitro Evaluation of vBA-MSCs Allogeneic and Xenogenic T Cell Modulatory Mechanisms The scope of the experiment described is to evaluate the potent immunomodulatory, properties of human vBA-MSC for suppression of xenogeneic T cell activation (FIG. 9) as well as for facilitating chimerism. Evaluating human VBA-MSC in a murine model as employed in this experiment allows for testing the actual therapeutic agent rather than the murine surrogate MSC. This is especially important given the fundamental difference in murine MSC immunomodulatory mechanisms compared to human MSC. Therapeutic action of xenogeneic MSC in immunocompetent models has been established previously. In addition to determining $T_{EFF}$ suppression, induction of $T_{REG}$ cells, are evaluated since these cells are important for graft survival as well as peripheral tolerance.

Figure 9:
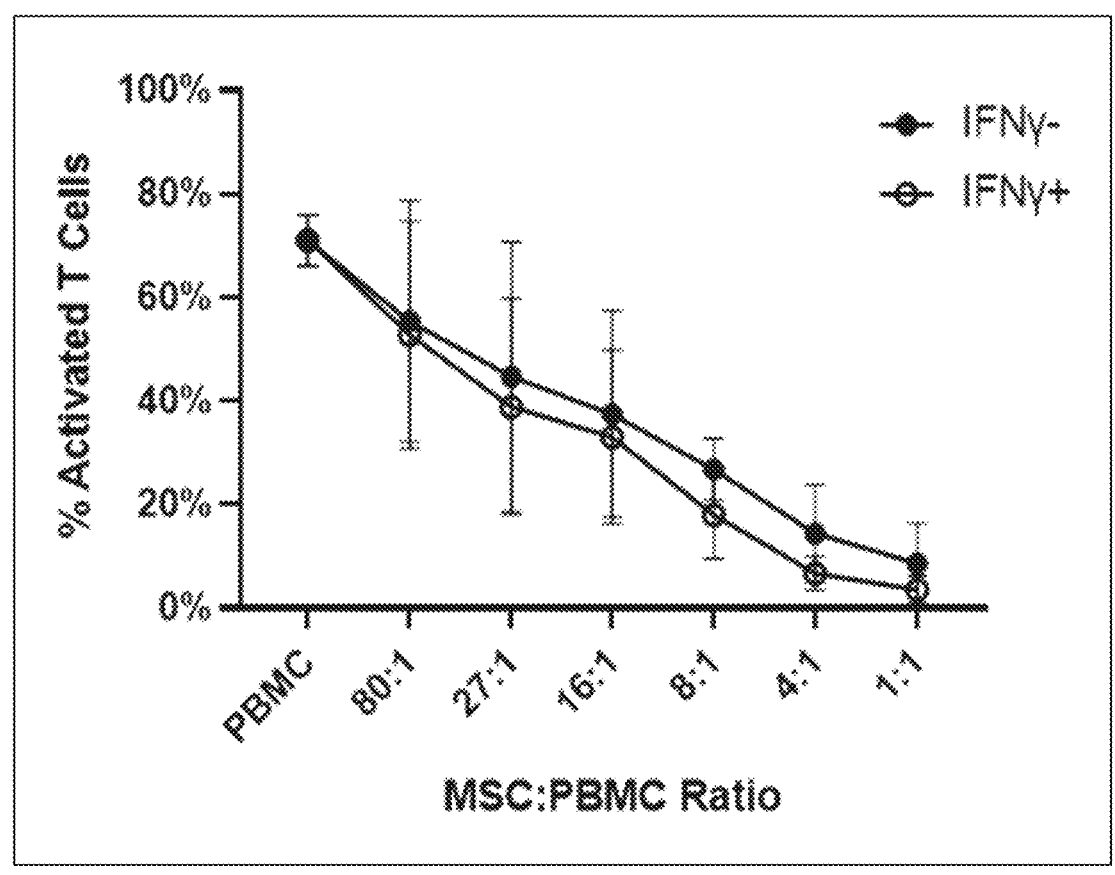
FIG. 9 is a chart showing potent suppression of stimulated T cells by vBA-MSC either with or without prior IFNγ simulation. Ratios of vBA-MSC:PBMC

Human and murine vBA-MSC suppression of antigen-independent and dependent activated murine lymphocytes are determined by analyzing peripheral blood mononuclear cells (PBMC) isolated from BALB/c (stimulator) and C57Bl/6 mice (responder) mice, Suppression of CD3/CD28-activated BALB/c CSFE-labeled PBMC is initially evaluated to establish a vBA-MSC:PBMC response curve (FIG. 9). Next, mixed lymphocyte reaction reactions (MLR) were performed with mitomycin-treated BALB/c PBMC and CSFE-labeled C57 Bl/6 PBMC (CFSE MLR). For both assays, responder cells are plated with activators after pre-attaching vBA-MSC and incubated for 4 days before analyzing for T cell proliferation. In separate experiments, $T_{REGS}$ and $T_{EM}$ cells populations are identified by flow cytometry using the respective antibody combinations of CD4+ FoxP3+ (eBioscience mouse regulatory T cell kit) and CD8+CD25–CD45RO+ (BD). It can be expected to observe levels of suppression with human vBA-MSCs similar to the results obtained for murine vBA-MSCs as seen in FIG. 9.

Example 4. Whole BM Transfusion and Co-Stimulation Blockade Effectively Modulate Immune Response to Animal Model VCA It has been previously demonstrated that whole BM transfusion and co-stimulation blockade effectively modulate the immune response to VCA when combined with other immunosuppressive modalities in large and small animal models as well as reduced requirement from immunosuppression in human. Success with these less toxic immunotherapies in VCA was demonstrated successfully with kidney and orthotopic hind limb transplantation models Additionally, such BM-derived MSC infusions showed enhanced nerve regeneration, an important component of VCA graft retention. The orthotopic hind limb transplant model implemented successfully provided a yield of 100% long-term animal survival in syngeneic donor-recipient combinations as well as demonstrated a characteristic pattern of graft acceptance and rejection in the allogeneic setting.

This highly, reliable mouse model for reconstructive transplantation provided a versatile immunological model system of a genetically defined inbred and transgenic mouse strain which opened the possibilities for diagnostic and interventional studies with translational impact on clinical VCA.

Example 5. The Combined Immunomodulatory Effect of vBA-MSC and BM In Vivo in a Mouse Orthotopic Hind Limb Model It has been previously shown that human vBA-MSC promote chimerism in irradiated mice receiving limiting doses of whole BM (FIG. 10. Very low levels (<1%) of chimerism were observed in BM of mice treated with 20,000 murine BM cells only. Chimerism increased to >8% with human vBA-MSC co-treatment.

This experiment builds off successes with abrogating specific immune responses, described in Example 3 and Example 4, using each modality to be tested in an established mouse orthotopic hind limb VCA model. All mice utilized in the experiment received a short-course (21 day) treatment with rapamycin (0.6 mg/kg), Postoperatively, mice are treated as described in the Table 4, with the VCA occurring on D0 ("Day 0")

TABLE 4

| | | | Treatment and Control Groups | | |
| --- | --- | --- | --- | --- |
| Grp | rapa (D0-21) | CTLA4-Ig | Murine BM (D14) | Human vBA-MSC |
| 1 | No | No | No | No |
| 2 | Yes | No | No | No |
| 3 | Yes | Yes | Yes | No |
| 4 | Yes | No | Low dose ($0.5 \times 10^6$) | No |
| 5 | Yes | No | Mid dose ($1 \times 10^6$) | No |
| 6 | Yes | No | High dose ($2 \times 10^6$) | No |
| 7 | Yes | No | Low dose ($0.5 \times 10^6$) | Yes (D14, D17) |
| 8 | Yes | No | Mid dose ($1 \times 10^6$) | Yes (D14, D17) |
| 9 | Yes | No | High dose ($2 \times 10^6$) | Yes (D14, D17) |
| 10 | Yes | No | No | Yes (D14, D17) |

Treatments with combinations of BM, vBA-MSC and CTLA4-Ig at times relevant to the clinical scenario requiring delayed BM and vBA-MSC infusion. Mice are randomly assigned to experimental groups (Table 4).

Surgical techniques and animal procedures involved recipient C57Bl/6 mice who receive fully mismatched hind limbs from donor BALB/c mice. Transplanted mice are monitored frequently over the first 4 hours and then daily thereafter until the end of the study at 120 days. Attrition due to mortality or morbidity in these surgical models was <10%.

For isolation of whole BM, donor BALB/c mice are euthanized and hind and fore limbs are removed and placed in plastic bags, which are placed in an insulated cooler with ice to be transported to appropriate clinic surgical suite. BM is isolated in a dedicated research space that is physically separated from the clinical tissue processing facilities.

Figure 10:
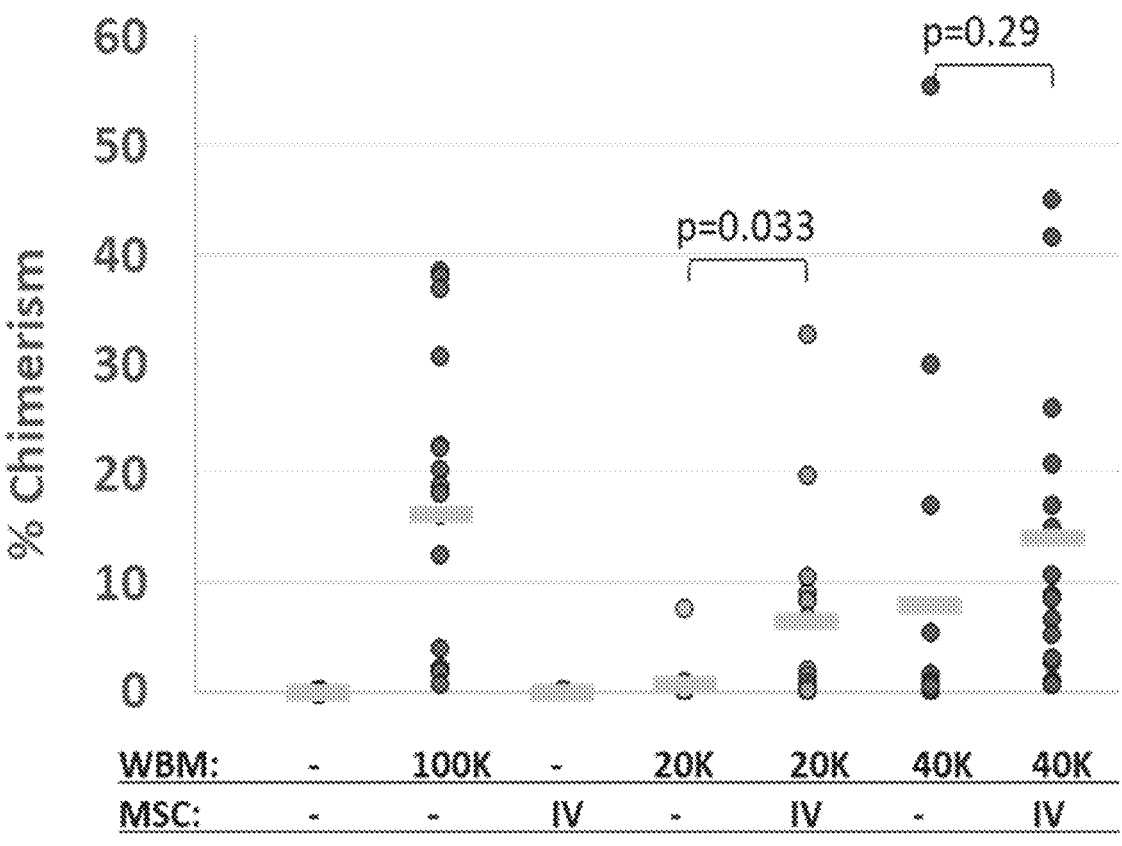
FIG. 10 is a chart showing that human vBA-MSC promote chimerism of murine BM HSC. C57Bl/6 (CD45.1) mice were lethally irradiated (872 cGy) and transplanted 24 hours later with either 100,000 (positive control), 20,000 or 40,000 whole BM cells from BoyJ (CD45.2) mice, One million human vBA-MSC were injected at 24 and 72 hours, Chimerism was measure in the BM of mice surviving 1 month.

BM is obtained by flushing BALB/c donor mouse humeri and femora with RPMI medium. Total nucleated counts and viability is determined. Banked human vBA-MSCs are obtained from cleaned and rinsed deceased donor VB fragments (FIG. 11) digested with DE10 collagenase (Vitacyte, Indianapolis, IN) and expanded in Mesencult medium (Stem Cell Technologies). Cells are cryopreserved at P2 after confirming quality by flow cytometry and CFU-F analyses. The low passage vBA-MSC used in this experiment is relatively small in size (average, 13 µm, range 6-29 µm) and are found to be well tolerated by recipient mice following intravenous delivery (FIG. 10).

Groups 2-10 mice receive intraperitoneal (i.p.) injections of rapamycin (06 mg/kg) for 21 days beginning immediately after transplantation. Groups 3 mice receive i.p injections of CTLA4-Ig (belatacept) on days 0, 2, 4 and 6 (500 µg ip on day 0 and 250 µg thereafter). Whole BM from BALB/c mice (low dose, $5 \times 10^5$; middle dose, $1 \times 10^6$; high dose, $2 \times 10^6$ total nucleated cells) is injected via the retro-orbital plexus on day 14, Human vBA-MSC is similarly injected on days 14 and 17. The high dose is chosen based on previous data demonstrating that this number of cells/body mass induced significantly reduced the allo-reactive immune response when injected individually. Lower BM doses are tested with a vBA-MSC dose that facilitated chimerism of congenic cells (FIG. 10).

Blood samples (25 µl) are withdrawn by cheek bleeding at weekly intervals and used for flow cytometric analysis of T cell subtypes. $T_{REGS}$ and $T_{EM}$ cells populations are identified by flow cytometry using the respective antibody combinations of CD4+ FoxP3+(eBioscience mouse regulatory 'T' cell kit) and CD8+CD25−CD45RO+(BD). Lymphocytes are assessed for alloantigen reactivity. BALE/c or OH enriched stimulator T cells are incubated with CSFE-labeled responder T cells from C57Bl/6 mice. The cultures are incubated for 4 days and analyzed for T cell proliferation as described above.

Allografts are monitored clinically by daily inspection. Craft acceptance is indicated by hair growth and intact transplanted skin. Graft rejection is indicated by skin erythema/necrosis and complete hair loss. Rejection is further confirmed by skin biopsies and histology. Donor antigen-specific immune tolerance is tested by secondary skin grafting on VCA recipients with grafts surviving to 120 days. Full-thickness tail skin (1 cm²) from BALB/c (H2d; donor-matched) or C311 (H2k; third-party) mice is transplanted onto the back of C57Bl/6 (H2h) recipients and secured with 6-0 prolene sutures. Skin graft survival is assessed daily by clinical inspection. Rejection is indicated by erythema and complete necrosis of the skin graft.

Immune monitoring assays (Luminex) are performed in investigate modulation of the immune response against donor antigens, or development of donor specific unresponsiveness, and to assess the immunocompetence of the recipient following transplantation. Peripheral blood mononuclear cells (PBMC) are isolated from recipient blood and plated in mixed lymphocyte reaction (CFSE MLR. Humoral reactivity is assessed by flow cytometric detection of serum antibody binding to donor and third party PBMC.

At the end of the study mice are sacrificed and fore and hind limbs are collected for isolation of BM and MSC as described above. Grafted limbs are processed separately. Chimerism of BM and engraftment of human vBA-MSC is evaluated by flow cytometry. The mononuclear fraction of whole BM and digested bone fragments was enriched by density gradient centrifugation with ficoll. The buffy coat is lysed and cells are labeled with fluorescently conjugated antibodies for flow cytometry. Whole BM is labeled with antibodies for CD45. H2b (C57bl/6 recipient) and H2d (BALB/c donor). Evidence of chimerism is determined through detection of CD45+H2d+ cells in a background of CD45+H2b+. The enriched digested bone fragments are labeled with the same markers as above with the inclusion of human specific CD73 and CD90 antibodies to detect vBA-MSC. Evidence of vBA-MSC persistence is determined based on the detection of CD45−huCD73+huCD90+ cells. For MSC anal sis a portion of the digest is plated at $3 \times 10^5$ cells/mi in Mesencult to select adherent cells which are expanded to P1 for flow analysis as described above.

It is found that a combination BM (any dose) and vBA-MSC results in >80% graft survival for 120 days and mice exhibit tolerance to 2° skirt grafts and lack alloantigen reactivity.

Example 6. vBA-MSC Induced Immune Tolerance in a Mouse Heterotopic Heart Transplantation Model The scope of this experiment encompasses the evaluation of a combined immunomodulatory effect a composition of vBA-MSC and BM exhibit in an in-vivo mouse heart transplantation model. Unlike VCA, the heart is not a pro-tolerogenic organ and, thus, represents a higher hurdle for tolerance induction, Nonetheless, there have been pre-clinical successes with prolonging survival of mismatched hearts in small animal models using BM transplantation to establish mixed chimerism. It has been shown previously that a murine cervical heart transplant model is capable to elucidate the immunological mechanisms of solid organ allograft survival in combination with costimulatory blockade and donor-specific blood infusion. Survival of mismatched hearts using this scheme have shown to correlate with enhanced intra-graft indolamine 2,3 deoxygenase (IDO) expression and $T_{REG}$ cell infiltration. This finding suggests a high probability of efficacy with vBA-MSC infusion along with establishing mixed chimerism, given the well-known immunomodulatory properties of MSC, including IDO expression and $T_{REG}$ modulation. Based on the findings from Example 5, the novel combination in mismatched heart transplantation is tested.

Surgical techniques and animal procedures for the modified mouse cervical heart transplantation model hold a major advantage of less occurrences of anastomosis related complications such as hemorrhages and thrombosis when compared to the abdominal transplant suture model. It was found that attrition due to mortality or morbidity after performing >1000 such surgeries is <20%.

Surgery and experimental procedures consist of dissecting and removing Fully mismatched hearts recovered from deeply anesthetized donor BALB/c mice. Hearts are flushed with cold cardioplegic solution. The IVC and superior vena cava as well as the pulmonary veins are ligated and transected. Hearts are then stored in 5 ml of 4° C. perfusion solution until transplantation to the recipient. Anesthetized recipient C57Bl/6 mice are prepared by shaving and disinfecting before making an incision from the jugular fossa to the mandibula. The right external jugular vein and the right common carotid artery are dissected and mobilized as far as possible. The distal ends are ligated twice and transected between the two ties. Two cuffs are placed over the vessels (24G arterial cuff; 22G venous cuff) and secured with a vessel clamp. Both vessels are everted over the distal end of the cuffs and fixed with a 6-0 silk ligature. The donor heart is then taken out of the cold preservation solution and first the aorta is pulled over the arterial cuff and secured with 6-0 silk. Thereafter, the pulmonary vein is anastomosed with the external jugular vein in a similar fashion. Finally, the vessel clamps are removed, and the heart allowed to reperfuse.

Mice are randomized to the treatment groups and subjected to the treatment regimens as described in Example 5. Transplanted mice are monitored frequently over the first 4 hours and then daily thereafter until the end of the study at 120 days. The function of the heart is assessed daily by visual and palpatory assessment for re-beating time—the time between reperfusion and first signs of cardiac contractions (either of the ventricle or atrium). In addition, cardiac function is assessed at after transplantation using a modified functional score (score 0: no beating, score 1: fibrillations, no real contractions, score 2: weak or partial contractions, score 3: homogenous contractions of both ventricles at reduced frequency and intensity, score 4: normal contraction intensity and frequency). Lymphocyte analysis, immune monitoring and 2° skin grafts are be performed as described in Example 5.

It is observed that the survival of transplanted hearts in groups followed, ranked lowest to highest: untreated<<<rapamycin alone<<vBA-MSC<CTLA4−Ig+ BM=vBA-MSC+BM (lower doses)<vBA-MSC+BM (highest dose). It is found that the vBA-MSC treated group reached significance with respect to all other groups, demonstrating >50% improvement in survival to the 120 day endpoint.

Example 7, vBA-MSC Induced Immune Tolerance in a Mouse Heterotopic Kidney Transplantation Model The scope of this experiment encompasses the evaluation of a combined immunomodulatory effect a composition of vBA-MSC and BM exhibit in an in-vivo mouse kidney transplantation model, Similar to VCA, the kidney is tolerogenic organ and, thus, pose a lower hurdle for tolerance induction. It has been shown previously that a murine kidney transplant model is capable to elucidate the immunological mechanisms of solid organ allograft survival in combination with costimulatory blockade and donor-specific blood infusion, Survival of mismatched kidneys using this scheme has shown to correlate with enhanced intra-graft indolamine 2,3 dioxygenase (IDO) expression and $T_{REG}$ cell infiltration. This finding suggests a high probability of efficacy with vBA-MSC infusion along with establishing mixed chimerism, given the well-known immunomodulatory properties of MSC, including IDO expression and $T_{REG}$ modulation. Based on the findings from Example 5, the novel combination in mismatched kidney transplantation is tested.

Surgery and experimental procedures consist of dissecting and removing fully mismatched kidneys recovered front deeply anesthetized donor BALB/c mice. Kidneys are then stored in 5 ml of 4° C. perfusion solution until transplantation to the recipient.

Mice are randomized to the treatment groups and subjected to the treatment regimens as described in Example 5. Transplanted mice are monitored frequently over the first 4 hours and then daily thereafter until the end of the study at 120 days. In addition, Lymphocyte analysis, immune monitoring and 2° skin grafts are performed as described in Example 5.

It is observed the survival of transplanted kidney in groups followed, ranked lowest to highest: untreated<<<rapamycin alone<<<vBA-MSC<CTLA4-Ig+ BM=vBA-MSC+BM (lower doses)<vBA-MSC+BM (highest dose). It is found that the vBA-MSC treated group reached significance with respect to all other groups, demonstrating >50% improvement in survival to the 120 day endpoint.

Example 8. Phenotype of vBA-MSCs

Cadaveric vBA-MSCs were extracted from t vertebral bodies as described herein, specifically as described in Example 2. Upon extraction, the vBA-MSCs were cultured in the culture medium comprising alpha MEM as described in Table 1, 10% Stemulate hPL, 2 ng/mL recombinant, carrier free FGF, and 2 ng/mL recombinant, carrier free EGF. An assay was ran to test the phenotype of the cadaveric vBA-MSCs. The assay tested for CD45+ cells, a well-documented phenotype specific to differentiated hematopoietic cells. A monoclonal antibody of CD45 was tested with vBA-MSCs from three distinct donors, two distinct samples were generated from a single donor, one sample that was passaged two times, and a distinct sample that was passaged three times. To test the phenotype of vBA-MSCs against bone marrow-derived MSCs, two samples of bone marrow-derived MSCs were also tested. The results of this assay, in terms of percent CD45+ cells are found in Table 5 below.

TABLE 5

| Donor | Cell Type | Passage | CD45+ |
|---|---|---|---|
| AGDF248 | vBA-MSC | P2 | 1.94% |
| AGDF248 | vBA-MSC | P3 | 1.98% |
| AGAX392 | vBA-MSC | P2 | 1.81% |
| AFLA403 | vBM-MSC | P4 | 1.75% |
| AGB2425 | vBM-MSC | P1 | 1.75% |
| AGEH235 | vBA-MSC | P3 | 1.95% |

Surprisingly, the vBA-MSC samples showed higher levels of CD45+ cells.

Example 9. Function of vBA-MSC Compositions Comprising Greater than 1.75% CD45+ Cells Higher CD45+ cell populations amongst a population of MSCs are known to result in decreased MSC function (e.g. lower colony forming units), Surprisingly, vBA-MSC compositions comprising CD45+ cells according to Table 5 showed levels of colony forming units greater than or substantially similar to colony forming units derived from a sample of bone marrow-derived MSCs. The results of the colony forming unit assay is described in Table 6 below.

TABLE 6

| Donor | Cell Type | Passage | CD45+ | CFU-F/ million cells |
|---|---|---|---|---|
| AGDF248 | vBA-MSC | P2 | 1.94% | 7.56E+05 |
| AGDF248 | vBA-MSC | P3 | 1.98% | Data not shown |
| AGAX392 | vBA-MSC | P2 | 1.81% | 1.67E+05 |
| AFLA403 | vBM-MSC | P4 | 1.75% | Data not shown |
| AGB2425 | vBM-MSC | P1 | 1.75% | 1.04E+05 |
| AGEH235 | vBA-MSC | P3 | 1.95% | 2.40E+05 |

Example 10 vBA-MSC Compositions Comprise Lower Levels of Senescent Cell Markers as Compared to Bone Marrow-Derived MSC Compositions vBA-MSC compositions are prepared according to the disclosure described herein, specifically Example 2, Samples from these compositions are tested for senescent cell markers MIC-A. MIC-B, and ULBP2. As a control, bone marrow-derived MSC compositions are tested for the same markers. The % BA-MSC compositions exhibit lower levels of MIC-A, MIC-B, and ULBP2 as compared to the bane marrow-derived MSC compositions.

Example 11 vBA-MSC Compositions Prepared and Maintained as Described Herein Exhibit Greater Doubling Times than Conventional MSC Compositions at Numerous Passages vBA-MSC compositions were prepared from 9 donor's according to Example 2. The vBA-MSC compositions were passaged up to 10 times. At each passage, the MSCs were plated onto either a 25 ml, 75 ml, or 225 ml flask at 3000 cells/cm². For cell counts at each passage, the MSCs were resuspended in either 1, 2, or 3 ml of buffer. The doubling rate of the MSCs at each passage was calculated, the results are summarized in Table %. Donor's with no passage 1 (P1) entry were removed from cryopreservation as described herein.

TABLE 7

| Donor | Passage | Days Between Passage | Viable TNCs/ ml | Total TNC/ ml | Total Viable TNCs | Total Cells | Cells Lifted/ cm2 | N | LN | CT (Hours) | Doubling Time |
|---|---|---|---|---|---|---|---|---|---|---|---|
| AGGM039 | P1 | | | | | | | | | | |
| | P2 | 4.00 | 2.28E+06 | 2.48E+06 | 4.56E+06 | 4.96E+06 | 6.61E+04 | 22.04 | 4.46 | 96.00 | 21.51 |
| | P3 | 2.95 | 4.25E+06 | 4.51E+06 | 4.25E+06 | 4.51E+06 | 6.01E+04 | 20.04 | 4.33 | 70.75 | 16.36 |
| | P4 | 3.88 | 2.06E+06 | 2.18E+06 | 2.06E+06 | 2.18E+06 | 8.72E+04 | 29.07 | 4.86 | 93.00 | 19.13 |
| | P5 | 3.91 | 1.14E+06 | 1.26E+06 | 1.14E+06 | 1.26E+06 | 5.04E+04 | 16.80 | 4.07 | 93.75 | 23.03 |
| | P6 | 4.09 | 1.23E+06 | 1.32E+06 | 1.23E+06 | 1.32E+06 | 5.28E+04 | 17.60 | 4.14 | 98.25 | 23.75 |
| | P7 | 3.90 | 1.15E+06 | 1.24E+06 | 1.15E+06 | 1.24E+06 | 4.96E+04 | 16.53 | 4.05 | 93.50 | 23.10 |
| | P8 | 4.02 | 1.11E+06 | 1.16E+06 | 1.11E+06 | 1.16E+06 | 4.64E+04 | 15.47 | 3.95 | 96.50 | 24.42 |
| | P9 | 4.09 | 9.76E+05 | 1.02E+06 | 9.76E+05 | 1.02E+06 | 4.08E+04 | 13.60 | 3.77 | 98.25 | 26.09 |
| | P10 | 3.99 | 8.54E+05 | 9.14E+05 | 8.54E+05 | 9.14E+05 | 3.66E+04 | 12.19 | 3.61 | 95.75 | 26.54 |
| AGB2425 | P1 | | | | | | | | | | |
| | P2 | 4.00 | 1.95E+06 | 2.18E+06 | 3.90E+06 | 4.36E+06 | 5.81E+04 | 19.38 | 4.28 | 96.00 | 22.45 |
| | P3 | 2.95 | 4.02E+06 | 4.35E+06 | 4.02E+06 | 4.35E+06 | 5.80E+04 | 19.33 | 4.27 | 70.75 | 16.56 |
| | P4 | 3.88 | 2.47E+06 | 2.60E+06 | 2.47E+06 | 2.60E+06 | 1.04E+05 | 34.67 | 5.12 | 93.00 | 18.18 |
| | P5 | 3.91 | 2.04E+06 | 2.22E+06 | 2.04E+06 | 2.22E+06 | 8.88E+04 | 29.60 | 4.89 | 93.75 | 19.18 |
| | P6 | 4.09 | 1.64E+06 | 1.78E+06 | 1.64E+06 | 1.78E+06 | 7.12E+04 | 23.73 | 4.57 | 98.25 | 21.50 |
| | P7 | 3.90 | 1.80E+06 | 1.96E+06 | 1.80E+06 | 1.96E+06 | 7.84E+04 | 26.13 | 4.71 | 93.50 | 19.86 |
| | P8 | 4.02 | 2.38E+06 | 2.59E+06 | 2.38E+06 | 2.59E+06 | 1.04E+05 | 34.53 | 5.11 | 96.50 | 18.88 |
| | P9 | 4.09 | 1.31E+06 | 1.43E+06 | 1.31E+06 | 1.43E+06 | 5.72E+04 | 19.07 | 4.25 | 98.25 | 23.10 |
| | P10 | 3.99 | 1.86E+06 | 1.99E+06 | 1.86E+06 | 1.99E+06 | 7.96E+04 | 26.53 | 4.73 | 95.75 | 20.24 |
| 4375119000058 | P1 | | | | | | | | | | |
| | P2 | 4.00 | 2.73E+06 | 2.95E+06 | 5.46E+06 | 5.90E+06 | 7.87E+04 | 26.22 | 4.71 | 96.00 | 20.37 |
| | P3 | 2.95 | 5.63E+06 | 5.93E+06 | 5.63E+06 | 5.93E+06 | 7.91E+04 | 26.36 | 4.72 | 70.75 | 14.99 |
| | P4 | 3.88 | 2.38E+06 | 2.51E+06 | 2.38E+06 | 2.51E+06 | 1.00E+05 | 33.47 | 5.06 | 93.00 | 18.36 |
| | P5 | 3.91 | 1.71E+06 | 1.83E+06 | 1.71E+06 | 1.83E+06 | 7.32E+04 | 24.40 | 4.61 | 93.75 | 20.34 |
| | P6 | 4.09 | 1.54E+06 | 1.67E+06 | 1.54E+06 | 1.67E+06 | 6.68E+04 | 22.27 | 4.48 | 98.25 | 21.95 |
| | P7 | 3.90 | 1.57E+06 | 1.69E+06 | 1.57E+06 | 1.69E+06 | 6.76E+04 | 22.53 | 4.49 | 93.50 | 20.81 |
| | P8 | 4.02 | 1.48E+06 | 1.60E+06 | 1.48E+06 | 1.60E+06 | 6.40E+04 | 21.33 | 4.42 | 96.50 | 21.86 |
| | P9 | 4.09 | 1.69E+06 | 1.81E+06 | 1.69E+06 | 1.81E+06 | 7.24E+04 | 24.13 | 4.59 | 98.25 | 21.39 |
| | P10 | 3.99 | 9.67E+05 | 1.01E+06 | 9.67E+05 | 1.01E+06 | 4.04E+04 | 13.47 | 3.75 | 95.75 | 25.52 |
| 4375119000060 | P1 | | | | | | | | | | |
| | P2 | 4.00 | 3.15E+06 | 3.32E+06 | 6.30E+06 | 6.64E+06 | 8.85E+04 | 29.51 | 4.88 | 96.00 | 19.66 |
| | P3 | 2.95 | 3.59E+06 | 3.82E+06 | 3.59E+06 | 3.82E+06 | 5.09E+04 | 16.98 | 4.09 | 70.75 | 17.32 |
| | P4 | 3.88 | 2.38E+06 | 2.45E+06 | 2.38E+06 | 2.45E+06 | 9.80E+04 | 32.67 | 5.03 | 93.00 | 18.49 |
| | P5 | 3.91 | 1.40E+06 | 1.56E+06 | 1.40E+06 | 1.56E+06 | 6.24E+04 | 20.80 | 4.38 | 93.75 | 21.41 |
| | P6 | 4.09 | 1.31E+06 | 1.47E+06 | 1.31E+06 | 1.47E+06 | 5.88E+04 | 19.60 | 4.29 | 98.25 | 22.89 |
| | P7 | 3.90 | 1.13E+06 | 1.26E+06 | 1.13E+06 | 1.26E+06 | 5.04E+04 | 16.80 | 4.07 | 93.50 | 22.97 |
| | P8 | 4.02 | 1.43E+06 | 1.55E+06 | 1.43E+06 | 1.55E+06 | 6.20E+04 | 20.67 | 4.37 | 96.50 | 22.09 |
| | P9 | 4.09 | 9.74E+05 | 1.08E+06 | 9.74E+05 | 1.08E+06 | 4.32E+04 | 14.40 | 3.85 | 98.25 | 25.53 |
| | P10 | 3.99 | 8.57E+05 | 9.14E+05 | 8.57E+05 | 9.14E+05 | 3.66E+04 | 12.19 | 3.61 | 95.75 | 26.54 |
| 4375119000073 | P1 | 3.90 | 7.45E+06 | 7.55E+06 | 7.45E+06 | 7.55E+06 | 1.01E+05 | 33.56 | 5.07 | 93.50 | 18.45 |
| | P2 | 3.86 | 3.59E+06 | 3.81E+06 | 7.18E+06 | 7.62E+06 | 6.39E+04 | 11.29 | 3.50 | 92.75 | 26.52 |
| | P3 | 3.03 | 7.24E+05 | 7.63E+05 | 7.24E+05 | 7.63E+05 | 3.05E+04 | 10.17 | 3.35 | 72.75 | 21.74 |
| | P4 | 2.96 | 8.84E+05 | 9.61E+05 | 8.84E+05 | 9.61E+05 | 3.84E+04 | 12.81 | 3.68 | 71.00 | 19.30 |
| | P5 | 4.01 | 1.70E+06 | 1.79E+06 | 1.70E+06 | 1.79E+06 | 7.16E+04 | 23.87 | 4.58 | 96.25 | 21.03 |
| | P6 | 3.05 | 6.73E+05 | 6.78E+05 | 6.73E+05 | 6.78E+05 | 2.71E+04 | 9.04 | 3.18 | 73.25 | 23.06 |
| | P7 | 3.07 | 1.03E+06 | 1.11E+06 | 1.03E+06 | 1.11E+06 | 4.44E+04 | 14.80 | 3.89 | 73.75 | 18.97 |
| | P8 | 3.85 | 1.28E+06 | 1.39E+06 | 1.28E+06 | 1.39E+06 | 5.56E+04 | 18.53 | 4.21 | 92.50 | 21.96 |
| | P9 | 5.10 | 1.53E+06 | 1.65E+06 | 1.53E+06 | 1.65E+06 | 6.60E+04 | 22.00 | 4.46 | 122.50 | 27.47 |
| | P10 | 5.00 | 8.89E+05 | 9.52E+05 | 8.89E+05 | 9.52E+05 | 3.81E+04 | 12.69 | 3.67 | 120.00 | 32.73 |
| AGFM119 | P1 | | | | | | | | | | |
| | P2 | 2.94 | 1.97E+06 | 2.09E+06 | 5.90E+06 | 6.27E+06 | 2.79E+04 | 9.29 | 3.22 | 70.50 | 21.93 |
| | P3 | 3.05 | 1.41E+06 | 1.56E+06 | 1.41E+06 | 1.56E+06 | 6.24E+04 | 20.80 | 4.38 | 73.25 | 16.73 |
| | P4 | 3.07 | 1.02E+06 | 1.12E+06 | 1.02E+06 | 1.12E+06 | 4.48E+04 | 14.93 | 3.90 | 73.75 | 18.91 |
| | P5 | 3.85 | 1.71E+06 | 1.87E+06 | 1.71E+06 | 1.87E+06 | 7.48E+04 | 24.93 | 4.64 | 92.50 | 19.94 |
| | P6 | 4.00 | 1.30E+06 | 1.42E+06 | 1.30E+06 | 1.42E+06 | 5.68E+04 | 18.93 | 4.24 | 96.00 | 22.63 |
| | P7 | 4.07 | 1.38E+06 | 1.52E+06 | 1.38E+06 | 1.52E+06 | 6.08E+04 | 20.27 | 4.34 | 97.75 | 22.52 |
| | P8 | 4.91 | 1.50E+06 | 1.60E+06 | 1.50E+06 | 1.60E+06 | 6.40E+04 | 21.33 | 4.42 | 117.75 | 26.67 |
| | P9 | 4.07 | 8.45E+05 | 9.16E+05 | 8.45E+05 | 9.16E+05 | 3.66E+04 | 12.21 | 3.61 | 97.75 | 27.07 |
| | P10 | 4.90 | 1.10E+06 | 1.25E+06 | 1.10E+06 | 1.25E+06 | 5.00E+04 | 16.67 | 4.06 | 117.50 | 28.95 |
| AGEE132 | P1 | 3.94 | 5.99E+06 | 6.37E+06 | 1.20E+07 | 1.27E+07 | 1.70E+05 | 56.62 | 5.82 | 94.50 | 16.23 |
| | P2 | 3.97 | 4.87E+06 | 5.43E+06 | 1.46E+07 | 1.63E+07 | 7.24E+04 | 24.13 | 4.59 | 95.25 | 20.74 |
| | P3 | 3.00 | 1.05E+06 | 1.12E+06 | 1.05E+06 | 1.12E+06 | 4.48E+04 | 14.93 | 3.90 | 72.00 | 18.46 |
| | P4 | 4.88 | 2.75E+06 | 2.98E+06 | 2.75E+06 | 2.98E+06 | 1.19E+05 | 39.73 | 5.31 | 117.00 | 22.02 |

TABLE 7-continued

| Donor | Passage | Days Between Passage | Viable TNCs/ ml | Total TNC/ ml | Total Viable TNCs | Total Cells | Cells Lifted/ cm2 | N | LN | CT (Hours) | Doubling Time |
|---|---|---|---|---|---|---|---|---|---|---|---|
| | P5 | 4.07 | 1.09E+06 | 1.16E+06 | 1.09E+06 | 1.16E+06 | 4.64E+04 | 15.47 | 3.95 | 97.75 | 24.74 |
| | P6 | 4.02 | 8.30E+05 | 9.18E+05 | 8.30E+05 | 9.18E+05 | 3.67E+04 | 12.24 | 3.61 | 96.50 | 26.71 |
| | P7 | 3.94 | 6.40E+05 | 6.91E+05 | 6.40E+05 | 6.91E+05 | 2.76E+04 | 9.21 | 3.20 | 94.50 | 29.50 |
| | P8 | 3.98 | 1.20E+06 | 1.27E+06 | 1.20E+06 | 1.27E+06 | 5.08E+04 | 16.93 | 4.08 | 95.50 | 23.40 |
| | P9 | 5.80 | 2.16E+06 | 2.33E+06 | 2.16E+06 | 2.33E+06 | 9.32E+04 | 31.07 | 4.96 | 139.25 | 28.09 |
| 20000003 | P1 | 3.83 | 3.53E+06 | 3.76E+06 | 7.06E+06 | 7.52E+06 | 1.00E+05 | 33.42 | 5.06 | 92.00 | 18.17 |
| | P2 | 3.94 | 3.23E+06 | 3.71E+06 | 9.69E+06 | 1.11E+07 | 4.95E+04 | 16.49 | 4.04 | 94.50 | 23.37 |
| | P3 | 4.13 | 1.52E+06 | 1.66E+06 | 1.52E+06 | 1.66E+06 | 6.64E+04 | 22.13 | 4.47 | 99.00 | 22.16 |
| | P4 | 4.91 | 1.85E+06 | 2.03E+06 | 1.85E+06 | 2.03E+06 | 8.12E+04 | 27.07 | 4.76 | 117.75 | 24.75 |
| | P5 | 4.07 | 7.66E+05 | 8.80E+05 | 7.66E+05 | 8.80E+05 | 3.52E+04 | 11.73 | 3.55 | 97.75 | 27.52 |
| | P6 | 4.90 | 1.15E+06 | 1.35E+06 | 1.15E+06 | 1.35E+06 | 5.40E+04 | 18.00 | 4.17 | 117.50 | 28.18 |
| | P7 | 4.90 | 1.78E+06 | 1.94E+06 | 1.78E+06 | 1.94E+06 | 7.76E+04 | 25.87 | 4.69 | 117.50 | 25.04 |
| | P8 | 4.06 | 7.57E+05 | 8.20E+05 | 7.57E+05 | 8.20E+05 | 3.28E+04 | 10.93 | 3.45 | 97.50 | 28.26 |
| | P9 | 3.88 | 1.24E+06 | 1.34E+06 | 1.24E+06 | 1.34E+06 | 5.36E+04 | 17.87 | 4.16 | 93.00 | 22.36 |
| 20000014 | P1 | 2.88 | 1.72E+06 | 1.86E+06 | 1.72E+06 | 1.86E+06 | 7.44E+04 | 24.80 | 4.63 | 69.00 | 14.90 |
| | P2 | 3.03 | 4.25E+06 | 4.55E+06 | 1.28E+07 | 1.37E+07 | 6.07E+04 | 20.22 | 4.34 | 72.75 | 16.77 |
| | P3 | 2.97 | 1.21E+06 | 1.29E+06 | 1.21E+06 | 1.29E+06 | 5.16E+04 | 17.20 | 4.10 | 71.25 | 17.36 |
| | P4 | 2.97 | 2.51E+06 | 2.83E+06 | 2.51E+06 | 2.83E+06 | 1.13E+05 | 37.73 | 5.24 | 71.25 | 13.60 |
| | P5 | 5.98 | 2.82E+06 | 3.21E+06 | 2.82E+06 | 3.21E+06 | 1.28E+05 | 42.80 | 5.42 | 143.50 | 26.48 |
| | P6 | 3.95 | 1.61E+06 | 1.76E+06 | 1.61E+06 | 1.76E+06 | 7.04E+04 | 23.47 | 4.55 | 94.75 | 20.81 |
| | P7 | 4.11 | 1.99E+06 | 2.22E+06 | 1.99E+06 | 2.22E+06 | 8.88E+04 | 29.60 | 4.89 | 98.75 | 20.20 |
| | P8 | 3.94 | 2.50E+06 | 2.28E+06 | 2.50E+06 | 2.28E+06 | 9.12E+04 | 30.40 | 4.93 | 94.50 | 19.18 |
| | P9 | 3.89 | 1.66E+06 | 1.83E+06 | 1.66E+06 | 1.83E+06 | 7.32E+04 | 24.40 | 4.61 | 93.25 | 20.23 |
| | P10 | 3.97 | 2.60E+06 | 2.80E+06 | 2.60E+06 | 2.80E+06 | 1.12E+05 | 37.33 | 5.22 | 95.25 | 18.24 |

The doubling time at each passage was averaged across all 9 donors. The average doubling times at each passage can be found in Table 8.

TABLE 8

| Average | P1 | 16.94 |
|---|---|---|
| | P2 | 21.48 |
| | P3 | 17.96 |
| | P4 | 19.19 |
| | P5 | 22.63 |
| | P6 | 23.50 |
| | P7 | 22.55 |
| | P8 | 22.97 |
| | P9 | 24.59 |
| | P10 | 25.54 |

Example 12 VBA-MSC Compositions Prepared and Maintained as Described Herein Exhibit Similar Cell Surface Markers as Compared to BM-MSC Compositions vBA-MSC compositions were prepared from 1 donor according to Example 2 along with vBM-MSC compositions (prepared using standard procedures in the art) from the same donor. The compositions for tested for the presence of classical MSC markers: CD86, CD140B, CD146, CD274, HLA-ABC, MICA-B, ULBP2/5/6 and CD199.

Both the vBA-MSC and the BM-MSC compositions expressed all of the markers, at all passages, without significant differences in expression level, evidencing that the distinct compositions maintain an "MSC-like" phenotype.

Example 13 vBA-MSC Compositions Prepared and Maintained as Described Herein Comprise More Cells in S Phase as Compared to BM-MSC Compositions at Passage 4

Figure 12:
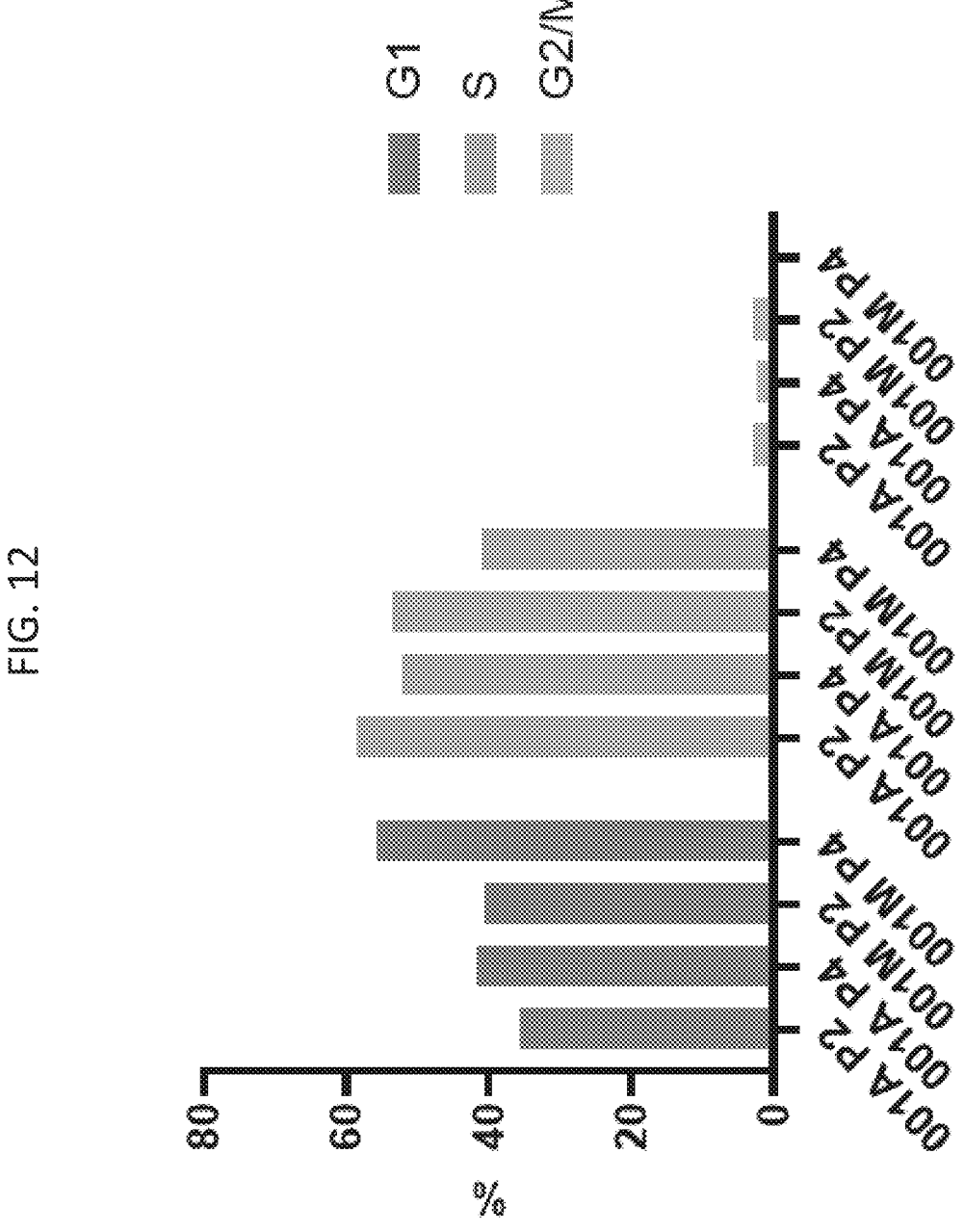
FIG. 12 illustrates a comparison between vBA-MSCs (marked as "001A") prepared by the methods described herein and bone marrow derived MSCs (derived from the same donor as the vBA-MSCs) (marked as "001M") prepared using standard procedures known in the an. Specifically.

VBA-MSC compositions were prepared from 1 donor according to Example 2 along with vBM-MSC compositions (prepared using standard procedures in the art) from the same donor. The compositions were passaged at least 4 times and assayed for percentage of cells in either G1, G2, or S phases of the cell cycle. The results are depicted in FIG. 12 indicating that the V-BA-MSC compositions comprised more cells in S Phase as compared to BM-MSC compositions at passage 4. These results are consistent with the doubling times disclosed in Example 11 which are faster than conventional MSC compositions.

Example 14 vBA-MSC Compositions Prepared and Maintained as Described Herein Retain Immuno-Suppressive Properties Similar to BM-MSC Compositions at Passage 4 Upon Stimulation with IFNγ

VBA-MSC compositions were prepared from 1 donor according to Example 2 along with vBM-MSC compositions (prepared using standard procedures in the art) from the same donor. The compositions were passaged at least 4 times, cultured with CD4+ and CD8+ T-cells, and assayed for T-cell suppression. T-cell suppression was represented by "fold-stimulation" by IFNγ. Fold stimulation by IFNγ is the "expansion index" of (IFNγ) unstimulated cells/expansion index of (IFNγ) stimulated cells. The "expansion index" is all generations greater than or equal to 1 divided by (the antilog (base n) of each generation 1 or greater+G0) e.g., G1+G2+G3, etc/(G1/2+G2/4+G3/8, etc+G0).

Figure 13:
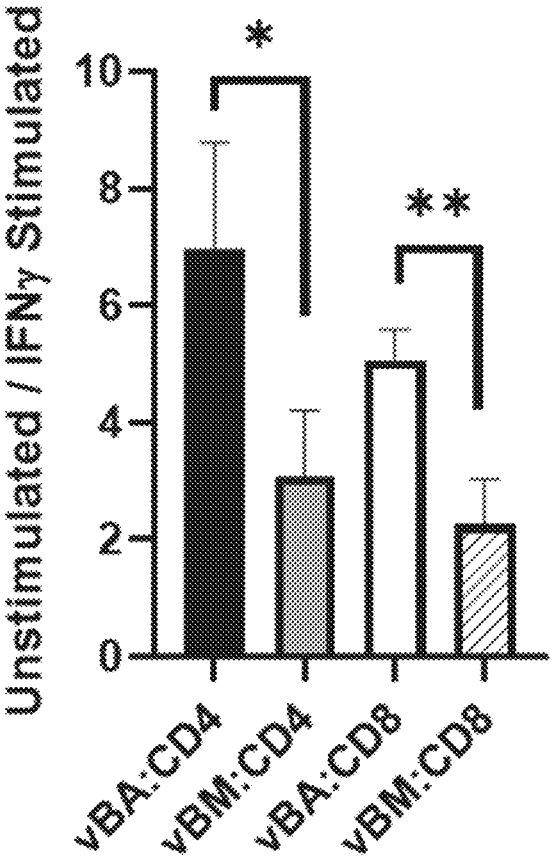
FIG. 13 illustrates a comparison between vBA-MSCs prepared by the methods described herein and BM-MSCs prepared using standard procedures known in the art. Specifically.

The results are depicted in FIG. 13 and indicated fold stimulation of >4-fold CD4 T cell suppression at P4 by vBA-MSC compositions (vBM was 3.07) and >3-fold for CD8 T cells by vBA-MSC compositions (vBM was 2.33).

While preferred embodiments oft the present invention have been shown and described herein, it will be obvious to those skilled in the art that such embodiments are provided by way of example only. It is not intended that the invention be limited by the specific examples provided within the specification. While the invention has been described with reference to the aforementioned specification, the descriptions and illustrations of the embodiments herein are not meant to be construed in a limiting sense. Numerous variations, changes, and substitutions will now occur to those skilled in the art without departing from the invention. Furthermore, it shall be understood that all aspects of the invention are not limited to the specific depictions, configurations or relative proportions set forth herein which depend upon a variety of conditions and variables. It should be understood that various alternatives to the embodiments of the invention described herein may be employed in practicing the invention. It is therefore contemplated that the invention shall also cover any such alternatives, modifications, variations or equivalents. It is intended that the following claims define the scope of the invention and that methods and structures within the scope of these claims and their equivalents be covered thereby.

What is claimed is:

1. A method of generating a population of mesenchymal stem cells (MSCs), the method comprising:
   a. obtaining a cadaver bone, cadaver bone fragments, or ground cadaver bone, optionally, preparing ground cadaver bone from the cadaver bone or cadaver bone fragments;
   b. contacting the ground cadaver bone with a grinding medium comprising at least one of Benzonase®, Iscove's Modified Dulbecco's Media (IMDM), PLASMA-LYTE™ A, or any combination thereof, under conditions sufficient to separate bone marrow from the ground cadaver bone;
   c. capturing the ground cadaver bone on a filter or sieve and collecting a filtrate that passes thru the filter or sieve, thereby recovering the bone marrow;
   d. contacting the captured ground cadaver bone with a digestion solution comprising a collagenase from *Clostridium histolyticum*, thereby obtaining fresh MSCs from the captured ground cadaver bone, wherein the digestion solution is present at a ratio of volume to weight of said the captured ground cadaver bone of about 1:1 to about 15:1; and
   e. passaging a sample of fresh MSCs at least 4 times, wherein the sample of fresh MSCs comprise a doubling rate of at least about 16 to 36 hours over the at least 4 passages, thereby generating the population of MSCs.

2. The method of claim 1, wherein the digestion solution comprises a neutral protease.

3. The method of claim 1, wherein the collagenase comprises collagenase isoforms C1 and C2 at a ratio comprising more collagenase isoform C1 than collagenase isoform C2.

4. The method of claim 3, wherein the ratio of collagenase isoform C1 to collagenase isoform C2 is about 30:10 to about 70:29.

5. The method of claim 4, wherein the ratio of collagenase isoform C1 to collagenase C2 is 35:15.

6. The method of claim 2, wherein the digestion solution comprises about 2 to about 20 U/ml of the neutral protease.

7. The method of claim 6, wherein the digestion solution comprises the neutral protease at an activity of about 19.6 U/ml.

8. The method of claim 1, wherein the digestion solution is present at a ratio of volume to weight of the captured ground cadaver bone is about 5:1.

9. The method of claim 1, wherein the digestion solution is contacted with the captured ground cadaver bone for up to about 2.5 hours.

10. The method of claim 1, wherein the population of MSCs are passaged at least 10 times.

11. The method of claim 1, wherein the population of MSCs comprises more than 1.75% CD45+ cells.

12. The method of claim 1, wherein the population of MSCs comprises at least 90% CD105+ cells.

13. The method of claim 1, wherein the population of MSCs comprises at least 90% CD166+ cells.

14. The method of claim 1, wherein the cadaver bone is a vertebral body.

15. The method of claim 1, wherein the doubling rate is less than about 29 hours.

16. The method of claim 1, wherein the grinding medium comprises an anticoagulant, wherein the anticoagulant is heparin.

17. The method of claim 1, wherein the grinding medium further comprises:
   a. a Denarase reagent (C-Lecta GmbH); and/or
   b. a DNase reagent.

18. The method of claim 1, wherein the grinding medium comprises a protein source and/or a reactive oxygen scavenger, optionally wherein the protein source and/or reactive oxygen scavenger is human serum albumin.

19. The method of claim 1, wherein the method further comprises contacting the ground cadaver bone with an isopropyl alcohol and/or a bleach prior to contacting the ground cadaver bone with a grinding medium.

20. The method of claim 1, wherein the method further comprises contacting the ground cadaver bone with hydrogen peroxide, then washing the bone at least once in a solution comprising PLASMA-LYTE™ A and/or IMDM, prior to contacting the ground cadaver bone with a grinding medium.

21. The method of claim 1, wherein the method further comprises an at least one rinse step after separating the bone marrow from the ground cadaver bone, wherein the rinse step comprising contacting the bone marrow with a rinse media comprising human serum albumin, and at least one of: IMDM, PLASMA-LYTE™ A, Benzonase®, heparin, or any combination thereof.

22. The method of claim 1, wherein the method further comprises collecting the filtrate that passes through the filter or sieve in a media comprising human serum albumin, and at least one of: IMDM, PLASMA-LYTE™ A, Benzonase®, heparin, or any combination thereof.

23. The method of claim 1, wherein the method further comprises contacting the captured ground cadaver bone with a digestion solution for 1 to 3 hours.

* * * * *